US010538574B2

(12) United States Patent
Bleakley et al.

(10) Patent No.: US 10,538,574 B2
(45) Date of Patent: Jan. 21, 2020

(54) TCRS SPECIFIC FOR MINOR HISTOCOMPATIBILITY (H) ANTIGEN HA-1 AND USES THEREOF

(71) Applicant: FRED HUTCHINSON CANCER RESEARCH CENTER, Seattle, WA (US)

(72) Inventors: Marie Bleakley, Seattle, WA (US); Robson Dossa, Shoreline, WA (US); Daniel Sommermeyer, Munich (DE)

(73) Assignee: FRED HUTCHINSON CANCER RESEARCH CENTER, Seattle, WA (US)

(*) Notice: Subject to any disclaimer, the term of this patent is extended or adjusted under 35 U.S.C. 154(b) by 0 days.

(21) Appl. No.: 16/362,551

(22) Filed: Mar. 22, 2019

(65) Prior Publication Data

US 2019/0211076 A1  Jul. 11, 2019

Related U.S. Application Data

(63) Continuation of application No. PCT/US2017/053112, filed on Sep. 22, 2017.

(60) Provisional application No. 62/399,291, filed on Sep. 23, 2016.

(51) Int. Cl.
| | |
|---|---|
| *C07K 14/725* | (2006.01) |
| *A61K 35/17* | (2015.01) |
| *C07K 14/705* | (2006.01) |
| *C12N 5/0783* | (2010.01) |
| *A61P 35/02* | (2006.01) |

(52) U.S. Cl.
CPC .......... *C07K 14/7051* (2013.01); *A61K 35/17* (2013.01); *A61P 35/02* (2018.01); *C07K 14/70517* (2013.01); *C12N 5/0636* (2013.01); *C07K 2319/41* (2013.01)

(58) Field of Classification Search
None
See application file for complete search history.

(56) References Cited

U.S. PATENT DOCUMENTS

| | | | |
|---|---|---|---|
| 5,420,032 A | 5/1995 | Marshall et al. | |
| 6,410,319 B1 | 6/2002 | Raubitschek et al. | |
| 6,833,252 B1 | 12/2004 | Dujon et al. | |
| 7,446,191 B2 | 11/2008 | Jensen | |
| 7,514,537 B2 | 4/2009 | Jensen | |
| 8,697,359 B1 | 4/2014 | Zhang | |
| 8,822,647 B2 | 9/2014 | Jensen | |
| 9,574,000 B2 | 2/2017 | Langermann et al. | |
| 10,189,880 B2 | 1/2019 | Heemskerk et al. | |
| 2004/0002092 A1 | 1/2004 | Arnould et al. | |
| 2004/0087025 A1 | 5/2004 | June et al. | |
| 2006/0078552 A1 | 4/2006 | Arnould et al. | |
| 2006/0153826 A1 | 7/2006 | Arnould et al. | |
| 2006/0206949 A1 | 9/2006 | Arnould et al. | |
| 2007/0117128 A1 | 5/2007 | Smith et al. | |
| 2011/0189141 A1 | 8/2011 | Kieback et al. | |
| 2011/0243972 A1 | 10/2011 | Jaffee | |
| 2011/0301073 A1 | 12/2011 | Gregory et al. | |
| 2014/0068797 A1 | 3/2014 | Doudna et al. | |
| 2014/0186843 A1 | 7/2014 | Zhang et al. | |
| 2016/0045594 A1 | 2/2016 | Geraghty et al. | |
| 2016/0046724 A1 | 2/2016 | Brogdon et al. | |
| 2016/0263155 A1 | 9/2016 | Heemskerk et al. | |

FOREIGN PATENT DOCUMENTS

| | | | | |
|---|---|---|---|---|
| EP | 2836511 B1 | 11/2017 | | |
| WO | WO-2007017201 A1 * | 2/2007 | ........... | C12N 5/0636 |
| WO | 2010/065818 A1 | 6/2010 | | |
| WO | 2013/025779 A1 | 2/2013 | | |
| WO | 2013/074916 A1 | 5/2013 | | |
| WO | 2014/031687 A1 | 2/2014 | | |
| WO | 2014/059173 A2 | 4/2014 | | |
| WO | 2015/066262 A1 | 5/2015 | | |
| WO | 2015/071474 A2 | 5/2015 | | |
| WO | 2016/040724 A1 | 3/2016 | | |
| WO | 2016/054638 A1 | 4/2016 | | |

OTHER PUBLICATIONS

Janeway et al., Immunobiology, 5th Ed., Garland Science, pp. 106-108 and 260-263, (2001). (Year: 2001).*
Manning et al., Immunity, vol. 8, 413-425, Apr. 1998. (Year: 1998).*
Garcia et al., Cell, vol. 122, 333-336, Aug. 12, 2005. (Year: 2005).*
Portolano et al., J Immunol. Feb. 1, 1993;150(3):880-7. (Year: 1993).*
Woodsworth et al., Genome Medicine 2013, 5:98. (Year: 2013).*
Kloosterboer et al. (Leukemia (2004) 18, 798-808). (Year: 2004).*
Robins et al., Blood. 2009;114:4099-4107. (Year: 2009).*
Argast et al., "I-Ppol and I-Crel Homing Site Sequence Degeneracy Determined by Random Mutagenesis and Sequential in Vitro Enrichment," *J. Mol. Biol.* 280:345-353, 1998.
Ashworth et al., "Computational redesign of endonuclease DNA binding and cleavage specificity,". *Nature.* 441(7093):656-659, 2006. (11 pges).
Belfort et al., "Homing endonucleases: keeping the house in order," *Nucleic Acids Research* 25(17):3379-3388, 1997.

(Continued)

*Primary Examiner* — Zachary S Skelding
(74) *Attorney, Agent, or Firm* — Seed IP Law Group LLP

(57) ABSTRACT

The present disclosure provides compositions and methods for targeting a minor histocompatibility (H) antigen (HA-$1^H$) to, for example, prevent or manage relapse of a hematological malignancy after allogeneic hematopoietic stem cell transplantation (HCT). Also provided are transgene constructs encoding engineered binding proteins, such as a T cell receptor or a chimeric antigen receptor, optionally encoding additional components such as a co-receptor and/or safety switch. Such transgene constructs can be transduced into an immune cell, such as a T cell, and used as an immunotherapy in a subject having a hematological malignancy or at risk for recurrence of the hematological malignancy (e.g., leukemia, lymphoma, myeloma).

19 Claims, 43 Drawing Sheets

Specification includes a Sequence Listing.

(56) References Cited

OTHER PUBLICATIONS

Bleakley et al., "Augmentation of anti-tumor immunity by adoptive T-cell transfer after allogeneic hematopoietic stem cell transplantation," *Expert Rev Hematol.* 5(4):409-425, 2012. (27 pages).
Bleakley et al., "Engineering Human Peripheral Blood Stem Cell Grafts That Are Depleted of Naïve T Cells and Retain Functional Pathogen-Specific Memory T cells," *Biol Blood Marrow Transplant.* 20(5):705-716, 2014. (24 pages).
Bleakley et al., "Exploiting T Cells Specific for Human Minor Histocompatibility Antigens for Therapy of Leukemia," *Immunol Cell Biol.* 89(3):396-407, 2011. (26 pages).
Bleakley et al., "Leukemia-associated minor histocompatibility antigen discovery using T-cell clones isolated by in vitro stimulation of naive $CD8^+$ T cells," *Blood* 115(23):4923-4933, 2010. (12 pages).
Bleakley et al., "Molecules and Mechanisms of the Graft-Versus-Leukaemia Effect," *Nature Reviews Cancer* 4:371-380, 2004.
Bleakley et al., "Outcomes of acute leukemia patients transplanted with naive T cell—depleted stem cell grafts," *The Journal of Clinical Investigation* 125(7): 2677-2689, 2015.
Bonini et al., "Safety of retroviral gene marking with a truncated NGF receptor," *Nature Medicine* 9(4):367-369, 2003.
Bowerman et al., "Engineering the Binding Properties of the T Cell Receptor:Peptide:MHC Ternary Complex that Governs T Cell Activity," *Mol Immunol.* 46(15):3000-3008, 2009. (23 pages).
Brentjens et al., "Genetically Targeted T Cells Eradicate Systemic Acute Lymphoblastic Leukemia Xenografts," *Clin Cancer Res* 13(18):5426-5435, 2007. (11 pages).
Chevalier et al., "Design, Activity, and Structure of a Highly Specific Artificial Endonuclease," *Molecular Cell* 10:895-905, 2002.
Cole et al., "The molecular determinants of CD8 co-receptor function," *Immunology* 137:139-148, 2012.
Dangaj et al., "Novel recombinant human B7-H4 antibodies overcome tumoral immune escape to potentiate T cell anti-tumor responses," *Cancer Res.* 73(15):4820-4829, 2013. (19 pages).
De Kreuk et al., "The Human Minor Histocompatibility Antigen1 Is a RhoGAP," *PLoS ONE* 8(9):e73962, 2013. (15 pages).
Desjarlais et al., "Use of a zinc-finger consensus sequence framework and specificity rules to design specific DNA binding proteins," *Proc. Natl. Acad. Sci. USA* 90:2256-2260, 1993.
Di Stasi et al., "Inducible Apoptosis as a Safety Switch for Adoptive Cell Therapy," *N Engl J Med.* 365(18):1673-1683, 2011. (16 pages).
Dickinson et al., "In situ dissection of the graft-versus-host activities of cytotoxic T cells specific for minor histocompatibility antigens," *Nature Medicine* 8(4):410-414, 2002.
Dossa et al., "Development of T-cell immunotherapy for hematopoietic stem cell transplantation recipients at risk of leukemia relapse," *Blood* 131(1):108-120, 2018. (14 pages).
Dossett et al., "Adoptive Immunotherapy of Disseminated Leukemia With TCR-transduced, $CD8^+$ T Cells Expressing a Known Endogenous TCR," *Molecular Therapy* 17(4): 742-749, 2009.
Dujon et al., "Mobile introns: definition of terms and recommended nomenclature," *Gene* 82:115-118, 1989.
Epinat et al., "A novel engineered meganuclease induces homologous recombination in yeast and mammalian cells," *Nucleic Acids Research* 31(11):2952-2962, 2003.
Fehse et al., "CD34 Splice Variant: An Attractive Marker for Selection of Gene-Modified Cells," *Molecular Therapy* 1(5):448-456, 2000.
Floros et al., "Anticancer Cytokines: Biology and Clinical Effects of IFN-α2, IL-2, IL-15, IL-21, and IL-12," *Semin Oncol.* 42(4):539-548, 2015. (17 pages).
Ghorashian et al., "CD8 T Cell Tolerance to a Tumor-Associated Self-Antigen Is Reversed by CD4 T Cells Engineered to Express the Same T Cell Receptor," *J Immunol* 194:1080-1089, 2015. (11 pages).
Gimble et al., "Substrate Recognition and Induced DNA Distortion by the PI-SceI Endonuclease, an Enzyme Generated by Protein Splicing," *J. Mol. Biol.* 263:163-180, 1996.

Giuntoli II et al., "Direct Costimulation of Tumor-reactive CTL by Helper T Cells Potentiate Their Proliferation, Survival, and Effector Function," *Clinical Cancer Research* 8:922-931, 2002. (11 pages).
Govers et al., "T cell receptor gene therapy: strategies for optimizing transgenic TCR pairing," *Trends in Molecular Medicine* 16(2):77-87, 2010.
Griffioen et al., "Autosomal Minor Histocompatibility Antigens: How Genetic Variants Create Diversity in Immune Targets," *Frontiers in Immunology* 7(100), 2016. (9 pages).
Griffioen et al., "Genetic engineering of virus-specific T cells with T-cell receptors recognizing minor histocompatibility antigens for clinical application," Haematologica 93(10):1535-1543, 2008.
Hambach et al., "Human cytotoxic T lymphocytes specific for a single minor histocompatibility antigen HA-1 are effective against human lymphoblastic leukaemia in NOD/scid mice," *Leukemia* 20:371-374, 2006.
Harris et al., "Adoptive T Cell Therapies: A Comparison of T Cell Receptors and Chimeric Antigen Receptors," *Trends Pharmacol Sci.* 37(3):220-230, 2016. (21 pages).
Hinrichs et al., "Adoptively transferred effector cells derived from naïve rather than central memory $CD8^+$ T cells mediate superior antitumor immunity," *PNAS* 106(41):17469-17474, 2009.
Inaguma et al., "Construction and molecular characterization of a T-cell receptor-like antibody and CAR-T cells specific for minor histocompatibility antigen HA-1H," *Gene Therapy* 21:575-584, 2014.
Jasin, "Genetic manipulation of genomes with rare-cutting endonucleases," *TIG* 12(6):224-228, 1996.
Jinek et al., "A Programmable Dual-RNA-Guided DNA Endonuclease in Adaptive Bacterial Immunity," *Science* 337:816-821, 2012.
Kennedy et al., "Multiple roles for $CD4^+$ T cells in anti-tumor immune responses," *Immunological Reviews* 222:129-144, 2008.
Kennedy et al., "T Helper Lymphocytes Rescue CTL from Activation-Induced Cell Death," *J Immunol.* 177(5):2862-2872, 2006. (25 pages).
Kessels et al., "Generation of T Cell Help through a MHC Class I-Restricted TCR," *J Immunol* 177:976-982, 2006. (8 pages).
Kieback et al., "A safeguard eliminates T cell receptor gene-modified autoreactive T cells after adoptive transfer," PNAS 105(2):623-628, 2008.
Kim et al., "High Cleavage Efficiency of a 2A Peptide Derived from Porcine Teschovirus-1 in Human Cell Lines, Zebrafish and Mice," *PLoS ONE* 6(4):e18556, 2011. (8 pages).
Kuball et al., "Facilitating matched pairing and expression of TCR chains introduced into human T cells," *Blood.* 109(6):2331-2338, 2007. (17 pages).
Leen et al., "Improving T Cell Therapy for Cancer," *Annu. Rev. Immunol.* 25:243-265, 2007. (26 pp.).
Li et al., "Memory T cells from minor histocompatibility antigen-vaccinated and virus-immune donors improve GVL and immune reconstitution," *Blood* 118(22):5965-5976, 2011. (22 pages).
Liu et al., "Selective inhibition of IDO1 effectively regulates mediators of antitumor immunity," *Blood* 115(17):3520-3530, 2010. (12 pages).
Liu et al., "Systematic comparison of 2A peptides for cloning multi-genes in a polycistronic vector," *Scientific Reports* 7:2193, 2017. (9 pages).
Marijt et al., "Hematopoiesis-restricted minor histocompatibility antigens HA-1- or HA-2-specific T cells can induce complete remissions of relapsed leukemia," *PNAS* 100(5):2742-2747, 2003.
Matte-Martone et al., "$CD8^+$ but not $CD4^+$ T cells require cognate interactions with target tissues to mediate GVHD across only minor H antigens, whereas both $CD4^+$ and $CD8^+$ T cells require direct leukemic contact to mediate GVL," *Blood.* 111(7):3884-3892, 2008. (18 pages).
Mautino et al., "Abstract 491: NLG919, a novel indoleamine-2,3-dioxygenase (IDO)-pathway inhibitor drug candidate for cancer therapy," *AACR 104th Annual Meeting,* Washington, D.C., Apr. 6-10, 2013. (4 pages) (Abstract Only).
Mavilio et al., "Peripheral Blood Lymphocytes as Target Cells of Retroviral Vector-Mediated Gene Transfer," *Blood* 83(7):1988-1997, 1994. (11 pages).

(56) References Cited

OTHER PUBLICATIONS

Morgan et al., "Cancer Regression in Patients After Transfer of Genetically Engineered Lymphocytes," *Science*. 314(5796): 126-129, 2006. (10 pages).

Morris et al., "A critical role of T cell antigen receptor-transduced MHC class I-restricted helper T cells in tumor protection," *PNAS* 102(22):7934-7939, 2005.

Mutis et al., "Generation of minor histocompatibility antigen HA-1-specific cytotoxic T cells restricted by nonself HLA molecules: a potential strategy to treat relapsed leukemia after HLA-mismatched stem cell transplantation," *Blood* 100:547-552, 2002. (7 pages).

Nakanishi et al., "CTL mobilization to virus-infected tissue requires $CD4^+$ T cell help," *Nature*. 462(7272):510-513, 2009. (12 pages).

Ochi et al., "Application of Adoptive T-Cell Therapy Using Tumor Antigen-Specific T-Cell Receptor Gene Transfer for the Treatment of Human Leukemia," *Journal of Biomedicine and Biotechnology 2010*, 2010. (10 pages).

Pâques et al., "Meganucleases and DNA Double-Strand Break-Induced Recombination: Perspectives for Gene Therapy," *Current Gene Therapy* 7(1):49-66, 2007.

Perler et al., "Protein splicing elements: inteins and exteins—a definition of terms and recommended nomenclature," *Nucleic Acids Research* 22(7):1125-1127, 1994.

Philip et al., "A highly compact epitope-based marker / suicide gene for easier and safer T-cell therapy," www.bloodjournal.org, 2014. (21 pages).

Philip et al., "A Highly Compact Epitope-Based Marker Suicide Gene for Safer and Easier Adoptive T-Cell Gene Therapy," *Molecular Therapy* 20(1): S35-S36, 2012.

Philip et al., "A highly compact epitope-based marker/suicide gene for easier and safer T-cell therapy," *Blood* 124(8):1277-1287, 2014. (12 pages).

Porteus et al, "Gene targeting using zinc finger nucleases," *Nature Biotechnology* 23(8): 967-973, 2005.

Ray et al., "MHC-I-restricted melanoma antigen specific TCR-engineered human $CD4^+$ T cells exhibit multifunctional effector and helper responses, in vitro," *Clinical Immunology* 136:338-347, 2010.

Sadelain et al., "The basic principles of chimeric antigen receptor (CAR) design," *Cancer Discov.* 3(4): 388-398, 2013. (21 pages).

Schmitt et al., "T Cell Receptor Gene Therapy for Cancer," *Human Gene Therapy* 20:1240-1248, 2009.

Scholten et al., "Codon modification of T cell receptors allows enhanced functional expression in transgenic human T cells," *Clinical Immunology* 119:135-145, 2006.

Sommermeyer et al., "Chimeric antigen receptor-modified T cells derived from defined $CD8^+$ and $CD4^+$ subsets confer superior antitumor reactivity in vivo," *Leukemia.* 30(2): 492-500, 2016. (20 pages).

Stone et al., "A novel T cell receptor single-chain signaling complex mediates antigen-specific T cell activity and tumor control," *Cancer Immunol Immunother.* 63(11):1163-1176, 2014. (23 pages).

Stone et al., "Role of T cell receptor affinity in the efficacy and specificity of adoptive T cell therapies," *Frontiers in Immunology T Cell Biology* 4(244), 2013. (15 pages).

Straathof et al., "An inducible caspase 9 safety switch for T-cell therapy," *Blood* 105(11):4247-4254, 2005. (20 pages).

Stromnes et al., "Re-adapting T cells for cancer therapy: from mouse models to clinical trials," *Immunol Rev.* 257(1):145-164, 2014. (34 pages).

Sussman et al., "Isolation and Characterization of New Homing Endonuclease Specificities at Individual Target Site Positions," *J. Mol. Biol.* 342:31-41, 2004.

Terentis et al., "The Selenazal Drug Ebselen Potently Inhibits Indoleamine 2,3-Dioxygenase by Targeting Enzyme Cysteine Residues," *Biochemistry* 49(3):591-600, 2010.

Tey et al., "Inducible caspase 9 suicide gene to improve the safety of allodepleted T cells after haploidentical stem cell transplantation," *Biol Blood Marrow Transplant.* 13(8):913-924, 2007. (22 pages).

Thakral et al., "Differential Expression of the Human $CD8\beta$ Splice Variants and Regulation of the M-2 Isoform by Ubiquitination," *The Journal of Immunology* 180:7431-7442, 2008.

Thakral et al., "The Human $CD8\beta$ M-4 Isoform Dominant in Effector Memory T Cells Has Distinct Cytoplasmic Motifs That Confer Unique Properties," *PLoS ONE* 8(3):e59374, 2013. (12 pages).

Till et al, "Adoptive immunotherapy for indolent non-Hodgkin lymphoma and mantle cell lymphoma using genetically modified autologous CD20-specific T cells," *Blood* 112(6):2261-2271, 2008. (12 pages).

Torikai et al., "A foundation for universal T-cell based immunotherapy: T cells engineered to express a CD19-specific chimeric-antigen-receptor and eliminate expression of endogenous TCR," *Blood* 119(24):5697-5705, 2012. (10 pages).

Torikai et al., "Aberrant expression of BCL2A1-restricted minor histocompatibility antigens in melanoma cells: application for allogeneic transplantation," *Int J Hematol* 87:467-473, 2008.

Torikai et al., "Genetic editing of HLA expression in hematopoietic stem cells to broaden their human application," *Scientific Reports* 6:21757, 2016. (11 pages).

Torikai et al., "The HLA-A*0201-restricted minor histocompatibility antigen HA-1H peptide can also be presented by another HLA-A2 subtype, A*0206," *Bone Marrow Transplantation* 40:165-174, 2007.

Torikai et al., "Toward eliminating HLA class I expression to generate universal cells from allogeneic donors," *Blood* 122(8):1341-1349, 2013. (10 pages).

Van der Torren et al., "Possible Role of Minor H Antigens in the Persistence of Donor Chimerism after Stem Cell Transplantation; Relevance for Sustained Leukemia Remission," *PLoS ONE* 10(3):e0119595, 2015. (18 pages).

Van Loenen et al., "Extracellular Domains of $CD8\alpha$ and $CD8\beta$ Subunits Are Sufficient for HLA Class I Restricted Helper Functions of TCR-Engineered $CD4^+$ T Cells," *PLoS ONE* 8(5):e65212, 2013. (7 pages).

Van Loenen et al., "Optimization of the HA-1-specific T-cell receptor for gene therapy of hematologic malignancies," *Haematologica* 96(3):477-481, 2011.

Wang et al., "A transgene-encoded cell surface polypeptide for selection, in vivo tracking, and ablation of engineered cells," *Blood.* 118(5):1255-1263, 2011. (18 pages).

Wang et al., "Engraftment of human central memory-derived effector $CD8^+$ T cells in immunodeficient mice," *Blood* 117(6): 1888-1898, 2011. (12 pages).

Wang et al., "Optimizing Adoptive Polyclonal T Cell Immunotherapy of Lymphomas, Using a Chimeric T Cell Receptor Possessing CD28 and CD137 Costimulatory Domains," *Human Gene Therapy* 18:712-725, 2007. (17 pages).

Warren et al., "Therapy of relapsed leukemia after allogeneic hematopoietic cell transplantation with T cells specific for minor histocompatibility antigens," *Blood.* 115(19):3869-3878, 2010. (22 pages).

Willemsen et al., "Redirecting human $CD4^+$ T lymphocytes to the MHC class I-restricted melanoma antigen MAGE-A1 by TCR $\alpha\beta$ gene transfer requires $CD8\alpha$," *Gene Therapy* 12:140-146, 2005.

Wolfe et al., "Analysis of Zinc Fingers Optimized via Phage Display: Evaluating the Utility of a Recognition Code," *J. Mol. Biol.* 285:1917-1934, 1999.

Xie et al., "sgRNAcas9: A Software Package for Designing CRISPR sgRNA and Evaluating Potential Off-Target Cleavage Sites, "*PLoS ONE* 9(6):e100448, 2014. (9 pages).

Xu et al., "Multiple pro-tumorigenic functions of the human minor Histocompatibility Antigen-1 (HA-1) in melanoma progression," *Journal of Dermatological Science* 88:216-224, 2017.

Zhou et al., "Improving the Safety of T Cell Therapies using an Inducible Caspase-9 Gene," *Exp Hematol.* 44(11):1013-1019, 2016. (14 pages).

Zhou et al., "Inducible caspase-9 suicide gene controls adverse effects from alloreplete T cells after haploidentical stem cell transplantation," *Blood.* 125(26):4103-4113, 2015. (20 pages).

(56) References Cited

OTHER PUBLICATIONS

Zhou et al., "Long-term outcome after haploidentical stem cell transplant and infusion of T cells expressing the inducible caspase 9 safety transgene," *Blood.* 123(25):3895-3905, 2014. (21 pages).
Zhou et al., "Serial Activation of the Inducible Caspase 9 Safety Switch After Human Stem Cell Transplantation," *Molecular Therapy* 24(4): 823-831, 2016.
The Union for International Cancer Control's (UICC), "4th International Conference on Immunotherapy in Pediatric Oncology (CIPO2015)," event information, last updated Mar. 10, 2015, event Sep. 25, 2015-Sep. 26, 2015, URL=https://www.uicc.org/4th-international-conference-immunotherapy-pediatric-oncology-cipo2015, download date May 13, 2019. (3 pages).
SeattleChildrens, "CIPO 2015: Adoptive T Cell Immunotherapy Targeting the Minor Histocompatibility Antigen HA-1," YouTube Video, Oct. 20, 2015, URL=https://www.youtube.com/watch?v=na6v_LcW4oQ, download date May 13, 2019, 2 pages. (Screenshot).
International Search Report and Written Opinion dated Jan. 3, 2018, in corresponding PCT Application No. PCT/US2017/053112, 16 pages.
Bonnet et al., "CD8+ minor histocompatibility antigen-specific cytotoxic T lymphocyte clones eliminate human acute myeloid leukemia stem cells," *Proc. Natl. Acad. Sci. USA* 96:8639-8644, 1999.
De Bueger et al., "Tissue distribution of human minor histocompatibility antigens. Ubiquitous versus restricted tissue distribution indicates heterogeneity among human cytotoxic T lymphocyte-defined non-MHC antigens," *The Journal of Immunology* 149(5):1788-1794, 1992. (8 pages).
Den Haan et al., "The Minor Histocompatibility Antigen HA-1: A Diallelic Gene with a Single Amino Acid Polymorphism," *Science* 279(5353):1054-1057, 1998. (5 pages).
Faber et al., "Recognition of Clonogenic Leukemic Cells, Remission Bone Marrow and HLA-identical Donor Bone Marrow by CD8+ or CD4+ Minor Histocompatibility Antigen-specific Cytotoxic T Lymphocytes," *J. Clin. Invest.* 96:877-883, 1995.
Falkenburg et al., "Growth Inhibition of Clonogenic Leukemic Precursor Cells by Minor Histocompatibility Antigen-specific Cytotoxic T Lymphocytes," *J. Exp. Med.* 174:27-33, 1991.
Franssen et al., "A phase I/II minor histocompatibility antigen-loaded dendritic cell vaccination trial to safely improve the efficacy of donor lymphocyte infusions in myeloma," *Bone Marrow Transplantation* 52:1378-1383, 2017.
Fujii et al., "Expression of Minor Histocompatibility Antigen, HA-1, in Solid Tumor Cells," *Transplantation* 73(7):1137-1141, 2002.
Hambach et al., "Targeting a single mismatched minor histocompatibility antigen with tumor-restricted expression eradicates human solid tumors," *Blood* 112(5):1844-1852, 2008. (10 pages).
Heemskerk et al., "Reprogramming of Virus-specific T Cells into Leukemia-reactive T Cells Using T Cell Receptor Gene Transfer," *J. Exp. Med.* 199(7):885-894, 2004.
Hobo et al., "Association of disparities in known minor histocompatibility antigens with relapse-free survival and graft-versus-host-disease after allogeneic stem cell transplantation," *Biol Blood Marrow Transplant.* 19(2):274-282, 2013. (21 pages).
Kircher et al., "Hematopoietic Lineage-Restricted Minor Histocompatibility Antigen HA-1 in Graft-Versus-Leukemia Activity After Donor Lymphocyte Infusion," *J Immunother* 27(2):156-160, 2004.
Kircher et al., "Induction of HA-1-specific cytotoxic T-cell clones parallels the therapeutic effect of donor lymphocyte infusion," *British Journal of Haematology* 117:935-939, 2002.
Klein et al., "The Hematopoietic System-specific Minor Histocompatibility Antigen HA-1 Shows Aberrant Expression in Epithelial Cancer Cells," *J. Exp. Med.* 196(3):359-368, 2002.
Kloosterboer et al., "Direct cloning of leukemia-reactive T cells from patients treated with donor lymphocyte infusion shows a relative dominance of hematopoiesis-restricted minor histocompatibility antigen HA-1 and HA-2 specific T cells," *Leukemia* 18:798-808, 2004.
Marijt et al., "Minor Histocompatibility Antigens HA-1-, -2-, and -4-, and HY-Specific Cytotoxic T-Cell Clones Inhibit Human Hematopoietic Progenitor Cell Growth by a Mechanism That Is Dependent on Direct Cell-Cell Contact," *Blood* 82(12):3778-3785, 1993. (9 pages).
Meij et al., "Generation and administration of HA-1-specific T-cell lines for the treatment of patients with relapsed leukemia after allogeneic stem cell transplantation: a pilot study," *haematologica* 97(8):1205-1208, 2012.
Mutis et al., "Tetrameric HLA class I-minor histocompatibility antigen peptide complexes demonstrate minor histocompatibility antigen-specific cytotoxic T lymphocytes in patients with graft-versus-host disease," *Nature Medicine* 5(7):839-842, 1999.
Nicholls et al., "Secondary anchor polymorphism in the HA-1 minor histocompatibility antigen critically affects MHC stability and TCR recognition," *PNAS* 106(10):3889-3894, 2009.
Pont et al., "Microarray Gene Expression Analysis to Evaluate Cell Type Specific Expression of Targets Relevant for Immunotherapy of Hematological Malignancies," *PLoS ONE* 11(5), e0155165, 2016. (20 pages).
Spierings et al., "Multicenter Analyses Demonstrate Significant Clinical Effects of Minor Histocompatibility Antigens on GvHD and GvL after HLA-Matched Related and Unrelated Hematopoietic Stem Cell Transplantation," *Biol Blood Marrow Transplant* 19:1244-1253, 2013.
Spierings et al., "Steric Hindrance and Fast Dissociation Explain the Lack of Immunogenicity of the Minor Histocompatibility HA-1$^{Arg}$ Null Allele," *The Journal of Immunology* 182:4809-4816, 2009.
Van Bergen et al., "Selective graft-versus-leukemia depends on magnitude and diversity of the alloreactive T cell response," *J Clin Invest.* 127(2):517-529, 2017.
Van der Harst et al., "Recognition of Minor Histocompatibility Antigens on Lymphocytic and Myeloid Leukemic Cells by Cytotoxic T-Cell Clones," *Blood* 83(4):1060-1066, 1994. (8 pages).
Van der Zouwen et al., "Collateral Damage of Nonhematopoietic Tissue by Hematopoiesis-Specific T Cells Results in Graft-versus-Host Disease During an Ongoing Profound Graft-versus-Leukemia Reaction," *Biol Blood Marrow Transplant* 20:760-769, 2014.
Van Lochem et al., "Functional expression of minor histocompatibility antigens on human peripheral blood dendritic cells and epidermal Langerhans cells," *Transplant Immunology* 4:151-157, 1996.
Van Loenen et al., "A Good Manufacturing Practice procedure to engineer donor virus-specific T cells into potent anti-leukemic effector cells," *haematologica* 99(4):759-768, 2014.
Voogt et al., "Cellularly Defined Minor Histocompatibility Antigens Are Differentially Expressed on Human Hematopoietic Progenitor Cells," *J. Exp. Med.* 168:2337-2347, 1988.
Wilke et al., "Quantification of the HA-1 gene product at the RNA level; relevance for immunotherapy of hematological malignancies," *The Hematology Journal* 4:315-320, 2003. (7 pages).
Medina et al., "Genetic Engineering of CD4+ T lymphocytes to Target MHC-class-I Restricted Tumor Antigens, *A Novel Approach to Prevent Leukemia Relapse After Allogeneic Hematopoietic Stem Cell Transplantation (HCT),*" *4th International Conference on Immunotherapy in Pediatric Oncology (CIPO2015)*, 2015. (27 pages).

\* cited by examiner

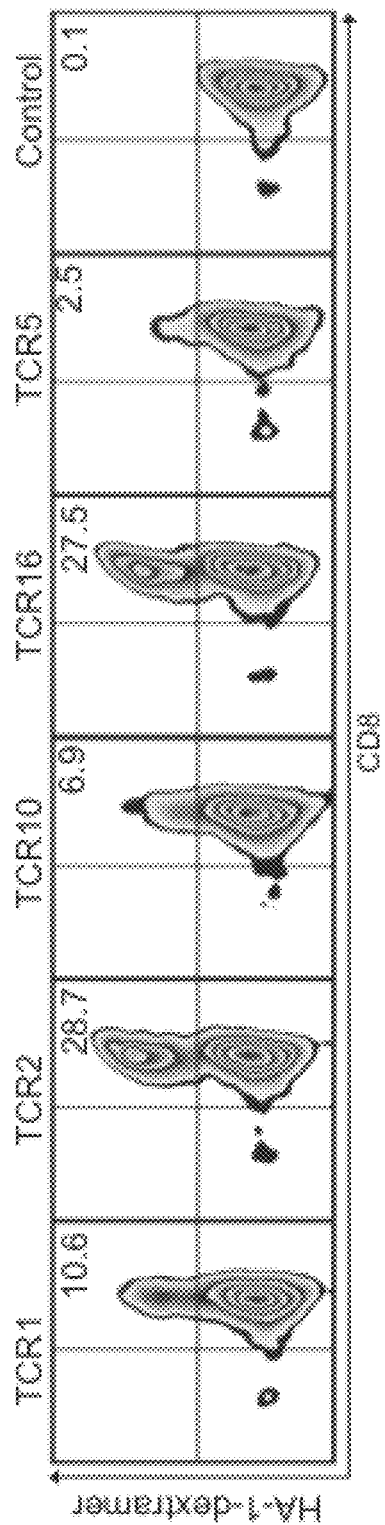
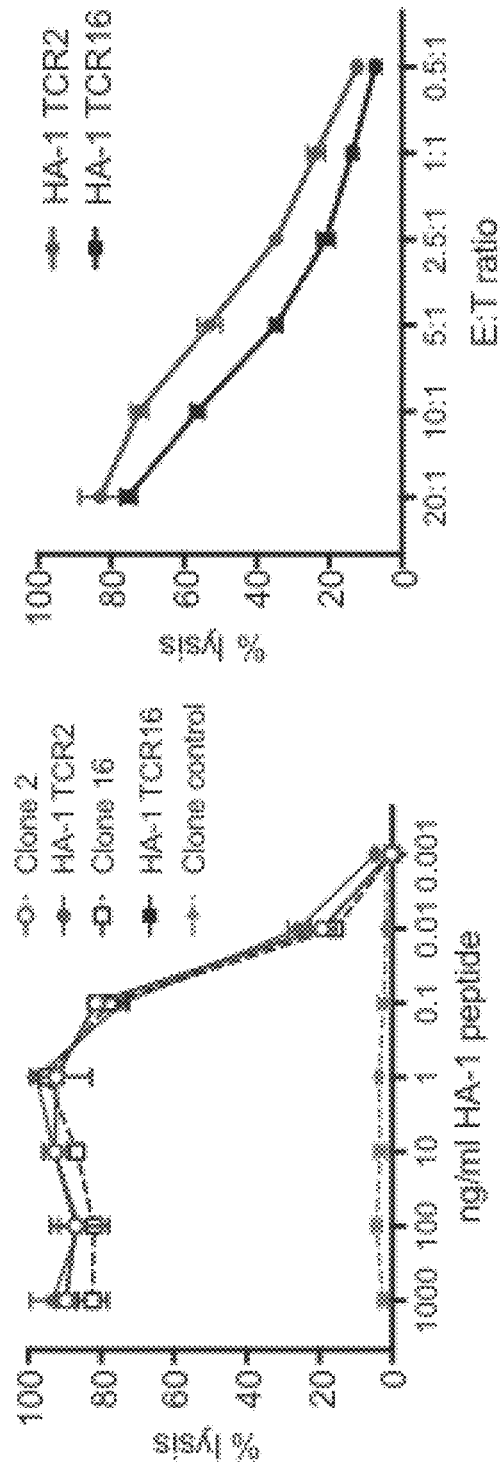
FIG. 6A
FIG. 6B
FIG. 6C 1- iCasp9-TCR 
2- TCR-CD8 
3- iCasp9-TCR-CD8

4- iCasp9-TCR-RQR_CD8 
5- iCasp9-CD34_TCR_CD8

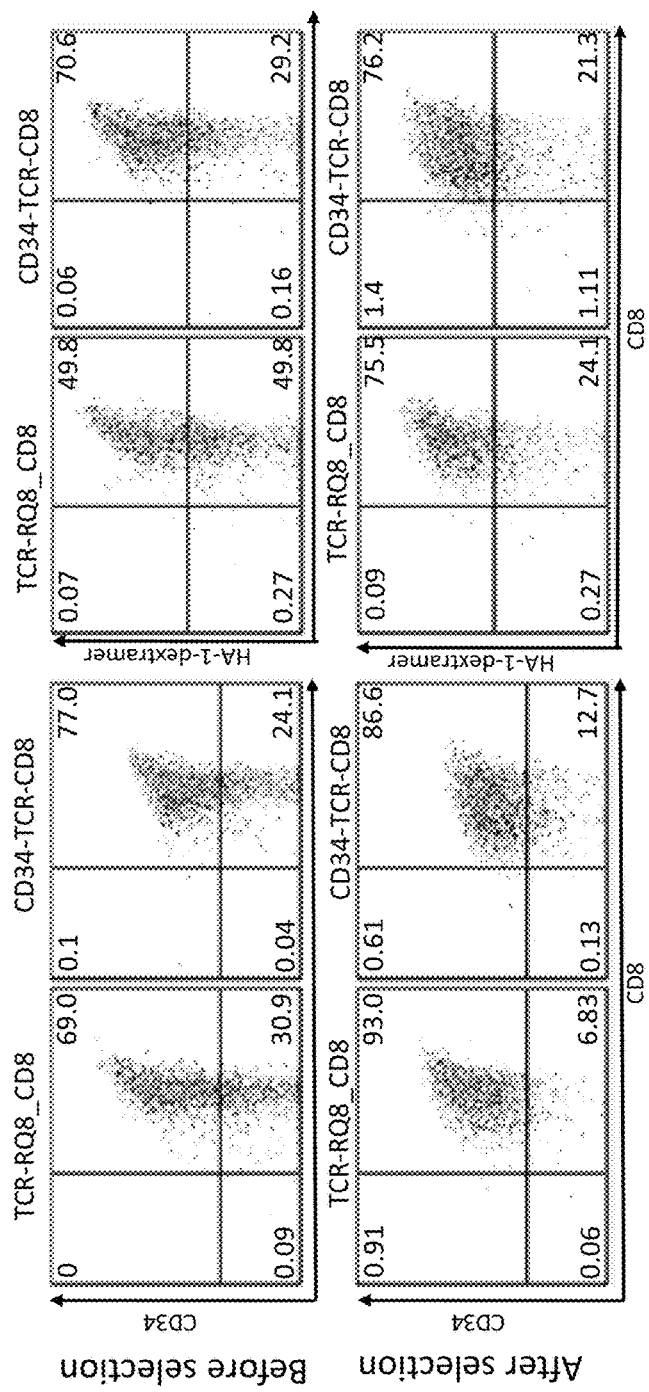
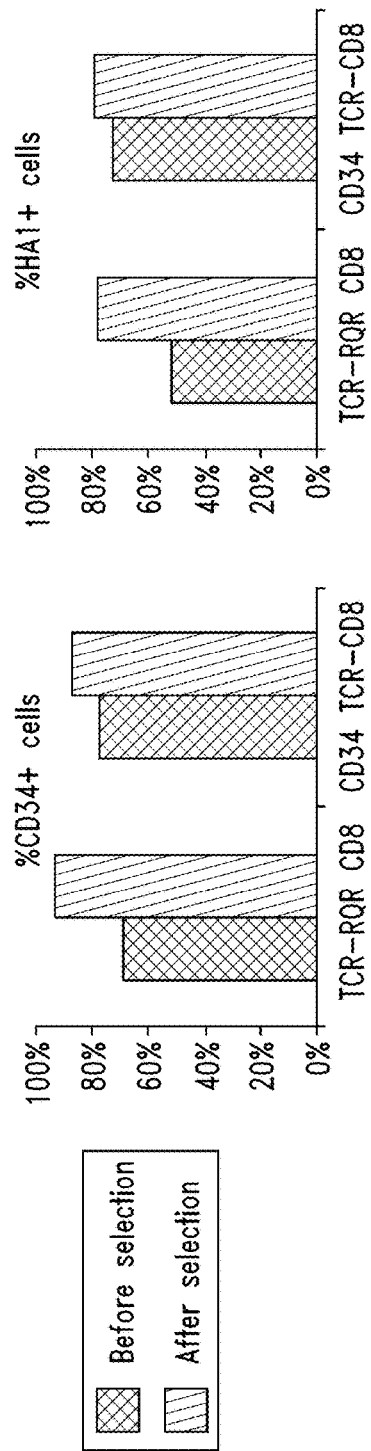
FIG. 28A
FIG. 28B

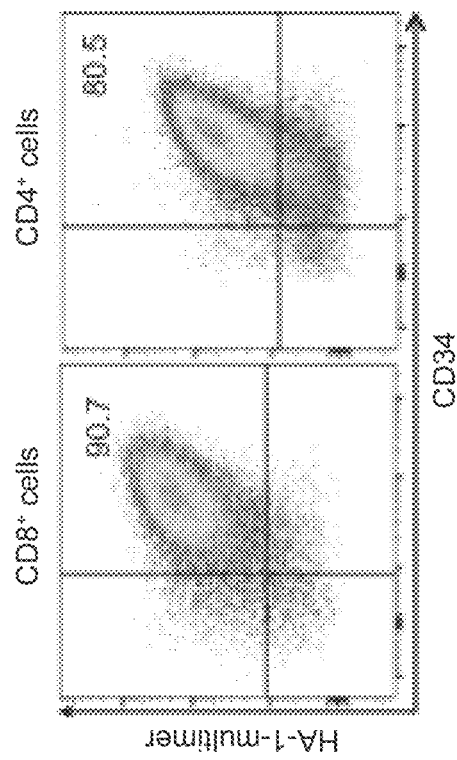
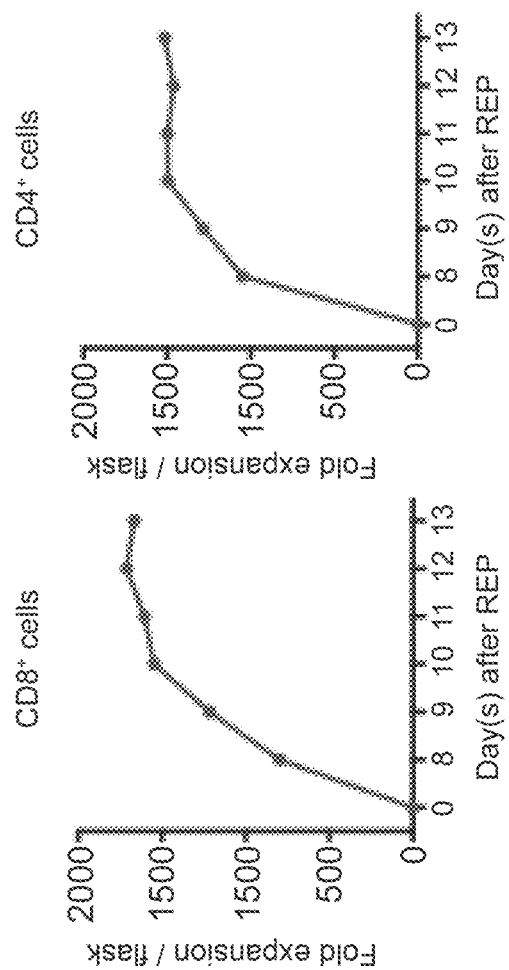
FIG. 32A
FIG. 32B

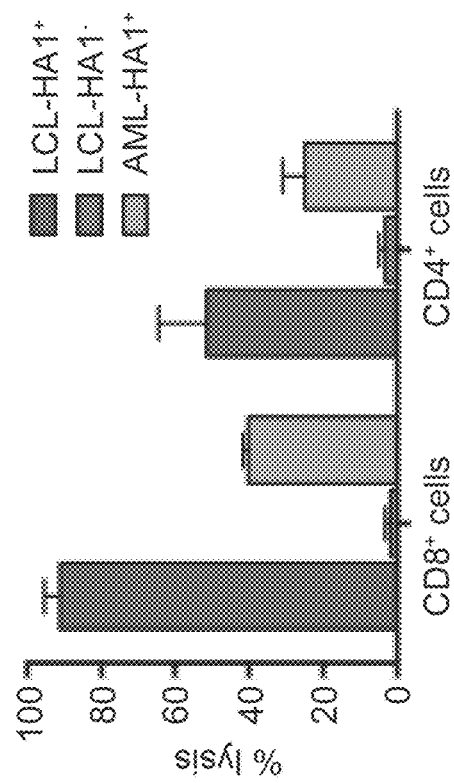
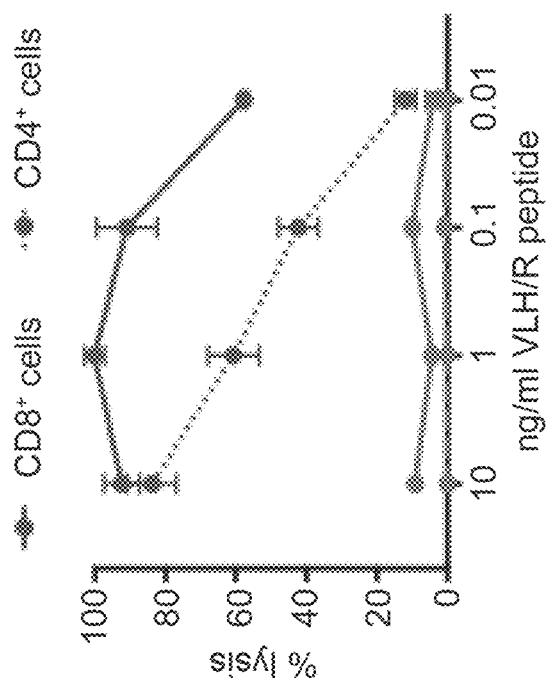
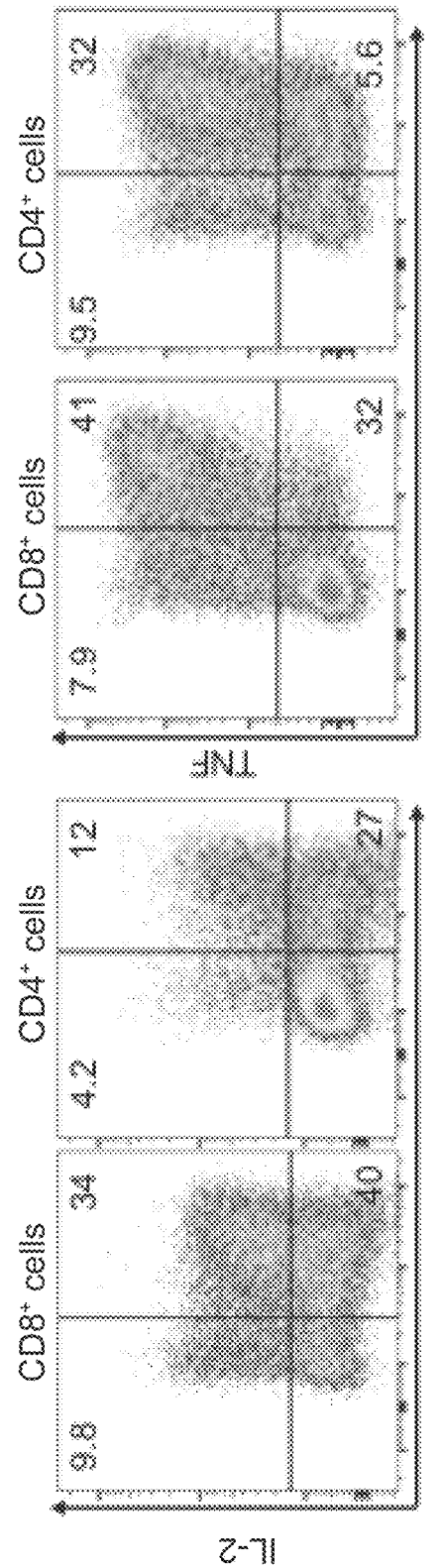
FIG. 33A
FIG. 33B
FIG. 33C

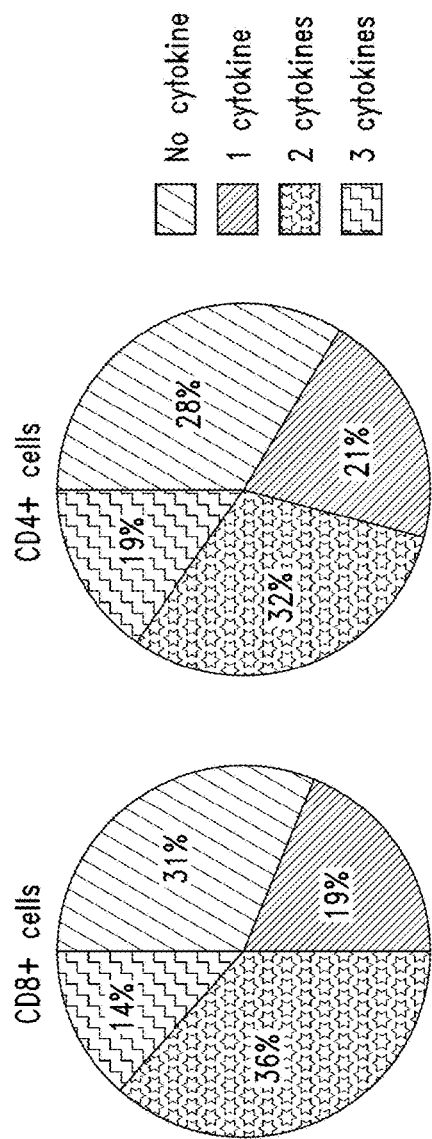
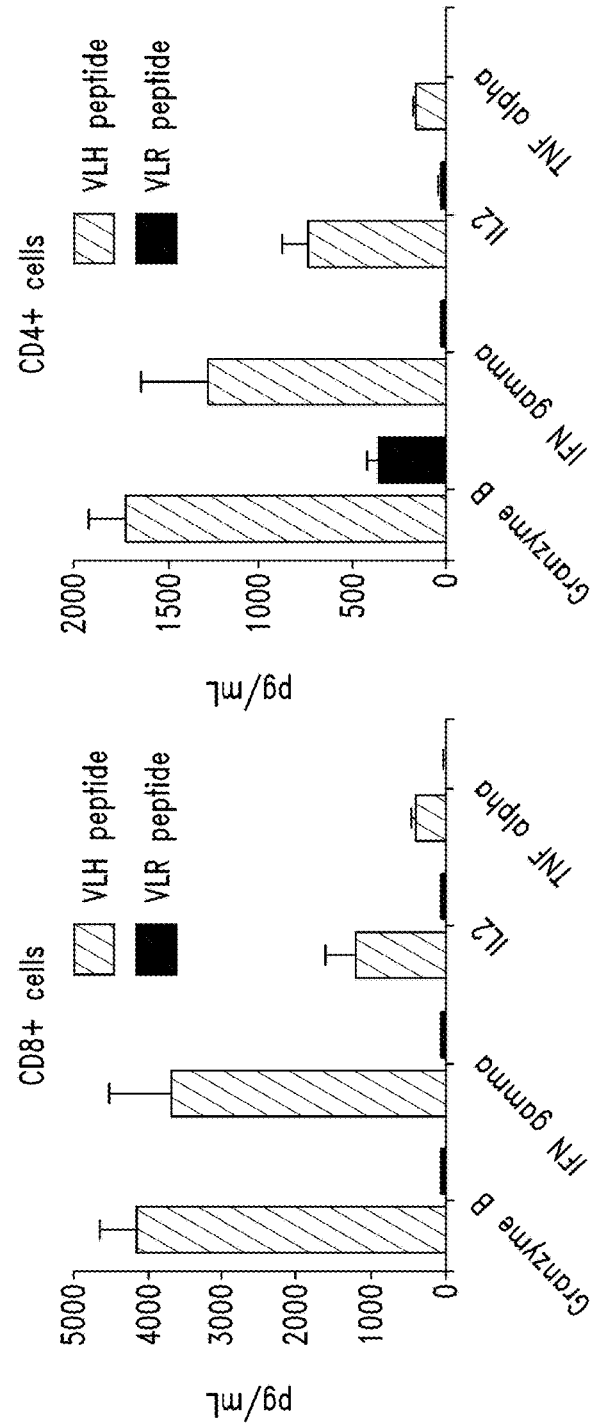
FIG. 33D
FIG. 33E

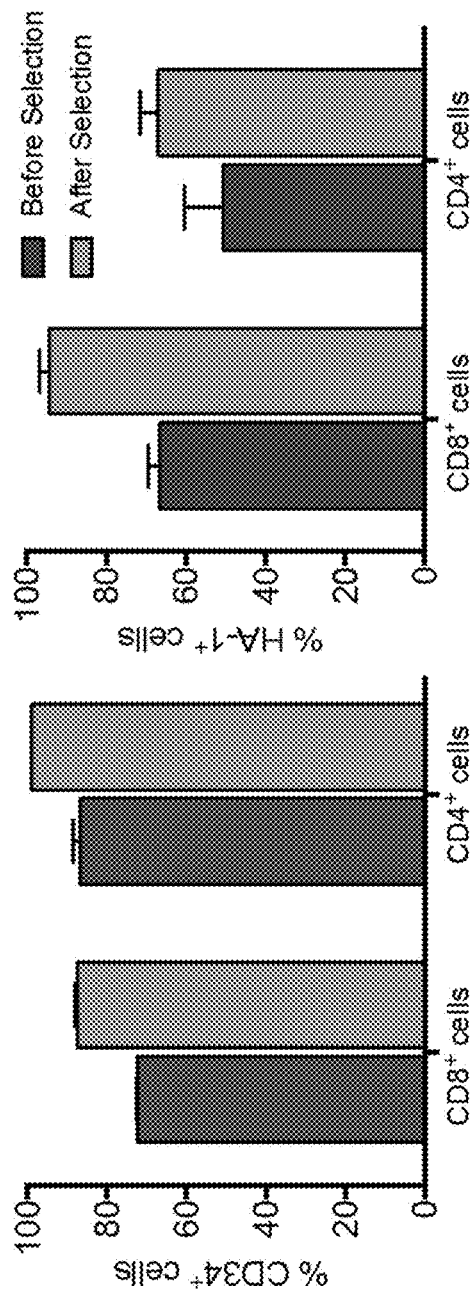
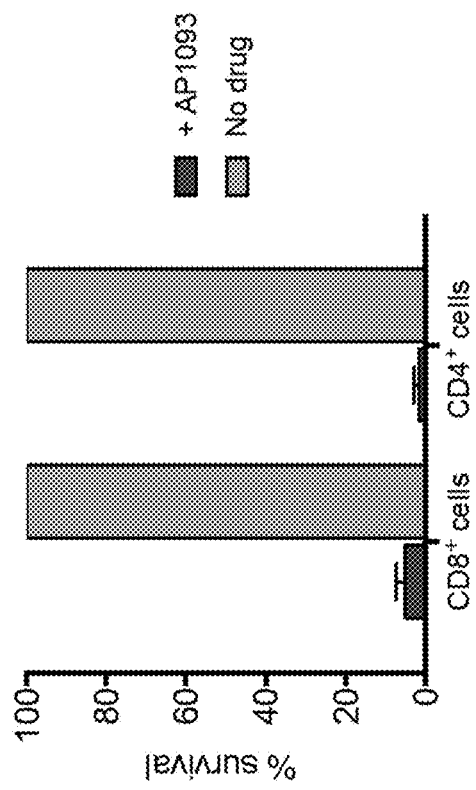
FIG. 34A
FIG. 34B

US 10,538,574 B2

TCRS SPECIFIC FOR MINOR HISTOCOMPATIBILITY (H) ANTIGEN HA-1 AND USES THEREOF

STATEMENT OF GOVERNMENT INTEREST

This invention was made with government support under CA154532 awarded by the National Institutes of Health. The government has certain rights in the invention.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 360056_455C1_SEQUENCE_LISTING.txt. The text file is 201KB, was created on Jul. 19, 2019, and is being submitted electronically via EFS-Web.

BACKGROUND

Patients with hematologic malignancies can be treated with allogeneic hematopoietic stem cell transplantation (HCT). In the United States, for example, allogeneic HCT transplants have risen steadily over the past 35 years, with approximately 8,000 transplants per year since 2013 (see CIBMTR 2016 Summary). However, relapse of the hematologic malignancy can occur thereafter. Currently, a significant number of patients who receive HCT for the treatment of acute leukemia relapse (approximately 2,000 patients relapse post-HCT each year in the U.S. alone, or about 25 to 50%; see Sucheston-Campbell et al., Curr. Hematol. Malig. Rep. 10:45-58, 2015). Relapse rates are especially high in patients who are not able to achieve deep complete remissions and/or are unable to tolerate intensive conditioning regimens prior to HCT. The prognosis for patients with post-HCT relapse is abysmal: two year survival rates for patients relapsing at <100, 100-200 and >200 days after HCT are 3%, 9% and 19%, respectively. Patients who receive a second HCT may have better outcomes, but to be eligible for a second HCT, the patient must first achieve remission, which typically only occurs in about 30% of patients.

Acute leukemia relapses can, in some cases, be treated with donor lymphocyte infusions from the original stem cell donor. This graft-versus-leukemia (GVL) effect of donor lymphocyte infusion, however, is often accompanied by graft-versus-host disease (GVHD), causing serious mortality and morbidity and is not always effective. If GVL could be selectively increased without enhancing immune responses against normal tissues (graft-versus-host disease, GVHD), post-HCT relapses might be prevented.

Certain minor H antigens are expressed on leukemic stem cells and blasts (see, e.g., Bleakley and Riddell, Nat. Rev. Cancer 4:371-380, 2004; Bleakley et al., Blood 115:4923-4933, 2010; Bleakley and Riddell, Immunol. Cell. Biol. 89:396-407, 2011; van der Harst et al., Blood 83:1060-1066, 1994; Bonnet et al., Proc. Natl. Acad. Sci. USA 96:8639-8644, 1999; Hambach et al., Leukemia 20:371-374, 2006), and have been targeted using cancer-specific T cells. In a small clinical trial of minor H antigen-targeted T cell immunotherapy in patients with post-HCT relapse, clinical responses were observed in some patients (Warren et al., Blood 115:3869-3878, 2010). Technical advances in genetic modification of T cells and growing knowledge of T cell biology means that therapeutic doses of antigen-specific T cells can now be prepared efficiently, given to patients, and persist and exert potent anti-tumor effects in vivo (Heemskerk et al., J. Exp. Med. 199:885-894, 2004; Morgan et al., Science 314:126-129, 2006; Griffioen et al., Haematologica 93:1535-131543, 2008; Ochi et al., J. Biomed. Biotechnol. 2010:5212248, 2010; Schmitt et al., Hum. Gene Ther. 20:1240-1248, 2009; Stromnes et al., Immunol Rev. 257: 145-164, 2014). However, there is a need for cell-based therapies that target leukemia-associated antigens. Presently disclosed embodiments address these needs and provide other related advantages.

BRIEF DESCRIPTION OF THE FIGURES

FIGS. 6A-6E show transduction and activity of the HA-1$^H$ TCRs into CD8$^+$ T cells using a lentiviral vector. (A) Flow cytometry showing HLA-A2/HA-1$^H$ multimer staining of CD8$^+$ T cells transduced to contain a polynucleotide encoding a HA-1$^H$ specific TCR (specifically, TCR clones 1, 2, 10, 16, and 5), which were delivered with a lentiviral vector (LV), or with a TCR specific for a different minor H antigen (control). (B-E) A chromium release assay (CRA) was used to evaluate specific lytic activity. (B) Lysis of T2 target cells pulsed with HA-1 peptide antigen at various concentrations by TCR-transduced CD8$^+$ T cells (solid lines and symbols-TCR2 circles, TCR16 squares), HA-1$^H$-specific T cell clones (dashed lines, open symbols-clone 2=circles, clone 16=squares), or T cell clone control (diamonds). (C) Lysis of HLA-A2$^+$HA-1$^{H+}$ LCL by CD8$^+$ T cells transduced with HA-1$^H$-specific TCR2 (circles) or HA-1$^H$-specific TCR16 (squares) at the indicated effector: target (E:T) ratios. (D) Lysis of HLA-A2$^+$/HA-1$^+$ homozygous (H/H) (circles n=7), HLA-A2$^+$/HA1$^{H+}$ heterozygous (H/R) (square n=22), HLA-A2$^+$/HA-1$^{H-}$ (R/R) (triangles n=17) or HLA-A2 negative (inverted triangles n=41) hematopoietic cell (LCL) targets by HA-1$^H$ TCR2 transduced CD8$^+$ T cells. (E) Lysis of LCL with common HLA alleles by HA-1$^H$ TCR2 transduced CD8$^+$ T cells. An E:T ratio of 20:1 was used unless otherwise specified. Data comparable to that shown in (D) and (E) were also obtained with HA-1$^H$ TCR16 (not shown).

FIGS. 28A and 28B provide flow cytometry data (28A) showing frequency of transduced T cells before (top row) and after (bottom row) magnetic selection. Four scatter plots at left: staining for CD34 selection marker and CD8. Four scatter plots at right: staining for HA-1$^{H}$ dextramer and CD8. Also shown (28B) are cell counts of cells expressing the CD34 selection marker (left) or being specific for HA-1$^{H}$ (right) before and after selection.

FIGS. 32A-32E show characterization of CD4$^+$ and CD8$^+$ T cells transduced with a (HA-1$^{H}$-specific TCR)-(RQR)-(CD8) and expanded to clinical scale. (A) Growth of transduced T cells. (B) HA-1$^{H}$ TCR multimer binding and CD34 expression on transduced T cells by flow cytometry with HA-1/HLA-A2 multimer staining. (C) Expression of co-stimulatory and homing molecules on T cells at the time of the apheresis, after CD45RA depletion and following transduction and expansion (N=5). (D, E) Expression of 'exhaustion' markers on HA-1$^{H}$ TCR CD8$^+$ and CD4$^+$ in the final cell product (N=3) (D) and a representative example (E).

FIGS. 33A-E show data from functional recognition assays in which the clinical-scale HA-1$^{H}$-TCR2-RQR-CD8-transduced T cells were incubated with target cells. (A) Lysis of target T2 cells pulsed with a range of VLH (solid lines, dark grey) and VLR (solid line, light grey) peptide concentrations by CD8$^+$ (solid lines) and CD4$^+$ T cells (dashed lines) in CRA at ET ratio 20:1. (B) Lysis of HA-1$^{H+}$A2$^-$ LCL, HA-1$^{H-}$-A2$^+$ LCL and AML HA-1$^{H}$+A2$^+$ cell line (THP-1) by CD8$^+$ (solid lines) in CRA (C) IL-2, IFN-γ, and TNFα production by T cells in response to stimulation by T2 cells pulsed with 10 ng/ml of HA-1 peptide. (D) Pie charts displaying the number of cytokine types secreted by T cells. (E) Concentration of cytokines and granzyme B in media 24 hours after stimulation of T cells by T2 cells pulsed with VLH or VLR peptides, as measured by multiplex immunoassay.

FIG. 34A shows (A) CD34 (left graph) and HA-1$^{H}$ TCR (right graph) expression on T cells in the final product before and after enrichment by CD34 immunomagnetic beads (N=3). FIG. 34B shows survival of T cells in the cell product after 24 hours of incubation with 5 ng/ml AP1903 or media control only.

DETAILED DESCRIPTION

Figure 1:
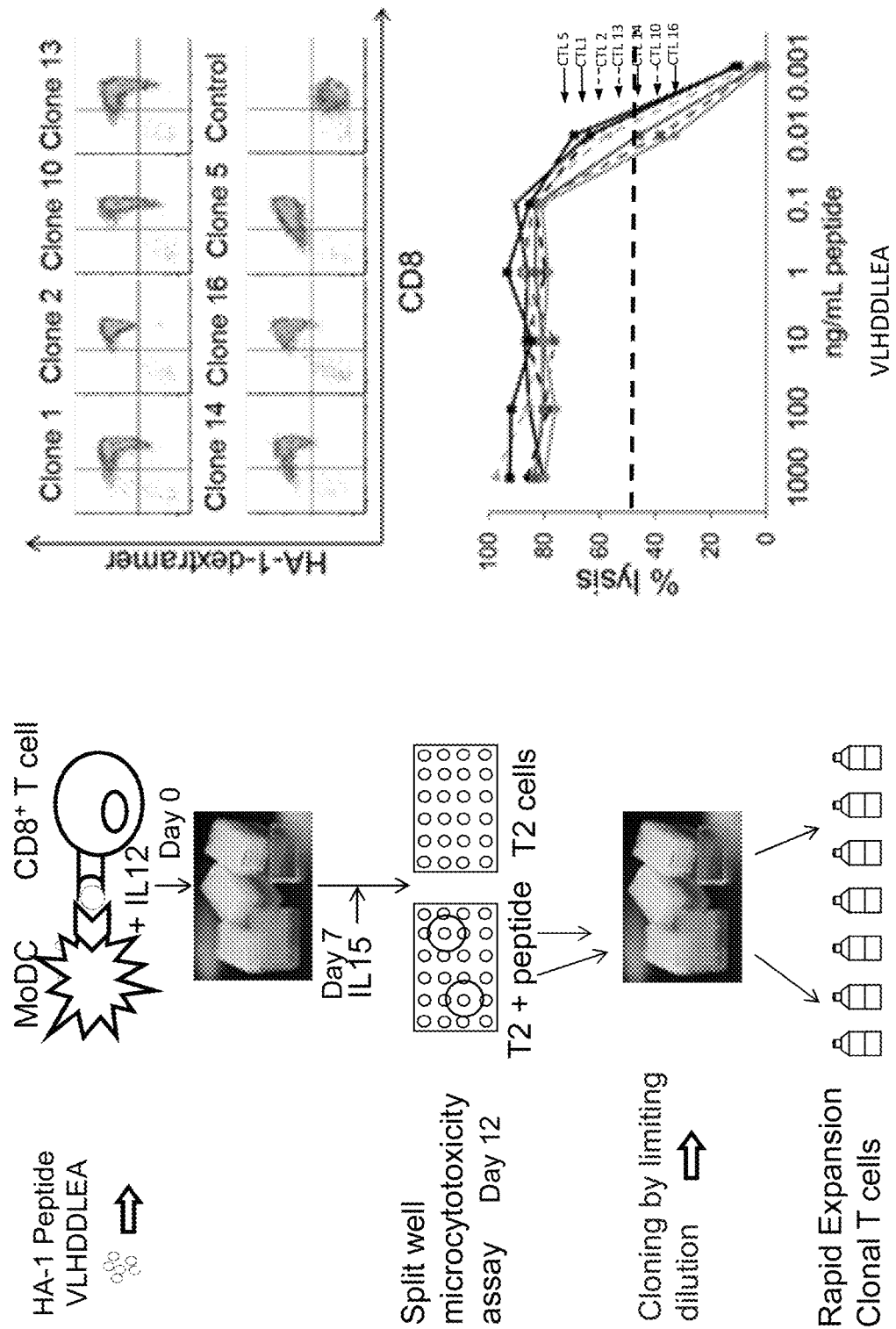
FIG. 1 depicts a process used to isolate and characterize HA-1$^H$-specific T cell clones of the present disclosure. (Top left of FIG. 1) To isolate HA-1$^H$-specific T cells, CD8$^+$ cells were primed with dendritic cells (DCs) pulsed with HA1$^H$ peptide (VLHDDLLEA; SEQ ID NO:1) and expanded in microcultures. (Middle left) Following 12 days of incubation in CTL media containing IL-12 and IL-15, aliquots of the T cells were evaluated in a split well microcytotoxicity assay, where T2 cells were pulsed with the VLHDDLLEA peptide or not. (Bottom left) Cells that specifically reacted against the T2$^+$ VLHDDLLEA were cloned by limiting dilution, reassessed for cytotoxicity, and rapidly expended for further evaluation (8 clones). (Top right) Flow cytometry data showing HA-1$^H$ specificity of the indicated seven (7) clones. Staining for HLA-A2-HA-1$^H$ dextramer staining (y-axis) and CD8 (x-axis). (Bottom right) Data from a chromium release assay (CRA) experiment wherein the indicated CTL clones were tested for specific lysis of $^{51}$CR-labeled T2 cells pulsed with the cognate peptide at the indicated titrations.

In some aspects, the present disclosure provides compositions and methods for treating hyperproliferative diseases characterized by expression of minor histocompatibility antigen HA-1$^{H}$. By way of background, human leukocyte antigen (HLA) testing is typically used to match organ, cell, and tissue transplant recipients with compatible donors. HLA testing identifies the major HLA genes a person has inherited and the corresponding antigens, or proteins, which are present on the surface of their cells. These antigens help the body's immune system distinguish which cells are "self", and which are "foreign" or "non-self." Any cells that are recognized as "non-self" can trigger an immune response, such as T cell-mediated cytotoxicity or the production of antibodies. Of note, tests for major HLA genes do not identify the minor HLA genes, which give rise to further antigens. Accordingly, even "HLA-matched" donor cells may attack healthy recipient cells expressing a perceived "foreign" minor HLA protein or peptide. Minor H antigens that are expressed on epithelial tissues are targets of alloreactive T cells, leading to graft-versus-host disease. However, some minor H antigens are associated with genes that are expressed predominantly or exclusively in the hematopoietic system, including hematopoietic cells that can be affected by hematological malignancies. Thus, minor H antigens with restricted expression are potential targets for therapies that seek to augment the graft-versus-leukemia effect and thereby prevent relapse.

The minor histocompatibility antigen HA-1$^{H}$ is encoded by the polymeric HMHA1 gene (also called Rho GTPase-activating protein 45) and is highly expressed in leukemia cells and normal hematopoietic cells (see, e.g, Griffioen et al., *Front. Immunol.* 7:100, 2016; Spierings et al. *Biol. Blood Marrow Transpl.* 19:1244-1253, 2013, the HA-1 expression disclosure of which is incorporated herein by reference), but not in normal non-hematopoietic cells. HMHA1 variants (rs1801284 A/A or A/G) present in 52% of individuals give rise to an immunogenic peptide containing a histidine residue in place of an arginine (VLHDDLLEA; SEQ ID NO:66) (R139H polymorphism) and HLA presentation of this peptide occurs in individuals with the common HLA-A*0201 (A2) allele (den Haan et al., *Science* 279:1054-1057, 1998). T cell therapies targeting HA-1$^H$ are therefore applicable to approximately 25% of subjects transplanted for hematological malignancies and require a T cell donor who is either HLA-A2 negative or HA-1$^H$ negative ("HA-1$^R$"; rs1801284 G/G-VLRDDLLEA; SEQ ID NO: 65).

In some aspects, the present disclosure provides engineered immune cells expressing binding proteins, such as TCRs and CARs, specific for HA-1$^H$. Such engineered immune cells can be used as a standalone therapy to treat a hematologic malignancy or to prevent a relapse or recurrence thereof, or such cells can be used as part of a therapeutic regimen comprising additional therapies or agents (e.g., following, or in combination with, allogeneic HCT).

Prior to setting forth this disclosure in more detail, it may be helpful to an understanding thereof to provide definitions of certain terms to be used herein. Additional definitions are set forth throughout this disclosure.

In the present description, any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated. As used herein, the term "about" means±20% of the indicated range, value, or structure, unless otherwise indicated. It should be understood that the terms "a" and "an" as used herein refer to "one or more" of the enumerated components. The use of the alternative (e.g., "or") should be understood to mean either one, both, or any combination thereof of the alternatives. As used herein, the terms "include", "have", and "comprise" are used synonymously, which terms and variants thereof are intended to be construed as non-limiting.

In addition, it should be understood that the individual compounds, or groups of compounds, derived from the various combinations of the structures and substituents described herein, are disclosed by the present application to the same extent as if each compound or group of compounds was set forth individually. Thus, selection of particular structures or particular substituents is within the scope of the present disclosure.

The term "consisting essentially of" is not equivalent to "comprising" and refers to the specified materials or steps of a claim, or to those that do not materially affect the basic characteristics of a claimed subject matter. For example, a protein domain, region, or module (e.g., a binding domain, hinge region, linker module) or a protein (which may have one or more domains, regions, or modules) "consists essentially of" a particular amino acid sequence when the amino acid sequence of a domain, region, module, or protein includes extensions, deletions, mutations, or a combination thereof (e.g., amino acids at the amino- or carboxy-terminus or between domains) that, in combination, contribute to at most 20% (e.g., at most 15%, 10%, 8%, 6%, 5%, 4%, 3%, 2% or 1%) of the length of a domain, region, module, or protein and do not substantially affect (i.e., do not reduce the activity by more than 50%, such as no more than 40%, 30%, 25%, 20%, 15%, 10%, 5%, or 1%) the activity of the domain(s), region(s), module(s), or protein (e.g., the target binding affinity of a binding protein).

As used herein, an "immune system cell" means any cell of the immune system that originates from a hematopoietic stem cell in the bone marrow, which gives rise to two major lineages, a myeloid progenitor cell (which give rise to myeloid cells such as monocytes, macrophages, dendritic cells, meagakaryocytes and granulocytes) and a lymphoid progenitor cell (which give rise to lymphoid cells such as T cells, B cells and natural killer (NK) cells). Exemplary immune system cells include a CD4$^+$ T cell, a CD8$^+$ T cell, a CD4–CD8– double negative T cell, a γδ T cell, a regulatory T cell, a natural killer cell, and a dendritic cell. Macrophages and dendritic cells can be referred to as "antigen presenting cells" or "APCs," which are specialized cells that can activate T cells when a major histocompatibility complex (MHC) receptor on the surface of the APC complexed with a peptide interacts with a TCR on the surface of a T cell.

A "T cell" or "T lymphocyte" is an immune system cell that matures in the thymus and produces T cell receptors (TCRs). T cells can be naive ("$T_N$"; not exposed to antigen; increased expression of CD62L, CCR7, CD28, CD3, CD127, and CD45RA and decreased or no expression of CD45RO as compared to $T_{CM}$ (described herein)), memory T cells ($T_M$) (antigen experienced and long-lived), and effector cells (antigen-experienced, cytotoxic). $T_M$ can be further divided into subsets of central memory T cells ($T_{CM}$ expresses CD62L, CCR7, CD28, CD45RO) and effector memory T cells ($T_{EM}$ express CD45RO, decreased expression of CD62L, CCR7, and CD28). Effector T cells ($T_E$) refers to antigen-experienced CD8$^+$ cytotoxic T lymphocytes that express CD45RA, have decreased expression of CD62L, CCR7, and CD28 as compared to $T_{CM}$, and are positive for granzyme and perforin. Helper T cells ($T_H$) are CD4$^+$ cells that influence the activity of other immune cells by releasing cytokines. CD4$^+$ T cells can activate and suppress an adaptive immune response, and which of those two functions is induced will depend on presence of other cells and signals. T cells can be collected using known techniques, and the various subpopulations or combinations thereof can be enriched or depleted by known techniques, such as by affinity binding to antibodies, flow cytometry, or immunomagnetic selection. Other exemplary T cells include regulatory T cells, such as CD4$^-$ CD25$^+$ (Foxp3$^+$) regulatory T cells and Treg17 cells, as well as Tr1, Th3, CD8$^-$CD28$^-$, and Qa-1 restricted T cells.

"T cell receptor" (TCR) refers to an immunoglobulin superfamily member (having a variable binding domain, a constant domain, a transmembrane region, and a short cytoplasmic tail; see, e. g., Janeway et al., Immunobiology: The Immune System in Health and Disease, 3rd Ed., Current Biology Publications, p. 433, 1997) capable of specifically binding to an antigen peptide bound to a MHC receptor. A TCR can be found on the surface of a cell or in soluble form and generally is comprised of a heterodimer having α and β chains (also known as TCRα and TCRβ, respectively), or γ and δ chains (also known as TCRγ and TCRδ, respectively).

Like other immunoglobulins (e.g., antibodies), the extracellular portion of TCR chains (e.g., α-chain, β-chain) contain two immunoglobulin domains, a variable domain (e.g., α-chain variable domain or $V_α$ chain variable domain or $V_β$; typically amino acids 1 to 116 based on Kabat numbering (Kabat et al., "Sequences of Proteins of Immunological Interest, US Dept. Health and Human Services, Public Health Service National Institutes of Health, 1991, 5$^{th}$ ed.) at the N-terminus, and one constant domain (e.g., α-chain constant domain or $C_\alpha$, typically 5 amino acids 117 to 259 based on Kabat, β-chain constant domain or $C_\beta$, typically amino acids 117 to 295 based on Kabat) adjacent the cell membrane. Also, like immunoglobulins, the variable domains contain complementary determining regions (CDRs) separated by frame work regions (FRs) (see, e.g., Jores et al., *Proc. Nat'l Acad. Sci. USA* 87:9138, 1990; Chothia et al., *EMBO J.* 7:3745, 1988; see also Lefranc et al., *Dev. Comp. Immunol.* 27:55, 2003).

"Antigen" or "Ag" as used herein refers to an immunogenic molecule that provokes an immune response. This immune response may involve antibody production, activation of specific immunologically-competent cells (e.g., T cells), or both. An antigen (immunogenic molecule) may be, for example, a peptide, glycopeptide, polypeptide, glycopolypeptide, polynucleotide, polysaccharide, lipid or the like. It is readily apparent that an antigen can be synthesized, produced recombinantly, or derived from a biological sample. Exemplary biological samples that can contain one or more antigens include tissue samples, tumor samples, cells, biological fluids, or combinations thereof. Antigens can be produced by cells that have been modified or genetically engineered to express an antigen, or that endogenously (e.g., without modification or genetic engineering by human intervention) express a mutation or polymorphism that is immunogenic.

"Major histocompatibility complex" (MHC) refers to glycoproteins that deliver peptide antigens to a cell surface of all nucleated cells. MHC class I molecules are heterodimers having a membrane spanning α chain (with three a domains) and a non-covalently associated $\beta_2$ microglobulin. MHC class II molecules are composed of two transmembrane glycoproteins, α and β, both of which span the membrane. Each chain has two domains. MHC class I molecules deliver peptides originating in the cytosol to the cell surface, where a peptide:MHC complex is recognized by $CD8^+$ T cells. MHC class II molecules deliver peptides originating in the vesicular system to the cell surface, where they are recognized by $CD4^+$ T cells. Human MHC is referred to as human leukocyte antigen (HLA).

The term "epitope" or "antigenic epitope" includes any molecule, structure, amino acid sequence or protein determinant that is recognized and specifically bound by a cognate binding molecule, such as an immunoglobulin, T cell receptor (TCR), chimeric antigen receptor, or other binding molecule, domain or protein. Epitopic determinants generally contain chemically active surface groupings of molecules, such as amino acids or sugar side chains, and can have specific three dimensional structural characteristics, as well as specific charge characteristics.

As used herein "specifically binds" or "specific for" refers to an association or union of a binding protein (e.g., TCR receptor) or a binding domain (or fusion protein thereof) to a target molecule with an affinity or $K_a$ (i.e., an equilibrium association constant of a particular binding interaction with units of 1/M) equal to or greater than $10^5$ $M^{-1}$ (which equals the ratio of the on-rate [$k_{on}$] to the off-rate [$k_{off}$] for this association reaction), while not significantly associating or uniting with any other molecules or components in a sample. Binding proteins or binding domains (or fusion proteins thereof) may be classified as "high affinity" binding proteins or binding domains (or fusion proteins thereof) or as "low affinity" binding proteins or binding domains (or fusion proteins thereof). "High affinity" binding proteins or binding domains refer to those binding proteins or binding domains having a $K_a$ of at least $10^7$ $M^{-1}$, at least $10^8$ $M^{-1}$, at least $10^9$ $M^{-1}$, at least $10^{10}$ $M^{-1}$, at least $10^{11}$ $M^{-1}$, at least $10^{12}$ $M^{-1}$, or at least $10^{13}$ $M^{-1}$. "Low affinity" binding proteins or binding domains refer to those binding proteins or binding domains having a $K_a$ of up to $10^7$ $M^{-1}$, up to $10^6$ $M^{-1}$, up to $10^5$ $M^{-1}$. Alternatively, affinity can be defined as an equilibrium dissociation constant ($K_d$) of a particular binding interaction with units of M (e.g., $10^{-5}$ M to $10^{-13}$ M).

In certain embodiments, a receptor or binding domain may have "enhanced affinity," which refers to selected or engineered receptors or binding domains with stronger binding to a target antigen than a wild type (or parent) binding domain. For example, enhanced affinity may be due to a $K_a$ (equilibrium association constant) for the target antigen that is higher than the wild type binding domain, due to a $K_d$ (dissociation constant) for the target antigen that is less than that of the wild type binding domain, due to an off-rate ($k_{off}$) for the target antigen that is less than that of the wild type binding domain, or a combination thereof. In certain embodiments, enhanced affinity TCRs can be codon optimized to enhance expression in a particular host cell, such as a cell of the immune system, a hematopoietic stem cell, a T cell, a primary T cell, a T cell line, a NK cell, or a natural killer T cell (Scholten et al., *Clin. Immunol.* 119:135, 2006). The T cell can be a CD4+ or a $CD8^+$ T cell.

A variety of assays are known for identifying binding domains of the present disclosure that specifically bind a particular target, as well as determining binding domain or fusion protein affinities, such as multimer/tetramer staining, Western blot, ELISA, analytical ultracentrifugation, spectroscopy and surface plasmon resonance (Biacore®) analysis (see, e.g., Dolton et al., *Immunology* 146:11-22, 2015, Scatchard et al., *Ann. NY Acad. Sci.* 51:660, 1949; Wilson, *Science* 20295:2103, 2002; Wolff et al., *Cancer Res.* 53:2560, 1993; and U.S. Pat. Nos. 5,283,173, 5,468,614, or the equivalent; all incorporated herein by reference).

The source of a TCR as used in the present disclosure can be from various animal species, such as a human, mouse, rat, rabbit or other mammal.

As used herein, the term "CD8 co-receptor" or "CD8" means the cell surface glycoprotein CD8, either as an alpha-alpha homodimer or an alpha-beta heterodimer. The CD8 co-receptor assists in the function of cytotoxic T cells ($CD8^+$) and functions through signaling via its cytoplasmic tyrosine phosphorylation pathway (Gao and Jakobsen, *Immunol. Today* 21:630-636, 2000; Cole and Gao, *Cell. Mol. Immunol.* 1:81-88, 2004). There are five (5) different CD8 beta chains (see UniProtKB identifier P10966) and a single CD8 alpha chain (see UniProtKB identifier P01732)

"CD4" is an immunoglobulin co-receptor glycoprotein that assists the TCR in communicating with antigen-presenting cells (see, Campbell & Reece, *Biology* 909 (Benjamin Cummings, Sixth Ed., 2002)). CD4 is found on the surface of immune cells such as T helper cells, monocytes, macrophages, and dendritic cells, and includes four immunoglobulin domains (D1 to D4) that are expressed at the cell surface. During antigen presentation, CD4 is recruited, along with the TCR complex, to bind to different regions of the MHCII molecule (CD4 binds MHCII β2, while the TCR complex binds MHCII α1/β1). Without wishing to be bound by theory, it is believed that close proximity to the TCR complex allows CD4-associated kinase molecules to phosphorylate the immunoreceptor tyrosine activation motifs (ITAMs) present on the cytoplasmic domains of CD3. This activity is thought to amplify the signal generated by the activated TCR in order to produce various types of T helper cells.

In certain embodiments, a TCR is found on the surface of T cells (or T lymphocytes) and associates with a CD3 complex. "CD3" is a multi-protein complex of six chains (see, Abbas and Lichtman, 2003; Janeway et al., p. 172 and 178, 1999) that is associated with antigen signaling in T cells. In mammals, the complex comprises a CD3γ chain, a CD3δ chain, two CD3ε chains, and a homodimer of CD3ζ chains. The CD3γ, CD3β, and CD3ε chains are highly related cell surface proteins of the immunoglobulin superfamily containing a single immunoglobulin domain. The transmembrane regions of the CD3γ, CD3β, and CD3ε chains are negatively charged, which is a characteristic that allows these chains to associate with the positively charged T cell receptor chains. The intracellular tails of the CD3γ, CD3β, and CD3ε chains each contain a single conserved motif known as an immunoreceptor tyrosine based activation motif or ITAM, whereas each CD3ζ chain has three. Without wishing to be bound by theory, it is believed that the ITAMs are important for the signaling capacity of a TCR complex. CD3 as used in the present disclosure may be from various animal species, including human, mouse, rat, or other mammals.

As used herein, "TCR complex" refers to a complex formed by the association of CD3 with TCR. For example, a TCR complex can be composed of a CD3γ chain, a CD3β chain, two CD3ε chains, a homodimer of CD3ζ chains, a TCRα chain, and a TCRβ chain. Alternatively, a TCR complex can be composed of a CD3γ chain, a CD3β chain, two CD3ε chains, a homodimer of CD3ζ chains, a TCRγ chain, and a TCRβ chain.

A "component of a TCR complex", as used herein, refers to a TCR chain (i.e., TCRα, TCRβ, TCRγ or TCRδ), a CD3 chain (i.e., CD3γ, CD3δ, CD3ε or CD3ζ), or a complex formed by two or more TCR chains or CD3 chains (e.g., a complex of TCRα and TCRβ, a complex of TCRγ and TCRδ, a complex of CD3ε and CD3δ, a complex of CD3γ and CD3ε, or a sub-TCR complex of TCRα, TCRβ, CD3γ, CD3δ, and two CD3ε chains).

As used herein, the term "HA-1$^H$ antigen" or "HA-1$^H$ peptide antigen" or "HA-1$^H$-containing peptide antigen" (or "minor HA-1$^H$ antigen" or "minor HA-1$^H$ peptide antigen" or "minor HA-1$^H$-containing peptide antigen" or "minor Histocompatibility HA-1$^H$ antigen peptide") refers to a naturally or synthetically produced peptide portion of a HMHA1 protein ranging in length from about 7 amino acids, about 8 amino acids, about 9 amino acids, about 10 amino acids, up to about 20 amino acids, and comprising the R139H substitution polymorphism), which can form a complex with a MEW (e.g., HLA) molecule, and a binding protein of this disclosure specific for a HA-1$^H$ peptide:MHC (e.g., HLA) complex can specifically bind to such as complex. An exemplary HA-1$^H$ HA-1 peptide antigen comprises a peptide having the amino acid VLHDDLLEA (SEQ ID NO: 66), wherein the bolded histidine in the sequence represents the R139H polymorphism.

The term "HA-1$^H$-specific binding protein," as used herein, refers to a protein or polypeptide, such as a TCR or CAR, that specifically binds to an HA-1$^H$ peptide antigen (or to an HA-1$^H$ peptide antigen:HLA complex, e.g., on a cell surface), and does not bind an HMHA peptide that does not contain the HA-1$^H$ polymorphism (e.g., a peptide comprising the amino acid sequence shown in SEQ ID NO:65) and does not bind to an HLA complex containing such an HMHA peptide.

In certain embodiments, a HA-1$^H$-specific binding protein specifically binds to an HA-1-containing peptide (or an HA-1$^H$ peptide:HLA complex) with a $K_d$ of less than about $10^{-8}$ M, less than about $10^{-9}$ M, less than about $10^{-10}$ M, less than about $10^{-11}$ M, less than about $10^{-12}$ M, or less than about $10^{-13}$ M, or with an affinity that is about the same as, at least about the same as, or is greater than at or about the affinity exhibited by an exemplary HA-1$^H$-specific binding protein provided herein, such as any of the HA-1$^H$-specific TCRs provided herein, for example, as measured by the same assay. In certain embodiments, a HA-1-specific binding protein comprises a HA-1-specific immunoglobulin superfamily binding protein or binding portion thereof.

Principles of antigen processing by antigen presenting cells (APC) (such as dendritic cells, macrophages, lymphocytes or other cell types), and of antigen presentation by APC to T cells, including major histocompatibility complex (MHC)-restricted presentation between immunocompatible (e.g., sharing at least one allelic form of an MHC gene that is relevant for antigen presentation) APC and T cells, are well established (see, e.g., Murphy, Janeway's Immunobiology (8$^{th}$ Ed.) 2011 Garland Science, NY; chapters 6, 9 and 16). For example, processed antigen peptides originating in the cytosol (e.g., tumor antigen, intracellular pathogen) are generally from about 7 amino acids to about 11 amino acids in length and will associate with class I MHC (HLA) molecules, whereas peptides processed in the vesicular system (e.g., bacterial, viral) will vary in length from about 10 amino acids to about 25 amino acids and associate with class II MHC (HLA) molecules.

An "altered domain" or "altered protein" refers to a motif, region, domain, peptide, polypeptide, or protein with a non-identical sequence identity to a wild type motif, region, domain, peptide, polypeptide, or protein (e.g., a wild type TCRα chain, TCRβ chain, TCRα constant domain, TCRβ constant domain) of at least 85% (e.g., 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%).

Altered domains or altered proteins or derivatives can include those based on all possible codon choices for the same amino acid and codon choices based on conservative amino acid substitutions. For example, the following six group's each contain amino acids that are conservative substitutions for one another: 1) alanine (ala; A), serine (ser; S), threonine (thr; T); 2) aspartic acid (asp; D), glutamic acid (glu; E); 3) asparagine (asn; N), glutamine (gln; Q); 4) arginine (arg; R), lysine (lys; K); 5) Isoleucine (ile; I), leucine (L), methionine (met; M), valine (val; V); and 6) phenylalanine (phe; F), tyrosine (tyr; Y), tryptophan (trp; W). (See also WO97/09433 at page 10, Lehninger, Biochemistry, 2$^{nd}$ Edition, Worth Publishers, Inc., NY, N.Y., pp. 71-77, 1975; Lewin Genes IV, Oxford University Press, NY and Cell Press, Cambridge, Mass., p.8, 1990; Creighton, Proteins, W.H. Freeman and Company 1984). In addition, individual substitutions, deletions or additions that alter, add or delete, a single amino acid or a small percentage of amino acids in an encoded sequence are also "conservative substitutions."

As used herein, "nucleic acid" or "nucleic acid molecule" refers to any of deoxyribonucleic acid (DNA), ribonucleic acid (RNA), oligonucleotides, polynucleotides, fragments thereof generated, for example, by the polymerase chain reaction (PCR) or by in vitro translation, and also to fragments generated by any of ligation, scission, endonuclease action, or exonuclease action. In certain embodiments, the nucleic acids of the present disclosure are produced by PCR. Nucleic acids can be composed of monomers that are naturally occurring nucleotides (such as deoxyribonucleotides and ribonucleotides), analogs of naturally occurring nucleotides (e.g., α-enantiomeric forms of naturally occurring nucleotides), or a combination of both. Modified nucleotides can have modifications in or replacement of sugar moieties, or pyrimidine or purine base moieties. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. Nucleic acid molecules can be either single stranded or double stranded.

The term "isolated" means that the material is removed from its original environment (e.g., the natural environment if it is naturally occurring). For example, a naturally occurring nucleic acid or polypeptide present in a living animal is not isolated, but the same nucleic acid or polypeptide, separated from some or all of the co-existing materials in the natural system, is isolated. Such a nucleic acid could be part of a vector and/or such nucleic acid or polypeptide could be part of a composition (e.g., a cell lysate), and still be isolated in that such vector or composition is not part of the natural environment for the nucleic acid or polypeptide. The term "gene" means the segment of DNA involved in producing a polypeptide chain; it includes regions preceding and following the coding region ("leader and trailer") as well as intervening sequences (introns) between individual coding segments (exons).

As used herein, the terms "recombinant" and "engineered" refer to a cell, microorganism, nucleic acid molecule, polypeptide, protein, plasmid, or vector that has been modified by introduction of an exogenous nucleic acid molecule, or refers to a cell or microorganism that has been genetically engineered by human intervention—that is, modified by introduction of a heterologous nucleic acid molecule, or refers to a cell or microorganism that has been altered such that expression of an endogenous nucleic acid molecule or gene is controlled, deregulated or constitutive, where such alterations or modifications can be introduced by genetic engineering. Human-generated genetic alterations can include, for example, modifications introducing nucleic acid molecules (which may include an expression control element, such as a promoter) encoding one or more proteins or enzymes, or other nucleic acid molecule additions, deletions, substitutions, or other functional disruption of or addition to a cell's genetic material. Exemplary modifications include those in coding regions or functional fragments thereof of heterologous or homologous polypeptides from a reference or parent molecule.

As used herein, "mutation" refers to a change in the sequence of a nucleic acid molecule or polypeptide molecule as compared to a reference or wild-type nucleic acid molecule or polypeptide molecule, respectively. A mutation can result in several different types of change in sequence, including substitution, insertion or deletion of nucleotide(s) or amino acid(s). In certain embodiments, a mutation is a substitution of one or three codons or amino acids, a deletion of one to about 5 codons or amino acids, or a combination thereof.

A "conservative substitution" is recognized in the art as a substitution of one amino acid for another amino acid that has similar properties. Exemplary conservative substitutions are well known in the art (see, e.g., WO 97/09433 at page 10; Lehninger, Biochemistry, $2^{nd}$ Edition; Worth Publishers, Inc. NY, N.Y., pp.71-77, 1975; Lewin, Genes IV, Oxford University Press, NY and Cell Press, Cambridge, Mass., p. 8, 1990).

The term "construct" refers to any polynucleotide that contains a recombinant nucleic acid molecule. A "transgene" or "transgene construct" refers to a construct that contains two or more genes operably linked in an arrangement that is not found in nature. The term "operably-linked" (or "operably linked" herein) refers to the association of two or more nucleic acid molecules on a single nucleic acid fragment so that the function of one is affected by the other. For example, a promoter is operably-linked with a coding sequence when it can affect the expression of that coding sequence (i.e., the coding sequence is under the transcriptional control of the promoter). "Unlinked" means that the associated genetic elements are not closely associated with one another and the function of one does not affect the other. In some embodiments, the genes present in a transgene are operably linked to an expression control sequence (e.g., a promoter).

A construct (e.g., a transgene) can be present in a vector (e.g., a bacterial vector, a viral vector) or can be integrated into a genome. A "vector" is a nucleic acid molecule that is capable of transporting another nucleic acid molecule. Vectors can be, for example, plasmids, cosmids, viruses, a RNA vector or a linear or circular DNA or RNA molecule that can include chromosomal, non-chromosomal, semi-synthetic or synthetic nucleic acid molecules. Exemplary vectors are those capable of autonomous replication (episomal vector) or expression of nucleic acid molecules to which they are linked (expression vectors). Vectors useful in the compositions and methods of this disclosure are described further herein.

The term "expression", as used herein, refers to the process by which a polypeptide is produced based on the encoding sequence of a nucleic acid molecule, such as a gene. The process can include transcription, post-transcriptional control, post-transcriptional modification, translation, post-translational control, post translational modification, or any combination thereof.

The term "introduced" in the context of inserting a nucleic acid molecule into a cell, means "transfection", or "transformation", or "transduction" and includes reference to the incorporation of a nucleic acid molecule into a eukaryotic or prokaryotic cell wherein the nucleic acid molecule can be incorporated into the genome of a cell (e.g., a chromosome, a plasmid, a plastid, or a mitochondrial DNA), converted into an autonomous replicon, or transiently expressed (e.g., transfected mRNA).

As used herein, "heterologous" or "exogenous" nucleic acid molecule, construct or sequence refers to a nucleic acid molecule or portion of a nucleic acid molecule that is not native to a host cell, but can be homologous to a nucleic acid molecule or portion of a nucleic acid molecule from the host cell. The source of the heterologous or exogenous nucleic acid molecule, construct or sequence can be from a different genus or species. In certain embodiments, a heterologous or exogenous nucleic acid molecule is added (i.e., not endogenous or native) to a host cell or host genome by, for example, conjugation, transformation, transfection, transduction, electroporation, or the like, wherein the added molecule can integrate into the host genome or exist as extra-chromosomal genetic material (e.g., as a plasmid or other form of self-replicating vector), and can be present in multiple copies. In addition, "heterologous" refers to a non-native enzyme, protein or other activity encoded by an exogenous nucleic acid molecule introduced into the host cell, even if the host cell encodes a homologous protein or activity.

As described herein, more than one heterologous or exogenous nucleic acid molecule can be introduced into a host cell as separate nucleic acid molecules, as a plurality of individually controlled genes, as a polycistronic nucleic acid molecule, as a single nucleic acid molecule encoding a fusion protein, or any combination thereof. For example, as disclosed herein, a host cell can be modified to express two or more heterologous or exogenous nucleic acid molecules encoding the desired TCR specific for a minor histocompatibility (H) antigen HA-1$^H$ peptide (e.g., TCRα and TCRβ). When two or more exogenous nucleic acid molecules are introduced into a host cell, it is understood that the two or more exogenous nucleic acid molecules can be introduced as a single nucleic acid molecule (e.g., on a single vector), on separate vectors, integrated into the host chromosome at a single site or multiple sites, or any combination thereof. The number of referenced heterologous nucleic acid molecules or protein activities refers to the number of encoding nucleic acid molecules or the number of protein activities, not the number of separate nucleic acid molecules introduced into a host cell.

As used herein, the term "endogenous" or "native" refers to a gene, protein, or activity that is normally present in a host cell. Moreover, a gene, protein or activity that is mutated, overexpressed, shuffled, duplicated or otherwise altered as compared to a parent gene, protein or activity is still considered to be endogenous or native to that particular host cell. For example, an endogenous control sequence from a first gene (e.g., a promoter, translational attenuation sequences) can be used to alter or regulate expression of a second native gene or nucleic acid molecule, wherein the expression or regulation of the second native gene or nucleic acid molecule differs from normal expression or regulation in a parent cell.

The term "homologous" or "homolog" refers to a molecule or activity found in or derived from a host cell, species or strain. For example, a heterologous or exogenous nucleic acid molecule can be homologous to a native host cell gene, and can optionally have an altered expression level, a different sequence, an altered activity, or any combination thereof.

"Sequence identity," as used herein, refers to the percentage of amino acid residues in one sequence that are identical with the amino acid residues in another reference polypeptide sequence after aligning the sequences and introducing gaps, if necessary, to achieve the maximum percent sequence identity, and not considering any conservative substitutions as part of the sequence identity. The percentage sequence identity values can be generated using the NCBI BLAST 2.0 software as defined by Altschul et al. (1997), *Nucl. Acids Res.* 25:3389-3402, with the parameters set to default values.

HA-1$^H$—Specific Binding Proteins, Accessory Proteins, and Engineered Host Cells In certain aspects, the present disclosure provides engineered immune cells comprising a heterologous polynucleotide that encodes a binding protein that specifically binds to an HA-1$^H$ antigen. In certain embodiments, the encoded binding protein is an HA-1$^H$ antigen-specific T cell receptor (TCR) or an HA-1$^H$ antigen-specific chimeric antigen receptor (CAR). In further embodiments, a binding protein is expressed as part of a transgene construct that encodes additional accessory proteins, such as a safety switch protein, a tag, a selection marker, a CD8 co-receptor β-chain, α-chain or both, or any combination thereof.

In any of the embodiments described herein, an encoded polypeptide of this disclosure (e.g., iCasp9, TCR β-chain, TCR α-chain, CD8 β-chain, CD8 α-chain) can comprise a "signal peptide" (also known as a leader sequence, leader peptide, or transit peptide). Signal peptides target newly synthesized polypeptides to their appropriate location inside or outside the cell. A signal peptide may be removed from the polypeptide during or once localization or secretion is completed. Polypeptides that have a signal peptide are referred to herein as a "pre-protein" and polypeptides having their signal peptide removed are referred to herein as "mature" proteins or polypeptides. Representative signal peptides include the amino acids from position 1 to position 21 of any one of SEQ ID NOS:1-3, 5-9, and 70-75, or the amino acids from position 1 to position 19 of any one of SEQ ID NOS:4, 10, and 12.

Binding proteins of this disclosure, such as TCRs and CARs, will contain a binding domain specific for a target (in this case, HA-1$^H$). A "binding domain" (also referred to as a "binding region" or "binding moiety"), as used herein, refers to a molecule or portion thereof (e.g., peptide, oligopeptide, polypeptide, protein) that possesses the ability to specifically and non-covalently associate, unite, or combine with a target (e.g., HA-1$^H$ peptide or HA-1$^H$ peptide:MHC complex). A binding domain includes any naturally occurring, synthetic, semi-synthetic, or recombinantly produced binding partner for a biological molecule, a molecular complex (i.e. complex comprising two or more biological molecules), or other target of interest. Exemplary binding domains include single chain immunoglobulin variable regions (e.g., single chain TCR (scTCR), single chain Fv (scFv)), receptor ectodomains, ligands (e.g., cytokines, chemokines), or synthetic polypeptides selected for their specific ability to bind to a biological molecule, a molecular complex or other target of interest.

In certain embodiments, an HA-1$^H$-specific binding domain alone (i.e., without any other portion of a HA-1-specific binding protein) can be soluble and can bind to HA-1$^H$ with a $K_d$ of less than about $10^{-8}$ M, less than about $10^{-9}$ M, less than about $10^{-10}$ M, less than about $10^{-11}$ M, less than about $10^{-12}$ M, or less than about $10^{-13}$ M. In particular embodiments, an HA-1$^H$-specific binding domain includes an HA-1$^H$-specific scTCR (e.g., single chain αβTCR proteins such as Vα-L-Vβ, Vβ-L-Vα, Vα-Cα-L-Vα, or Vα-L-Vβ-Cβ, wherein Vα and Vβ are TCRα and β variable domains respectively, Cα and Cβ are TCRα and β constant domains, respectively, and L is a linker).

The term "variable region" or "variable domain" refers to the domain of an immunoglobulin superfamily binding protein (e.g., a TCR α-chain or β-chain (or γ chain and δ chain for γδ TCRs)) that is involved in binding of the immunoglobulin superfamily binding protein (e.g., TCR) to antigen. The variable domains of the α-chain and β-chain ($V_α$, and $V_β$, respectively) of a native TCR generally have similar structures, with each domain comprising four conserved framework regions (FRs) and three CDRs. The $V_α$ domain is encoded by two separate DNA segments, the variable gene segment and the joining gene segment (V-J); the $V_β$ domain is encoded by three separate DNA segments, the variable gene segment, the diversity gene segment, and the joining gene segment (V-D-J). A single $V_α$ or $V_β$ domain may be sufficient to confer antigen-binding specificity. Furthermore, TCRs that bind a particular antigen may be isolated using a $V_α$ or $V_β$ domain from a TCR that binds the antigen to screen a library of complementary $V_α$ or $V_β$ domains, respectively.

The terms "complementarity determining region," and "CDR," are synonymous with "hypervariable region" or "HVR," and are known in the art to refer to non-contiguous sequences of amino acids within TCR variable regions, which confer antigen specificity and/or binding affinity. In general, there are three CDRs in each α-chain variable region (αCDR1, αCDR2, αCDR3) and three CDRs in each β-chain variable region (βCDR1, βCDR2, βCDR3). CDR3 is thought to be the main CDR responsible for recognizing processed antigen. CDR1 and CDR2 mainly interact with the MHC.

In certain embodiments, an encoded binding protein comprises: (a) a T cell receptor (TCR) α chain variable (Vα) domain having an amino acid sequence encoded by a TRAV17 gene, a TRAV21 gene, or a TRAV10 gene, and a TCR β-chain variable (Vβ) domain comprising a CDR3 amino acid sequence as shown in any one of SEQ ID NOS:13-17 and 86; (b) a TCR Vα domain comprising a CDR3 amino acid sequence as shown in any one of SEQ ID NOS:87-92, and a TCR Vβ domain having an amino acid sequence encoded by a TRBV7-9 gene; or (c) a TCR Vα domain comprising a CDR3 amino acid sequence of any one of SEQ ID NOS:87-92, and a TCR Vβ domain comprising a CDR3 amino acid sequence of any one of SEQ ID NOS:13-17 and 86, wherein the encoded binding protein is capable of specifically binding to a peptide containing an HA-1$^H$ minor antigen and does not bind to a peptide that does not contain an HA-1$^H$ minor antigen.

In further embodiments, an encoded binding protein comprises a TCR V$_\alpha$ domain and a TCR V$_\beta$ domain, wherein: (a) the encoded V$_\beta$ CDR3 comprises the amino acid sequence of SEQ ID NO:13, and the encoded V$_\alpha$ CDR3 comprises the amino acid sequence of SEQ ID NO:87; (b) the encoded V$_\beta$ CDR3 comprises the amino acid sequence shown in SEQ ID NO:14, and the encoded V$_\alpha$ CDR3 comprises the amino acid sequence of SEQ ID NO:88; (c) the encoded V$_\beta$ CDR3 comprises the amino acid sequence shown in SEQ ID NO:15, and the encoded V$_\alpha$ CDR3 comprises the amino acid sequence of SEQ ID NO:89; (d) the encoded V$_\beta$ CDR3 comprises the amino acid sequence shown in SEQ ID NO:16, and the encoded V$_\alpha$ CDR3 comprises the amino acid sequence of SEQ ID NO:90; (e) the encoded V$_\beta$ CDR3 comprises the amino acid sequence shown in SEQ ID NO:17, and the encoded V$_\alpha$ CDR3 comprises the amino acid sequence of SEQ ID NO:91; or (f) the encoded V$_\beta$ CDR3 comprises the amino acid sequence shown in SEQ ID NO:86, and the encoded V$_\alpha$ CDR3 comprises the amino acid sequence of SEQ ID NO:92.

In further embodiments, an encoded binding protein comprises a V$_\alpha$ domain, wherein the encoded V$_\alpha$ domain comprises an amino acid sequence that has at least about 90% sequence identity to the amino acid sequence of any one of SEQ ID NOS:2, 4, 6, 8, 10, and 12. In additional embodiments, an encoded binding protein comprises a V$_\beta$ domain, wherein the encoded V$_\beta$ domain comprises an amino acid sequence that has at least about 90% sequence identity to the amino acid sequence of any one of SEQ ID NOS:1, 3, 5, 7, 9, and 11.

In some embodiments, the encoded V$_\alpha$ domain comprises no change in amino acid sequence of CDR1, the encoded V$_\beta$ domain comprises no change in amino acid sequence of CDR1, or the CDR1 of the encoded V$_\alpha$ domain and the CDR1 of the encoded V$_\beta$ domain comprise no change in amino acid sequence. In further embodiments, the encoded V$_\alpha$ domain comprises no change in amino acid sequence of CDR2, the encoded V$_\beta$ domain comprises no change in amino acid sequence of CDR2, or the CDR2 of the encoded V$_\alpha$ domain and the CDR2 of the encoded V$_\beta$ domain comprise no change in amino acid sequence.

In particular embodiments, an encoded binding protein comprises a TCR V$_\alpha$ domain and a TCR V$_\beta$ domain, wherein: (a) the encoded V$_\beta$ domain comprises or consists of the amino acid sequence of SEQ ID NO:1, and the encoded V$_\alpha$ domain comprises or consists of the amino acid sequence of SEQ ID NO:2; (b) the encoded V$_\beta$ domain comprises or consists of the amino acid sequence of SEQ ID NO:3, and the encoded V$_\alpha$ domain comprises or consists of the amino acid sequence of SEQ ID NO:4; (c) the encoded V$_\beta$ domain comprises or consists of the amino acid sequence of SEQ ID NO:5, and the encoded Vα domain comprises or consists of the amino acid sequence of SEQ ID NO:6; (d) the encoded V$_\beta$ domain comprises or consists of the amino acid sequence of SEQ ID NO:7, and the encoded V$_\alpha$ domain comprises or consists of the amino acid sequence of SEQ ID NO:8; (e) the encoded V$_\beta$ domain comprises or consists of the amino acid sequence of SEQ ID NO:9, and the encoded V$_\alpha$ domain comprises or consists of the amino acid sequence of SEQ ID NO:10; or (f) the encoded V$_\beta$ domain comprises or consists of the amino acid sequence of SEQ ID NO:11, and the encoded V$_\alpha$ domain comprises or consists of the amino acid sequence of SEQ ID NO:12.

Exemplary binding proteins of this disclosure expressed by a cell may include a signal peptide (e.g., binding preproteins), and the cell may remove the signal peptide to generate a mature binding protein. In certain embodiments, a binding protein comprises two components, such as an α-chain and a β-chain, which can associate on the cell surface to form a functional binding protein. The two associated components may comprise mature proteins. In certain embodiments, a binding protein of this disclosure comprises a mature V$_\beta$ domain, wherein the mature V$_\beta$ domain comprises or consists of the amino acid sequence of any one of SEQ ID NOS:96, 98, 100, 102, 104, or 106. In further embodiments, a binding protein of this disclosure comprises a mature V$_\alpha$ domain, wherein the mature V$_\alpha$ domain comprises or consists of the amino acid sequence of any one of SEQ ID NOS:97, 99, 101, 103, 105, or 107. In still further embodiments, a binding protein of this disclosure comprises a mature V$_\beta$ domain and a mature V$_\alpha$ domain, wherein the mature V$_\beta$ domain comprises or consists of the amino acid sequence of any one of SEQ ID NOS:96, 98, 100, 102, 104, or 106, and the mature V$_\alpha$ domain comprises or consists of the amino acid sequence of any one of SEQ ID NOS:97, 99, 101, 103, 105, or 107. In certain embodiments, a binding protein of this disclosure comprises a mature TCR β-chain, wherein the mature TCR β-chain comprises or consists of the amino acid sequence of any one of SEQ ID NOS:108, 110, 112, 114, 116, or 118. In further embodiments, a binding protein of this disclosure comprises a mature TCR α-chain, wherein the mature TCR α-chain comprises or consists of the amino acid sequence of any one of SEQ ID NOS:109, 111, 113, 115, 117, or 119. In yet further embodiments, a binding protein of this disclosure comprises a mature TCR β-chain and a mature TCR α-chain, wherein the mature TCR β-chain comprises or consists of the amino acid sequence of any one of SEQ ID NOS:108, 110, 112, 114, 116, or 118, and the mature TCR α-chain comprises or consists of the amino acid sequence of any one of SEQ ID NOS:109, 111, 113, 115, 117, or 119. In certain embodiments, a binding protein of this disclosure is expressed with a CD8 β-chain and the CD8 β-chain comprises a mature CD8 β-chain, wherein the mature CD8 β-chain comprises or consists of the amino acid sequence shown in any one of SEQ ID NOS:121-125. In further embodiments, a binding protein of this disclosure is expressed with a CD8 α-chain and the CD8 α-chain comprises a mature CD8 α-chain, wherein the mature CD8 α-chain comprises or consists of the amino acid sequence of SEQ ID NO:120. In more embodiments, a binding protein of this disclosure is expressed with a CD8 β-chain and a CD8 α-chain, wherein the CD8 β-chain and α-chain comprises a mature CD8 β-chain and α-chain, wherein the mature CD8

β-chain comprises or consists of the amino acid sequence shown in any one of SEQ ID NOS:121-125, and the mature CD8 α-chain comprises or consists of the amino acid sequence of SEQ ID NO:120.

In further embodiments, an encoded binding protein comprises a mature TCR $V_\alpha$ domain and a mature TCR $V_\beta$ domain, wherein: (a) the $V_\beta$ domain comprising or consisting of the amino acid sequence of SEQ ID NO:96, and the $V_\alpha$ domain comprising or consisting of the amino acid sequence of SEQ ID NO:97; (b) the $V_\beta$ domain comprising or consisting of the amino acid sequence of SEQ ID NO:98, and the $V_\alpha$ domain comprising or consisting of the amino acid sequence of SEQ ID NO:99; (c) the $V_\beta$ domain comprising or consisting of the amino acid sequence of SEQ ID NO:100, and the Vα domain comprising or consisting of the amino acid sequence of SEQ ID NO:101; (d) the $V_\beta$ domain comprising or consisting of the amino acid sequence of SEQ ID NO:102, and the $V_\alpha$ domain comprising or consisting of the amino acid sequence of SEQ ID NO:103; (e) the $V_\beta$ domain comprising or consisting of the amino acid sequence of SEQ ID NO:104, and the $V_\alpha$ domain comprising or consisting of the amino acid sequence of SEQ ID NO:105; or (f) the $V_\beta$ domain comprising or consisting of the amino acid sequence of SEQ ID NO:106, and the $V_\alpha$ domain comprising or consisting of the amino acid sequence of SEQ ID NO:107.

An encoded binding protein contained in an engineered immune cell of the present disclosure may, in some embodiments, comprise a TCR constant domain. In certain embodiments, a TCR constant domain is modified to enhance pairing of desired TCR chains. For example, enhanced pairing between a heterologous TCR α-chain and a heterologous TCR β-chain due to a modification results in the preferential assembly of a TCR comprising two heterologous chains over an undesired mispairing of a heterologous TCR chain with an endogenous TCR chain (see, e.g., Govers et al., Trends Mol. Med. 16(2):77 (2010), the TCR modifications of which are herein incorporated by reference). Exemplary modifications to enhance pairing of heterologous TCR chains include the introduction of complementary cysteine residues in each of the heterologous TCR α-chain and β-chain. In some embodiments, a polynucleotide encoding a heterologous TCR α-chain encodes a cysteine at amino acid position 48 (corresponding to the full-length, mature human TCR α-chain sequence) and a polynucleotide encoding a heterologous TCR β-chain encodes a cysteine at amino acid position 57 (corresponding to the full-length mature human TCR β-chain sequence).

In certain embodiments, the encoded binding protein comprises a TCR α-chain constant ($C_\alpha$) domain having at least about 90% sequence identity to the amino acid sequence of any one of SEQ ID NOS:19, 22, 24 and 26. In further embodiments, the encoded binding protein comprises a TCR $C_\alpha$ domain having at least about 90% sequence identity to the amino acid sequence of any one of SEQ ID NOS:19, 22, 24 and 26, provided that the TCR $C_\alpha$ domain retains the introduced cysteine residue at position 48. In still further embodiments, the encoded binding protein comprises a TCR $C_\alpha$ domain comprising or consisting of the amino acid sequence of any one of SEQ ID NOS:19, 22, 24 and 26.

In certain embodiments, the encoded binding protein comprises a TCR β-chain constant ($C_\alpha$) domain having at least about 90% sequence identity to the amino acid sequence of any one of SEQ ID NOS:18, 23 and 25. In further embodiments, the encoded binding protein comprises a TCR $C_\beta$ domain having at least about 90% sequence identity to the amino acid sequence of any one of SEQ ID NOS:18, 23 and 25, provided that the TCR $C_\beta$ domain retains the introduced cysteine residue at position 57. In still further embodiments, the encoded binding protein comprises a TCR $C_\beta$ domain comprising or consisting of the amino acid sequence of any one of SEQ ID NOS:18, 23 and 25.

In certain embodiments, an encoded binding protein comprises a TCR α-chain (e.g., a TCR $V_\alpha$ domain operatively associated with a TCR $C_\alpha$ domain) having an amino acid sequence that is at least about 90% identical to the amino acid sequence of any one of SEQ ID NOS:28, 30, 32, 34, 36 and 38, optionally wherein the TCR $C_\alpha$ domain retains the cysteine at position 47 (as counted from the beginning of the $C_\alpha$ domain). In further embodiments, an encoded binding protein comprises a TCR α-chain comprising or consisting of the amino acid sequence of any one of SEQ ID NOS:28, 30, 32, 34, 36 and 38. In other embodiments, an encoded binding protein comprises a TCR β-chain (e.g., a TCR $V_\beta$ domain operatively associated with a TCR $C_\beta$ domain) having an amino acid sequence that is at least about 90% identical to the amino acid sequence of any one of SEQ ID NOS:27, 29, 31, 33, 35, and 37, optionally wherein the TCR $C_\beta$ domain retains the cysteine at position 57 (as counted from the beginning of the $C_\beta$ domain). In still further embodiments, the encoded binding protein comprises a TCR β-chain comprising or consisting of the amino acid sequence of any one of SEQ ID NOS:27, 29, 31, 33, 35, and 37.

A binding protein encoded by an engineered immune cell of this disclosure may comprise any of the presently disclosed TCR α-chains in association with any of the disclosed TCR β-chains. For example, in certain embodiments, an encoded binding protein comprises: (a) a TCR β-chain comprising or consisting of the amino acid sequence shown in SEQ ID NO:27, and a TCR α-chain comprising or consisting of the amino acid sequence shown in SEQ ID NO:28; (b) a TCR β-chain comprising or consisting of the amino acid sequence shown in SEQ ID NO:29, and a TCR α-chain comprising or consisting of the amino acid sequence shown in SEQ ID NO:30; (c) a TCR β-chain comprising or consisting of the amino acid sequence shown in SEQ ID NO:31, and the TCR α-chain comprising or consisting of the amino acid sequence shown in SEQ ID NO:32; (d) a TCR β-chain comprising or consisting of the amino acid sequence shown in SEQ ID NO:33, and a TCR α-chain comprising or consisting of the amino acid sequence shown in SEQ ID NO:34; (e) a TCR β-chain comprising or consisting of the amino acid sequence shown in SEQ ID NO:35, and a TCR-α chain comprising or consisting of the amino acid sequence shown in SEQ ID NO:36; or (f) a TCR β-chain comprising or consisting of the amino acid sequence shown in SEQ ID NO:37, and a TCR-α chain comprising or consisting of the amino acid sequence shown in SEQ ID NO:38.

An engineered immune cell of the present disclosure may comprise a single polynucleotide that encodes a binding protein as described herein, or the binding protein may be encoded by more than one polynucleotide. In other words, components or portions of a binding protein may be encoded by two or more polynucleotides, which may be contained on a single nucleic acid molecule or may be contained on two or more nucleic acid molecules.

In certain embodiments, a polynucleotide encoding two or more components or portions of a binding protein of the present disclosure comprises the two or more coding sequences operatively associated in a single open reading frame. Such an arrangement can advantageously allow coordinated expression of desired gene products, such as, for example, contemporaneous expression of alpha- and beta-chains of a TCR, such that they are produced in about a 1:1 ratio. In certain embodiments, two or more substituent gene products of a binding protein of this disclosure, such as a TCR (e.g., alpha- and beta-chains) or CAR, are expressed as separate molecules and associate post-translationally. In further embodiments, two or more substituent gene products of a binding protein of this disclosure are expressed as a single peptide with the parts separated by a cleavable or removable segment. For instance, self-cleaving peptides useful for expression of separable polypeptides encoded by a single polynucleotide or vector are known in the art and include, for example, a Porcine teschovirus-1 2A (P2A) peptide, such as a peptide encoded by a polynucleotide having the nucleotide sequence shown in any one of SEQ ID NOS:76-81, a Thoseaasigna virus 2A (T2A) peptide, such as a peptide encoded by a polynucleotide having the nucleotide sequence shown in SEQ ID NO:82, an Equine rhinitis A virus (ERAV) 2A (E2A) peptide, such as a peptide encoded by a polynucleotide having the nucleotide sequence shown in SEQ ID NO:83, and a Foot-and-Mouth disease virus 2A (F2A) peptide, such as a peptide encoded by a polynucleotide having the nucleotide sequence shown in SEQ ID NO:84.

In certain embodiments, a binding protein of the present disclosure comprises one or more junction amino acids. "Junction amino acids" or "junction amino acid residues" refer to one or more (e.g., 2 to about 10) amino acid residues between two adjacent motifs, regions or domains of a polypeptide, such as between a binding domain and an adjacent constant domain or between a TCR chain and an adjacent self-cleaving peptide. Junction amino acids can result from the design of a construct that encodes a fusion protein (e.g., amino acid residues resulting from the use of a restriction enzyme site during the construction of a nucleic acid molecule encoding a fusion protein), or from cleavage of, for example, a self-cleaving peptide adjacent one or more domains of an encoded binding protein of this disclosure (e.g., a P2A peptide disposed between a TCR α-chain and a TCR β-chain, the self-cleavage of which can leave one or more junction amino acids in the α-chain, the TCR β-chain, or both).

Binding proteins contained in engineered immune cells of this disclosure can, in certain embodiments, specifically bind to an HA-1$^H$ peptide:HLA complex. For example, in specific embodiments, a binding protein of this disclosure is capable of specifically binding to an HA-1$^H$ peptide:HLA complex, wherein the HLA can comprise HLA-A*0201. In particular embodiments, the HA-1$^H$ peptide comprises the amino acid sequence VLHDDLLEA (SEQ ID NO:66).

In any of the aforementioned embodiments, an encoded binding protein contained in an engineered immune cell can comprise a TCR, an antigen-binding fragment of a TCR (e.g., a single chain TCR ("scTCR")), or a chimeric antigen receptor ("CAR").

In certain embodiments, an antigen-binding fragment of a TCR comprises a single chain TCR (scTCR), which comprises both the TCR $V_\alpha$ and TCR $V_\beta$ domains, but only a single TCR constant domain ($C_\alpha$ or $C_\beta$). In further embodiments, an antigen-binding fragment of a TCR or a chimeric antigen receptor is chimeric (e.g., comprises amino acid residues or motifs from more than one donor or species), humanized (e.g., comprises residues from a non-human organism that are altered or substituted so as to reduce the risk of immunogenicity in a human), or human.

"Chimeric antigen receptor" (CAR) refers to a fusion protein that is engineered to contain two or more naturally-occurring amino acid sequences linked together in a way that does not occur naturally or does not occur naturally in a host cell, which fusion protein can function as a receptor when present on a surface of a cell. CARs of the present disclosure include an extracellular portion comprising an antigen binding domain (i.e., obtained or derived from an immunoglobulin or immunoglobulin-like molecule, such as an scFv derived from an antibody or TCR specific for a cancer antigen, or an antigen binding domain derived or obtained from a killer immunoreceptor from an NK cell) linked to a transmembrane domain and one or more intracellular signaling domains (optionally containing co-stimulatory domain(s)) (see, e.g., Sadelain et al., *Cancer Discov.*, 3(4):388 (2013); see also Harris and Kranz, *Trends Pharmacol. Sci.*, 37(3):220 (2016), and Stone et al., *Cancer Immunol. Immunother.*, 63(11):1163 (2014)).

Methods for producing engineered TCRs are described in, for example, Bowerman et al., *Mol. Immunol.*, 46(15):3000 (2009), the techniques of which are herein incorporated by reference. Methods for making CARs are well known in the art and are described, for example, in U.S. Pat. Nos. 6,410, 319; 7,446,191; U.S. Patent Publication No. 2010/065818; U.S. Pat. No. 8,822,647; PCT Publication No. WO 2014/031687; U.S. Pat. No. 7,514,537; and Brentjens et al., 2007, *Clin. Cancer Res.* 13:5426, the techniques of which are herein incorporated by reference.

Engineered immune cells of this disclosure can be administered as therapies for, e.g., cancer. In some circumstances, it may be desirable to reduce or stop the activity associated with a cellular immunotherapy. Thus, in certain embodiments, an engineered immune cell of the present disclosure comprises a heterologous polynucleotide encoding a binding protein and an accessory protein, such as a safety switch protein, which can be targeted using a cognate drug or other compound to selectively modulate the activity (e.g., lessen or ablate) of such cells when desirable. Safety switch proteins used in this regard include, for example, a a truncated EGF receptor polypeptide (huEGFRt) that is devoid of extracellular N-terminal ligand binding domains and intracellular receptor tyrosine kinase activity but retains the native amino acid sequence, type I transmembrane cell surface localization, and a conformationally intact binding epitope for pharmaceutical-grade anti-EGFR monoclonal antibody, cetuximab (Erbitux) tEGF receptor (tEGFr; Wang et al., *Blood* 118:1255-1263, 2011), a caspase polypeptide (e.g., iCasp9; Straathof et al., *Blood* 105:4247-4254, 2005; Di Stasi et al., *N. Engl. J. Med.* 365:1673-1683, 2011; Zhou and Brenner, *Exp. Hematol.* pii:S0301-472X(16)30513-6. doi:10.1016/j.exphem.2016.07.011), RQR8 (Philip et al., *Blood* 124:1277-1287, 2014), a 10 amino acid tag of the human c-myc protein (Myc) (Kieback et al., *Proc. Natl. Acad. Sci. USA* 105:623-628, 2008), as discussed herein, and a marker/safety switch polypeptide, such as RQR (CD20+ CD34; Philip et al., 2014).

Other accessory components useful for therapeutic cells comprise a tag or selection marker that allows the cells to be identified, sorted, isolated, enriched, or tracked. For example, marked immune cells having desired characteristics (e.g., an antigen-specific TCR and a safety switch protein) can be sorted away from unmarked cells in a sample and more efficiently activated and expanded for inclusion in a therapeutic product of desired purity.

As used herein, the term "selection marker" comprises a nucleic acid construct that confers an identifiable change to a cell permitting detection and positive selection of immune cells transduced with a polynucleotide comprising a selection marker. RQR is a selection marker that comprises a major extracellular loop of CD20 and two minimal CD34 binding sites. In some embodiments, an RQR-encoding polynucleotide comprises a polynucleotide that encodes the 16 amino acid CD34 minimal epitope. In some embodiments, such as certain embodiments provided in the examples herein, the CD34 minimal epitope is incorporated at the amino terminal position of the CD8 stalk domain (Q8). In further embodiments, the CD34 minimal binding site sequence can be combined with a target epitope for CD20 to form a compact marker/suicide gene for T cells (RQR8) (Philip et al., 2014, incorporated by reference herein). This construct allows for the selection of immune cells expressing the construct, with for example, CD34 specific antibody bound to magnetic beads (Miltenyi) and that utilizes clinically accepted pharmaceutical antibody, rituximab, that allows for the selective deletion of a transgene expressing engineered T cell (Philip et al., 2014).

Further exemplary selection markers also include several truncated type I transmembrane proteins normally not expressed on T cells: the truncated low-affinity nerve growth factor, truncated CD19, and truncated CD34 (see for example, Di Stasi et al., *N. Engl. J. Med.* 365:1673-1683, 2011; Mavilio et al., *Blood* 83:1988-1997, 1994; Fehse et al., *Mol. Ther.* 1:448-456, 2000; each incorporated herein in their entirety). A particularly attractive feature of CD19 and CD34 is the availability of the off-the-shelf Miltenyi CliniMACs™ selection system that can target these markers for clinical-grade sorting. However, CD19 and CD34 are relatively large surface proteins that may tax the vector packaging capacity and transcriptional efficiency of an integrating vector. Surface markers containing the extracellular, non-signaling domains or various proteins (e.g., CD19, CD34, LNGFR) also can be employed. Any selection marker may be employed and should be acceptable for Good Manufacturing Practices. In certain embodiments, selection markers are expressed with a polynucleotide that encodes a gene product of interest (e.g., a binding protein of the present disclosure, such as a TCR or CAR). Further examples of selection markers include, for example, reporters such as GFP, EGFP, β-gal or chloramphenicol acetyl-transferase (CAT). In certain embodiments, a selection marker, such as, for example, CD34 is expressed by a cell and the CD34 can be used to select enrich for, or isolate (e.g., by immunomagnetic selection) the transduced cells of interest for use in the methods described herein. As used herein, a CD34 marker is distinguished from an anti-CD34 antibody, or, for example, a scFv, TCR, or other antigen recognition moiety that binds to CD34.

In certain embodiments, a selection marker comprises an RQR polypeptide, a truncated low-affinity nerve growth factor (tNGFR), a truncated CD19 (tCD19), a truncated CD34 (tCD34), or any combination thereof.

By way of background, inclusion of CD4$^+$ T cells in an immunotherapy cell product can provide antigen-induced IL-2 secretion and augment persistence and function of transferred cytotoxic CD8$^+$ T cells (see, e.g., Kennedy et al., *Immunol. Rev.* 222:129 (2008); Nakanishi et al., *Nature* 462(7272):510 (2009)). In certain circumstances, a class I restricted TCR in CD4$^-$ T cells may require the transfer of a CD8 co-receptor to enhance sensitivity of the TCR to class I HLA peptide complexes. CD4 co-receptors differ in structure to CD8 and cannot effectively substitute for CD8 co-receptors (see, e.g., Stone & Kranz, Front. *Immunol.* 4:244 (2013); see also Cole et al., *Immunology* 137(2):139 (2012). Thus, another accessory protein for use in the compositions and methods of this disclosure comprises a CD8 co-receptor or component thereof.

Engineered immune cells comprising a heterologous polynucleotide encoding a binding protein of the present disclosure may, in certain embodiments, further comprise a heterologous polynucleotide encoding a CD8 co-receptor protein, or a beta-chain or alpha-chain component thereof. An encoded CD8 co-receptor includes, in some embodiments, a β-chain comprising the amino acid sequence of any one of SEQ ID NOS:71-75. In further embodiments, the encoded CD8 co-receptor is a recombinant CD8 co-receptor further comprising a RQR polypeptide having the amino acid sequence of SEQ ID NO:69. Without wishing to be bound by theory, it is believed that distance from the host cell surface is important for RQR polypeptides to function as selection markers/safety switches (Philip et al., 2010 (supra)). In some embodiments, the encoded RQR polypeptide is contained in a β-chain, an α-chain, or both, of the encoded CD8 co-receptor. In specific embodiments, an engineered immune cell comprises a heterologous polynucleotide encoding iCasp9 and a heterologous polynucleotide encoding a recombinant CD8 co-receptor protein that comprises a β-chain containing a RQR polypeptide and further comprises a CD8 α-chain. In particular embodiments, the encoded CD8 α-chain comprises the amino acid sequence shown in SEQ ID NO:70.

In further embodiments, an engineered immune cell comprises a heterologous polynucleotide encoding iCasp9 and a heterologous polynucleotide encoding a recombinant CD8 co-receptor protein that comprises an α-chain containing a RQR polypeptide and further comprises a CD8 β-chain. In some embodiments, both of the encoded CD8 α-chain and the encoded CD8 β-chain contain a RQR polypeptide.

An engineered immune cell may be efficiently transduced to contain, and may efficiently express, a single polynucleotide that encodes the binding protein, safety switch protein, selection marker, and CD8 co-receptor protein. For example, in some embodiments, an engineered immune cell of the present disclosure comprises a heterologous polynucleotide that encodes, from 5' to 3', ([an iCasp9 polypeptide]-[a porcine teschovirus 2A (P2A) peptide]-[a TCR β-chain]-[a P2A peptide]-[a TCR α-chain]-[a P2A peptide]-[a CD8 β-chain comprising an RQR polypeptide]-[a P2A peptide]-[a CD8 α-chain]). In specific embodiments, the TCRβ-chain-encoding polynucleotide comprises or consists of the nucleotide sequence of SEQ ID NO:41, and the TCRα-chain-encoding polynucleotide comprises or consists of the nucleotide sequence of SEQ ID NO:42.

In particular embodiments, an engineered immune cell contains a heterologous polynucleotide that comprises or consists of the nucleotide sequence of SEQ ID NO:85.

Any suitable immune cell may be engineered to include a heterologous polynucleotide encoding a binding protein of this disclosure, including, for example, a T cell, a NK cell, or a NK-T cell. In some embodiments, an engineered immune cell comprises a CD4$^+$T cell, a CD8$^-$ T cell, or both. Methods for transfecting/transducing T cells with desired nucleic acids have been described (e.g., U.S. Patent Application Pub. No. US 2004/0087025) as have adoptive transfer procedures using T cells of desired target-specificity (e.g., Schmitt et al., *Hum. Gen.* 20:1240, 2009; Dossett et al., *Mol. Ther.* 17:742, 2009; Till et al., *Blood* 112:2261, 2008; Wang et al., *Hum. Gene Ther.* 18:712, 2007; Kuban et al., *Blood* 109:2331, 2007; US 2011/0243972; US 2011/0189141; Leen et al., *Ann. Rev. Immunol.* 25:243, 2007), such that adaptation of these methodologies to the presently disclosed embodiments is contemplated, based on the teachings herein.

Any appropriate method can be used to transfect or transduce the cells, for example, the T cells, or to administer the polynucleotides or compositions of the present methods. Known methods for delivering polynucleotides to host cells include, for example, use of cationic polymers, lipid-like molecules, and certain commercial products such as, for example, IN-VIVO-JET PEI. Other methods include ex vivo transduction, injection, electroporation, DEAE-dextran, sonication loading, liposome-mediated transfection, receptor-mediated transduction, microprojectile bombardment, transposon-mediated transfer, and the like. Still further methods of transfecting or transducing host cells employ vectors, described in further detail herein.

In any of the foregoing embodiments, an engineered immune cell may be a "universal donor" cell that is modified to reduce or eliminate expression of one or more endogenous genes that encode a polypeptide involved in immune signaling or other related activities. Exemplary gene knock-outs include those that encode PD-1, LAG-3, CTLA4, TIM3, an HLA molecule, a TCR molecule, or the like. Without wishing to be bound by theory, certain endogenously expressed immune cell proteins may be recognized as foreign by an allogeneic host receiving the engineered immune cells, which may result in elimination of the engineered immune cells (e.g., an HLA allele), or may down-regulate the immune activity of the engineered immune cells (e.g., PD-1, LAG-3, CTLA4), or may interfere with the binding activity of a heterologously expressed binding protein of the present disclosure (e.g., an endogenous TCR that binds a non-HA-1$^H$ antigen and thereby interferes with the engineered immune cell binding a cell that expresses HA-1$^H$ antigen). Accordingly, decreasing or eliminating expression or activity of such endogenous genes or proteins can improve the activity, tolerance, and persistence of the engineered immune cells within an allogeneic host, and allows for universal, "off-the-shelf" cells for administration (e.g., to any recipient regardless of HLA type).

In certain embodiments, an engineered immune cell of this disclosure comprises a chromosomal gene knockout of one or more of a gene that encodes PD-1, LAG-3, CTLA4, TIM3, an HLA component (e.g., a gene that encodes an α1 macroglobulin, an α2 macroglobulin, an α3 macroglobulin, a β1 microglobulin, or a β2 microglobulin), or a TCR component (e.g., a gene that encodes a TCR variable region or a TCR constant region) (see, e.g., Torikai et al., *Nature Sci. Rep.* 6:21757 (2016); Torikai et al., *Blood* 119(24):5697 (2012); and Torikai et al., *Blood* 122(8):1341 (2013), the gene editing techniques and compositions of which are herein incorporated by reference in their entirety). As used herein, the term "chromosomal gene knockout" refers to a genetic alteration in an engineered immune cell that prevents production, by the engineered immune cell, of a functionally active endogenous polypeptide product. Alterations resulting in a chromosomal gene knockout can include, for example, introduced nonsense mutations (including the formation of premature stop codons), missense mutations, gene deletion, and strand breaks, as well as the heterologous expression of inhibitory nucleic acid molecules that inhibit endogenous gene expression in the engineered immune cell.

A chromosomal gene knockout may be introduced by chromosomal editing of the immune cell. In certain embodiments, the chromosomal gene knockout is made by chromosomal editing of the immune cell. Chromosomal editing can be performed using, for example, endonucleases. As used herein "endonuclease" refers to an enzyme capable of catalyzing cleavage of a phosphodiester bond within a polynucleotide chain. In certain embodiments, an endonuclease is capable of cleaving a targeted gene thereby inactivating or "knocking out" the targeted gene. An endonuclease may be a naturally occurring, recombinant, genetically modified, or fusion endonuclease. The nucleic acid strand breaks caused by the endonuclease are commonly repaired through the distinct mechanisms of homologous recombination or non-homologous end joining (NHEJ). During homologous recombination, a donor nucleic acid molecule may be used for gene "knock-in" to inactivate a target gene. NHEJ is an error-prone repair process that often results in changes to the DNA sequence at the site of the cleavage, e.g., a substitution, deletion, or addition of at least one nucleotide. NHEJ may be used to "knock-out" a target gene. Methods of disrupting or knocking out genes or gene expression in immune cells using endonucleases are known in the art and described, for example, in PCT Publication Nos. WO 2015/066262; WO 2013/074916; and WO 2014/059173; methods from each of which is incorporated by reference. Examples of endonucleases include zinc finger nucleases, TALE-nucleases, CRISPR-Cas nucleases, and meganucleases.

As used herein, a "zinc finger nuclease" (ZFN) refers to a fusion protein comprising a zinc finger DNA-binding domain fused to a non-specific DNA cleavage domain, such as a FokI endonuclease. Each zinc finger motif of about 30 amino acids binds to about 3 base pairs of DNA, and amino acids at certain residues can be changed to alter triplet sequence specificity (see, e.g., Desjarlais et al., *Proc. Natl. Acad. Sci.* 90:2256-2260, 1993; Wolfe et al., *J. Mol. Biol.* 285:1917-1934, 1999). Multiple zinc finger motifs can be linked in tandem to create binding specificity to desired DNA sequences, such as regions having a length ranging from about 9 to about 18 base pairs. By way of background, ZFNs mediate genome editing by catalyzing the formation of a site-specific DNA double strand break (DSB) in the genome, and targeted integration of a transgene comprising flanking sequences homologous to the genome at the site of DSB is facilitated by homology directed repair. Alternatively, a DSB generated by a ZFN can result in knock out of target gene via repair by non-homologous end joining (NHEJ), which is an error-prone cellular repair pathway that results in the insertion or deletion of nucleotides at the cleavage site. In certain embodiments, a gene knockout comprises an insertion, a deletion, a mutation or a combination thereof, made using a ZFN molecule.

As used herein, a "transcription activator-like effector nuclease" (TALEN) refers to a fusion protein comprising a TALE DNA-binding domain and a DNA cleavage domain, such as a FokI endonuclease. A "TALE DNA binding domain" or "TALE" is composed of one or more TALE repeat domains/units, each generally having a highly conserved 33-35 amino acid sequence with divergent 12$^{th}$ and 13$^{th}$ amino acids. The TALE repeat domains are involved in binding of the TALE to a target DNA sequence. The divergent amino acid residues, referred to as the Repeat Variable Diresidue (RVD), correlate with specific nucleotide recognition. The natural (canonical) code for DNA recognition of these TALEs has been determined such that an HD sequence at positions 12 and 13 leads to a binding to cytosine (C), NG binds to T, NI to A, NN binds to G or A, and NG binds to T and non-canonical (atypical) RVDs are also known (see, e.g., U.S. Patent Publication No. US 2011/0301073, which atypical RVDs are incorporated by reference herein in its entirety). TALENs can be used to direct site-specific double-strand breaks (DSB) in the genome of T cells. Non-homologous end joining (NHEJ) ligates DNA from both sides of a double-strand break in which there is little or no sequence overlap for annealing, thereby introducing errors that knock out gene expression. Alternatively, homology directed repair can introduce a transgene at the site of DSB providing homologous flanking sequences are present in the transgene. In certain embodiments, a gene knockout comprises an insertion, a deletion, a mutation or a combination thereof, and made using a TALEN molecule.

As used herein, a "clustered regularly interspaced short palindromic repeats/Cas" (CRISPR/Cas) nuclease system refers to a system that employs a CRISPR RNA (crRNA)-guided Cas nuclease to recognize target sites within a genome (known as protospacers) via base-pairing complementarity and then to cleave the DNA if a short, conserved protospacer associated motif (PAM) immediately follows 3' of the complementary target sequence. CRISPR/Cas systems are classified into three types (i.e., type I, type II, and type III) based on the sequence and structure of the Cas nucleases. The crRNA-guided surveillance complexes in types I and III need multiple Cas subunits. Type II system, the most studied, comprises at least three components: an RNA-guided Cas9 nuclease, a crRNA, and a trans-acting crRNA (tracrRNA). The tracrRNA comprises a duplex forming region. A crRNA and a tracrRNA form a duplex that is capable of interacting with a Cas9 nuclease and guiding the Cas9/crRNA:tracrRNA complex to a specific site on the target DNA via Watson-Crick base-pairing between the spacer on the crRNA and the protospacer on the target DNA upstream from a PAM. Cas9 nuclease cleaves a double-stranded break within a region defined by the crRNA spacer. Repair by NHEJ results in insertions and/or deletions which disrupt expression of the targeted locus. Alternatively, a transgene with homologous flanking sequences can be introduced at the site of DSB via homology directed repair. The crRNA and tracrRNA can be engineered into a single guide RNA (sgRNA or gRNA) (see, e.g., Jinek et al., Science 337:816-21, 2012). Further, the region of the guide RNA complementary to the target site can be altered or programed to target a desired sequence (Xie et al., PLOS One 9:e100448, 2014; U.S. Pat. Appl. Pub. No. US 2014/0068797, U.S. Pat. Appl. Pub. No. US 2014/0186843; U.S. Pat. No. 8,697,359, and PCT Publication No. WO 2015/071474; the techniques and compositions of each of which are incorporated by reference). In certain embodiments, a gene knockout comprises an insertion, a deletion, a mutation or a combination thereof, and made using a CRISPR/Cas nuclease system.

As used herein, a "meganuclease," also referred to as a "homing endonuclease," refers to an endodeoxyribonuclease characterized by a large recognition site (double stranded DNA sequences of about 12 to about 40 base pairs). Meganucleases can be divided into five families based on sequence and structure motifs: LAGLIDADG (SEQ ID NO;131), GIY-YIG, HNH, His-Cys box and PD-(D/E)XK (SEQ ID NO;132). Exemplary meganucleases include I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII, whose recognition sequences are known (see, e.g., U.S. Pat. Nos. 5,420,032 and 6,833,252; Belfort et al., Nucleic Acids Res. 25:3379-3388, 1997; Dujon et al., Gene 82:115-118, 1989; Perler et al., Nucleic Acids Res. 22:1125-1127, 1994; Jasin, Trends Genet. 12:224-228, 1996; Gimble et al., J. Mol. Biol. 263:163-180, 1996; Argast et al., J. Mol. Biol. 280:345-353, 1998).

In certain embodiments, naturally-occurring meganucleases may be used to promote site-specific genome modification of a target selected from PD-1, LAG3, TIM3, CTLA4, an HLA-encoding gene, or a TCR component-encoding gene. In other embodiments, an engineered meganuclease having a novel binding specificity for a target gene is used for site-specific genome modification (see, e.g., Porteus et al., Nat. Biotechnol. 23:967-73, 2005; Sussman et al., J. Mol. Biol. 342:31-41, 2004; Epinat et al., Nucleic Acids Res. 31:2952-62, 2003; Chevalier et al., Molec. Cell 10:895-905, 2002; Ashworth et al., Nature 441:656-659, 2006; Paques et al., Curr. Gene Ther. 7:49-66, 2007; U.S. Patent Publication Nos. US 2007/0117128; US 2006/0206949; US 2006/0153826; US 2006/0078552; and US 2004/0002092).

In certain embodiments, a chromosomal gene knockout comprises an inhibitory nucleic acid molecule that is introduced into an engineered immune cell comprising a heterologous polynucleotide encoding an antigen-specific receptor that specifically binds to a tumor associated antigen, wherein the inhibitory nucleic acid molecule encodes a target-specific inhibitor and wherein the encoded target-specific inhibitor inhibits endogenous gene expression (i.e., of PD-1, TIM3, LAG3, CTLA4, an HLA component, a TCR component, or any combination thereof) in the engineered immune cell.

A chromosomal gene knockout can be confirmed directly by DNA sequencing of the engineered immune cell following use of the knockout procedure or agent. Chromosomal gene knockouts can also be inferred from the absence of gene expression (e.g., the absence of an mRNA or polypeptide product encoded by the gene) following the knockout.

In another aspect, compositions are provided herein that comprise an engineered immune cell of the present disclosure and a pharmaceutically acceptable carrier, diluent, or excipient. Also provided herein are unit doses that comprise an effective amount of an engineered immune cell or of a composition comprising the engineered immune cell. In certain embodiments, a unit dose comprises (i) a composition comprising at least about 30%, at least about 40%, at least about 50%, at least about 60%, at least about 70%, at least about 80%, at least about 85%, at least about 90%, or at least about 95% engineered CD4$^+$ T cells, combined with (ii) a composition comprising at least about 30%, at least about 40%, at least about 50%, at least about 60%, at least about 70%, at least about 80%, at least about 85%, at least about 90%, or at least about 95% engineered CD8$^+$ T cells, in about a 1:1 ratio, wherein the unit dose contains a reduced amount or substantially no naive T cells (i.e., has less than about 50%, less than about 40%, less than about 30%, less then about 20%, less than about 10%, less than about 5%, or less then about 1% the population of naive T cells present in a unit dose as compared to a patient sample having a comparable number of PBMCs).

In some embodiments, a unit dose comprises (i) a composition comprising at least about 50% engineered CD4$^+$ T cells, combined with (ii) a composition comprising at least about 50% engineered CD8$^+$ T cells, in about a 1:1 ratio, wherein the unit dose contains a reduced amount or substantially no naive T cells. In further embodiments, a unit dose comprises (i) a composition comprising at least about 60% engineered CD4$^+$ T cells, combined with (ii) a composition comprising at least about 60% engineered CD8$^+$ T cells, in about a 1:1 ratio, wherein the unit dose contains a reduced amount or substantially no naive T cells. In still further embodiments, a unit dose comprises (i) a composition comprising at least about 70% engineered CD4$^+$ T cells, combined with (ii) a composition comprising at least about 70% engineered CD8$^-$ T cells, in about a 1:1 ratio, wherein the unit dose contains a reduced amount or substantially no naive T cells. In some embodiments, a unit dose comprises (i) a composition comprising at least about 80% engineered CD4+ T cells, combined with (ii) a composition comprising at least about 80% engineered CD8− T cells, in about a 1:1 ratio, wherein the unit dose contains a reduced amount or substantially no naive T cells. In some embodiments, a unit dose comprises (i) a composition comprising at least about 85% engineered CD4+ T cells, combined with (ii) a composition comprising at least about 85% engineered CD8+ T cells, in about a 1:1 ratio, wherein the unit dose contains a reduced amount or substantially no naive T cells. In some embodiments, a unit dose comprises (i) a composition comprising at least about 90% engineered CD4+ T cells, combined with (ii) a composition comprising at least about 90% engineered CD8− T cells, in about a 1:1 ratio, wherein the unit dose contains a reduced amount or substantially no naive T cells.

In any of the embodiments described herein, a unit dose comprises equal, or approximately equal numbers of engineered CD45RA− CD3+ CD8+ and engineered CD45RA− CD3− CD4+ $T_M$ cells.

Polynucleotides, Transgenes and Vectors

In further aspects, the present disclosure provides an isolated polynucleotide that encodes a binding protein as described herein (e.g., an HA-1$^H$-specific TCR, scTCR, or CAR that comprises TCR $V_\alpha$ and $V_\beta$ domains as described herein (and optionally further comprises constant domains or other components as described herein)), and may additionally encoded a safety switch protein, a selection marker, a CD8 co-receptor β-chain, or a CD8 co-receptor α-chain, or any combination thereof, provided that at least a portion of the isolated polynucleotide is codon-optimized for expression in a host cell (e.g., an engineered immune cell as disclosed herein).

In particular, any of the aforementioned heterologous polynucleotides comprised in the engineered immune cells (e.g., encoding any of the binding proteins of the present disclosure) may also or alternatively be provided in an isolated form, wherein the polynucleotide is codon-optimized for expression in a host cell. For example, in certain embodiments, an isolated polynucleotide encodes a TCR β-chain of an HA-1$^H$-specific binding protein and comprises or consists of the nucleotide sequence of any one of SEQ ID NOS:39, 41, 43, 45, 47, 49, or 51. In further embodiments, an isolated polynucleotide encodes a TCR α-chain of an HA-1$^H$-specific binding protein and comprises or consists of the nucleotide sequence of any one of SEQ ID NOS:40, 42, 46, 48, 50, or 52.

In certain embodiments, a heterologous polynucleotide encoding a TCR α-chain and a heterologous polynucleotide encoding a TCR β-chain are contained in a single open reading frame comprised in the engineered immune cell, wherein the single open reading frame further comprises a polynucleotide encoding a self-cleaving peptide disposed between the α-chain-encoding polynucleotide and the β-chain-encoding polynucleotide. In some embodiments, the polynucleotide encoding the self-cleaving peptide comprises or consists of the nucleotide sequence of any one of SEQ ID NOS:76-84.

In further embodiments, the single open reading frame comprises a nucleotide sequence that is at least about 80% identical to the nucleotide sequence of any one of SEQ ID NOS:59-63. In specific embodiments, the single open reading frame comprises or consists of the nucleotide sequence of any one of SEQ ID NOS: 59-63. In still further embodiments, the encoded ([TCR β-chain]-[self-cleaving-peptide]-[TCR α-chain]) comprises or consists of the amino acid sequence of any one of SEQ ID NOS: 53-57, which exists before the cell removes the signal peptide, and before the β-chain and α-chains are separated by the self cleaving peptide.

An isolated polynucleotide of this disclosure may further comprise a polynucleotide encoding a safety switch protein, a selection marker, a CD8 co-receptor beta chain (e.g., SEQ ID NOs:71-75), or a CD8 co-receptor alpha chain (e.g., SEQ ID NO:70) as disclosed herein, or may comprise a polynucleotide encoding any combination thereof. In specific embodiments, an isolated comprising a heterologous polynucleotide encoding iCasp9 and a heterologous polynucleotide encoding a recombinant CD8 co-receptor protein that comprises a β-chain or α-chain that contains a RQR polypeptide.

In some embodiments, an isolated polynucleotide comprises a single open reading frame containing, from 5' to 3', ([a polynucleotide encoding a safety switch protein]-[a polynucleotide encoding a self-cleaving peptide]-[the polynucleotide encoding a TCR β-chain]-[a polynucleotide encoding a self-cleaving polypeptide]-[a polynucleotide encoding a TCR α-chain]-[a polynucleotide encoding a self-cleaving polypeptide]-[a polynucleotide encoding a CD8 β-chain that contains an RQR polypeptide]-[a polynucleotide encoding a self-cleaving polypeptide]-[a polynucleotide encoding a CD8 α-chain]).

In further embodiments, an isolated polynucleotide comprises a single open reading frame that encodes, from 5' to 3', ([an iCasp9 polypeptide]-[a porcine teschovirus 2A (P2A) peptide]-[a TCR β chain]-[a P2A peptide]-[a TCR α-chain]-[a P2A peptide]-[a CD8 β-chain comprising an RQR polypeptide]-[a P2A peptide]-[a CD8 α-chain]). In certain embodiments, the TCR β-chain-encoding polynucleotide comprises or consists of the nucleotide sequence of SEQ ID NO:41, and wherein the TCR α-chain-encoding polynucleotide comprises or consists of the nucleotide sequence of SEQ ID NO:42.

In specific embodiments, an isolated polynucleotide comprises or consists of the nucleotide sequence of SEQ ID NO:85.

In any of the embodiments described herein, an isolated polynucleotide is codon-optimized for expression in an immune cell, such as a T cell.

In another aspect, transgene constructs are provided herein, wherein a transgene construct comprises an expression control sequence (e.g., a promoter sequence) operatively linked to a single open reading frame comprising (a) a polynucleotide encoding a safety switch protein; (b) a polynucleotide encoding a TCR β-chain; (c) a polynucleotide encoding a TCR α-chain; (b) a polynucleotide encoding a selection marker; (c) a polynucleotide encoding a CD8 co-receptor β-chain; and (d) a polynucleotide encoding a CD8 co-receptor α-chain.

Construction of an transgene construct for genetically engineering and producing a polypeptide of interest can be accomplished by using any suitable molecular biology engineering technique known in the art. To obtain efficient transcription and translation, a polynucleotide in each transgene construct of the present disclosure includes, in certain embodiments, at least one appropriate expression control sequence (also called a regulatory sequence), such as a leader sequence and particularly a promoter operably (i.e., operatively) linked to the nucleotide sequence encoding the polypeptide of interest. In certain embodiments, a transgene construct comprises a polynucleotide that encodes a safety switch protein, wherein the encoded safety switch protein comprises: (i) a truncated EGF receptor (tEGFR); (ii) iCasp9; (iii) a RQR polypeptide; (iv) a myc epitope; or (v) any combination thereof.

In further embodiments, the encoded selection marker comprises: (i) a RQR polypeptide; (ii) a truncated low-affinity nerve growth factor (tNGFR); (iii) a truncated CD19 (tCD19); (iv) a truncated CD34 (tCD34); or (v) any combination thereof.

In some embodiments, the encoded CD8 co-receptor is a recombinant CD8 co-receptor comprising a RQR polypeptide having the amino acid sequence shown in SEQ ID NO:69. In particular embodiments, a transgene construct includes a polynucleotide that encodes an RQR polypeptide that is contained in an encoded CD8 β-chain. In further embodiments, a transgene construct includes a polynucleotide that encodes an RQR polypeptide that is contained in an encoded CD8 α-chain.

For example, a transgene construct of the present disclosure comprises, in certain embodiments, an open reading frame containing (a) a polynucleotide encoding a safety switch protein; (b) a polynucleotide encoding a TCRβ-chain; (c) a polynucleotide encoding a TCRα-chain; (d) a polynucleotide encoding a CD8 β-chain that contains an RQR polypeptide; and (e) a polynucleotide encoding a CD8 α-chain. Any arrangement of the component polynucleotides is contemplated herein, including, for example, a single open reading frame that comprises, from 5' to to 3', ([the polynucleotide encoding a safety switch protein]-[a polynucleotide encoding a self-cleaving peptide]-[the polynucleotide encoding a TCR β-chain]-[the polynucleotide encoding a self-cleaving polypeptide]-[the polynucleotide encoding a TCR α-chain]-[a polynucleotide encoding a self-cleaving polypeptide]-[the polynucleotide encoding a CD8 β-chain that contains an RQR polypeptide]-[a polynucleotide encoding a self-cleaving polypeptide]-[the polynucleotide encoding a CD8 α-chain]).

In specific embodiments, a transgene construct of the instant disclosure comprises a single open reading frame that encodes, from 5'to 3', ([an iCasp9 polypeptide]-[a P2A peptide]-[a TCR β-chain]-[a P2A peptide]-[a TCR α-chain]-[a P2A peptide]-[a CD8 β-chain comprising an RQR polypeptide]-[a P2A peptide]-[a CD8 α-chain]).

In further embodiments, a transgene construct can comprise an expression control sequence operatively linked to a polynucleotide as described herein. For example, a transgene construct can comprise an expression control sequence operatively linked to a polynucleotide that encodes a binding protein of the present disclosure, wherein the binding protein includes (a) a T cell receptor (TCR) α chain variable ($V_\alpha$) domain having an amino acid sequence encoded by a TRAV17 gene, a TRAV21 gene, or a TRAV10 gene, and a TCR β-chain variable ($V_\beta$) domain comprising a CDR3 amino acid sequence as shown in any one of SEQ ID NOS:13-17 and 86; (b) a TCR $V_\alpha$ domain comprising a CDR3 amino acid sequence as shown in any one of SEQ ID NOS:87-92, and a TCR $V_\beta$ domain having an amino acid sequence encoded by a TRBV7-9 gene; or (c) a TCR $V_\alpha$ domain comprising a CDR3 amino acid sequence of any one of SEQ ID NOS:87-92, and a TCR $V_\beta$ domain comprising a CDR3 amino acid sequence of any one of SEQ ID NOS:13-17 and 86, wherein the encoded binding protein is capable of specifically binding to a peptide containing an HA-1$^H$ antigen and does not bind to a peptide that does not contain an HA-1$^H$ antigen.

Also provided herein are vectors that comprise a transgene construct of the instant disclosure. Some examples of vectors include plasmids, viral vectors, cosmids, and others. Some vectors may be capable of autonomous replication in a host cell into which they are introduced (e.g., bacterial vectors having a bacterial origin of replication and episomal mammalian vectors), whereas other vectors may be integrated into the genome of a host cell or promote integration of the polynucleotide insert upon introduction into the host cell and thereby replicate along with the host genome (e.g., lentiviral vector, retroviral vector). Additionally, some vectors are capable of directing the expression of genes to which they are operatively linked (these vectors may be referred to as "expression vectors"). According to related embodiments, it is further understood that, if one or more agents (e.g., polynucleotides encoding binding proteins as described herein) are co administered to a subject, that each agent may reside in separate or the same vectors, and multiple vectors (each containing a different agent or the same agent) may be introduced to a cell or cell population or administered to a subject.

In certain embodiments, polynucleotides of the present disclosure may be operatively linked to certain elements of a vector. For example, polynucleotide sequences that are needed to effect the expression and processing of coding sequences to which they are ligated may be operatively linked. Expression control sequences may include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequences); sequences that enhance protein stability; and possibly sequences that enhance protein secretion. Expression control sequences may be operatively linked if they are contiguous with the gene of interest and expression control sequences that act in trans or at a distance to control the gene of interest.

In certain embodiments, the vector comprises a plasmid vector or a viral vector (e.g., a vector selected from lentiviral vector or a y-retroviral vector). Viral vectors include retrovirus, adenovirus, parvovirus (e.g., adeno-associated viruses), coronavirus, negative strand RNA viruses such as ortho-myxovirus (e.g., influenza virus), rhabdovirus (e.g., rabies and vesicular stomatitis virus), paramyxovirus (e.g., measles and Sendai), positive strand RNA viruses such as picornavirus and alphavirus, and double-stranded DNA viruses including adenovirus, herpesvirus (e.g., Herpes Simplex virus types 1 and 2, Epstein-Barr virus, cytomeg¬lovirus), and poxvirus (e.g., vaccinia, fowlpox and canarypox). Other viruses include Norwalk virus, togavirus, flavivirus, reoviruses, papovavirus, hepadnavirus, and hepatitis virus, for example. Examples of retroviruses include avian leukosis-sarcoma, mammalian C-type, B-type viruses, D type viruses, HTLV-BLV group, lentivirus, and spumavirus (Coffin, J. M., Retroviridae: The viruses and their replication, In Fundamental Virology, Third Edition, B. N. Fields et al., Eds., Lippincott-Raven Publishers, Philadelphia, 1996).

"Retroviruses" are viruses having an RNA genome, which is reverse-transcribed into DNA using a reverse transcriptase enzyme, the reverse-transcribed DNA is then incorporated into the host cell genome. "Gammaretrovirus" refers to a genus of the retroviridae family. Examples of gammaretroviruses include mouse stem cell virus, murine leukemia virus, feline leukemia virus, feline sarcoma virus, and avian reticuloendotheliosis viruses. "Lentiviral vector," as used herein, means HIV-based lentiviral vectors for gene delivery, which can be integrative or non-integrative, have relatively large packaging capacity, and can transduce a range of different cell types. Lentiviral vectors are usually generated following transient transfection of three (packaging, envelope and transfer) or more plasmids into producer cells. Like HIV, lentiviral vectors enter the target cell through the interaction of viral surface glycoproteins with receptors on the cell surface. On entry, the viral RNA undergoes reverse transcription, which is mediated by the viral reverse transcriptase complex. The product of reverse transcription is a double-stranded linear viral DNA, which is the substrate for viral integration into the DNA of infected cells.

In certain embodiments, the viral vector can be a gammaretrovirus, e.g., Moloney murine leukemia virus (MLV)-derived vectors. In other embodiments, the viral vector can be a more complex retrovirus-derived vector, e.g., a lentivirus-derived vector. HIV-1-derived vectors belong to this category. Other examples include lentivirus vectors derived from HIV-2, FIV, equine infectious anemia virus, SIV, and Maedi-Visna virus (ovine lentivirus). Methods of using retroviral and lentiviral viral vectors and packaging cells for transducing mammalian host cells with viral particles containing TCR or CAR transgenes are known in the art and have been previous described, for example, in: U.S. Pat. No. 8,119,772; Walchli et al., *PLoS One* 6:327930, 2011; Zhao et al., *J. Immunol.* 174:4415, 2005; Engels et al., *Hum. Gene Ther.* 14:1155, 2003; Frecha et al., *Mol. Ther.* 18:1748, 2010; and Verhoeyen et al., *Methods Mol. Biol.* 506:97, 2009. Retroviral and lentiviral vector constructs and expression systems are also commercially available. Other viral vectors also can be used for polynucleotide delivery including DNA viral vectors, including, for example adenovirus-based vectors and adeno-associated virus (AAV)-based vectors; vectors derived from herpes simplex viruses (HSVs), including amplicon vectors, replication-defective HSV and attenuated HSV (Krisky et al., Gene Ther. 5:1517, 1998).

Other vectors recently developed for gene therapy uses can also be used with the compositions and methods of this disclosure. Such vectors include those derived from baculoviruses and α-viruses. (Jolly, D J. 1999. Emerging Viral Vectors. pp 209-40 in Friedmann T. ed. The Development of Human Gene Therapy. New York: Cold Spring Harbor Lab), or plasmid vectors (such as Sleeping Beauty or other transposon vectors).

When a viral vector genome comprises a plurality of polynucleotides to be expressed in a host cell as separate transcripts, the viral vector may also comprise additional sequences between the two (or more) transcripts allowing for bicistronic or multicistronic expression. Examples of such sequences used in viral vectors include internal ribosome entry sites (IRES), furin cleavage sites, viral 2A peptide, or any combination thereof.

In certain embodiments, a vector is capable of delivering the transgene construct to a host cell (e.g., a hematopoietic progenitor cell or a human immune system cell). In specific embodiments, a vector is capable of delivering a transgene construct to human immune system cell, such as, for example, a CD4+ T cell, a CD8+ T cell, a CD4− CD8− double negative T cell, a γδ T cell, a natural killer cell, a dendritic cell, or any combination thereof. In further embodiments, a vector is capable of delivering a transgene construct to a naive T cell, a central memory T cell, an effector memory T cell, or any combination thereof. In some embodiments, a vector that encodes a polynucleotide or transgene construct of the present disclosure may further comprise a polynucleotide that encodes a nuclease that can be used to perform a chromosomal knockout in a host cell (e.g., a CRISPR-Cas endonuclease or another endonuclease as disclosed herein) or that can be used to to deliver a therapeutic transgene or portion thereof to a host cell in a gene therapy replacement or gene repair therapy. Alternatively, a nuclease used for a chromosomal knockout or a gene replacement or gene repair therapy can be delivered to a host cell independent of a vector that encodes a polynucleotide or transgene construct of this disclosure.

Uses

In still other aspects, the present disclosure provides methods for treating or for preventing a relapse of a hyperproliferative disorder characterized by expression of an HA-1 antigen in a subject, the method comprising administering to the subject a unit dose comprising an engineered immune cell of this disclosure (or a composition comprising an engineered immune cell), thereby treating the hyperproliferative disorder.

"Treat" or "treatment" or "ameliorate" refers to medical management of a disease, disorder, or condition of a subject (e.g., a human or non-human mammal, such as a primate, horse, cat, dog, goat, mouse, or rat). In general, an appropriate dose or treatment regimen comprising an engineered immune cell of the present disclosure, and optionally an adjuvant, is administered in an amount sufficient to elicit a therapeutic or prophylactic benefit. Therapeutic or prophylactic/preventive benefit includes improved clinical outcome; lessening or alleviation of symptoms associated with a disease; decreased occurrence of symptoms; improved quality of life; longer disease-free status; diminishment of extent of disease, stabilization of disease state; delay of disease progression; remission; survival; prolonged survival; or any combination thereof.

A "therapeutically effective amount" or "effective amount", as used herein, refers to an amount of engineered immune cells sufficient to result in a therapeutic effect, including improved clinical outcome; lessening or alleviation of symptoms associated with a disease; decreased occurrence of symptoms; improved quality of life; longer disease-free status; diminishment of extent of disease, stabilization of disease state; delay of disease progression; remission; survival; or prolonged survival in a statistically significant manner. When referring to an individual active ingredient or a cell expressing a single active ingredient, administered alone, a therapeutically effective amount refers to the effects of that ingredient or cell expressing that ingredient alone. When referring to a combination, a therapeutically effective amount refers to the combined amounts of active ingredients or combined adjunctive active ingredient with a cell expressing an active ingredient that results in a therapeutic effect, whether administered serially or simultaneously. A combination may also be a cell expressing more than one active ingredient.

The term "pharmaceutically acceptable excipient or carrier" or "physiologically acceptable excipient or carrier" refer to biologically compatible vehicles, e.g., physiological saline, which are described in greater detail herein, that are suitable for administration to a human or other non-human mammalian subject and generally recognized as safe or not causing a serious adverse event.

As used herein, "statistically significant" refers to a p value of 0.050 or less when calculated using the Students t-test and indicates that it is unlikely that a particular event or result being measured has arisen by chance.

The presently disclosed methods may be useful to, for example, treat or prevent a relapse of a hyperproliferative disorder characterized by expression of HA-1 antigen in a subject, wherein the HA-1$^H$ antigen is present in an HLA complex expressed by hyperproliferating cells in the subject.

Examples of hyperproliferative disorders characterized by HA-1$^H$:HLA complexes include hematological malignancies. In certain embodiments, the hematological malignancy comprises a leukemia (e.g., an acute leukemia or a chronic leukemia). In specific embodiments, the leukemia comprises acute myeloid leukemia (AML), acute lymphocytic leukemia (ALL), mixed phenotype acute leukemia (MPAL), chronic myeloid leukemia (CML), B cell prolymphocytic leukemia, hairy cell leukemia, or chronic lymphocytic leukemia (CLL). In certain embodiments, the hematological malignancy comprises a lymphoma. In certain embodiments, the lymphoma comprises Hodgkin's lymphoma (HL), non-Hodgkin's lymphoma (NHL), a central nervous system lymphoma, small lymphocytic lymphoma (SLL), CD37+ dendritic cell lymphoma, lymphoplasmacytic lymphoma, splenic marginal zone lymphoma, plasma cell myeloma, extraosseous plasmacytoma, extra-nodal marginal zone B-cell lymphoma of mucosa-associated (MALT) lymphoid tissue, nodal marginal zone B-cell lymphoma, follicular lymphoma, mantle cell lymphoma, diffuse large B-cell lymphoma, mediastinal (thymic) large B-cell lymphoma, precursor B-lymphoblastic lymphoma, immunoblastic large cell lymphoma, intravascular large B-cell lymphoma, primary effusion lymphoma, Burkitt's lymphoma/leukemia, B-cell proliferations of uncertain malignant potential, lymphomatoid granulomatosis, and post-transplant lymphoproliferative disorder. In certain embodiments, the hematological malignancy comprises a myelodysplastic disorder, such as, for example, refractory cytopenia with unilineage dysplasia (refractory anemia, refractory neutropenia, and refractory thrombocytopenia), refractory anemia with ring sideroblasts (RARS), refractory anemia with ring sideroblasts-thrombocytosis (RARS-t), refractory cytopenia with multinieage dysplasia (RCMD), refractory cytopenia with multinieage dysplasia and ring sideroblasts (RCMD-RS), refractory anemia with excess blasts (RAEB), myelodysplasia unclassifiable, and refractory cytopenia of childhood. In further embodiments, the hematological malignancy comprises a myeloma. Subjects that can be treated by the present invention are, in general, human and other primate subjects, such as monkeys and apes for veterinary medicine purposes. In any of the aforementioned embodiments, the subject may be a human subject. The subjects can be male or female and can be any suitable age, including infant, juvenile, adolescent, adult, and geriatric subjects. Cells according to the present disclosure may be administered in a manner appropriate to the disease, condition, or disorder to be treated as determined by persons skilled in the medical art. In any of the above embodiments, an engineered immune cell or unit dose as described herein is administered intravenously, intraperitoneally, intratumorally, into the bone marrow, into a lymph node, or into the cerebrospinal fluid so as to encounter target cells (e.g., leukemia cells). An appropriate dose, suitable duration, and frequency of administration of the compositions will be determined by such factors as a condition of the patient; size, type, and severity of the disease, condition, or disorder; the particular form of the active ingredient; and the method of administration.

The amount of cells in a composition or unit dose is at least one cell (for example, one engineered CD8$^+$ T cell subpopulation; one engineered CD4$^+$ T cell subpopulation) or is more typically greater than $10^2$ cells, for example, up to $10^6$, up to $10^7$, up to $10^8$ cells, up to $10^9$ cells, or more than $10^{10}$ cells. In certain embodiments, the cells are administered in a range from about 106 to about $10^{10}$ cells/m$^2$, preferably in a range of about $10^5$ to about $10^9$ cells/m$^2$. The number of cells will depend upon the ultimate use for which the composition is intended as well the type of cells included therein. For example, cells modified to contain a fusion protein specific for a particular antigen will comprise a cell population containing at least 30%, 35%, 40%, 45%, 50%, 55%, 60%, 65%, 70%, 75%, 80%, 85%, 90%, 95% or more of such cells. For uses provided herein, cells are generally in a volume of a liter or less, 500 mls or less, 250 mls or less, or 100 mls or less. In embodiments, the density of the desired cells is typically greater than 104 cells/ml and generally is greater than 107 cells/ml, generally $10^8$ cells/ml or greater. The cells may be administered as a single infusion or in multiple infusions over a range of time. A clinically relevant number of immune cells can be apportioned into multiple infusions that cumulatively equal or exceed $10^6$, $10^7$, $10^8$, $10^9$, $10^{10}$, or $10^{11}$ cells. In certain embodiments, a unit dose of the engineered immune cells can be co-administered with (e.g., simultaneously or contemporaneously) hematopoietic stem cells from an allogeneic donor (e.g., a donor that is HA1$^H$-negative, HLA-A2-negative, or both).

Also contemplated are pharmaceutical compositions (i.e., compositions) that engineered immune cells as disclosed herein and a pharmaceutically acceptable carrier, diluents, or excipient. Suitable excipients include water, saline, dextrose, glycerol, or the like and combinations thereof. In embodiments, compositions comprising fusion proteins or host cells as disclosed herein further comprise a suitable infusion media. Suitable infusion media can be any isotonic medium formulation, typically normal saline, Normosol R (Abbott) or Plasma-Lyte A (Baxter), 5% dextrose in water, Ringer's lactate can be utilized. An infusion medium can be supplemented with human serum albumin or other human serum components.

Pharmaceutical compositions may be administered in a manner appropriate to the disease or condition to be treated (or prevented) as determined by persons skilled in the medical art. An appropriate dose and a suitable duration and frequency of administration of the compositions will be determined by such factors as the health condition of the patient, size of the patient (i.e., weight, mass, or body area), the type and severity of the patient's condition, the particular form of the active ingredient, and the method of administration. In general, an appropriate dose and treatment regimen provide the composition(s) in an amount sufficient to provide therapeutic and/or prophylactic benefit (such as described herein, including an improved clinical outcome, such as more frequent complete or partial remissions, or longer disease-free and/or overall survival, or a lessening of symptom severity).

An effective amount of a pharmaceutical composition refers to an amount sufficient, at dosages and for periods of time needed, to achieve the desired clinical results or beneficial treatment, as described herein. An effective amount may be delivered in one or more administrations. If the administration is to a subject already known or confirmed to have a disease or disease-state, the term "therapeutic amount" may be used in reference to treatment, whereas "prophylactically effective amount" may be used to describe administrating an effective amount to a subject that is susceptible or at risk of developing a disease or disease-state (e.g., recurrence) as a preventative course.

The pharmaceutical compositions described herein may be presented in unit-dose or multi-dose containers, such as sealed ampoules or vials. Such containers may be frozen to preserve the stability of the formulation until infusion into the patient. In certain embodiments, a unit dose comprises an engineered immune cell as described herein at a dose of about $10^7$ cells/m$^2$ to about $10^{11}$ cells/m$^2$. The development of suitable dosing and treatment regimens for using the particular compositions described herein in a variety of treatment regimens, including e.g., parenteral or intravenous administration or formulation.

If the subject composition is administered parenterally, the composition may also include sterile aqueous or oleaginous solution or suspension. Suitable non-toxic parenterally acceptable diluents or solvents include water, Ringer's solution, isotonic salt solution, 1,3-butanediol, ethanol, propylene glycol or polythethylene glycols in mixtures with water. Aqueous solutions or suspensions may further comprise one or more buffering agents, such as sodium acetate, sodium citrate, sodium borate or sodium tartrate. Of course, any material used in preparing any dosage unit formulation should be pharmaceutically pure and substantially non-toxic in the amounts employed. In addition, the active compounds may be incorporated into sustained-release preparation and formulations. Dosage unit form, as used herein, refers to physically discrete units suited as unitary dosages for the subject to be treated; each unit may contain a predetermined quantity of engineered immune cells or active compound calculated to produce the desired effect in association with an appropriate pharmaceutical carrier.

In general, an appropriate dosage and treatment regimen provides the active molecules or cells in an amount sufficient to provide a benefit. Such a response can be monitored by establishing an improved clinical outcome (e.g., more frequent remissions, complete or partial, or longer disease-free survival) in treated subjects as compared to non-treated subjects. Increases in preexisting immune responses to a tumor protein generally correlate with an improved clinical outcome. Such immune responses may generally be evaluated using standard proliferation, cytotoxicity or cytokine assays, which are routine.

For prophylactic use, a dose should be sufficient to prevent, delay the onset of, or diminish the severity of a disease associated with disease or disorder. Prophylactic benefit of the immunogenic compositions administered according to the methods described herein can be determined by performing pre-clinical (including in vitro and in vivo animal studies) and clinical studies and analyzing data obtained therefrom by appropriate statistical, biological, and clinical methods and techniques, all of which can readily be practiced by a person skilled in the art.

As used herein, administration of a composition refers to delivering the same to a subject, regardless of the route or mode of delivery. Administration may be effected continuously or intermittently, and parenterally. Administration may be for treating a subject already confirmed as having a recognized condition, disease or disease state, or for treating a subject susceptible to or at risk of developing such a condition, disease or disease state. Co-administration with an adjunctive therapy may include simultaneous and/or sequential delivery of multiple agents in any order and on any dosing schedule (e.g., engineered immune cells with one or more cytokines; immunosuppressive therapy such as calcineurin inhibitors, corticosteroids, microtubule inhibitors, low dose of a mycophenolic acid prodrug, or any combination thereof).

In certain embodiments, a plurality of doses of an engineered immune cell described herein is administered to the subject, which may be administered at intervals between administrations of about two to about four weeks.

Treatment or prevention methods of this disclosure may be administered to a subject as part of a treatment course or regimen, which may comprise additional treatments prior to, or after, administration of the instantly disclosed unit doses, cells, or compositions. For example, in certain embodiments, a subject receiving a unit dose of the engineered immune cell is receiving or had previously received a hematopoietic cell transplant (HCT; including myeloablative and non-myeloablative HCT). In specific embodiments, the HCT comprises donor cells that are HA-1$^-$, HLA-A2$^-$, or both, and the subject receiving the HCT donor cells is HA-1$^+$/HLA-A2$^+$. In any of the foregoing embodiments, a hematopoietic cell used in an HCT may be a "universal donor" cell that is modified to reduce or eliminate expression of one or more endogenous genes that encode a polypeptide product selected from an HLA molecule or a TCR molecule (e.g., by a chromosomal gene knockout according to the methods described herein). Techniques and regimens for performing HCT are known in the art and can comprise transplantation of any suitable donor cell, such as a cell derived from umbilical cord blood, bone marrow, or peripheral blood, a hematopoietic stem cell, a mobilized stem cell, or a cell from amniotic fluid. Accordingly, in certain embodiments, an engineered immune cell of the present disclosure can be administered with or shortly after hematopoietic stem cells in a modified HCT therapy.

In further embodiments, the subject had previously received lymphodepleting chemotherapy prior to receiving the engineered immune cells or HCT. In certain embodiments, a lymphodepleting chemotherapy comprises a conditioning regimen comprising cyclophosphamide, fludarabine, anti-thymocyte globulin, or a combination thereof.

Methods according to this disclosure may further include administering one or more additional agents to treat the disease or disorder in a combination therapy. For example, in certain embodiments, a combination therapy comprises administering an engineered immune cell with (concurrently, simultaneously, or sequentially) an immune checkpoint inhibitor. In some embodiments, a combination therapy comprises administering an engineered immune cell with an agonist of a stimulatory immune checkpoint agent. In further embodiments, a combination therapy comprises administering an engineered immune cell with a secondary therapy, such as chemotherapeutic agent, a radiation therapy, a surgery, an antibody, or any combination thereof.

As used herein, the term "immune suppression agent" or "immunosuppression agent" refers to one or more cells, proteins, molecules, compounds or complexes providing inhibitory signals to assist in controlling or suppressing an immune response. For example, immune suppression agents include those molecules that partially or totally block immune stimulation; decrease, prevent or delay immune activation; or increase, activate, or up regulate immune suppression. Exemplary immunosuppression agents to target (e.g., with an immune checkpoint inhibitor) include PD-1, PD-L1, PD-L2, LAG3, CTLA4, B7-H3, B7-H4, CD244/ 2B4, HVEM, BTLA, CD160, TIM3, GALS, KIR, PVR1G (CD112R), PVRL2, adenosine, A2aR, immunosuppressive cytokines (e.g., IL-10, IL-4, IL-IRA, IL-35), IDO, arginase, VISTA, TIGIT, LAIR1, CEACAM-1, CEACAM-3, CEACAM-5, Treg cells, or any combination thereof.

An immune suppression agent inhibitor (also referred to as an immune checkpoint inhibitor) may be a compound, an antibody, an antibody fragment or fusion polypeptide (e.g., Fc fusion, such as CTLA4-Fc or LAG3-Fc), an antisense molecule, a ribozyme or RNAi molecule, or a low molecular weight organic molecule. In any of the embodiments disclosed herein, a method may comprise an engineered immune cell with one or more inhibitor of any one of the following immune suppression components, singly or in any combination.

In certain embodiments, an engineered immune cell is used in combination with a PD-1 inhibitor, for example a PD-1-specific antibody or binding fragment thereof, such as pidilizumab, nivolumab, pembrolizumab, MEDI0680 (formerly AMP-514), AMP-224, BMS-936558 or any combination thereof. In further embodiments, an engineered immune cell of the present disclosure (or an engineered host cell expressing the same) is used in combination with a PD-L1 specific antibody or binding fragment thereof, such as BMS-936559, durvalumab (MEDI4736), atezolizumab (RG7446), avelumab (MSB0010718C), MPDL3280A, or any combination thereof.

In certain embodiments, an engineered immune cell of the present disclosure is used in combination with a LAG3 inhibitor, such as LAG525, IMP321, IMP701, 9H12, BMS-986016, or any combination thereof.

In certain embodiments, an engineered immune cell is used in combination with an inhibitor of CTLA4. In particular embodiments, an engineered immune cell is used in combination with a CTLA4 specific antibody or binding fragment thereof, such as ipilimumab, tremelimumab, CTLA4-Ig fusion proteins (e.g., abatacept, belatacept), or any combination thereof.

In certain embodiments, an engineered immune cell is used in combination with a B7-H3 specific antibody or binding fragment thereof, such as enoblituzumab (MGA271), 376.96, or both. A B7-H4 antibody binding fragment may be a scFv or fusion protein thereof, as described in, for example, Dangaj et al., Cancer Res. 73:4820, 2013, as well as those described in U.S. Pat. No. 9,574,000 and PCT Patent Publication Nos. WO/201640724A1 and WO 2013/025779A1.

In certain embodiments, an engineered immune cell is used in combination with an inhibitor of CD244.

In certain embodiments, an engineered immune cell is used in combination with an inhibitor of BLTA, HVEM, CD160, or any combination thereof. Anti CD-160 antibodies are described in, for example, PCT Publication No. WO 2010/084158.

In certain embodiments, an engineered immune cell is used in combination with an inhibitor of TIM3.

In certain embodiments, an engineered immune cell is used in combination with an inhibitor of Gal9.

In certain embodiments, an engineered immune cell is used in combination with an inhibitor of adenosine signaling, such as a decoy adenosine receptor.

In certain embodiments, an engineered immune cell is used in combination with an inhibitor of A2aR.

In certain embodiments, an engineered immune cell is used in combination with an inhibitor of KIR, such as lirilumab (BMS-986015).

In certain embodiments, an engineered immune cell is used in combination with an inhibitor of an inhibitory cytokine (typically, a cytokine other than TGFβ) or Treg development or activity.

In certain embodiments, an engineered immune cell is used in combination with an IDO inhibitor, such as levo-1-methyl tryptophan, epacadostat (INCB024360; Liu et al., *Blood* 115:3520-30, 2010), ebselen (Terentis et al., *Biochem.* 49:591-600, 2010), indoximod, NLG919 (Mautino et al., American Association for Cancer Research 104th Annual Meeting 2013; Apr. 6-10, 2013), 1-methyl-tryptophan (1-MT)-tira-pazamine, or any combination thereof.

In certain embodiments, an engineered immune cell is used in combination with an arginase inhibitor, such as N(omega)-Nitro-L-arginine methyl ester (L-NAME), N-omega-hydroxy-nor-1-arginine (nor-NOHA), L-NOHA, 2(S)-amino-6-boronohexanoic acid (ABH), S-(2-boronoethyl)-L-cysteine (BEC), or any combination thereof.

In certain embodiments, an engineered immune cell is used in combination with an inhibitor of VISTA, such as CA-170 (Curis, Lexington, Mass.).

In certain embodiments, an engineered immune cell is used in combination with an inhibitor of TIGIT such as, for example, COM902 (Compugen, Toronto, Ontario Canada), an inhibitor of CD155, such as, for example, COM701 (Compugen), or both.

In certain embodiments, an engineered immune cell is used in combination with an inhibitor of PVRIG, PVRL2, or both. Anti-PVRIG antibodies are described in, for example, PCT Publication No. WO 2016/134333. Anti-PVRL2 antibodies are described in, for example, PCT Publication No. WO 2017/021526.

In certain embodiments, an engineered immune cell is used in combination with a LAIR1 inhibitor.

In certain embodiments, an engineered immune cell is used in combination with an inhibitor of CEACAM-1, CEACAM-3, CEACAM-5, or any combination thereof.

In certain embodiments, an engineered immune cell is used in combination with an agent that increases the activity (i.e., is an agonist) of a stimulatory immune checkpoint molecule. For example an engineered immune cell can be used in combination with a CD137 (4-1BB) agonist (such as, for example, urelumab), a CD134 (OX-40) agonist (such as, for example, MEDI6469, MEDI6383, or MEDI0562), lenalidomide, pomalidomide, a CD27 agonist (such as, for example, CDX-1127), a CD28 agonist (such as, for example, TGN1412, CD80, or CD86), a CD40 agonist (such as, for example, CP-870,893, rhuCD40L, or SGN-40), a CD122 agonist (such as, for example, IL-2) an agonist of GITR (such as, for example, humanized monoclonal antibodies described in PCT Patent Publication No. WO 2016/054638), an agonist of ICOS (CD278) (such as, for example, GSK3359609, mAb 88.2, JTX-2011, Icos 145-1, Icos 314-8, or any combination thereof). In any of the embodiments disclosed herein, a method may comprise administering an engineered immune cell with one or more agonist of a stimulatory immune checkpoint molecule, including any of the foregoing, singly or in any combination.

In certain embodiments, a combination therapy comprises an engineered immune cell and a secondary therapy comprising one or more of: an antibody or antigen binding-fragment thereof that is specific for a cancer antigen expressed by the non-inflamed solid tumor, a radiation treatment, a surgery, a chemotherapeutic agent, a cytokine, RNAi, or any combination thereof.

In certain embodiments, a combination therapy method comprises administering a fusion protein and further administering a radiation treatment or a surgery. Radiation therapy is well-known in the art and includes X-ray therapies, such as gamma-irradiation, and radiopharmaceutical therapies. Surgeries and surgical techniques appropriate to treating a given cancer in a subject are well-known to those of ordinary skill in the art.

In certain embodiments, a combination therapy method comprises administering an engineered immune cell and further administering a chemotherapeutic agent. A chemotherapeutic agent includes, but is not limited to, an inhibitor of chromatin function, a topoisomerase inhibitor, a microtubule inhibiting drug, a DNA damaging agent, an antimetabolite (such as folate antagonists, pyrimidine analogs, purine analogs, and sugar-modified analogs), a DNA synthesis inhibitor, a DNA interactive agent (such as an intercalating agent), and a DNA repair inhibitor. Illustrative chemotherapeutic agents include, without limitation, the following groups: anti-metabolites/anti-cancer agents, such as pyrimidine analogs (5-fluorouracil, floxuridine, capecitabine, gemcitabine and cytarabine) and purine analogs, folate antagonists and related inhibitors (mercaptopurine, thioguanine, pentostatin and 2-chlorodeoxyadenosine (cladribine)); antiproliferative/antimitotic agents including natural products such as vinca alkaloids (vinblastine, vincristine, and vinorelbine), microtubule disruptors such as taxane (paclitaxel, docetaxel), vincristin, vinblastin, nocodazole, epothilones and navelbine, epidipodophyllotoxins (etoposide, teniposide), DNA damaging agents (actinomycin, amsacrine, anthracyclines, bleomycin, busulfan, camptothecin, carboplatin, chlorambucil, cisplatin, cyclophosphamide, Cytoxan, dactinomycin, daunorubicin, doxorubicin, epirubicin, hexamethylmelamineoxaliplatin, iphosphamide, melphalan, merchlorehtamine, mitomycin, mitoxantrone, nitrosourea, plicamycin, procarbazine, taxol, taxotere, temozolamide, teniposide, triethylenethiophosphoramide and etoposide (VP 16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); anti-angiogenic compounds (TNP470, genistein) and growth factor inhibitors (vascular endothelial growth factor (VEGF) inhibitors, fibroblast growth factor (FGF) inhibitors); angiotensin receptor blocker; nitric oxide donors; anti-sense oligonucleotides; antibodies (trastuzumab, rituximab); chimeric antigen receptors; cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin, irinotecan (CPT-11) and mitoxantrone, topotecan, irinotecan), corticosteroids (cortisone, dexamethasone, hydrocortisone, methylpednisolone, prednisone, and prenisolone); growth factor signal transduction kinase inhibitors; mitochondrial dysfunction inducers, toxins such as Cholera toxin, ricin, *Pseudomonas exotoxin*, *Bordetella pertussis* adenylate cyclase toxin, or *diphtheria* toxin, and caspase activators; and chromatin disruptors.

Cytokines are increasingly used to manipulate host immune response towards anticancer activity. See, e.g., Floros & Tarhini, *Semin. Oncol.* 42(4):539-548, 2015. Cytokines useful for promoting immune anticancer or antitumor response include, for example, IFN-α, IL-2, IL-3, IL-4, IL-10, IL-12, IL-13, IL-15, IL-16, IL-17, IL-18, IL-21, IL-24, and GM-CSF, singly or in any combination with an engineered immune cell of this disclosure.

Also provided herein are methods for modulating an adoptive immunotherapy, wherein the methods comprise administering, to a subject who has previously received an engineered immune cell of the present disclosure that comprises a heterologous polynucleotide encoding a safety switch protein, a cognate compound of the safety switch protein in an amount effective to ablate in the subject the previously administered engineered immune cell.

As used herein, the term "adoptive immune therapy" or "adoptive immunotherapy" refers to administration of naturally occurring or genetically engineered, disease- or antigen-specific immune cells (e.g., T cells). Adoptive cellular immunotherapy may be autologous (immune cells are from the recipient), allogeneic (immune cells are from a donor of the same species) or syngeneic (immune cells are from a donor genetically identical to the recipient).

In certain embodiments, the safety switch protein comprises tEGFR and the cognate compound is cetuximab, or the safety switch protein comprises iCasp9 and the cognate compound is AP1903 (e.g., dimerized AP1903), or the safety switch protein comprises a RQR polypeptide and the cognate compound is rituximab, or the safety switch protein comprises a myc binding domain and the cognate compound is an antibody specific for the myc binding domain.

In still further aspects, methods are provided for manufacturing a composition, or unit dose of the present disclosure. In certain embodiments, the methods comprise combining (i) an aliquot of a host cell transduced with a vector of the present disclosure with (ii) a pharmaceutically acceptable carrier. In certain embodiments, vectors of the present disclosure are used to transfect/transduce a host cell (e.g., a T cell) for use in adoptive transfer therapy (e.g., targeting a cancer antigen).

In some embodiments, the methods further comprise, prior to the aliquotting, culturing the transduced host cell and selecting the transduced cell as having incorporated (i.e., expressing) the vector. In further embodiments, the methods comprise, following the culturing and selection and prior to the aliquotting, expanding the transduced host cell. In any of the embodiments of the instant methods, the manufactured composition or unit dose may be frozen for later use. Any appropriate host cell can be used for manufacturing a composition or unit dose according to the instant methods, including, for example, a hematopoietic stem cell, a T cell, a primary T cell, a T cell line, a NK cell, or a NK-T cell. In specific embodiments, the methods comprise a host cell which is a $CD4^+$ T cell or a $CD8^+$ T cell.

EXAMPLES

Example 1

Isolation and Cloning of HA-$1^H$—Specific TCRs

HA-$1^H$-specific $CD8^+$ T cell clones were isolated using in vitro methods previously described (Bleakley et al., *Blood* 115:4923-4933, 2010 (FIG. 1). Specifically, $CD8^+$ T cells were isolated from HLA-A2+ donor (2 donors) peripheral blood mononuclear cells (PBMC), using a $CD8^+$ T cell isolation kit and anti-CD45RO immunomagnetic beads (Miltenyi Biotec). Autologous dendritic cells (DCs) were pulsed with 1 μg/mL HA-$1^H$ peptide (VLHDDLLEA) for 3-6 hours at 37° C. Purified $CD8^+$ $T_N$ were combined in complete T lymphocyte (CTL) medium with peptide-pulsed DCs at a $T_N$ to DC ratio of 30:1, and co-cultured in 96-well plates at 6×10⁴ T cells/well, supplemented with 10 ng/mL IL-12 from initiation and 10 ng/mL IL-15 from day 7. On day 11-13, cells were evaluated for HA-1$^H$-specific cytotoxicity in split-well micro-chromium release assays (CRA; μCRA). T cell lines that lysed T2 cells pulsed with 1 ug/mL HA-1$^H$ peptide (>20% lysis and >5 fold more lysis of peptide-pulsed versus unpulsed targets) were subsequently cloned by limiting dilution using anti-CD3 monoclonal antibody (mAb), interleukin-2 (IL-2) and feeder cells.

Figure 2A:
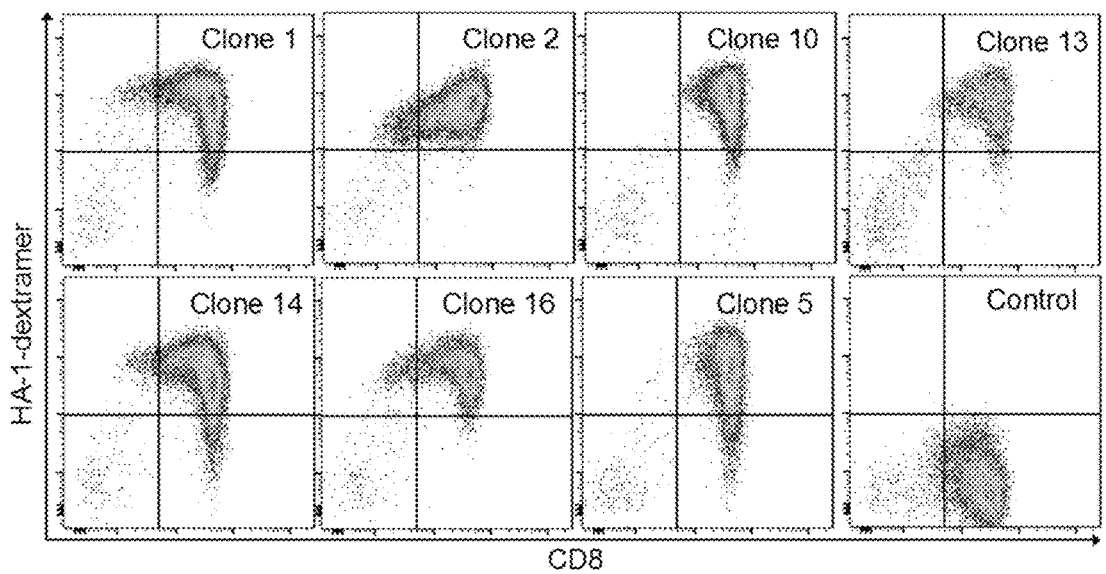
FIGS. 2A-2C show characterization of isolated cytotoxic T cell clones that were obtained using the method shown in FIG. 1. (A) HLA-A2/HA-1$^H$ multimer and CD8$^+$ monoclonal antibody staining of seven (7) representative HA-1$^H$ specific clones (1, 2, 10, 13, 4, 16, and 5) and a control clone specific for another tumor antigen. (B) Data from a chromium release assay in which the seven HA-1$^H$-specific clones were tested for killing HA-1 peptide-pulsed target cells. (C) Data from cytotoxicity assays in which the HA-1$^H$-specific CTL clones were incubated with peptide-pulsed T2 cells, HA-1$^{H+}$ AML cell line THP-1, HA-1$^{H+}$ primary AML, or HA-1$^-$ AML.

Clones were screened by μCRA on day 11-13. T cell clones from wells showing specific cytotoxicity, using the above criteria, were expanded using anti-CD3 mAb, IL-2 and feeder cells, by the Rapid Expansion Protocol (REP). The specificity of expanded clones was evaluated by CRA, HA-1/HLA-A2 multimer staining, and intracellular cytokine staining (ICC). The HA-1$^H$ specificity of the CTL clones was verified with HA-1$^H$/HLA A2 multimers. In particular, HLA-A2/HA-1$^H$ multimer and CD8$^+$ monoclonal antibody (mAb) were used to stain HA-1 specific clones (clones 1, 2, 10, 13, 14, 16, and 5) and a control clone specific for another tumor antigen (FIG. 2A).

Figure 2B:
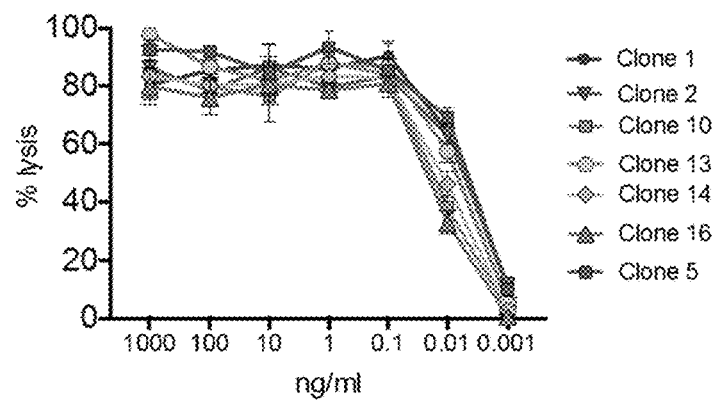
Figure 2C:
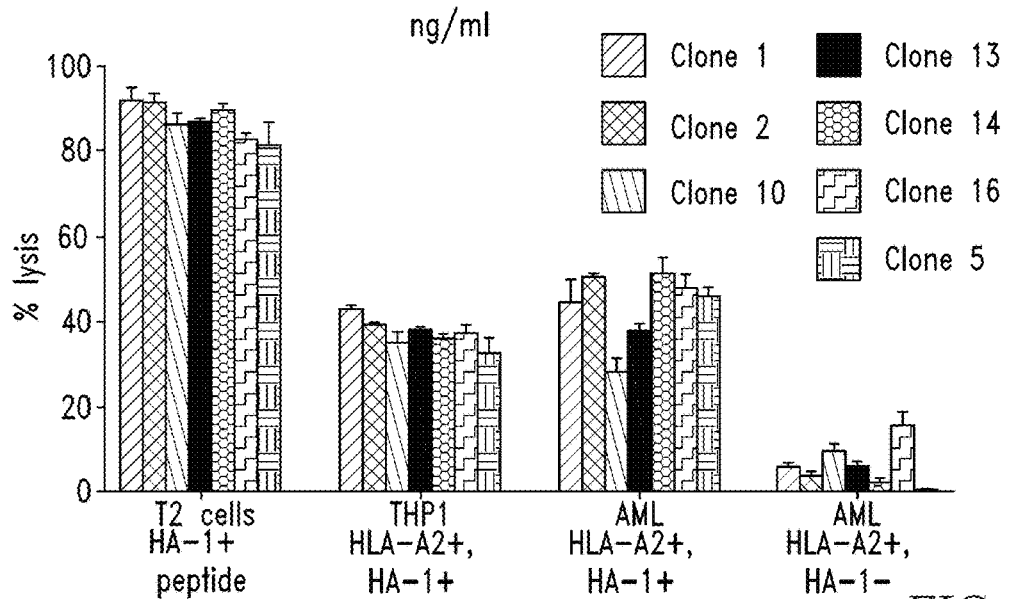
Figure 3:
FIG. 3 depicts a representative HA-1$^H$ TCR-encoding lentiviral construct of the present disclosure.

In addition, a chromium release assay (CRA) was used to test 7 of the HA-1-specific CTL clones (1, 2, 10, 13, 14, 16 and 5) for killing of HA-1$^H$ peptide-pulsed targets. The T cell clones recognized HA-1$^H$ peptide (VL HDDLLEA)-pulsed target cells at very low peptide concentrations and half-maximal lysis is seen at a peptide concentration of 10 pM. (FIG. 2B) (ICC data not shown). Cytotoxicity of the the isolated clones against cells with or without endogenous HA-1$^H$ expression was also examined. The assays show 7 HA-1$^H$-specific CTL clones (TCR1, TCR2, TCR10, TCR13, TCR14, TCR16 and TCR5) lysing HA-1$^{H+}$ acute myeloid leukemia (AML) cell line (THP-1) and HA-1$^{H+}$ primary AML but not HA-1$^{H-}$ AML (FIG. 2C).

Next, the isolated HA-1$^H$ TCRs were cloned. The TCR V$_\beta$ and V$_\alpha$ genes of the 8 CTL were sequenced and 6 distinct TCRs were identified (TCR1 and TCR13 were found to be identical, as were TCR2 and TCR14). The genes (and specific alleles) encoding the 6 TCRs, as well as the V$_\beta$ CDR3 amino acid sequences of the TCRs, are shown in Table 1:

TABLE 1

Genes and βCDR3 sequences of isolated TCRs

| | Alpha | | Beta | | | |
|---|---|---|---|---|---|---|
| | V gene | J gene | V gene | D gene | J gene | CDR3 (aa) |
| TCR 1 | TRAV17*01 F | TRAJ28*01 F | TRVB7-9*03 | TRBD1*01 | TRBJ21*01 | CASSSTGGHNEQFF |
| TCR 13 | TRAV17*01 F | TRAJ28*01 F | TRVB7-9*03 | TRBD1*01 | TRBJ21*01 | CASSSTGGHNEQFF |
| TCR 2 | TRAV21*02 F | TRAJ40*01 F | TRVB7-9*03 | TRBD1*01 | TRBJ1-4*01 | CASSLVKGEKLFF |
| TCR 14 | TRAV21*02 F | TRAJ40*01 F | TRVB7-9*03 | TRBD1*01 | TRBJ1-4*01 | CASSLVKGEKLFF |
| TCR 10 | TRAV10*01F | TRAG45*01 F | TRVB7-9*03 | TRBD2*01 | TRBJ27*01 | CASSMLTNYEQYF |
| TCR 16 | TRAV21*01 or *02 | TRAF20*01 F | TRVB7-9*03 | TRBD1*01 F | TRBJ21*01 | CASSLVVGNEQFF |
| TCR 5 | TRAV17 | TRAJ29 | TRVB7-9*03 | TRBD1/2 | TRBJ2-7 | CASSLTTLDEQY |
| TCR 24 | TRAV8-3 | TRAJ27 | TRBV15 | TRBD1*01 | TRBJ2-5 | ATSKTRIAQETQYF |

A seventh TCR, "TCR29" was also identified and sequenced. After sequencing, the genes encoding the HA-1$^H$ TCRs (except for TCR24, which had poor function in transduced CD8$^+$ T cells) were codon optimized to maximize expression and cysteine modifications were introduced and to reduce the risk of mispairing with endogenous TCR chains, as described below. The nucleotide sequences of the CTL clone TCRβ and TCRα genes after codon optimization and cysteine modification are provided in SEQ ID NOs 39-48 and 51-52.

RNA was extracted from each HA-1$^H$-specific T cell clone. 5'-first-strand cDNA amplification and Rapid Amplification of cDNA Ends (RACE) PCR were performed to identify full-length TCR regions, using a SMARTer RACE cDNA Amplification Kit (Clontech Laboratories). cDNA was synthesized from RNA using 5' CDS Primer A, SMARTer IIA oligo and SMARTScribe Reverse Transcriptase. Subsequently, the cDNA was used to perform a RACE PCR reaction, using Phusion® High Fidelity DNA polymerase, and Gene-Specific Primers for the TCR alpha (α)-(5'-GGTGAATAGGCAGACAGACTT-3') (SEQ ID NO:93) or TCR beta (β)-chain (GTGGCCAGGCACACCA-GTGT) (SEQ ID NO:94). The RACE PCR product was purified and sequenced to identify the TCR α- and β-chains. IMGT/V-QUEST was used to define the TCR variable (V), diversity (D) and joining (J) regions.

Complementary cysteine residues at positions 48 (Thr to Cys) and 57 (Ser to Cys) were incorporated into the constant domains of the TCR α and β genes to increase exogenous TCR pairing and decrease mispairing with the endogenous TCR. To ensure coordinated gene expression, the TCR chains were separated by 2A elements from the porcine teschovirus (P2A). The transgenes were codon-optimized to enhance expression and synthesized by GeneArt (Life Technologies), and were cloned into the pRRLSIN.cPPT.M-

SCV.WPRE LV vector by restriction digestion and ligation. The amino acid sequences of the encoded TCR constructs are provided in SEQ ID NOS: 53-57.

Example 2

Heterologous Expression and Activity of HA-1$^H$—Specific TCRs

Next, codon-optimized and cysteine modified TCRs were tested for expression and activity.

Figure 4:
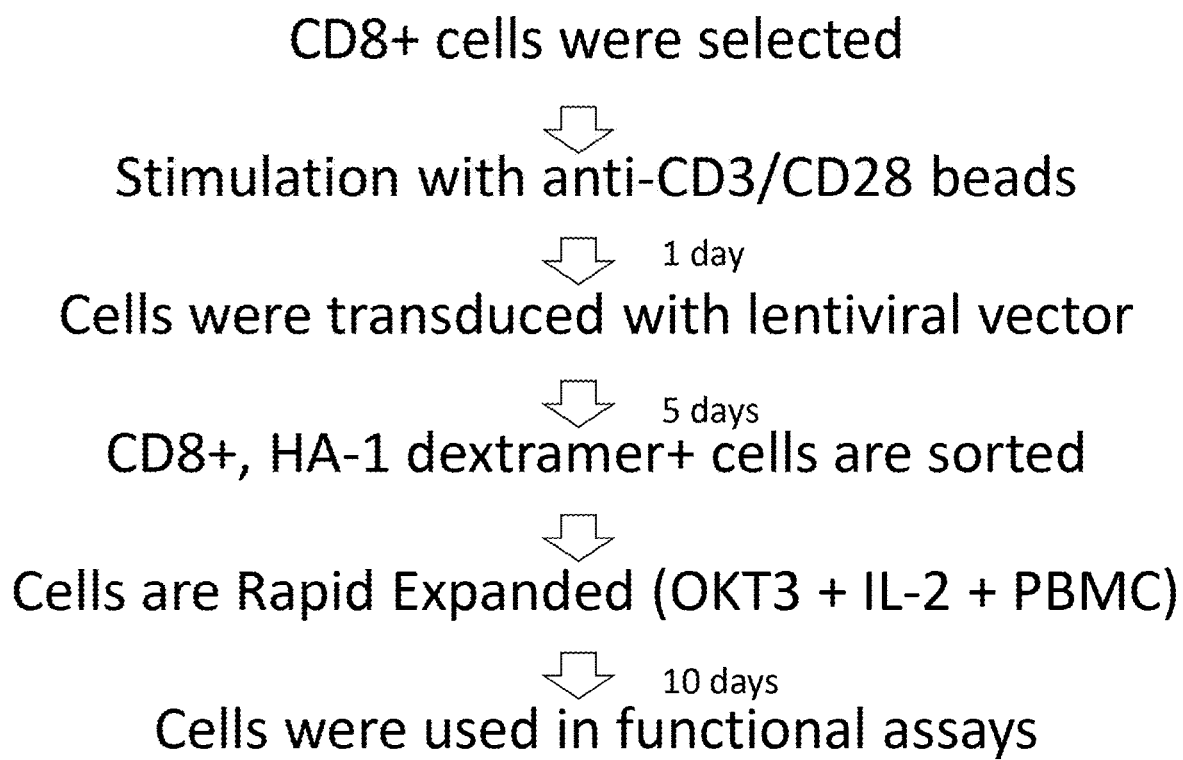
FIG. 4 shows a procedure for evaluating T cells transduced to express HA-1 TCRs.
Figure 5A:
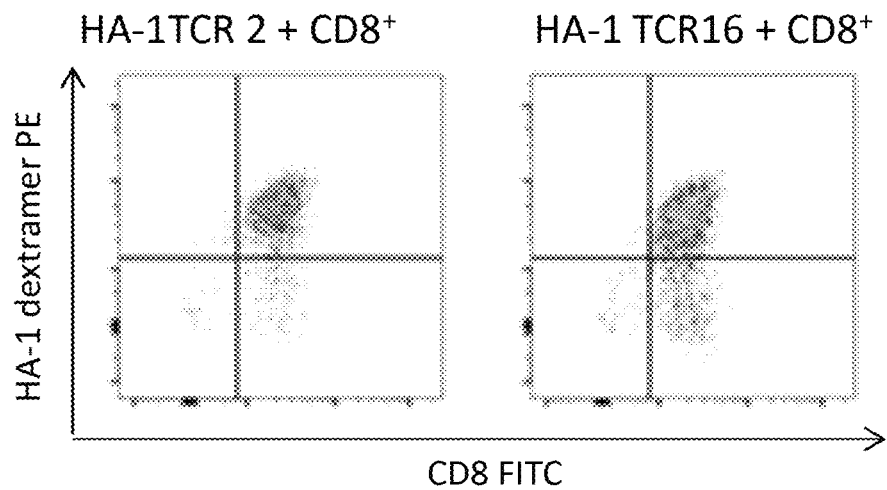
FIGS. 5A-5C show expression and activity of HA-1$^H$-transduced CD8$^+$ T cells. (A) Flow cytometry data showing HA-1$^H$ dextramer binding and CD8 expression of T cells transduced with TCR2 or TCR16. (B) Killing activity of CD8$^+$ T cells transduced with TCR2 or TCR16, as well as of the corresponding 'parental clones', i.e., the T cell clones from which TCR2 and TCR16 were isolated and of a control clone specific for a control a different antigen (SMCY). Left, lysis of HA-1$^H$-pulsed T2 cells. Right, T2 cells pulsed with irrelevant SMCY peptide. (C) Specific lysis of T2 cells pulsed with the indicated amount of HA-1$^H$ peptide (x-axis) by HA-1$^H$ TCR2 (dashed line with circles), HA-1$^H$ TCR16 (dashed line with squares), parental TCR2 clone (solid line with circles), parental TCR16 clone (solid line with squares), and a heterologous or parent clone specific for SMCY peptide (lower two lines on graph).
Figure 5B:
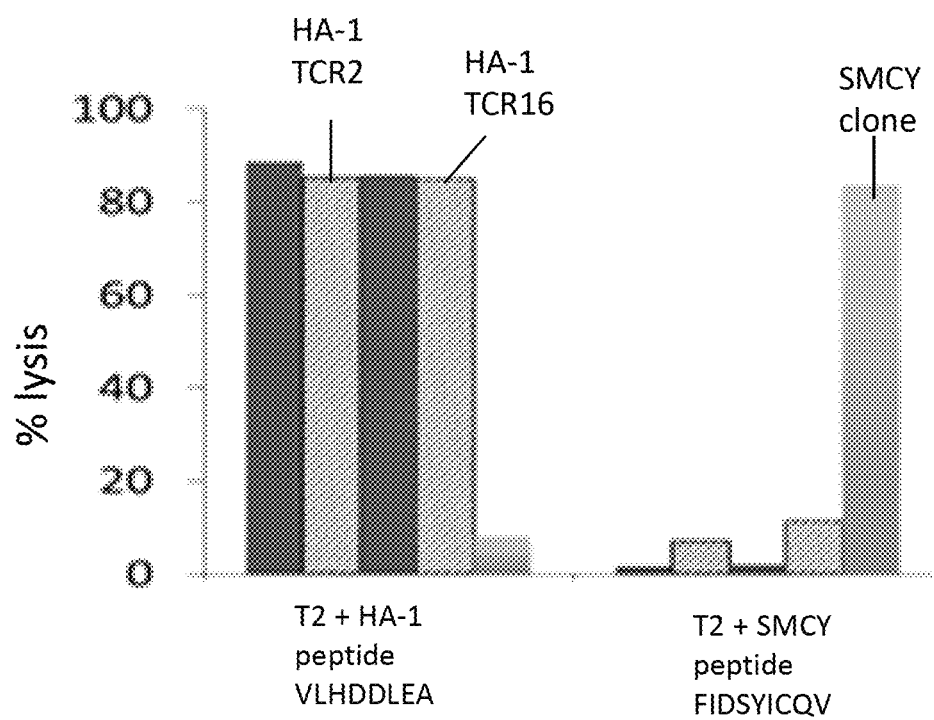
Figure 5C:
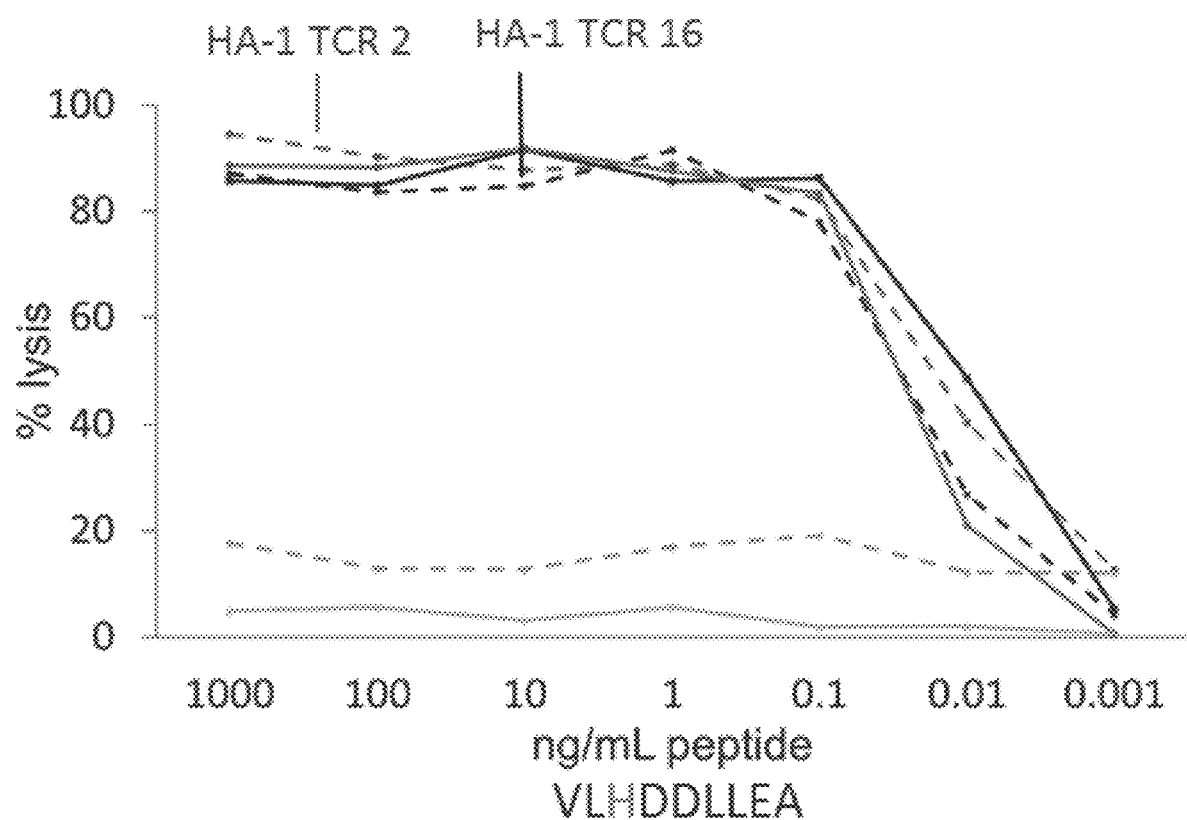
Figure 6E:
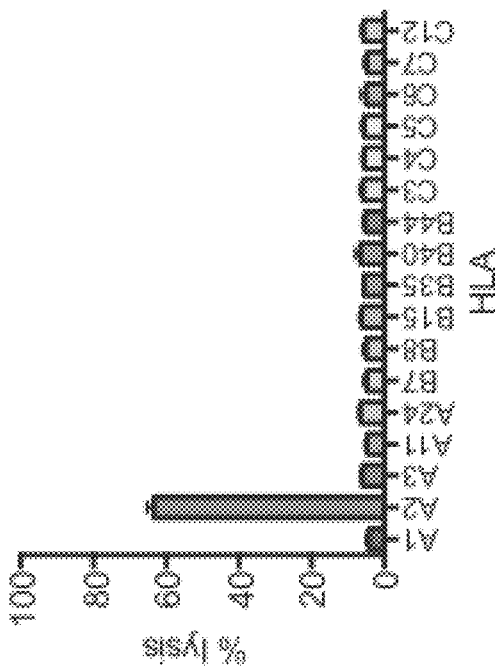
Figure 6D:
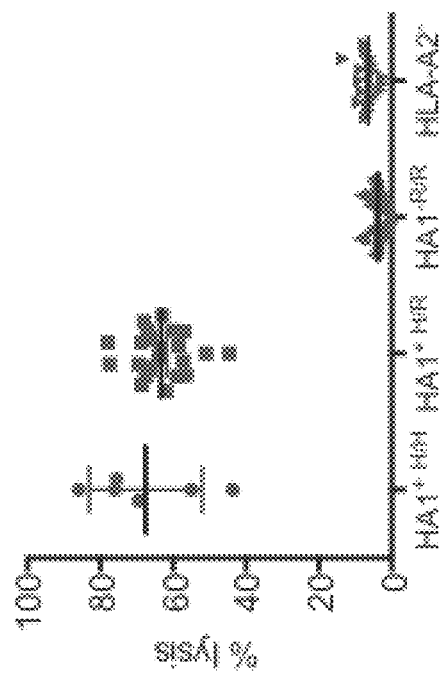
Figure 7:
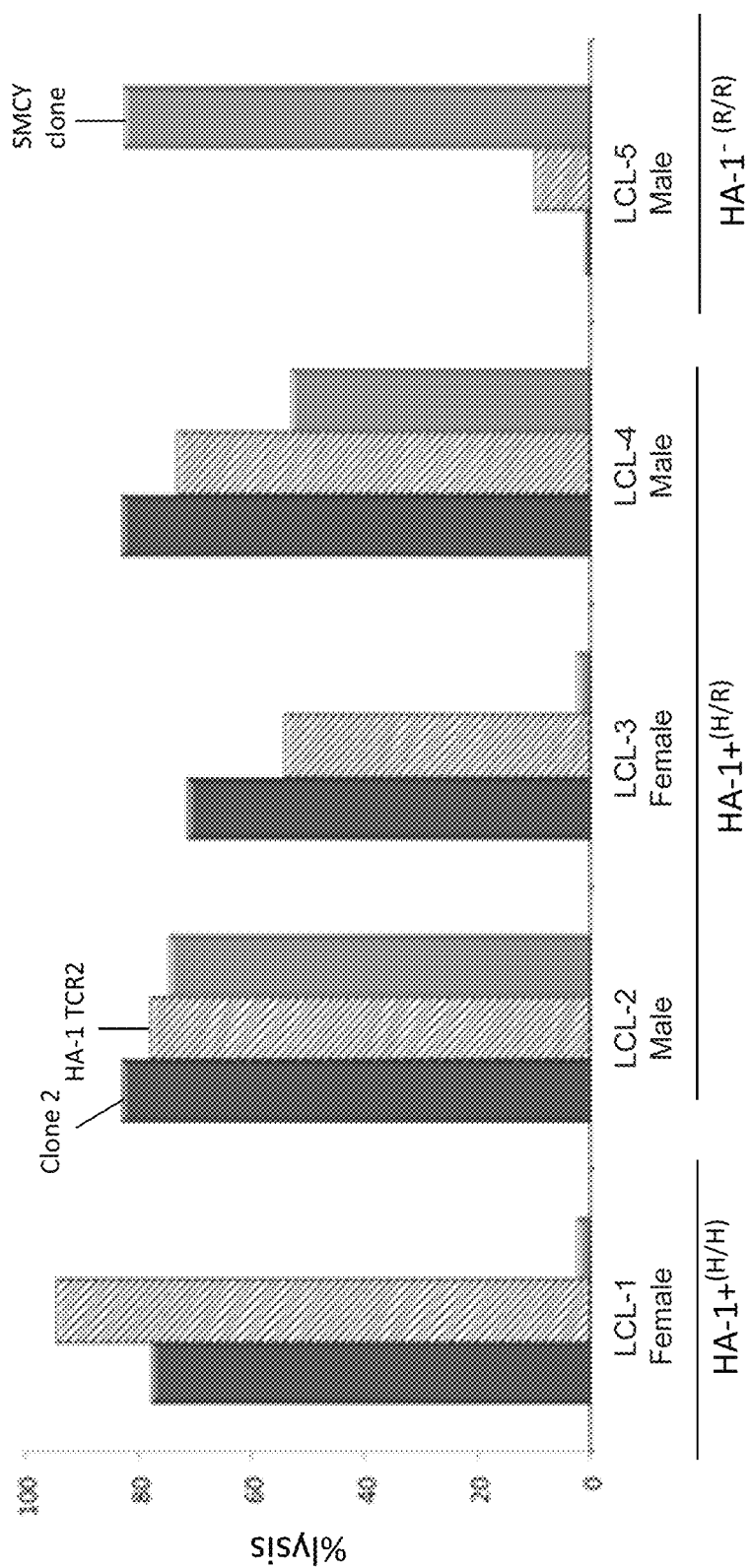
FIG. 7 provides data from cytotoxicity experiments in which target cells that endogenously express HA-1 (HA-1$^{H+}$ LCL (H/H or H/R) and HA-1$^{H-}$LCL (R/R) by were incubated with TCR2 transduced cells or with 'parental' clone 2 cells. Also shown is a control clone specific for a Y chromosome-associated minor H antigen (FIDSYICQV) (SEQ IS NO: 128).
Figure 8A:
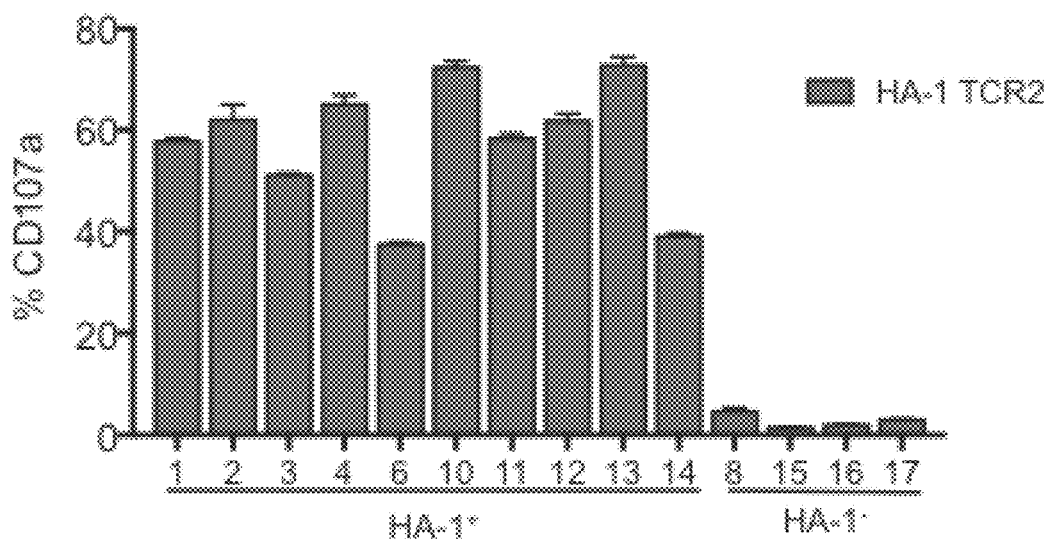
FIGS. 8A-8E show specific killing of HA-1$^+$ leukemia cells by HA-1$^H$-TCR2-transduced CD8$^+$ T cells. (A) HA-1$^H$-specific expression of CD107a on HA-1$^H$-TCR2 transduced CD8$^+$ T cells showing degranulation after 5 h co-culture (1:1) with a panel of primary AML samples. (B-E) CRA showing lysis of leukemia and lymphoma targets by HA-1 TCR-transduced CD8$^+$ T cells; (B) Lysis of primary HA-1$^{H+}$ AML or HA-1$^-$ AML by HA-1$^H$TCR-transduced CD8$^+$ T cells (dark grey bars) and HA-1$^H$-specific T cell clone 2 (light grey bars); (C) HLA-A2$^+$/HA-1$^{H+}$ primary AML (AML1) at various E:T ratios; (D) B-ALL lines (1) BALL-1, (2) RS4;11, T-ALL lines (1) MOLT4, (2) CEM (3) RPMI-8402 (4) HSB-2 and AML line NB-4; (E) T cell lymphoma (SUP-M2 HLA-A2$^+$, HA-1$^+$; SU-DHL-1 HLA-A2$^-$ HA-1$^-$) cell lines. In (D) HLA-A2$^-$ and/or HA-1$^{H-}$ (WT) cell lines were transduced (TD) with LV encoding *HLA-A2 or **HLA-A2 and HA-1$^H$minigene if the WT was HLA-A2- or had a HA-1$^H$-genotype. An E:T ratio of 20:1 was used, unless otherwise specified.
Figure 8B:
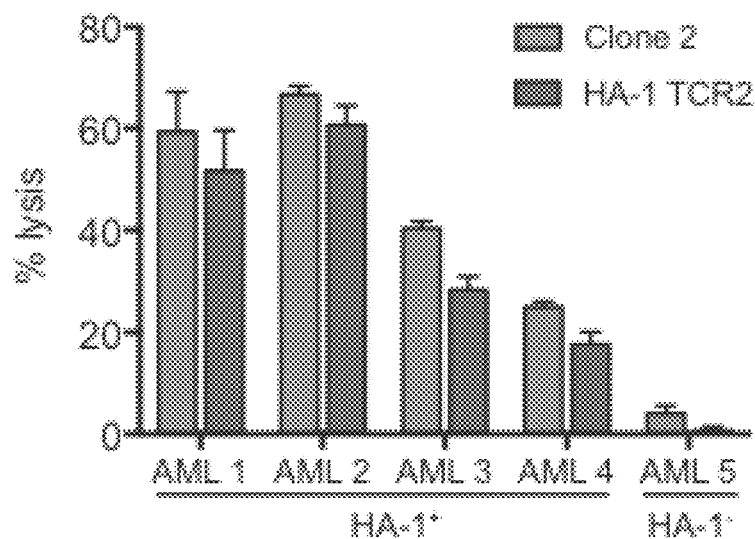
Figure 8C:
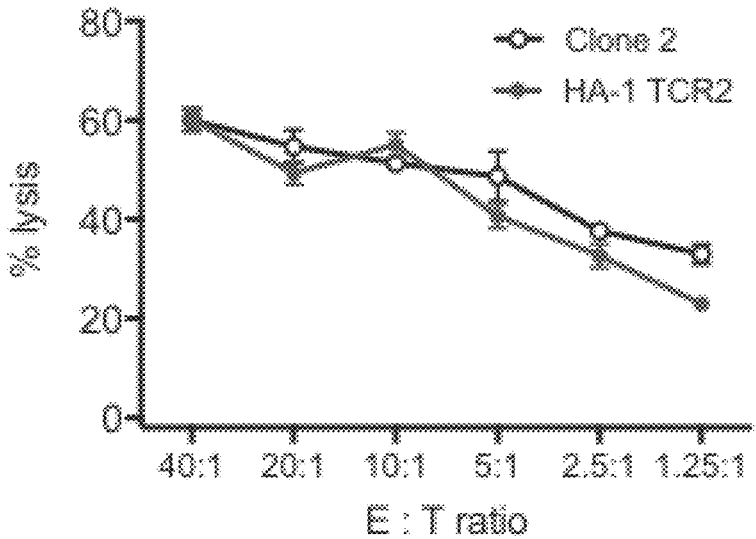
Figures 8D, 8E:
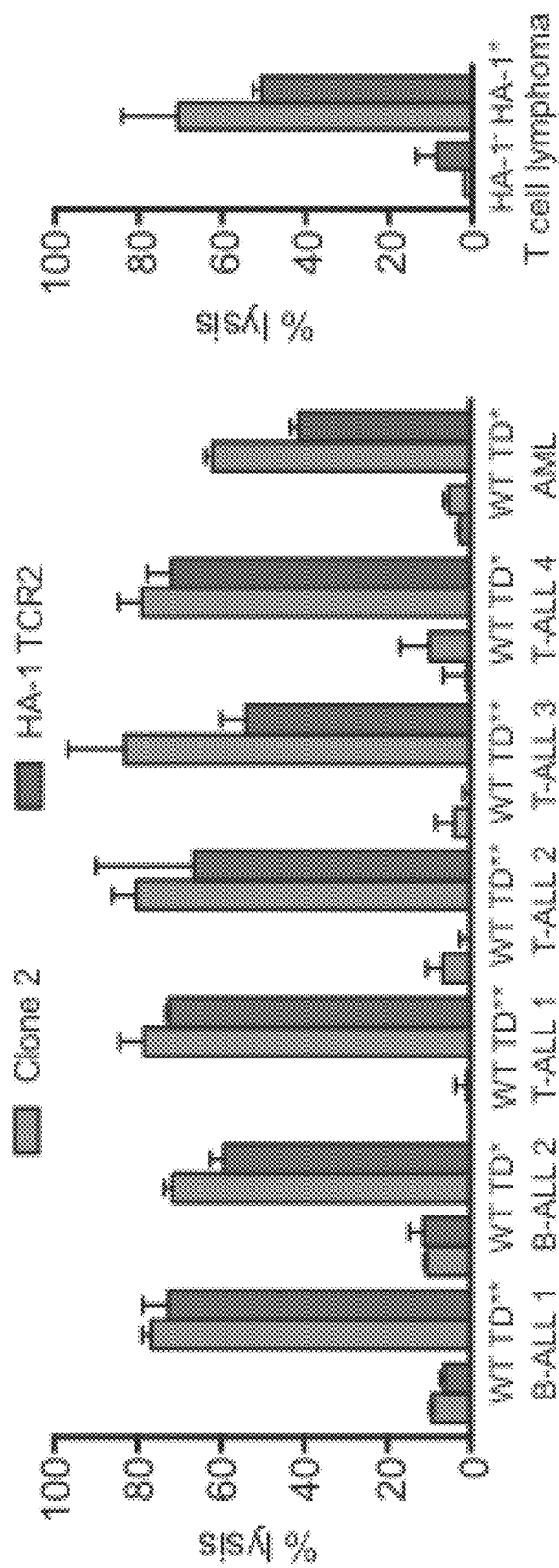
Figure 9A:
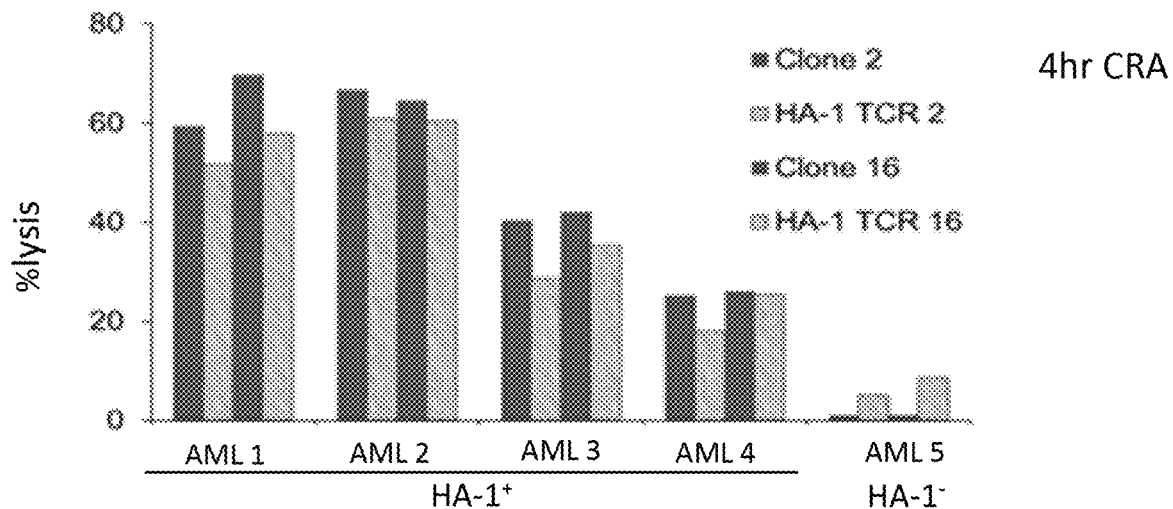
FIGS. 9A and 9B show cytotoxicity of T cells transduced with TCR2 or TCR16 (as well as of the corresponding parental clones) against HA-1$^{H+}$ or HA-1$^{H-}$ primary leukemia cells. 9A: specific lysis (4 h CRA) of the indicated cell lines. 9B: specific lysis of target cells at the indicated effector:target ratios.
Figure 9B:
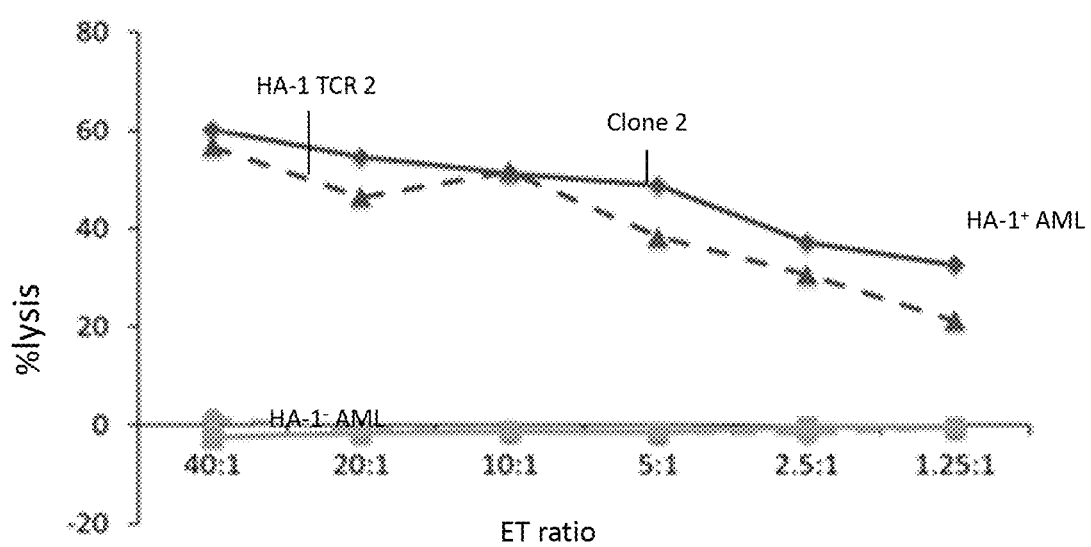
Figure 10:
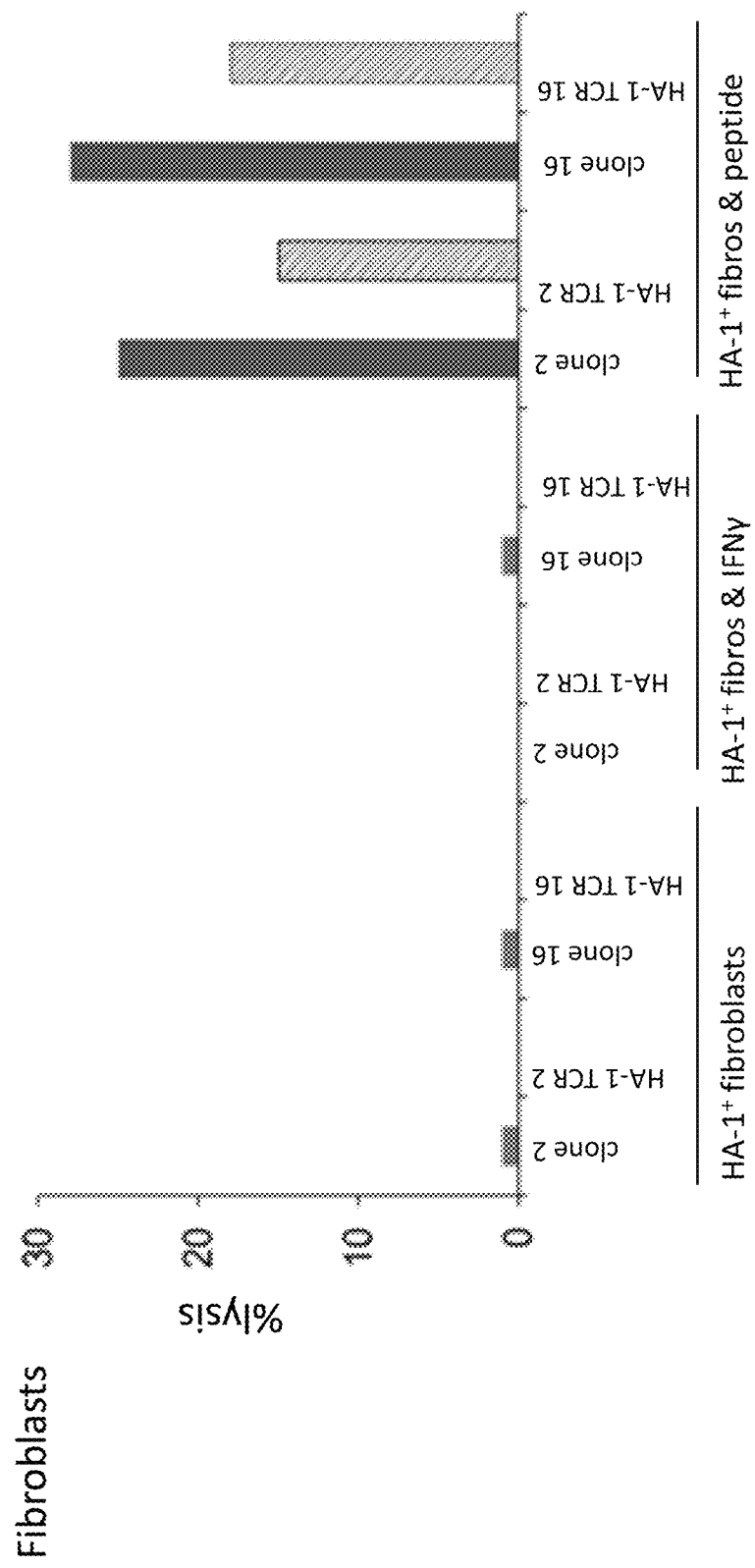
FIG. 10 shows data from a cytotoxicity assay in which TCR2- and TCR16-transduced cells (and parental clones) were incubated with HA-1$^H$ genotypically positive dermal fibroblasts, with or without exposure of the fibroblasts to interferon gamma (IFNγ).

Lentiviral (LV) vectors were used to transduce primary T cells to deliver a polynucleotide encoding the engineered HA-1$^H$specific TCR constructs. The transduced T cells were sorted, expanded, and tested for HA-1$^H$specificity (FIG. 4). Five of six HA-1$^H$ TCR LVs efficiently transduced primary CD8$^+$ and CD4$^+$ T cells (FIGS. 5A and 6A), and conferred specific recognition of HLA-A2$^+$ cells pulsed with low amounts of HA-1$^H$ peptide. TCR2 and TCR16 showed the strongest cytotoxic activity and were selected for further experiments. T cells transduced with these TCRs killed HA-1$^H$-pulsed cells (FIGS. 5B, 5C, 6B, and 35), cell lines with endogenous HA-1$^H$ expression (FIGS. 6C-6E and FIG. 7) and primary leukemia cells with endogenous HA-1$^H$ (FIGS. 8A-8E, FIG. 9), but these engineered cells were not activated by, and did not kill, HA-1$^H$-negative cells (FIG. 7), primary leukemia cells (FIGS. 8A, 8B and 9) or fibroblasts (FIG. 10). In addition, CD8$^+$ and CD4+ HA-1$^H$ TCR T cells secreted IFNγ and IL-2 in response to HA-1$^H$ peptide stimulation (data not shown). HA-1$^H$ TCR CD4$^+$ cells killed target cells pulsed with high peptide concentrations, although LV transduction with the HA-1$^H$ TCR alone did not make CD4$^+$ T cells responsive to primary leukemia cells with native levels of antigen (data not shown).

In sum, these data demonstrate that T cells effectively express transduced HA-1$^H$ TCRs and have antigen-specific killing activity against lymphoid cells.

Example 3

CD8 Co-Receptor Function in CD4$^+$HA-1$^H$ TCR Cells

Inclusion of CD4$^+$ T cells in an immunotherapy cell product can provide antigen-induced IL-2 secretion and augment persistence and function of transferred cytotoxic CD8$^+$ T cells (see, e.g., Kennedy et al., *Immunol. Rev.* 222:129 (2008); Nakanishi et al., *Nature* 462(7272): 510 (2009)). However, optimal function of many class I restricted TCR in CD4$^+$ T cells requires the transfer of a CD8 co-receptor to enhance sensitivity of the TCR to class I HLA peptide complexes. CD4 co-receptors differ in structure to CD8 and cannot effectively substitute for CD8 co-receptors (see, e.g., Stone & Kranz, *Front. Immunol.* 4:244 (2013); see also Cole et al., *Immunology* 137(2):139 (2012). Relatively high HA-1$^H$ peptide concentrations were required to induce cytolytic activity in CD4$^+$ T cells transduced with an HA-1$^H$ TCR alone, and HA-1 TCR CD4$^+$ T cells did not recognize cell lines or leukemia, implying CD8 co-receptor dependency of the TCR (data not shown).

Various options for including a CD8 co-receptor in the transgene construct were explored. CD8 co-receptors exist on the surface of human conventional αβ TCR T cells, typically as dimers of CD8α- and β-chains, and there are five β-chain variants with different intracytoplasmic tail sequences (βM1-5) (see, e.g., Thakral et al., *J. Immunol.* 180(11):7431 (2008); see also Thakral et al., *PLoS One* 8(3):e59374 (2013)). The amino acid sequences of the CD8 co-receptor chains are provided in SEQ ID NOs: 48-53.

Figure 11A:
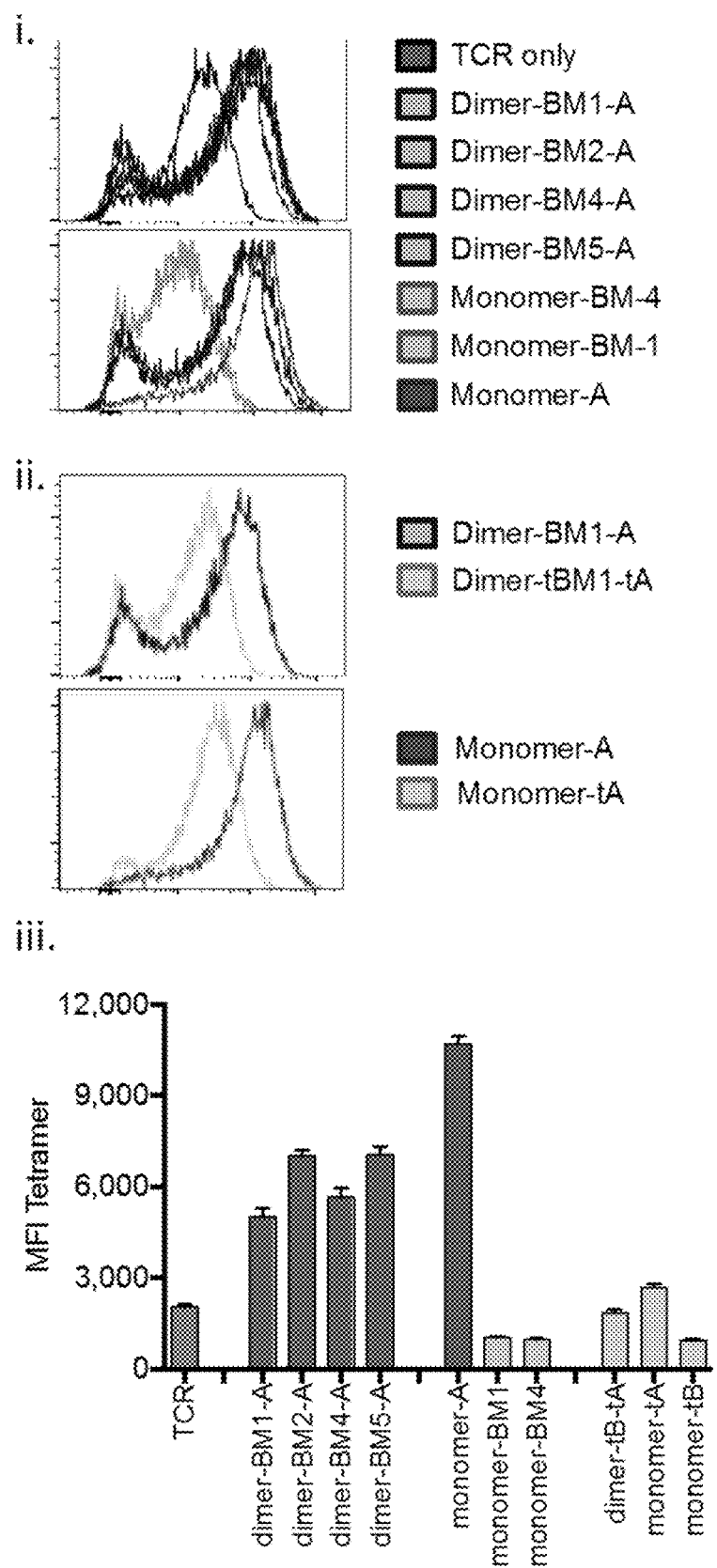
FIGS. 11A-11C show characterization of CD4$^+$ T cells transduced with the HA-1$^H$ TCR2 and CD8 co-receptor variants. (A) (i, ii) Mean fluorescence intensity (MFI) of HA-1$^H$/HLA-A2 multimer staining of CD4$^+$ T cells transduced with CD8α and/or βM1-M5 chains as indicated. (iii) MFI of the various CD8 co-receptor constructs is summarized in the graph. (B) CRA showing lysis of T2 pulsed with HA-1$^H$ peptide at various concentrations by HA-1$^H$-specific CD8$^+$T cells (solid circles), CD4+ T cells transduced with the CD8α and β chains (squares, diamonds, downward triangles), CD8α chains alone (upward triangles), or HA-1$^H$ TCR only (open circle). (C) Proliferation assay showing dilution of the carboxyfluorescein (CFSE) dye with cell division in CD4$^+$ T cells transduced with (top to bottom) the HA-1$^H$ TCR alone, with CD8α chain, CD8α and βM1 chain, or CD8α and βM4 chain, in response to stimulation with HLA-A2$^+$HA-1$^{H+}$ LCL, HA-1$^{H-}$ LCL, or media only.
Figure 11B:
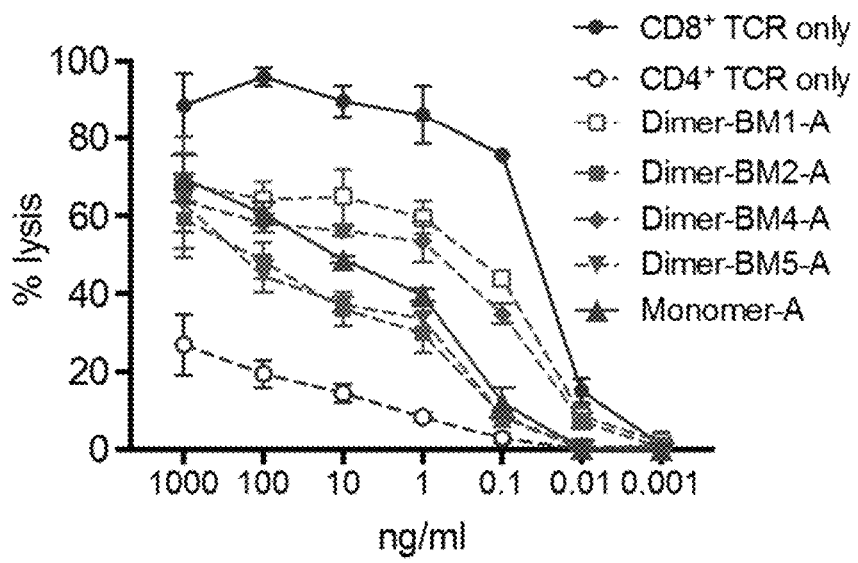
Figure 11C:
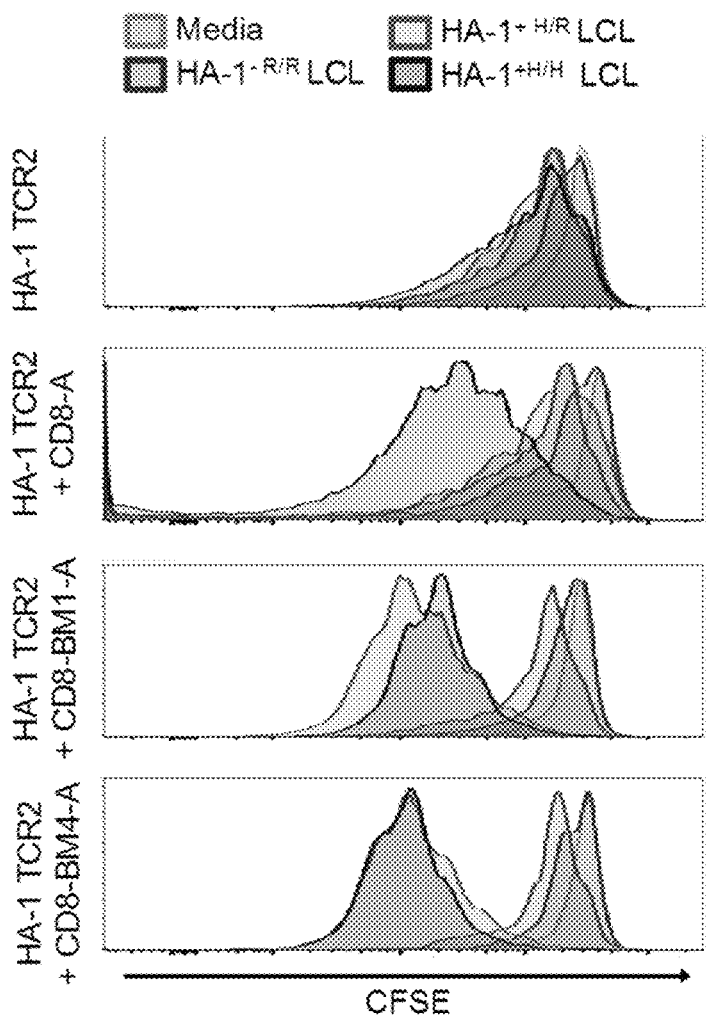
Figure 12A:
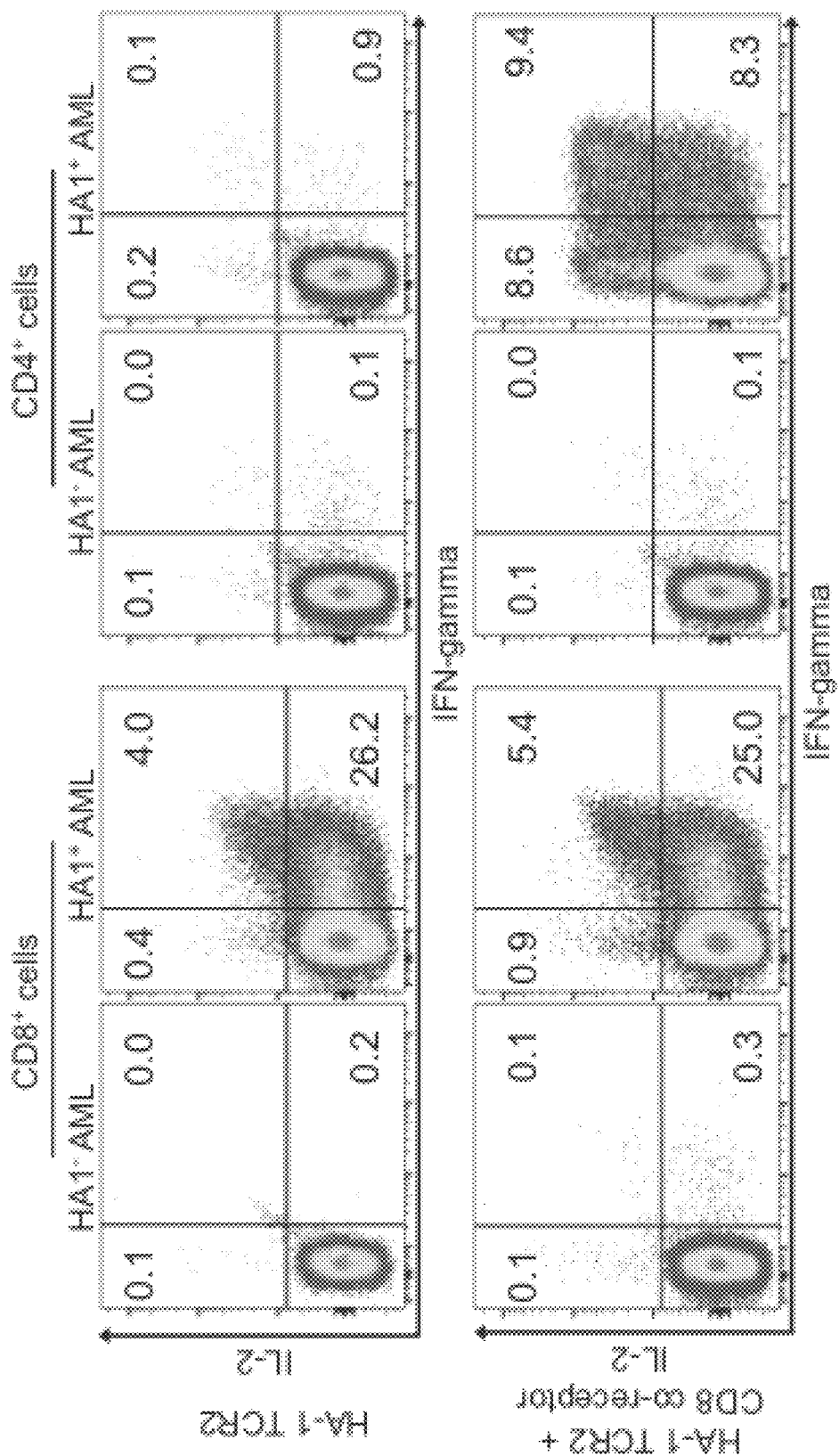
FIGS. 12A and 12B show further functional characterization of CD4$^+$ T cells transduced with the HA-1$^H$-TCR2 and a CD8 co-receptor. (A) Intracellular cytokine assay showing IL-2 and IFN-γ production by CD8$^+$ T cells (left) and CD4$^+$ T cells (right) transduced with HA-1$^H$TCR2 LV (upper panels) or HA-1$^H$TCR2-CD8 co-receptor LV (lower panels) in response to HLA-A2$^-$/HA-1$^{H+}$ AML or HLA-A2$^-$/HA-1$^-$ AML; (B) CFSE assay showing proliferation of CD8$^+$ T cells (left) and CD4$^+$ T cells (right) transduced with HA-1$^H$-specific TCR2 LV (upper panels) or HA-1$^H$TCR2-CD8 co-receptor LV (lower panels) in response to HLA-A2$^+$/HA-1$^{H+}$ primary AML, HLA-A2+/HA-1$^{H-}$ AML or media control.
Figure 12B:
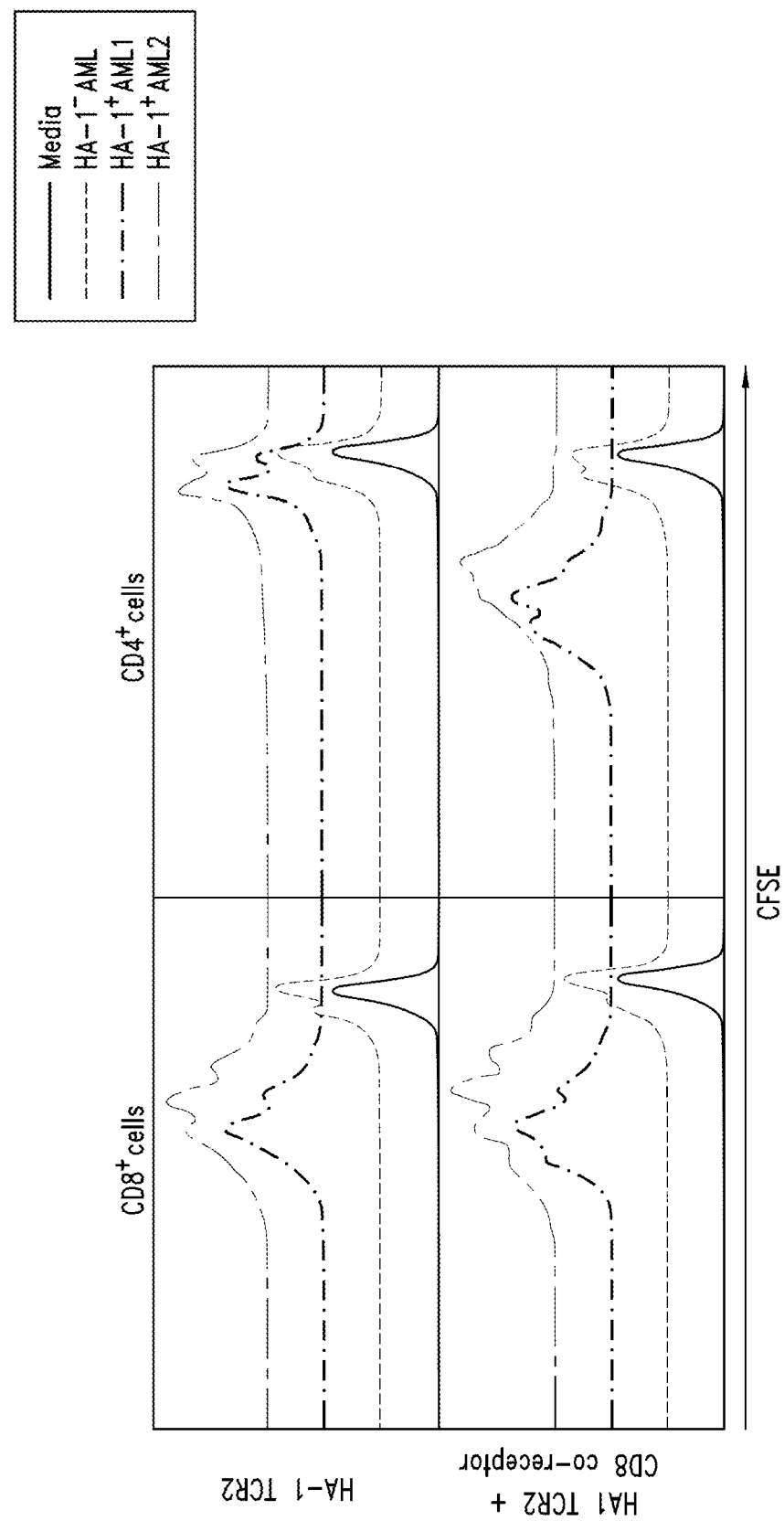
Figure 13:
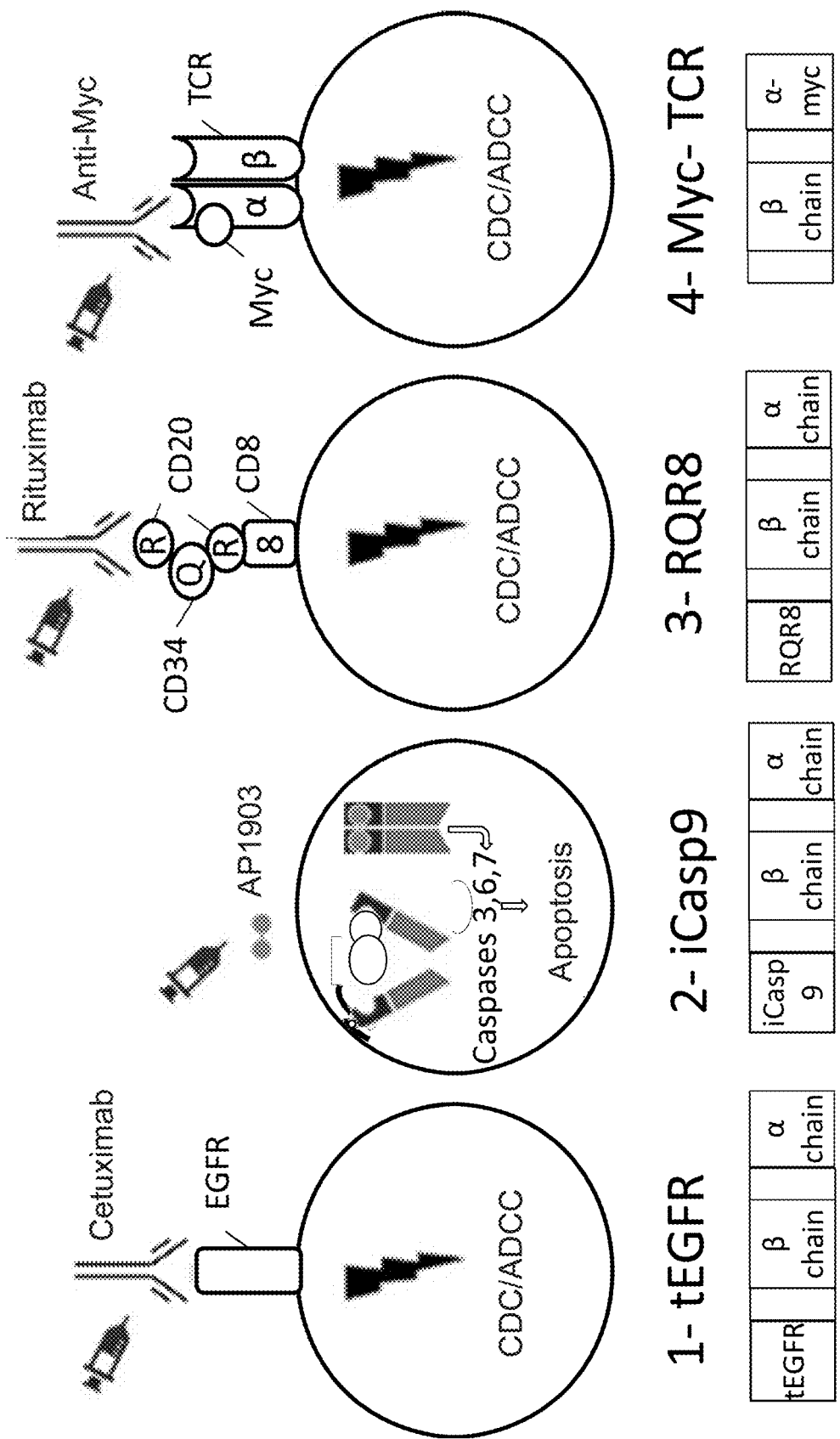
FIG. 13 provides representative diagrams of safety switch gene constructs of the present disclosure (bottom) and schema using the safety switch gene constructs to kill T cells (top).

HA-1$^H$ TCR2 constructs were generated that included one or both of the CD8 α-chain and the CD8 β-chain as full-length or truncated variants. When used to transduce primary CD4$^+$ T cells, the α- and β-chains were expressed on the cell surface; αβ dimers and a monomers increased HA-1$^H$/HLA-A2 multimer binding by TCR-transduced T cells to a greater extent than did β monomers (FIG. 11A(i-ii)). CD8 α- and β-chains with truncations of the intracellular chain components did not increase multimer binding above the TCR alone (FIG. 11A(iii)). Transduction with the CD8 α and βM1 or βM4 variants improved HA-1$^H$ TCR function in CD4$^+$ T cells more than did the CD8 α and βM2 or βM5 chains (FIG. 11B). In functional assays, incorporation of the βM1 or βM4 chain improved the CD4$^+$ T cell function to a greater extent than CD8 α monomers (FIGS. 11B and 11C). βM1 provided greater specificity of response than did βM4. The βM1 variant was therefore selected and used in a multi-cistronic LV that included CD8 a and βM1 sequences as well as the HA-1$^H$ TCR. CD4$^-$ T cells transduced with the vector secreted IL-2 and interferon gamma (IFNγ) (FIG. 12A) and proliferated when co-cultured with HA-1$^{H+}$ AML cells (FIG. 12B).

Example 4

Introduction of a Safety Switch into the HA-1$^H$ TCR Constructs

To ensure that HA-1$^H$ TCR-transduced T cells can be rapidly depleted in case of any unexpected toxicity, four codon-optimized "safety switch" HA-1$^H$ TCR constructs were generated: (1) The inducible caspase 9 (iCasp9) is based on the fusion of human caspase 9 to a modified human FK-binding protein, allowing conditional dimerization; when exposed to a synthetic dimerizing drug, iCasp9 becomes activated and initiates rapid death of cells expressing this construct (see, e.g., Straathof et al., *Blood* 105(11): 4247 (2005)); (2) The truncated human EGFR ("tEGFR") is a polypeptide devoid of extracellular N-terminal ligand binding domains and intracellular receptor tyrosine kinase activity, but retains type I transmembrane cell surface localization and a binding epitope for pharmaceutical-grade anti-EGFR mAb, cetuximab (see Wang et al., *Blood* 118(5): 4255 (2011)); (3) RQR8 is a compact combined marker and safety switch for T cells, combining target epitopes from both CD34 (a marker recognized by antibody QBEnd10) and CD20 antigens (extracellular loop mimotopes) presented on a truncated CD8 co-receptor stalk; RQR8 is bound by the pharmaceutical-grade anti-CD20 mAb, rituximab (see Philip et al., *Blood* 124(8):1255 (2011)); (4) Myc-tagged TCR incorporate a 10-amino acid tag of the human c-Myc protein that is bound by a tag-specific mAb (see Kieback et al., *PNAS* 105(2):623 (2008)).

Figure 14:
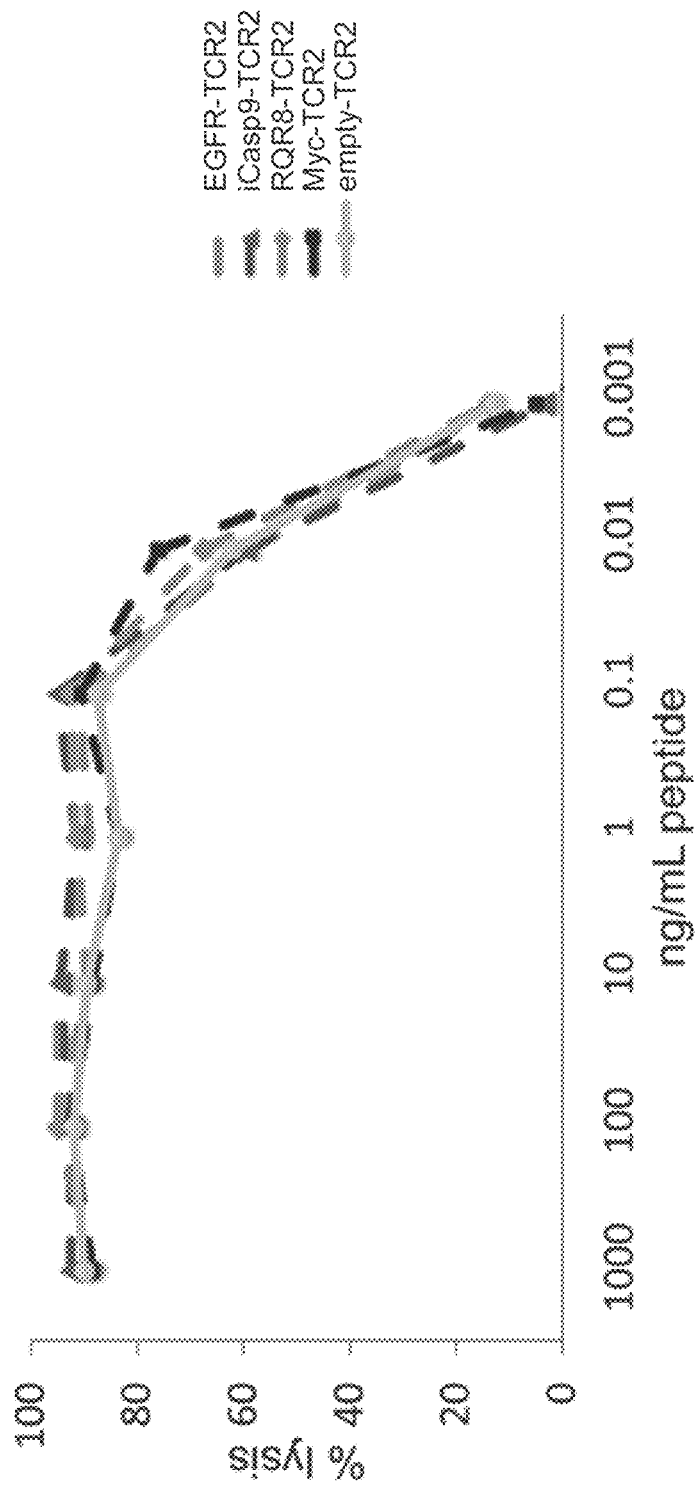
FIG. 14 provides data from a cytotoxicity assay in which primary T cells were transduced with transgene constructs expressing safety switch genes and the HA-1$^H$ specific TCR2 (or were transduced with TCR2 alone) and incubated with T2 cells pulsed with HA-1$^H$ peptide.

Binding of the respective mAbs to tEGFR, RQR8 or myc-tag provides a target for complement-dependent or antibody-dependent cellular cytotoxicity and elimination of transduced cells. The safety switch molecules were cloned into TCR2 LV constructs upstream of, and operatively associated with, the the TCRβ and TCRα coding sequences. The TCRβ and TCRα sequences were separated by P2A elements from the porcine teschovirus to ensure coordinated gene expression. T cells transduced with iCasp9-HA-1$^H$ TCR, tEGFR-HA-1$^H$ TCR, RQR8-HA-1$^H$ TCR or Myc-tagged HA-1$^H$-TCR all demonstrated HA-1$^H$ TCR expression and HA-1$^{H+}$ target cell recognition similar to recognition by T cells transduced with the HA-1$^H$ TCR alone (FIG. 14).

Figure 15:
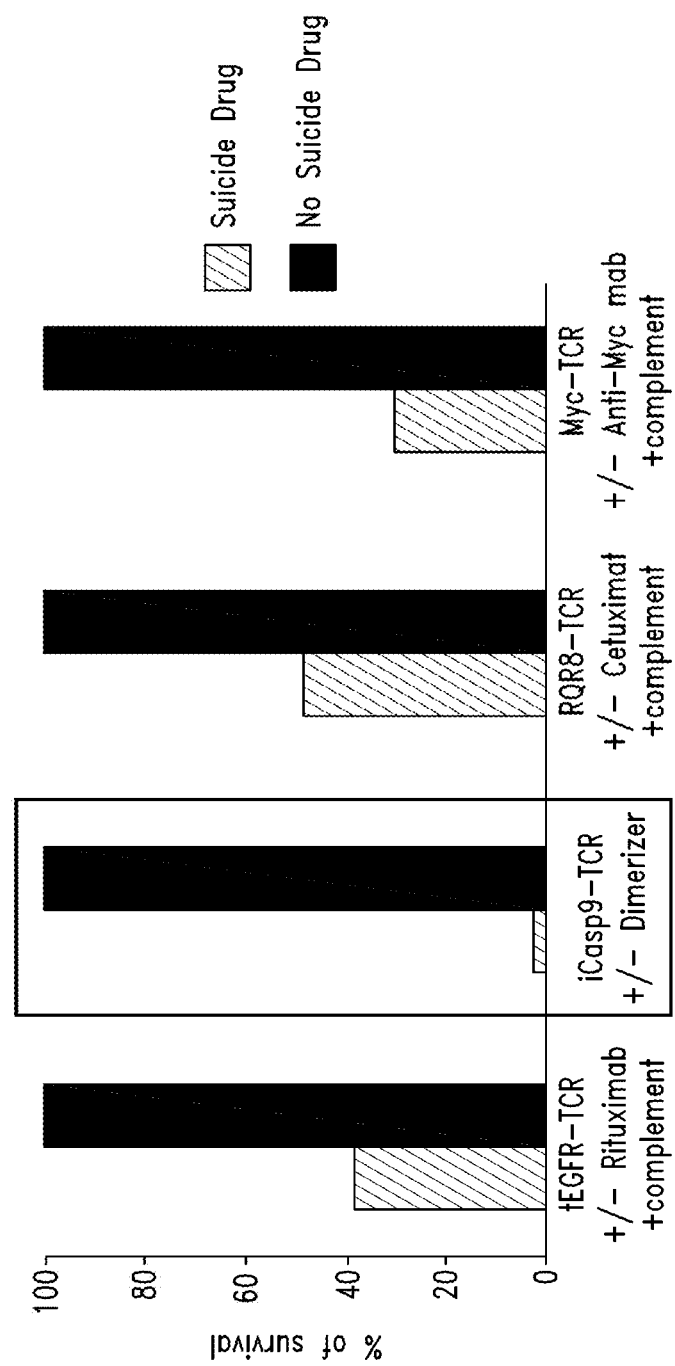
FIG. 15 shows percent survival of the transduced TCRs in the presence or absence of a "suicide drug" that activates the encoded safety switch.
Figure 16:
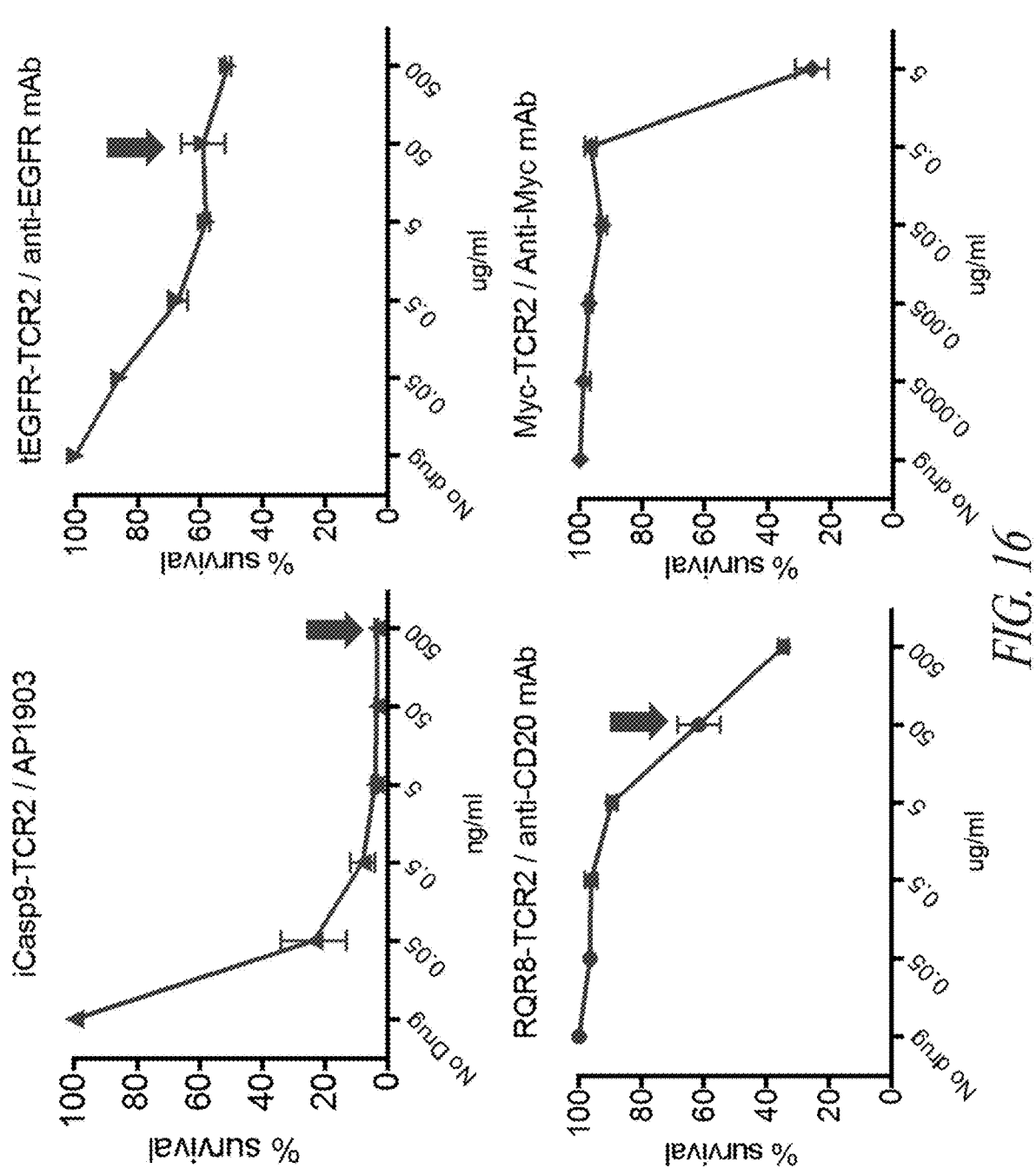
FIG. 16 shows survival of CD8$^+$ T cells transduced with HA-1$^H$ TCR2 plus safety genes after exposure to the cognate safety-switch activating drug at the indicated concentrations. Survival of iCasp9-TCR2, tEGFR-TCR2, RQR8-TCR2 and Myc-TCR2 CD8$^+$-transduced T cells was measured after 24 hours of incubation with the indicated concentrations of the respective safety switch activating drug: AP1903; anti-EGFR mAb (Cetuximab)+complement; anti-CD20Mab (Rituximab) +complement; anti-myc mAb+complement. Residual HA-1 TCR2 transduced T cells were quantified by flow cytometry. The arrows indicate the drug concentrations that can be achieved and tolerated in humans in vivo.

To test the ability of the safety switches to eliminate T cells, transduced T cells were incubated for 24 hours with the optimal concentration (FIG. 16) of the respective cognate drug (the dimerizer AP1903 for iCasp9/HA-1$^H$ TCR; complement plus appropriate mAb (anti-EGFR mAb for tEGFR-HA-1$^H$ TCR; anti-CD20 mAb plus for RQR8-HA-1$^H$ TCR; and anti-Myc tag mAb for Myc-tagged HA-1$^H$-TCR in all other constructs). All of the safety switch transduced T cells were susceptible to their respective trigger (FIG. 16, see also FIG. 15). However, iCasp9 with AP1903 consistently provided the most rapid and complete elimination of transduced T cells and was selected for further evaluation.

Example 5

Design and Selection of a Transgene Construct

Figure 17:
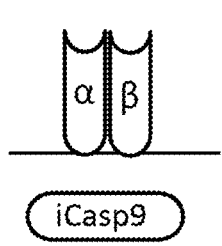
FIG. 17 shows five (5) different types of constructs for the evaluation of iCasp 9-HA-1$^H$ TCR-CD8+ expression constructs: (i) iCasp 9 and TCR2; (ii) TCR 2 and CD8 co-receptor; (iii) iCasp 9, TCR 2 and CD8 co-receptor; (iv) iCasp 9, TCR 2 and CD8 co-receptor with RQR tag on the CD8 co-receptor; and (v) iCasp 9, TCR 2 and CD8 co-receptor with Q (CD34) tag on the alpha chain of the TCR.
Figure 17:
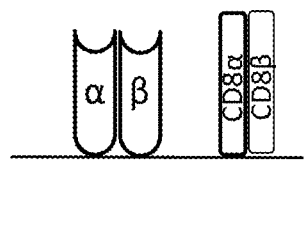
Figure 17:
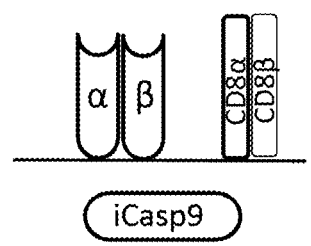
Figure 17:
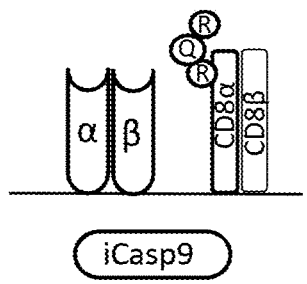
Figure 17:
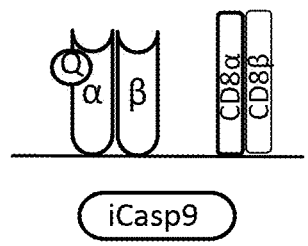
Figure 18:
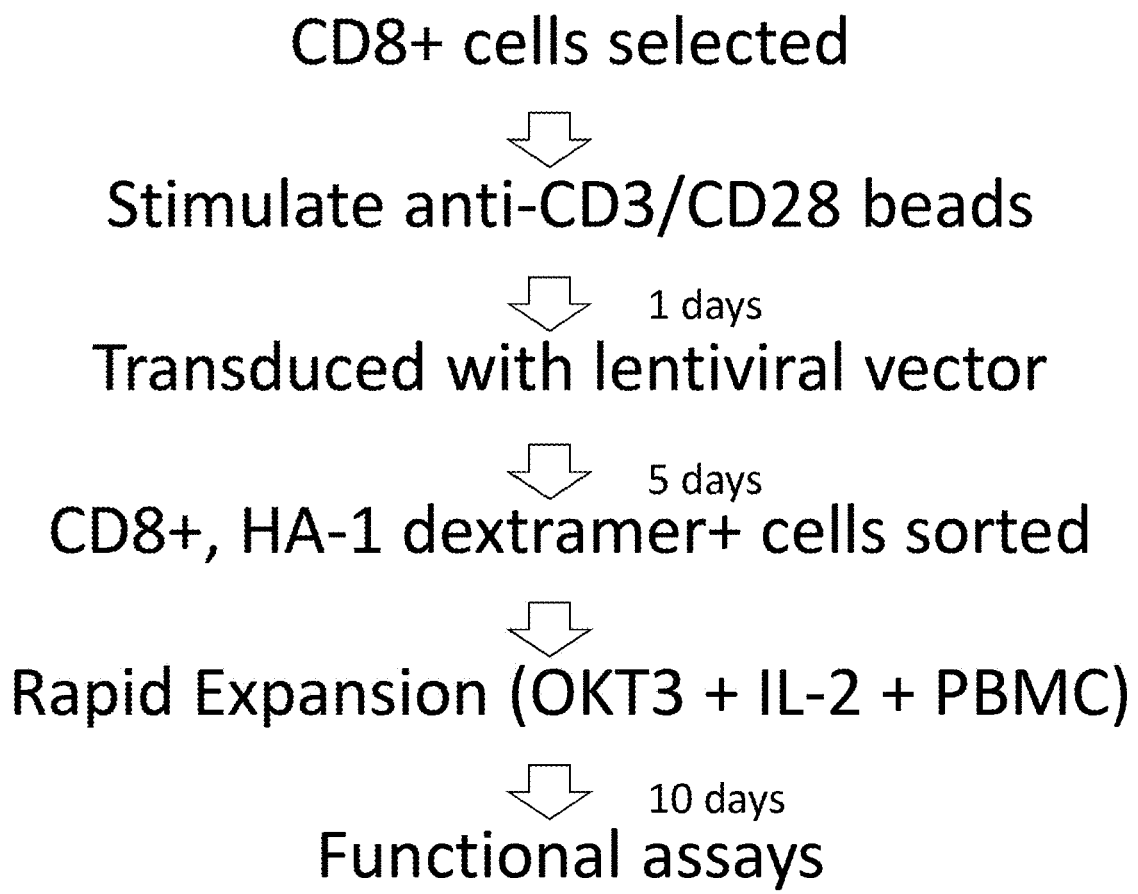
FIG. 18 depicts a flow chart for evaluating TCR-transduced cells of the present disclosure.
Figure 19:
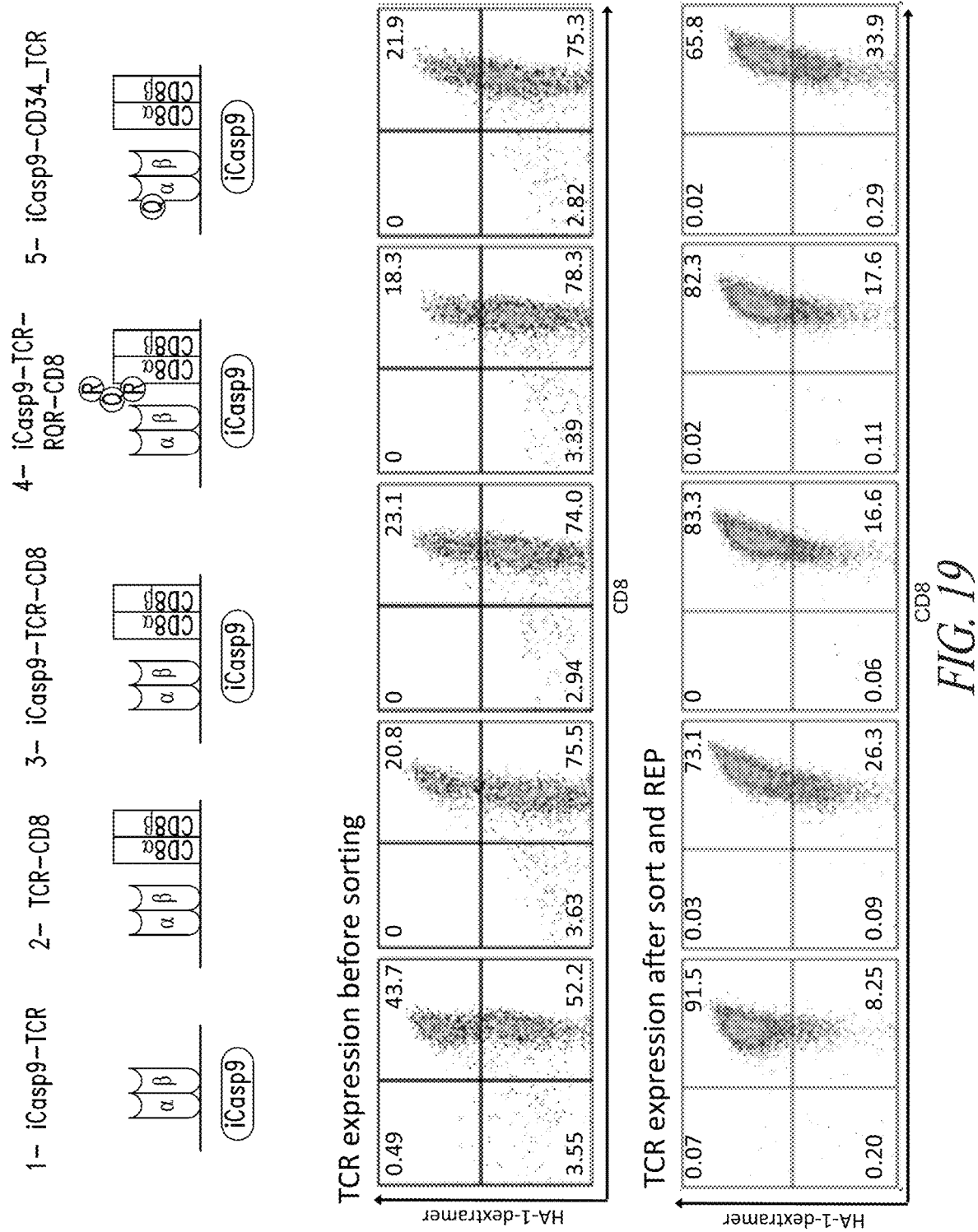
FIG. 19 provides flow cytometry data showing expression of the engineered TCR in each of the indicated transgene constructs before (top row) and after (bottom row) enrichment with an HA-1 dextramer.
Figure 20A:
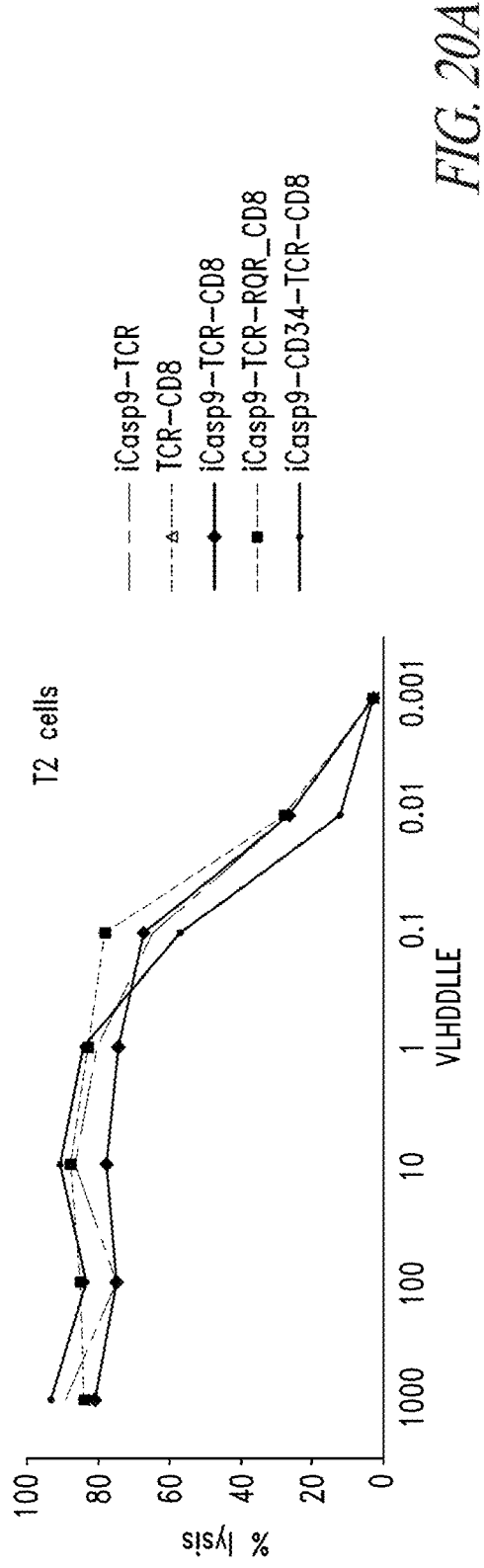
FIGS. 20A and 20B show specific lysis of peptide-pulsed target cells (20A) and LCL lines (20B) by T cells transduced with transgene constructs: iCasp-9-TCR (- -; first bar); TCR and CD8 co-receptor (-▲-; second bar); iCasp-9-TCR-CD8 co-receptor (-♦-; third bar); iCasp9-TCR-RQR-CD8 co-receptor (-■-; fourth bar); and iCas9-CD 34tag-TCR-CD8 co-receptor (-●-; fifth bar).
Figure 20B:
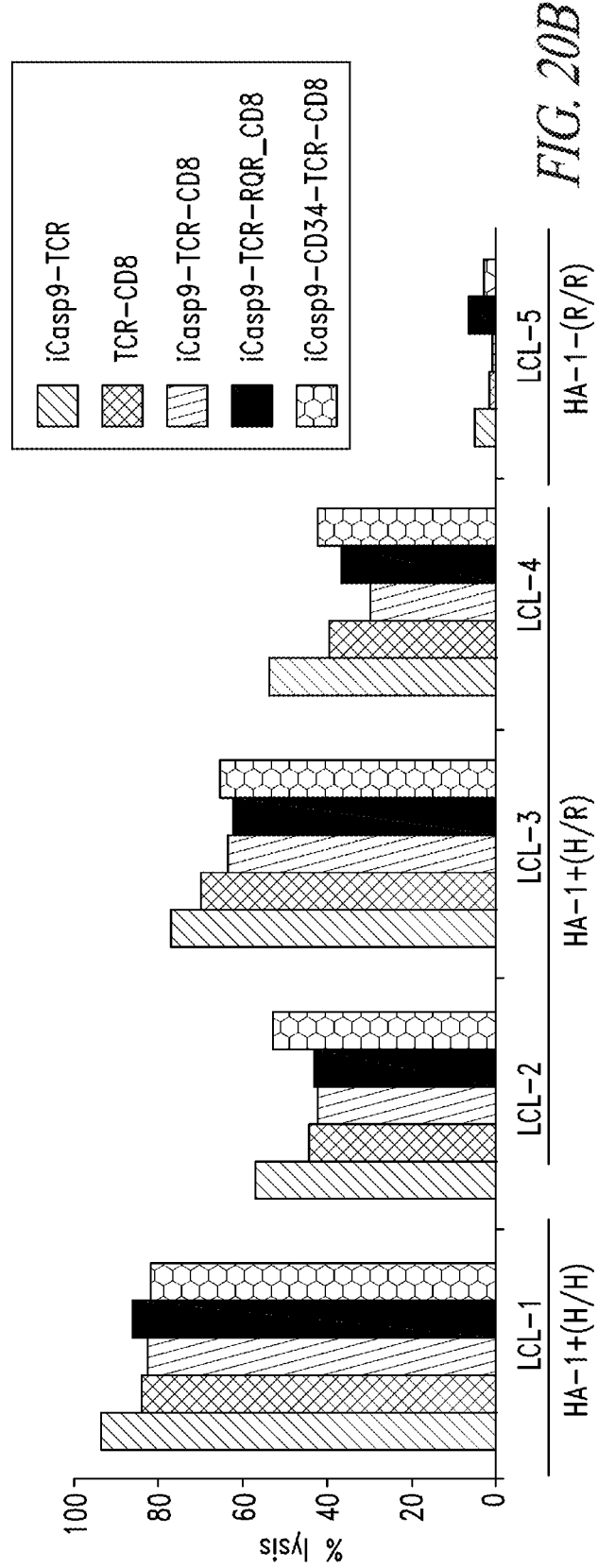
Figure 21:
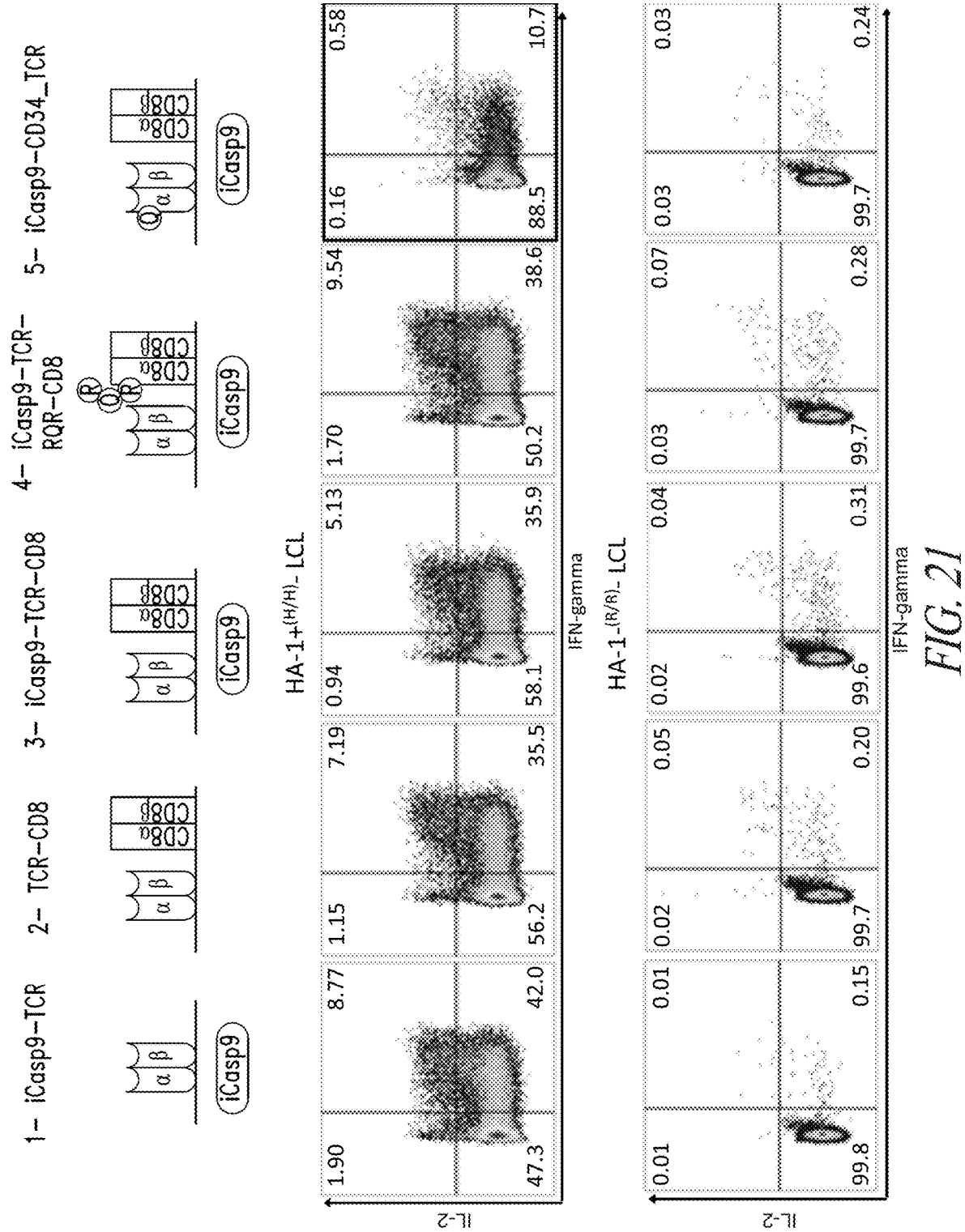
FIG. 21 shows cytokine elaboration by T cells transduced with the indicated transgene constructs following stimulation with HA-1$^{H+}$ (top) or HA-1$^{H-}$ (bottom) cell lines.
Figure 22:
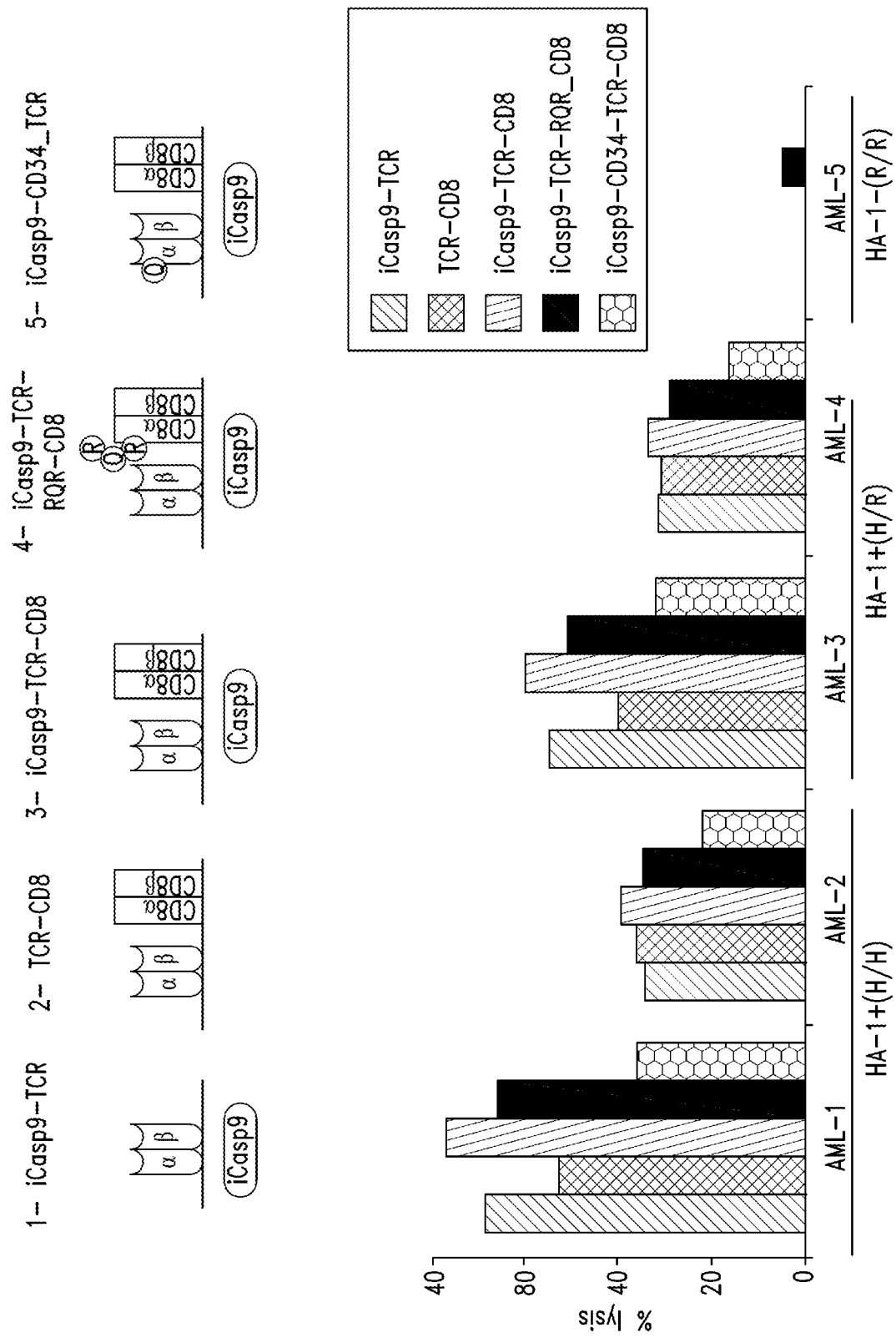
FIG. 22 shows cytolytic activity (bottom) of T cells transduced with the transgene constructs (top) against indicated target cell lines.
Figure 23:
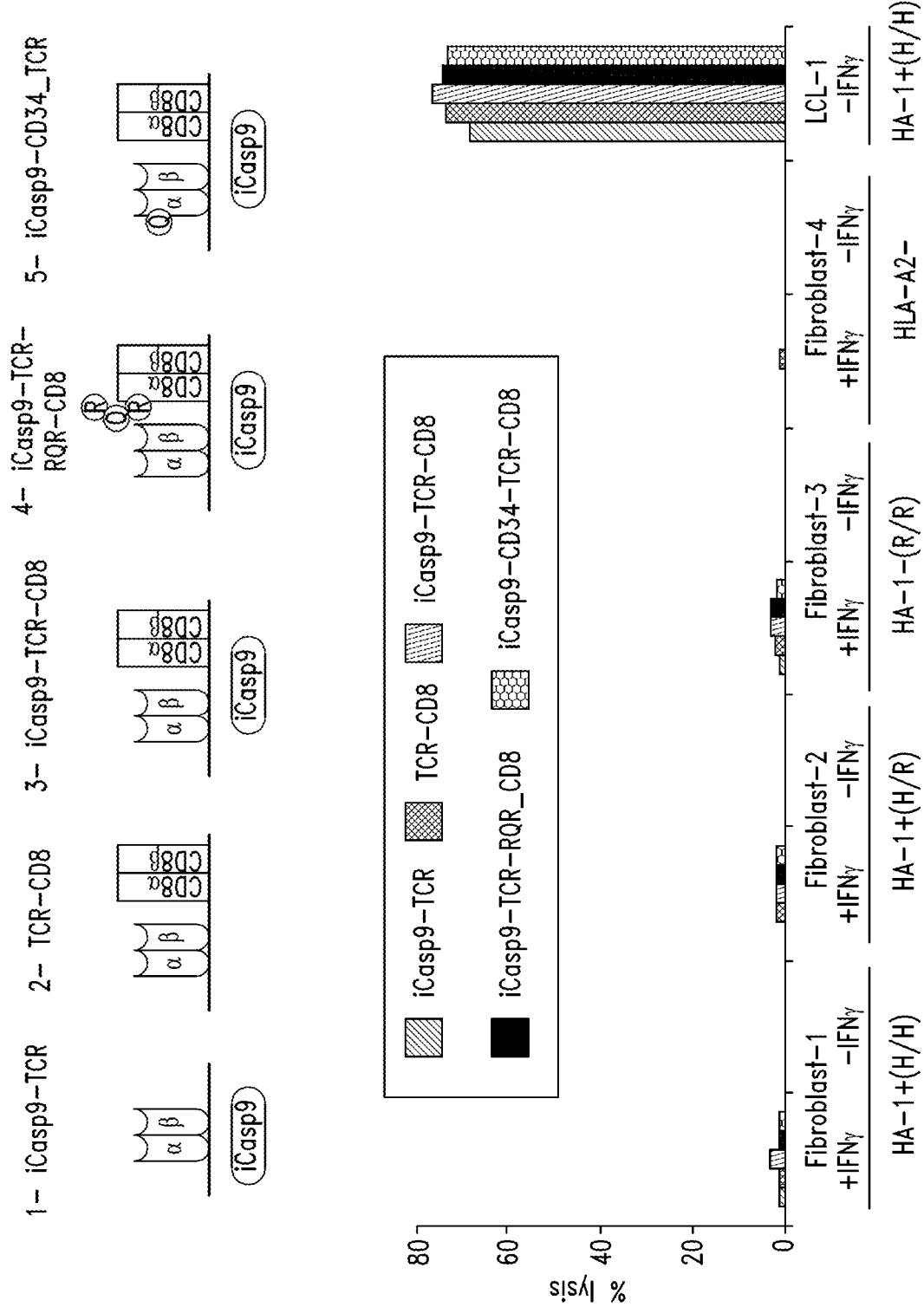
FIG. 23 shows the absence of cytolytic activity of T cells transduced with the indicated transgene constructs against indicated non-hematopoietic cells in the presence or absence of interferon-gamma. HA-1$^{H+}$ hematopoietic control cells were killed by the T cells.
Figure 24:
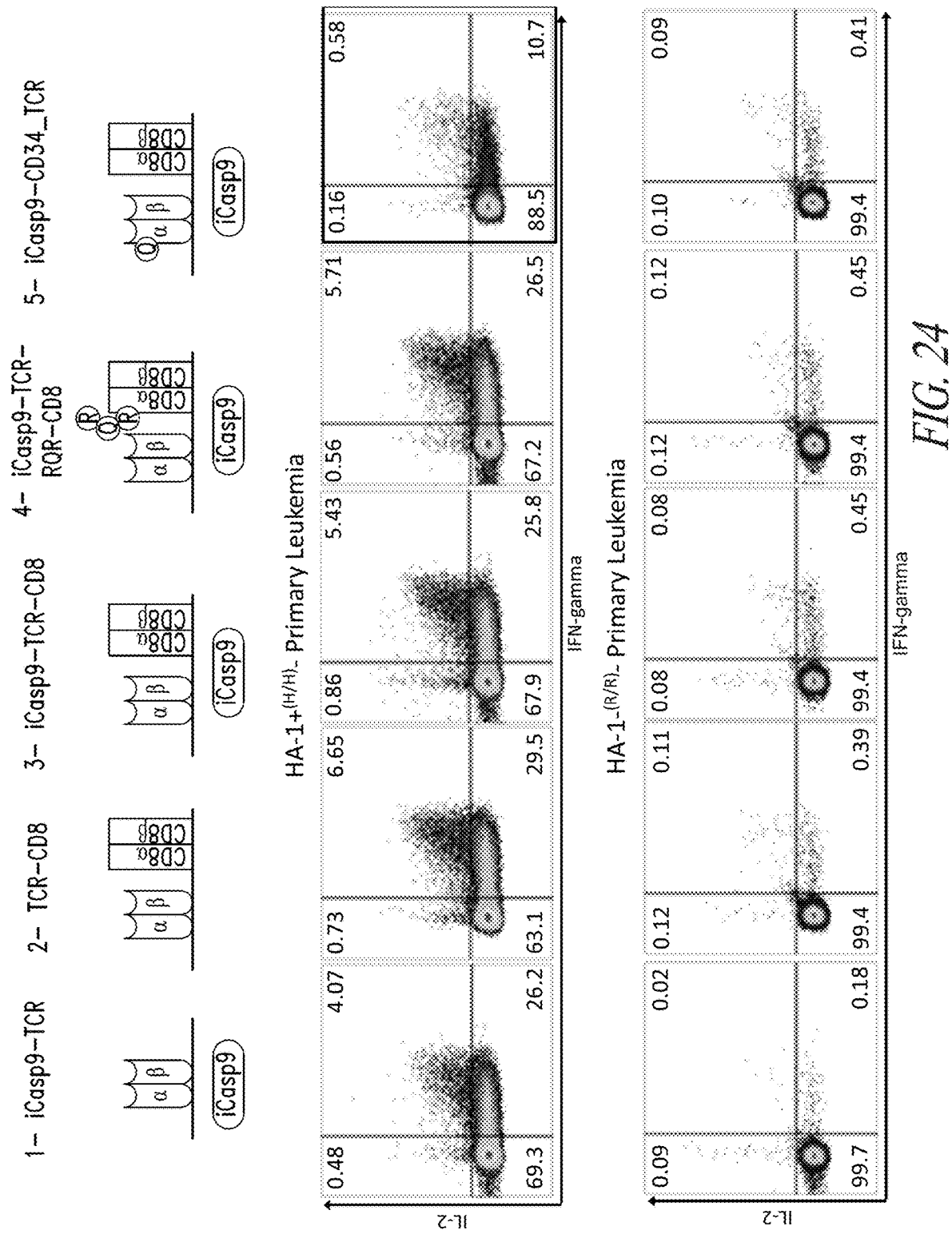
FIG. 24 shows cytokine elaboration by cells transduced with the indicated transgene constructs when exposed to primary leukemia cells.
Figure 25:
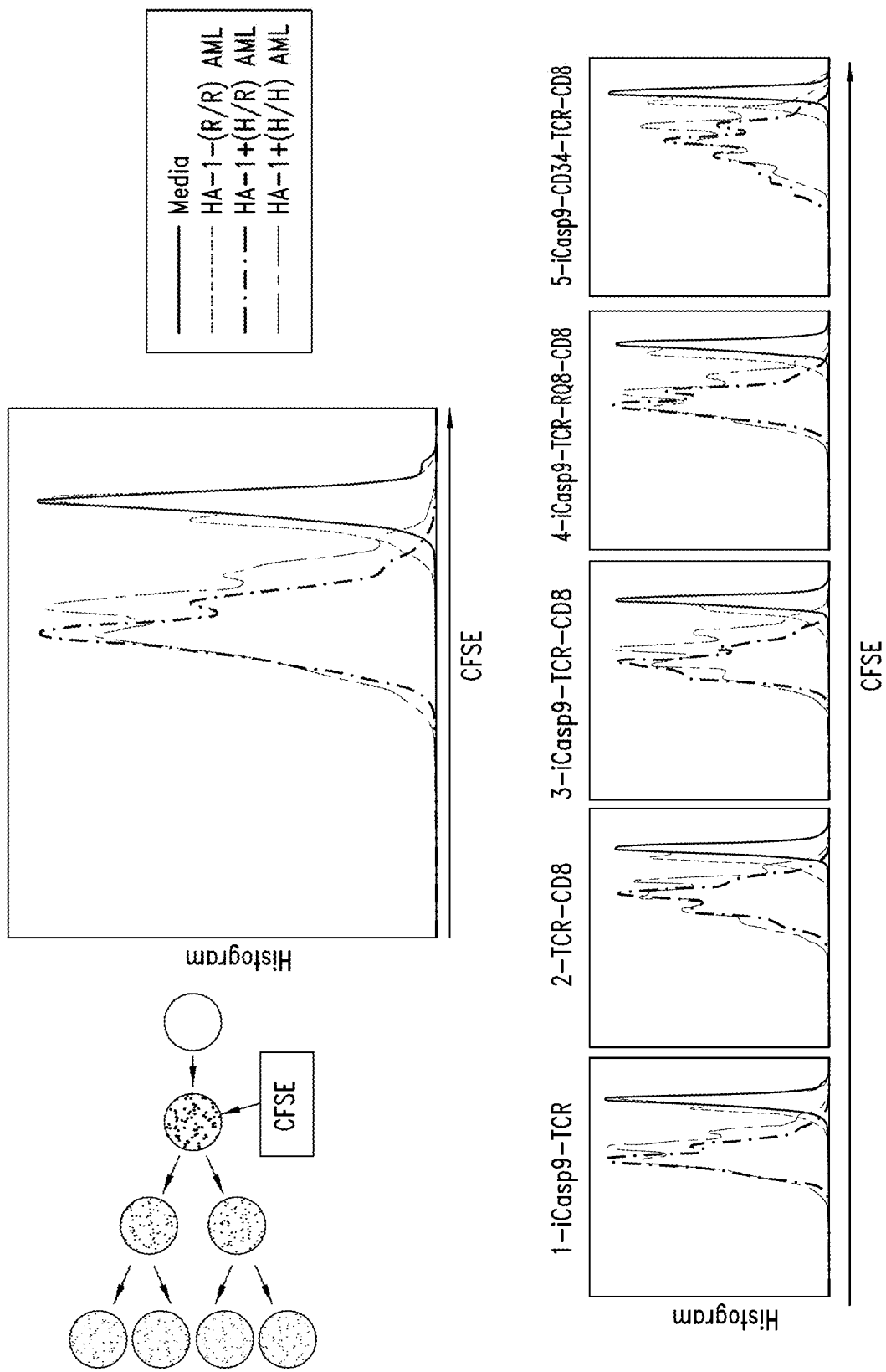
FIG. 25 provides flow cytometry histograms showing proliferation of transduced T cells when stimulated with HA-1$^{H-}$ primary leukemia cells. Top: scheme for measuring proliferation by staining F1 cells with CFSE (left), and representative proliferation data from a T cell transduced with a transgene constructs of the present disclosure. Bottom: proliferation of T cells transduced with the indicated transgene constructs.
Figure 26:
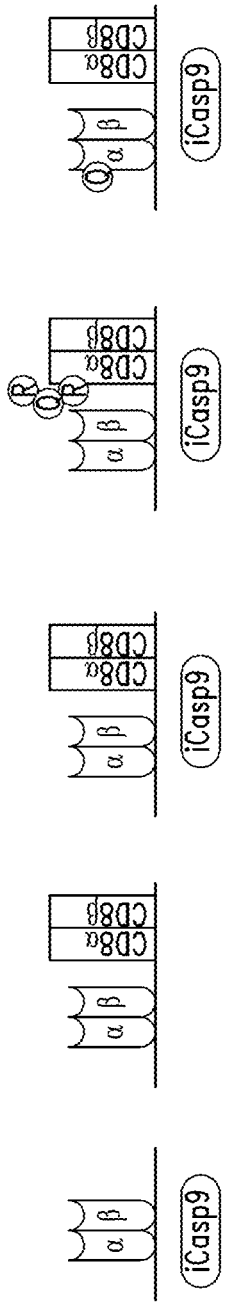
FIG. 26 shows survival (bottom) of T cells transduced with transgene constructs as shown (top) following introduction of the cognate suicide drug at the indicated concentrations.
Figure 26:
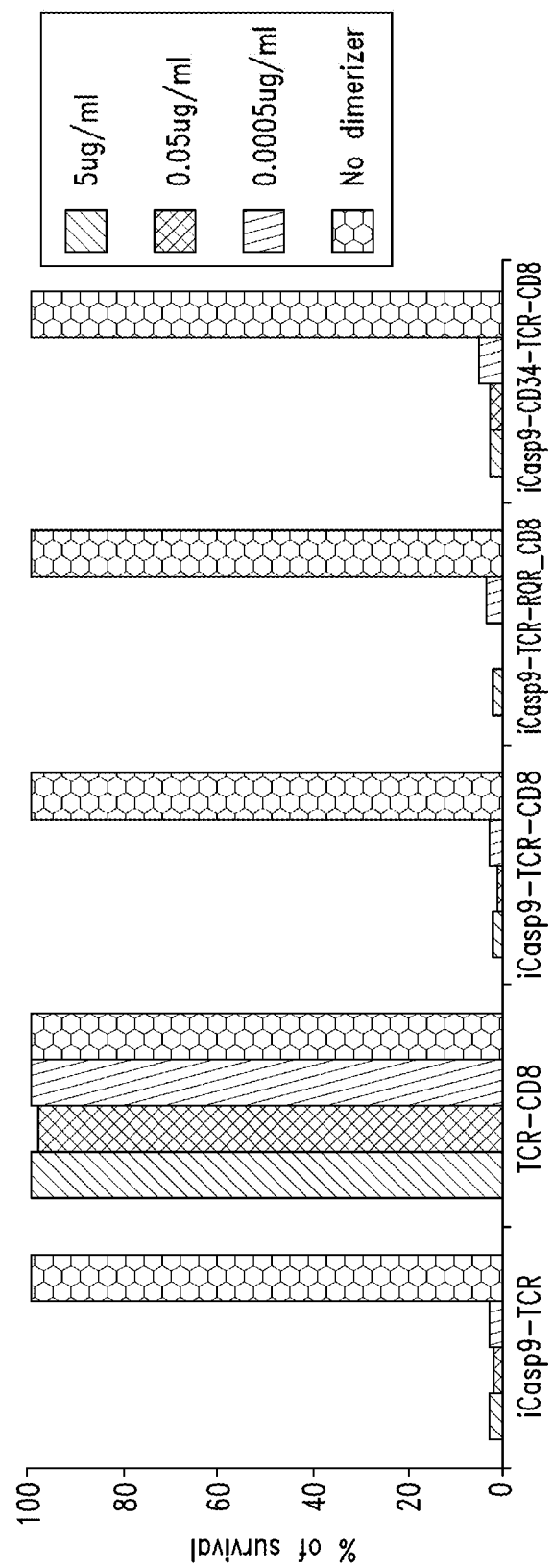

Next, the HA-1$^H$ TCR transgenes incorporating both iCasp9 and the CD8αβM1 co-receptor were analyzed for functionality. To assist in the selection and tracking of transduced T cells, two marker configurations were designed. In one, the minimal CD34 epitope ("Q") of the RQR polypeptide was nested into the α-chain of the HA-1$^H$ TCR. In the other, the RQR polypeptide was incorporated into the β-chain of the full-length functional CD8 αβM1 co-receptor. Five LV transgene constructs were then created, used to transduce CD8$^+$ T cells, and compared: (1) iCasp9-HA-1$^H$ TCR2; (2) HA-1$^H$-TCR2-CD8 co-receptor; (3) iCasp9-HA-1$^H$TCR2-CD8; (4) iCasp9-HA-1$^H$TCR2-RQR-CD8; and (5) iCasp9-CD34-HA-1$^H$ TCR2-CD8 (see FIGS. 17 and 18).

Figure 27:
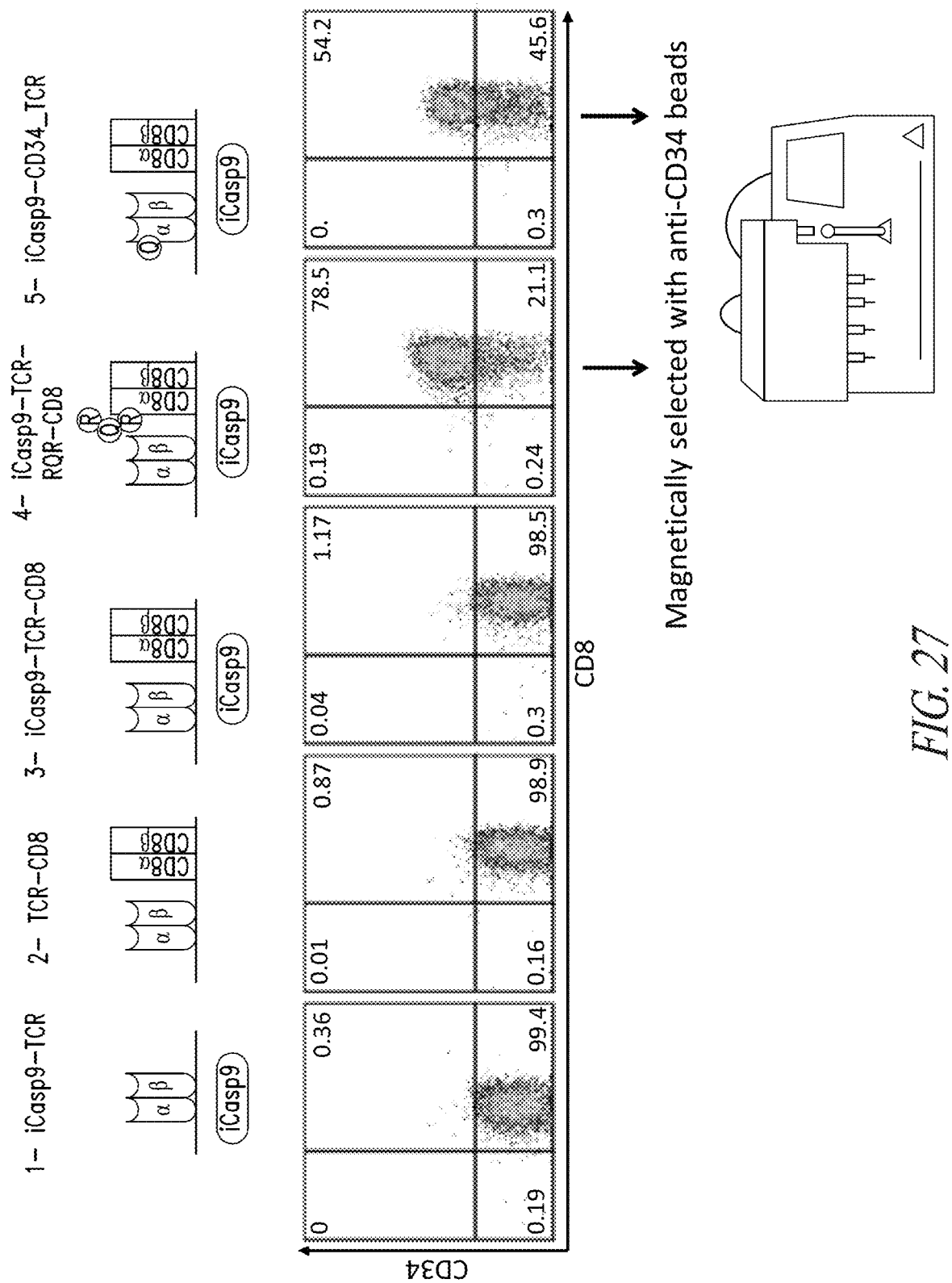
FIG. 27 shows an enrichment scheme for engineered T cells of the present disclosure. T cells are transduced with the indicated transgene constructs (top) and examined for expression (middle). Cells expressing a selectable transduction marker (CD34 epitope; two right-most scatter plots) are selected using magnetic beads with anti-CD34 antibody.
Figure 29:
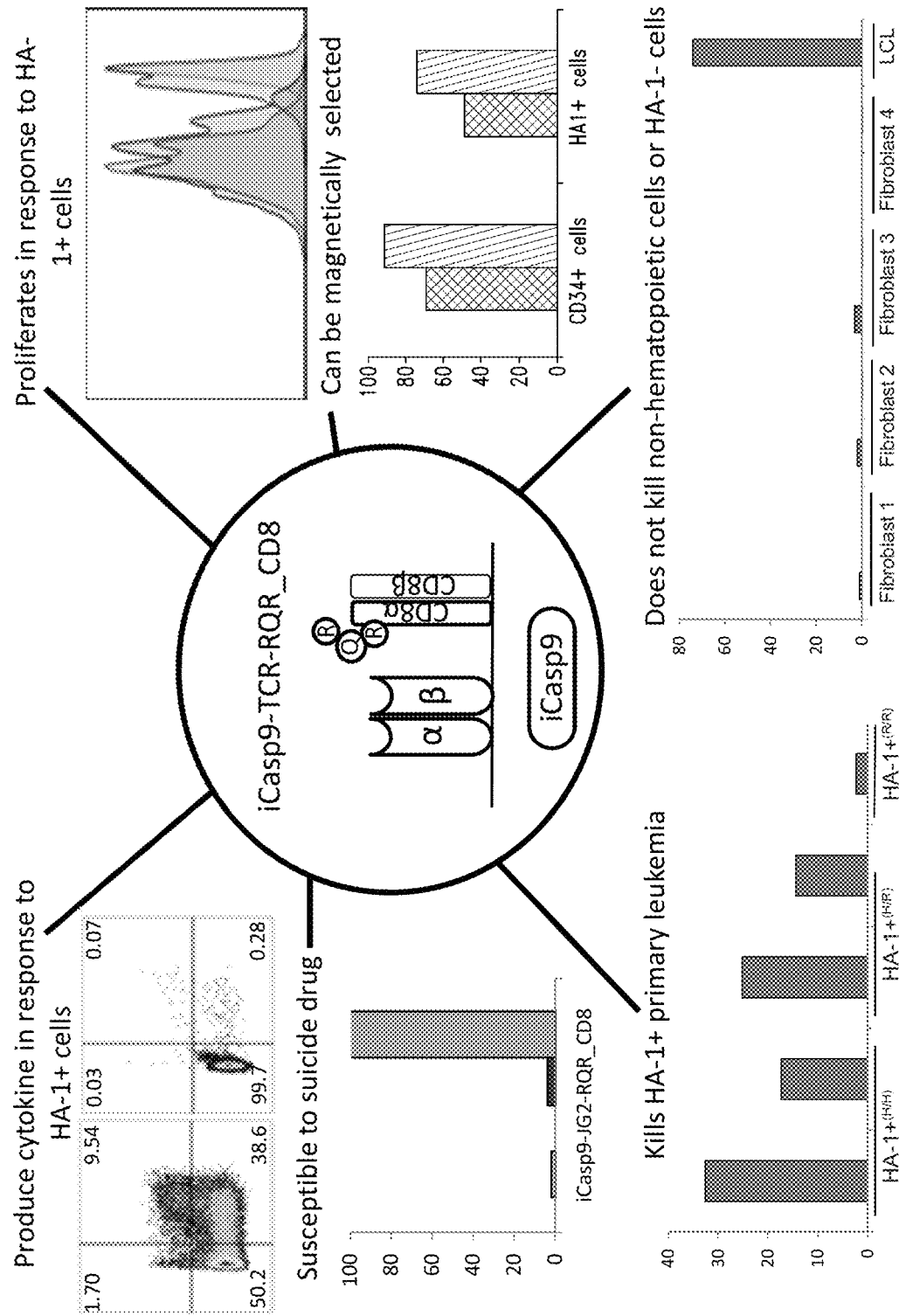
FIG. 29 provides a schematic showing various functionalities of a TCR-safety gene construct of the present disclosure.
Figure 30:
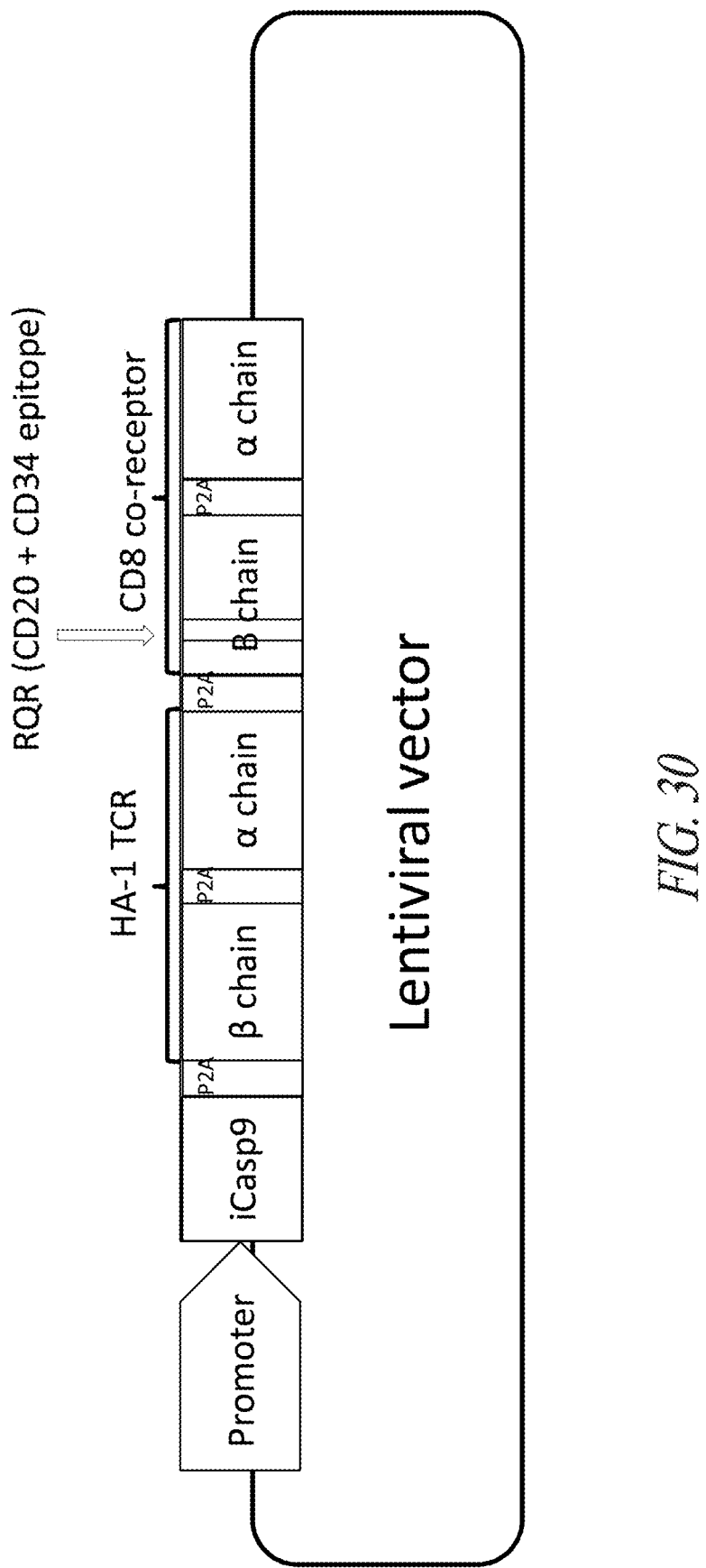
FIG. 30 provides a diagram of a lentiviral delivery vector encoding an exemplary iC9-HA-1$^{H}$-TCR-RQR-CD8 construct of the present disclosure.

All of the constructs produced T cells that specifically secreted cytokines and killed HA-1$^{H+}$, but not HA-1$^{H-}$ AML cells or fibroblasts, and had similar function (see FIGS. 19-26), except the iCasp9-CD34-HA-1$^H$ TCR2-CD8 construct (with the CD34 epitope embedded in the TCR α-chain), which performed poorly. The iCasp9-HA-1$^H$ TCR2-RQR-CD8 transgene, which contains all of the desired elements (including the capacity for immunomagnetic selection; see FIGS. 27-29) and functioned as well as the less complex constructs, was selected for further studies. A schematic diagram of this construct is shown in FIG. 30, and the nucleotide sequence of the construct is provided in SEQ ID NO:85.

Example 6

Clinical-Scale Production and Testing of HA-1$^H$ TCR T Cells

The cellular composition of T cell immunotherapy products can have important downstream effects on the persistence and function of antigen-specific T cells after adoptive T cell transfer (see, e.g., Sommermeyer et al., *Leukemia* 30(2):492 (2016); see also Wang et al., *Blood* 117(6):1888 (2011) and Hinrichs et al., *PNAS* 106*41):17469 (2009)). In general, infusion of antigen-specific T cells derived from "younger" T cell subsets, including $T_N$, T memory stem cells ($T_{SCM}$) and central memory T cells ($T_{CM}$), appears advantageous. In the context of post-HCT T cell immunotherapy, it is also important to consider the potential for GVHD mediated by the native TCR of donor T cells. $T_N$ cause severe GVHD in murine models and depletion of CD45RA$^+$ $T_N$ from PBSC grafts reduces the risk of severe and/or chronic GVHD in humans (see, e.g., Bleakley et al., *J. Clin. Invest.* 125(7):2677 (2015). It is also desirable to include both CD4$^+$ and CD8$^+$ cells specific for the same antigen, as CD4$^+$ T helper cells can enhance anti-tumor CTL responses by enhancing clonal expansion at the tumor site and preventing activation-induced cell death (see, e.g., Giuntoli et al., *Clin. Cancer Res.* 8(3):922 (2002); see also Kennedy and Celis, *J. Immunol.* 177(5):2862 (2006)). Therefore, the T cell product (1-2 ×10$^9$PBSC/PBMC) was first depleted of CD45RA$^+$ $T_N$ cells to minimize the risk of serious GVHD, and depleted of CD14$^+$ monocytes to optimize LV transduction efficiency, prior to separating CD8$^+$ and CD4$^+$ enriched fractions to ensure a consistent CD4:CD8 composition (approx. 3×10$^6$ cells of each cell type), and stimulating (CD3/CD28 microbeads beads) and transducing the T cells with the iCasp9-HA1 TCR2-RQR-CD8 LV.

Figure 31:
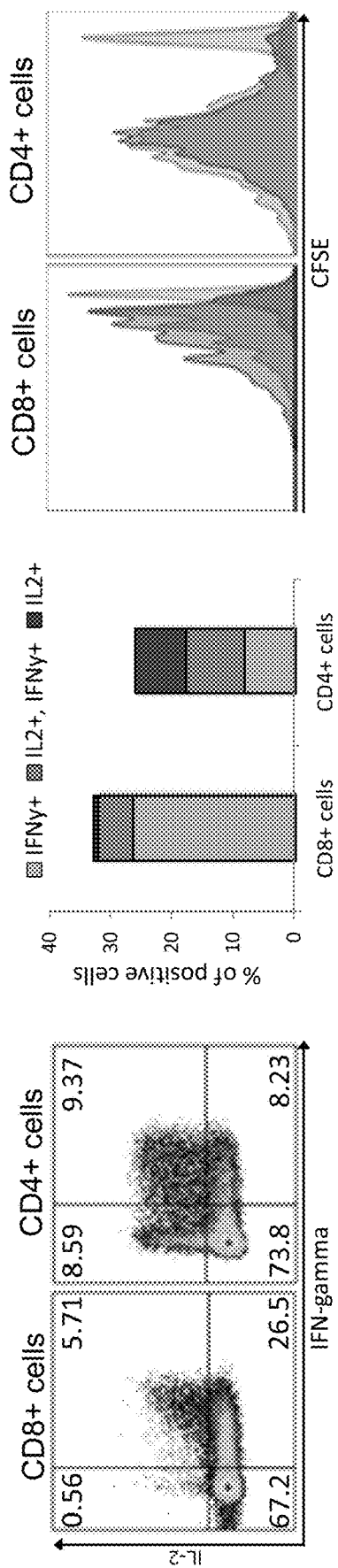
FIG. 31 shows the functional characterization of CD8$^-$ and CD4$^+$ cells transduced with a TCR2-CD8 transgene construct of the present disclosure. Left panel: flow cytometry data showing cytokine release (IL-2; IFN-γ) in response to HA-1$^{H}$ peptide antigen. Middle panel: quantification of the flow cytometry data. Right panels: proliferation of transduced cells in response to HA-1$^{H}$.
Figure 32C:
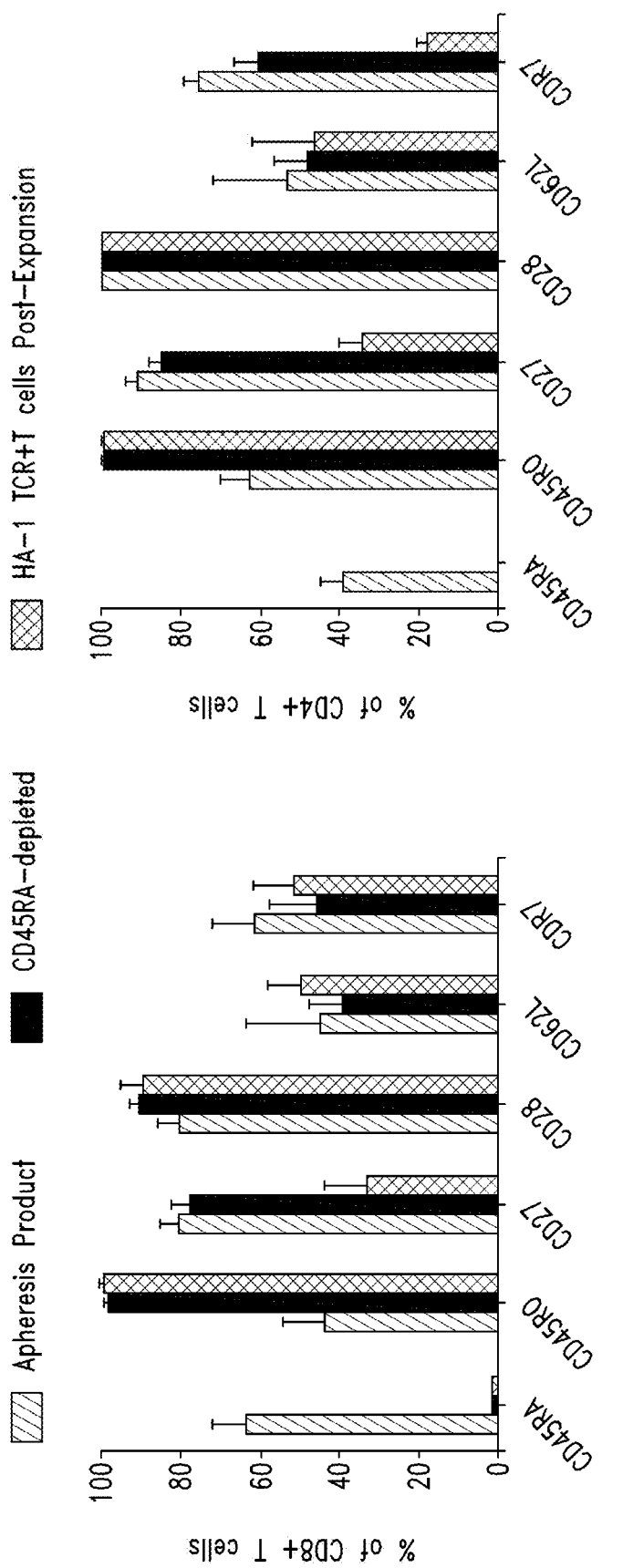
Figures 32D, 32E:
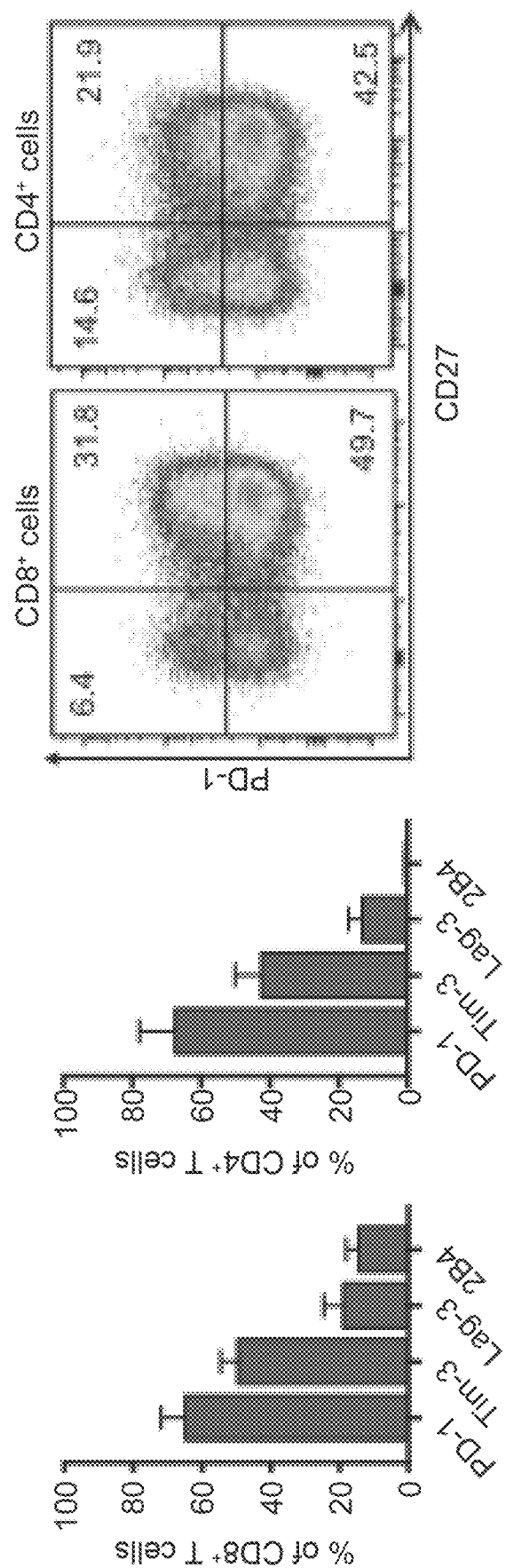
Figure 35:
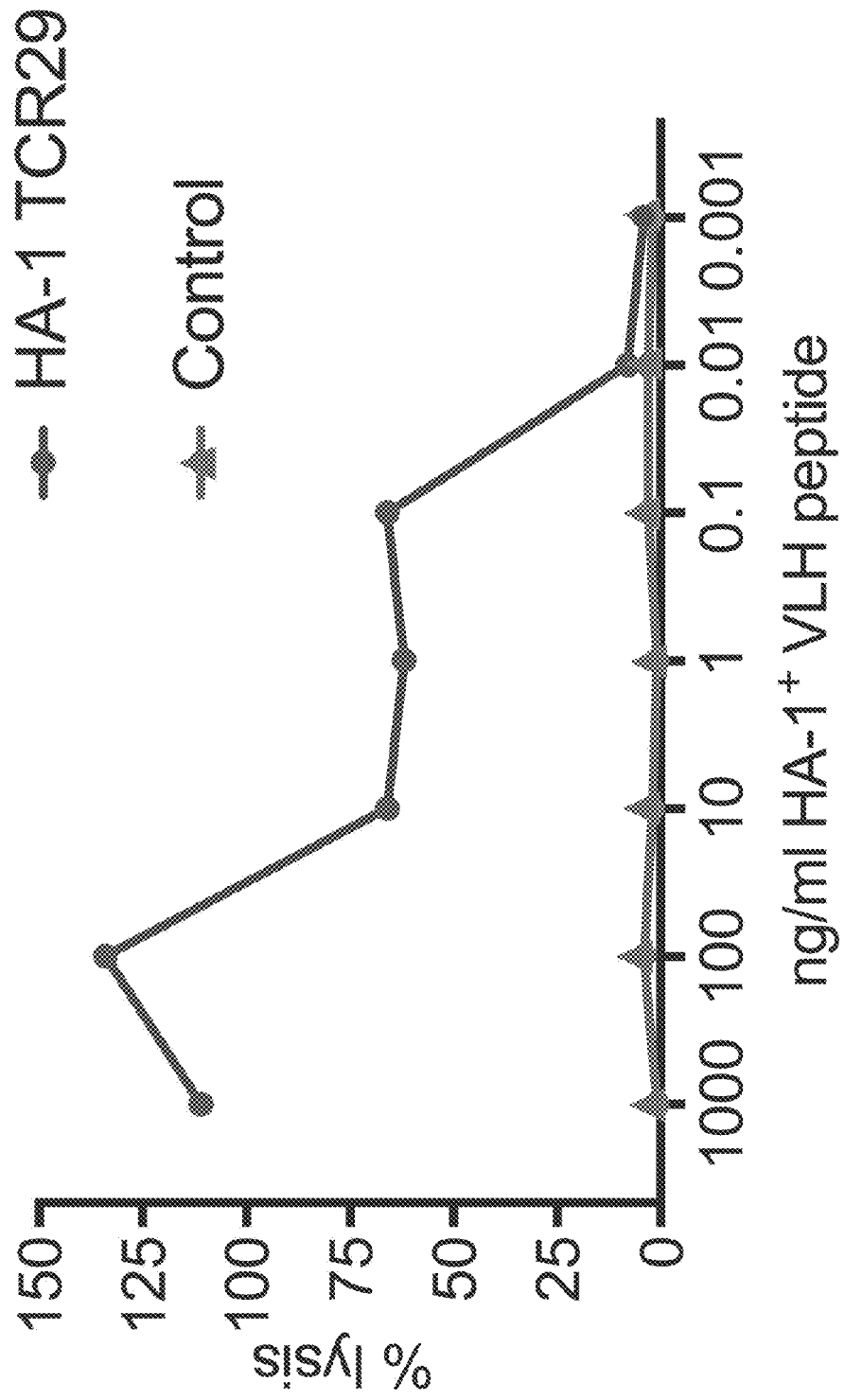
FIG. 35 shows cytolytic activity of T cells transduced with another HA-1$^{H}$ TCR of the present disclosure (circles) and of control cells (triangles) against T2 cells pulsed with the HA-1$^{H}$ antigen at the indicated concentrations.

The transduced cells were flow-sorted using HA-1$^H$/HLA-A2 multimers and CD34 mAb 4-5 days later, and cultured in G-Rex flasks using REP (Rapid Expansion Protocol) comprising OKT3 cells, PBMC, HA-1$^+$LCL, and IL-2. The CD4$^+$ and CD8$^+$ HA-1$^H$TCR memory T cells expanded efficiently, with an average 2000-fold expansion (FIG. 32A; see also FIG. 31, left-most panels). The CD4$^+$ and CD8$^+$-transduced T cells were harvested and combined (total 3-6×10$^9$ cells at days 16-20), then enriched via selection for CD34 to produce an enriched population of ≥1.5× 10$^9$ cells. Release assays were then performed to test for purity (>75%), viability, function, specificity, presence or absence of virus, and sterility. The final T cell product retained expression of the HA-1$^H$ TCR (FIG. 32B), had a predominantly CD45RO$^+$CD28$^+$ phenotype with variable expression of CD62L, CCR7 and CD27 (FIG. 32C), and included cells that did not express exhaustion markers such as PD-1 (FIGS. 32D, 32E).

The expanded CD8$^+$ and CD4$^+$ HA-1$^H$ TCR T cells retained their ability to specifically kill and secrete cytokines in response to stimulation with HA-1$^H$-pulsed cells (FIG. 33A) or HA-1$^{H+}$ leukemia cell lines (FIG. 33B), and many HA-1$^H$ TCR CD8$^+$ and CD4$^+$ cells secreted multiple cytokines (FIG. 33C; see also FIG. 31 middle and right-hand panels). Further, the cells could be enriched using anti-CD34 immunomagnetic beads (FIG. 34A) and were efficiently eliminated by exposure to the AP1903 dimerizer drug (FIG. 34B). Finally, the native TCR in HA-1$^H$ TCR CD4$^+$ and CD8$^+$ T cells in the cell product was evaluated using TCR immunosequencing (Adaptive Biotechnologies) and a diverse polyclonal population was observed (data not shown). Moreover, the product contained numerous very-low-frequency TCR, a finding that has recently been associated with the potential for persistence and expansion after adoptive T cell transfer (Chapuis et al., *Sci. Immunol.* 2(8) (2017).

Example 7

Clinical Study Using the HA-1$^H$ T Cell Therapy Product

A feasibility and safety study is conducted using the HA-1$^H$ cell therapy product described in Example 5 (CD8$^+$ and CD4$^+$ memory T cells transduced with pRRLSIN iC9-HA-1$^H$-TCR2-RQR-CD8; abbreviated hereafter as "HA-1$^H$ TCR LV"). The patient sample comprises children, adolescents and adults with recurrent leukemia (AML, ALL, another acute leukemia, or CML). Specifically, patients aged 0-70 are enrolled into two age groups of approximately 12 subjects each: one group aged ≥16 years, and one group aged <16 years. group. All patients express HLA-A*0201 and have the HA-1(H) genotype (RS_1801284: A/G, A/A). The patients also have an adult donor for HCT who is adequately HLA-matched by institutional standards, and are currently undergoing or have previously undergone allogeneic HCT for AML, ALL, another type of acute leukemia, or chronic myeloid leukemia.

Bone marrow samples are taken subsequent to a suspected relapse. Patients then generally receive lymphodepleting chemotherapy (fludarabine) prior to infusion with the T cell product. Thereafter, patients are administered a single dose of HA-1$^H$ TCR LV-T cells (approx. 1:1 CD4$^+$:CD8$^+$ T$_M$) when three criteria are satisfied: (1) there is evidence of recurrent or refractory disease after HCT; (2) HA-1$^H$ TCR T cells have been generated; and (3) lymphodepleting chemotherapy has been administered (if indicated). HA-1$^H$ TCR LV-T cells are administered by infusion (as rapidly as tolerated through a central venous catheter via gravity or a syringe pump) according to the dosage schedule provided in Table 2.

TABLE 2

Clinical Dosing Schedule

| Dose level | Dose (HA-1$^H$ TCR T cells) | |
| --- | --- | --- |
| −1 | Up to 3 × 10$^5$/kg | |
| 0 | Up to 1 × 10$^6$/kg | |
| 1 | Up to 3 × 10$^6$/kg | Starting dose |
| 2 | Up to 10 × 10$^6$/kg | |
| 3 | Up to 30 × 10$^6$/kg | |

At least 1-2 subjects ≥16 y. o. are treated prior to treatment of a subject in the younger cohort. In each age group (≥16 and <16 years old), patients are treated in cohorts of three or more patients at one of five dose levels of HA-1$^H$ TCR T cells, starting at dose level 1 (3 ×10$^6$ HA-1$^H$ TCR T cells/kg). A 28-day period between administration of the investigational agent to consecutive subjects within each age group is observed. Bone marrow samples are taken at days 4, 18, and 32 following infusion of the T cell product. Other aspects of the study include monitoring: the in vivo persistence of transferred HA-1$^H$ TCR T cells in peripheral blood; the ability of HA-1$^H$ TCR T cells to migrate to bone marrow; the function of HA-1$^H$ TCR T cells before and, if possible, after adoptive T cell transfer; whether infusion of HA-1$^H$ TCR T cells is followed by a reduction of leukemia burden; whether infusion of HA-1$^H$ TCR T cells is followed by a reduction of recipient hematopoietic chimerism; and whether infusion of HA-1$^H$ TCR T cells is followed by the appearance or recurrence of signs or symptoms of graft-versus-host disease (GVHD).

U.S. Provisional Patent Application No. 62/399,291, filed Sep. 23, 2016, to which the present application claims priority, is hereby incorporated herein by reference in its entirety.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. An engineered immune cell, comprising a heterologous polynucleotide encoding a binding protein that includes:
   (a) a TCR α-chain variable (Vα) domain comprising a CDR3 amino acid sequence of SEQ ID NO: 88, a CDR2 amino acid sequence of SEQ ID NO: 136, and a CDR1 amino acid sequence of SEQ ID NO: 135; and
   (b) a TCR β-chain variable (Vβ) domain comprising a CDR3 amino acid sequence of SEQ ID NO: 14, a CDR2 amino acid sequence of SEQ ID NO: 134, and a CDR1 amino acid sequence of SEQ ID NO: 133,
   wherein the encoded binding protein is capable of specifically binding to a peptide containing an HA-1H antigen and does not bind to a peptide that does not contain an HA-1H antigen.

2. The engineered immune cell of claim 1, wherein the encoded binding protein is capable of specifically binding to a HA-1H peptide:HLA complex.

3. The engineered immune cell of claim 2, wherein the HLA comprises HLA-A*0201.

4. The engineered immune cell of claim 1, further comprising a heterologous polynucleotide encoding:
   (a) a safety switch protein;
   (b) a selection marker;
   (c) a CD8 co-receptor β-chain; and/or
   (d) a CD8 co-receptor α-chain.

5. The engineered immune cell of claim 1, wherein
   the encoded Vβ domain has at least 90% identity to the amino acid sequence of SEQ ID NO: 3 or 98, and the encoded Vα domain has at least 90% identity to the amino acid sequence of SEQ ID NO: 4 or 99.

6. The engineered immune cell of claim 5, wherein
   the encoded Vβ domain comprises the amino acid sequence of SEQ ID NO: 3 or 98, and the encoded Vα domain comprises the amino acid sequence of SEQ ID NO: 4 or 99.

7. The engineered immune cell of claim 1, wherein the encoded binding protein comprises a TCR α-chain having at least 90% identity to the amino acid sequence of SEQ ID NO: 30 or 111.

8. The engineered immune cell of claim 1, wherein the encoded binding protein comprises a TCR β-chain having at least 90% identity to the amino acid sequence of SEQ ID NO: 29 or 110.

9. The engineered immune cell of claim 1, wherein the encoded binding protein comprises:
   (i) a TCR β-chain comprising or consisting of the amino acid sequence of SEQ ID NO: 29, and a TCR α-chain comprising or consisting of the amino acid sequence of SEQ ID NO: 30; or
   (ii) a TCR β-chain comprising or consisting of the amino acid sequence of SEQ ID NO: 110, and a TCR α-chain comprising or consisting of the amino acid sequence of SEQ ID NO: 111.

10. The engineered immune cell of claim 9, wherein the (i) heterologous polynucleotide encoding the TCR α-chain and the (ii) heterologous polynucleotide encoding the TCR β-chain are contained in a single open reading frame, wherein the single open reading frame further comprises a polynucleotide encoding a self-cleaving peptide disposed between (i) and (ii).

11. The engineered immune cell of claim 10, wherein the encoded binding protein comprises the amino acid sequence of SEQ ID NO: 54.

12. An engineered immune cell, comprising a heterologous transgene polynucleotide comprising or consisting of the nucleotide sequence of SEQ ID NO: 85.

13. The engineered immune cell of claim 1, wherein the immune cell is a T cell, a NK cell, or a NK-T cell.

14. The engineered immune cell of claim 1, wherein the peptide containing an HA-1H antigen comprises the amino acid sequence VLHDDLLEA (SEQ ID NO:66).

15. The engineered immune cell of claim 1, wherein the Vα domain is encoded by a TRAV21 gene, and the Vβ domain is encoded by a TRBV7-9 gene.

16. The engineered immune cell of claim 15, wherein the TRAV21 gene comprises TRAV21*02 and the TRBV7-9 gene comprises TRB7*03.

17. The engineered immune cell of claim 15, wherein the heterologous polynucleotide encoding a binding protein further comprises a TRAJ40*01 gene, a TRBD1*01 gene, and a TRBJ1-4*01 gene.

18. A composition, comprising an engineered immune cell of claim 1 and a pharmaceutically acceptable carrier, diluent, or excipient.

19. An engineered immune cell, comprising a heterologous polynucleotide encoding a binding protein that includes:
   (a) a TCR α-chain variable (Vα) domain, wherein the encoded Vα domain
      (i) comprises a CDR3 amino acid sequence of SEQ ID NO: 88, and (ii) has at least about 90% sequence identity to the Vα domain amino acid sequence of SEQ ID NOs: 3 or 98, provided that the encoded Vα domain comprises no change in amino acid sequence of CDR1 and CDR2, and;

(b) a TCR β-chain variable (Vβ) domain, wherein encoded the Vβ domain (i) comprises a CDR3 amino acid sequence of SEQ ID NO: 14, and (ii) has at least about 90% sequence identity to the amino acid sequence of SEQ ID NOs: 3 or 98, provided that the encoded Vβ domain comprises no change in amino acid sequence of CDR1 and CDR2, wherein the encoded binding protein is capable of specifically binding to a peptide containing an HA-1H antigen and does not bind to a peptide that does not contain an HA-1H antigen.

* * * * *

UNITED STATES PATENT AND TRADEMARK OFFICE
CERTIFICATE OF CORRECTION

PATENT NO. : 10,538,574 B2  
APPLICATION NO. : 16/362551  
DATED : January 21, 2020  
INVENTOR(S) : Marie Bleakley Page 1 of 1

It is certified that error appears in the above-identified patent and that said Letters Patent is hereby corrected as shown below:

On the Title Page

Page 3, item [56], Line 23:
"HA-1H" should read --HA-1$^H$--

In the Claims

Column 209, Claim 19, Lines 2-3, part (a)(ii):
"SEQ ID NOs: 3 or 98" should read --SEQ ID NO:4 or 99--

Column 209, Claim 19, Line 11, part (b)(ii):
"SEQ ID NOs: 3 or 98" should read --SEQ ID NO:3 or 98--

Signed and Sealed this  
Seventeenth Day of November, 2020

Andrei Iancu  
*Director of the United States Patent and Trademark Office*

SEQUENCE LISTING

```
<160> NUMBER OF SEQ ID NOS: 136

<210> SEQ ID NO 1
<211> LENGTH: 133
<212> TYPE: PRT
<213> ORGANISM: Artificial Sequence
<220> FEATURE:
<223> OTHER INFORMATION: Synthetic sequence TCR1,13 beta chain variable
      region with signal peptide

<400> SEQUENCE: 1

Met Gly Thr Ser Leu Leu Cys Trp Met Ala Leu Cys Leu Leu Gly Ala
1               5                   10                  15

Asp His Ala Asp Thr Gly Val Ser Gln Asp Pro Arg His Lys Ile Thr
            20                  25                  30

Lys Arg Gly Gln Asn Val Thr Phe Arg Cys Asp Pro Ile Ser Glu His
        35                  40                  45

Asn Arg Leu Tyr Trp Tyr Arg Gln Thr Leu Gly Gln Gly Pro Glu Phe
    50                  55                  60

Leu Thr Tyr Phe Gln Asn Glu Ala Gln Leu Glu Lys Ser Arg Leu Leu
65                  70                  75                  80

Ser Asp Arg Phe Ser Ala Glu Arg Pro Lys Gly Ser Phe Ser Thr Leu
                85                  90                  95
```

```
Glu Ile Gln Arg Thr Glu Gln Gly Asp Ser Ala Met Tyr Leu Cys Ala
                100                 105                 110

Ser Ser Ser Thr Gly Gly His Asn Glu Gln Phe Phe Gly Pro Gly Thr
        115                 120                 125

Arg Leu Thr Val Leu
        130

<210> SEQ ID NO 2
<211> LENGTH: 134
<212> TYPE: PRT
<213> ORGANISM: Artificial Sequence
<220> FEATURE:
<223> OTHER INFORMATION: Synthetic sequence TCR1,13 alpha chain variable
      region with signal peptide

<400> SEQUENCE: 2

Met Glu Thr Leu Leu Gly Val Ser Leu Val Ile Leu Trp Leu Gln Leu
1               5                   10                  15

Ala Arg Val Asn Ser Gln Gln Gly Glu Glu Asp Pro Gln Ala Leu Ser
            20                  25                  30

Ile Gln Glu Gly Glu Asn Ala Thr Met Asn Cys Ser Tyr Lys Thr Ser
        35                  40                  45

Ile Asn Asn Leu Gln Trp Tyr Arg Gln Asn Ser Gly Arg Gly Leu Val
    50                  55                  60

His Leu Ile Leu Ile Arg Ser Asn Glu Arg Glu Lys His Ser Gly Arg
65                  70                  75                  80

Leu Arg Val Thr Leu Asp Thr Ser Lys Lys Ser Ser Ser Leu Leu Ile
                85                  90                  95

Thr Ala Ser Arg Ala Ala Asp Thr Ala Ser Tyr Phe Cys Ala Thr Lys
            100                 105                 110

Arg Asp Ser Gly Ala Gly Ser Tyr Gln Leu Thr Phe Gly Lys Gly Thr
        115                 120                 125

Lys Leu Ser Val Ile Pro
        130

<210> SEQ ID NO 3
<211> LENGTH: 132
<212> TYPE: PRT
<213> ORGANISM: Artificial Sequence
<220> FEATURE:
<223> OTHER INFORMATION: Synthetic sequence TCR2,14 beta chain variable
      region with signal peptide

<400> SEQUENCE: 3

Met Gly Thr Ser Leu Leu Cys Trp Met Ala Leu Cys Leu Leu Gly Ala
1               5                   10                  15

Asp His Ala Asp Thr Gly Val Ser Gln Asp Pro Arg His Lys Ile Thr
            20                  25                  30

Lys Arg Gly Gln Asn Val Thr Phe Arg Cys Asp Pro Ile Ser Glu His
        35                  40                  45

Asn Arg Leu Tyr Trp Tyr Arg Gln Thr Leu Gly Gln Gly Pro Glu Phe
    50                  55                  60

Leu Thr Tyr Phe Gln Asn Glu Ala Gln Leu Glu Lys Ser Arg Leu Leu
65                  70                  75                  80

Ser Asp Arg Phe Ser Ala Glu Arg Pro Lys Gly Ser Phe Ser Thr Leu
                85                  90                  95

Glu Ile Gln Arg Thr Glu Gln Gly Asp Ser Ala Met Tyr Leu Cys Ala
            100                 105                 110
```

Ser Ser Leu Val Lys Gly Glu Lys Leu Phe Phe Gly Ser Gly Thr Gln Leu
            115                 120                 125

Ser Val Leu
    130

<210> SEQ ID NO 4
<211> LENGTH: 132
<212> TYPE: PRT
<213> ORGANISM: Artificial Sequence
<220> FEATURE:
<223> OTHER INFORMATION: Synthetic sequence TCR2,14 alpha chain variable
      region with signal peptide

<400> SEQUENCE: 4

Met Glu Thr Leu Leu Gly Leu Leu Ile Leu Trp Leu Gln Leu Gln Trp
1               5                   10                  15

Val Ser Ser Lys Gln Glu Val Thr Gln Ile Pro Ala Ala Leu Ser Val
            20                  25                  30

Pro Glu Gly Glu Asn Leu Val Leu Asn Cys Ser Phe Thr Asp Ser Ala
        35                  40                  45

Ile Tyr Asn Leu Gln Trp Phe Arg Gln Asp Pro Gly Lys Gly Leu Thr
    50                  55                  60

Ser Leu Leu Leu Ile Gln Ser Ser Gln Arg Glu Gln Thr Ser Gly Arg
65                  70                  75                  80

Leu Asn Ala Ser Leu Asp Lys Ser Ser Gly Arg Ser Thr Leu Tyr Ile Ala
                85                  90                  95

Ala Ser Gln Pro Gly Asp Ser Ala Thr Tyr Leu Cys Ala Val Ile Gly
            100                 105                 110

Leu Gly Gly Thr Tyr Lys Tyr Ile Phe Gly Thr Gly Thr Arg Leu Lys
        115                 120                 125

Val Leu Ala
    130

<210> SEQ ID NO 5
<211> LENGTH: 132
<212> TYPE: PRT
<213> ORGANISM: Artificial Sequence
<220> FEATURE:
<223> OTHER INFORMATION: Synthetic sequence TCR5 beta chain variable
      region with signal peptide

<400> SEQUENCE: 5

Met Gly Thr Ser Leu Leu Cys Trp Met Ala Leu Cys Leu Leu Gly Ala
1               5                   10                  15

Asp His Ala Asp Thr Gly Val Ser Gln Asp Pro Arg His Lys Ile Thr
            20                  25                  30

Lys Arg Gly Gln Asn Val Thr Phe Arg Cys Asp Pro Ile Ser Glu His
        35                  40                  45

Asn Arg Leu Tyr Trp Tyr Arg Gln Thr Leu Gly Gln Gly Pro Glu Phe
    50                  55                  60

Leu Thr Tyr Phe Gln Asn Glu Ala Gln Leu Glu Lys Ser Arg Leu Leu
65                  70                  75                  80

Ser Asp Arg Phe Ser Ala Glu Arg Pro Lys Gly Ser Phe Ser Thr Leu
                85                  90                  95

Glu Ile Gln Arg Thr Glu Gln Gly Asp Ser Ala Met Tyr Leu Cys Ala
            100                 105                 110

Ser Ser Leu Thr Thr Leu Asp Glu Gln Tyr Val Gly Pro Gly Thr Arg
        115                 120                 125

```
Leu Thr Val Thr
    130

<210> SEQ ID NO 6
<211> LENGTH: 130
<212> TYPE: PRT
<213> ORGANISM: Artificial Sequence
<220> FEATURE:
<223> OTHER INFORMATION: Synthetic sequence TCR5 alpha chain variable
      region with signal peptide

<400> SEQUENCE: 6

Met Glu Thr Leu Leu Gly Val Ser Leu Val Ile Leu Trp Leu Gln Leu
1               5                   10                  15

Ala Arg Val Asn Ser Gln Gln Gly Glu Glu Asp Pro Gln Ala Leu Ser
            20                  25                  30

Ile Gln Glu Gly Glu Asn Ala Thr Met Asn Cys Ser Tyr Lys Thr Ser
        35                  40                  45

Ile Asn Asn Leu Gln Trp Tyr Arg Gln Asn Ser Gly Arg Gly Leu Val
    50                  55                  60

His Leu Ile Leu Ile Arg Ser Asn Glu Arg Glu Lys His Ser Gly Arg
65                  70                  75                  80

Leu Arg Val Thr Leu Asp Thr Ser Lys Lys Ser Ser Ser Leu Leu Ile
                85                  90                  95

Thr Ala Ser Arg Ala Ala Asp Thr Ala Ser Tyr Phe Cys Ala Thr Asn
            100                 105                 110

Ser Gly Asn Thr Pro Leu Val Phe Gly Lys Gly Thr Arg Leu Ser Val
        115                 120                 125

Ile Ala
    130

<210> SEQ ID NO 7
<211> LENGTH: 132
<212> TYPE: PRT
<213> ORGANISM: Artificial Sequence
<220> FEATURE:
<223> OTHER INFORMATION: Synthetic sequence TCR10 beta chain variable
      region with signal peptide

<400> SEQUENCE: 7

Met Gly Thr Ser Leu Leu Cys Trp Met Ala Leu Cys Leu Leu Gly Ala
1               5                   10                  15

Asp His Ala Asp Thr Gly Val Ser Gln Asp Pro Arg His Lys Ile Thr
            20                  25                  30

Lys Arg Gly Gln Asn Val Thr Phe Arg Cys Asp Pro Ile Ser Glu His
        35                  40                  45

Asn Arg Leu Tyr Trp Tyr Arg Gln Thr Leu Gly Gln Gly Pro Glu Phe
    50                  55                  60

Leu Thr Tyr Phe Gln Asn Glu Ala Gln Leu Glu Lys Ser Arg Leu Leu
65                  70                  75                  80

Ser Asp Arg Phe Ser Ala Glu Arg Pro Lys Gly Ser Phe Ser Thr Leu
                85                  90                  95

Glu Ile Gln Arg Thr Glu Gln Gly Asp Ser Ala Met Tyr Leu Cys Ala
            100                 105                 110

Ser Ser Met Leu Thr Asn Tyr Glu Gln Tyr Phe Gly Pro Gly Thr Arg
        115                 120                 125

Leu Thr Val Thr
    130
```

<210> SEQ ID NO 8
<211> LENGTH: 134
<212> TYPE: PRT
<213> ORGANISM: Artificial Sequence
<220> FEATURE:
<223> OTHER INFORMATION: Synthetic sequence TCR10 alpha chain variable
      region with signal peptide

<400> SEQUENCE: 8

Met Lys Lys His Leu Thr Thr Phe Leu Val Ile Leu Trp Leu Tyr Phe
1               5                   10                  15

Tyr Arg Gly Asn Gly Lys Asn Gln Val Glu Gln Ser Pro Gln Ser Leu
                20                  25                  30

Ile Ile Leu Glu Gly Lys Asn Cys Thr Leu Gln Cys Asn Tyr Thr Val
            35                  40                  45

Ser Pro Phe Ser Asn Leu Arg Trp Tyr Lys Gln Asp Thr Gly Arg Gly
50                  55                  60

Pro Val Ser Leu Thr Ile Met Thr Phe Ser Glu Asn Thr Lys Ser Asn
65                  70                  75                  80

Gly Arg Tyr Thr Ala Thr Leu Asp Ala Asp Thr Lys Gln Ser Ser Leu
                85                  90                  95

His Ile Thr Ala Ser Gln Leu Ser Asp Ser Ala Ser Tyr Ile Cys Val
            100                 105                 110

Val Asp Ser Gly Gly Gly Ala Asp Gly Leu Thr Phe Gly Lys Gly Thr
        115                 120                 125

His Leu Ile Ile Gln Pro
    130

<210> SEQ ID NO 9
<211> LENGTH: 132
<212> TYPE: PRT
<213> ORGANISM: Artificial Sequence
<220> FEATURE:
<223> OTHER INFORMATION: Synthetic sequence TCR16 beta chain variable
      region with signal peptide

<400> SEQUENCE: 9

Met Gly Thr Ser Leu Leu Cys Trp Met Ala Leu Cys Leu Leu Gly Ala
1               5                   10                  15

Asp His Ala Asp Thr Gly Val Ser Gln Asp Pro Arg His Lys Ile Thr
                20                  25                  30

Lys Arg Gly Gln Asn Val Thr Phe Arg Cys Asp Pro Ile Ser Glu His
            35                  40                  45

Asn Arg Leu Tyr Trp Tyr Arg Gln Thr Leu Gly Gln Gly Pro Glu Phe
50                  55                  60

Leu Thr Tyr Phe Gln Asn Glu Ala Gln Leu Glu Lys Ser Arg Leu Leu
65                  70                  75                  80

Ser Asp Arg Phe Ser Ala Glu Arg Pro Lys Gly Ser Phe Ser Thr Leu
                85                  90                  95

Glu Ile Gln Arg Thr Glu Gln Gly Asp Ser Ala Met Tyr Leu Cys Ala
            100                 105                 110

Ser Ser Leu Val Val Gly Asn Glu Gln Phe Phe Gly Pro Gly Thr Arg
        115                 120                 125

Leu Thr Val Leu
    130

<210> SEQ ID NO 10
<211> LENGTH: 131

```
<212> TYPE: PRT
<213> ORGANISM: Artificial Sequence
<220> FEATURE:
<223> OTHER INFORMATION: Synthetic sequence TCR16 alpha chain variable
      region with signal peptide

<400> SEQUENCE: 10

Met Glu Thr Leu Leu Gly Leu Leu Ile Leu Trp Leu Gln Leu Gln Trp
1               5                   10                  15

Val Ser Ser Lys Gln Glu Val Thr Gln Ile Pro Ala Ala Leu Ser Val
            20                  25                  30

Pro Glu Gly Glu Asn Leu Val Leu Asn Cys Ser Phe Thr Asp Ser Ala
        35                  40                  45

Ile Tyr Asn Leu Gln Trp Phe Arg Gln Asp Pro Gly Lys Gly Leu Thr
    50                  55                  60

Ser Leu Leu Leu Ile Gln Ser Ser Gln Arg Glu Gln Thr Ser Gly Arg
65                  70                  75                  80

Leu Asn Ala Ser Leu Asp Lys Ser Ser Gly Arg Ser Thr Leu Tyr Ile
                85                  90                  95

Ala Ala Ser Gln Pro Gly Asp Ser Ala Thr Tyr Leu Cys Ala Val His
            100                 105                 110

Leu Leu Asn Asp Tyr Lys Leu Ser Phe Gly Ala Gly Thr Thr Val Thr
        115                 120                 125

Val Arg Ala
    130

<210> SEQ ID NO 11
<211> LENGTH: 132
<212> TYPE: PRT
<213> ORGANISM: Artificial Sequence
<220> FEATURE:
<223> OTHER INFORMATION: Synthetic sequence TCR29 beta chain variable
      region with signal peptide

<400> SEQUENCE: 11

Met Gly Thr Ser Leu Leu Cys Trp Met Ala Leu Cys Leu Leu Gly Ala
1               5                   10                  15

Asp His Ala Asp Thr Gly Val Ser Gln Asp Pro Arg His Lys Ile Thr
            20                  25                  30

Lys Arg Gly Gln Asn Val Thr Phe Arg Cys Asp Pro Ile Ser Glu His
        35                  40                  45

Asn Arg Leu Tyr Trp Tyr Arg Gln Thr Leu Gly Gln Gly Pro Glu Phe
    50                  55                  60

Leu Thr Tyr Phe Gln Asn Glu Ala Gln Leu Glu Lys Ser Arg Leu Leu
65                  70                  75                  80

Ser Asp Arg Phe Ser Ala Glu Arg Pro Lys Gly Ser Phe Ser Thr Leu
                85                  90                  95

Glu Ile Gln Arg Thr Glu Gln Gly Asp Ser Ala Met Tyr Leu Cys Ala
            100                 105                 110

Ser Ser Leu Val Ser Gly Asn Thr Ile Tyr Phe Gly Glu Gly Ser Trp
        115                 120                 125

Leu Thr Val Val
    130

<210> SEQ ID NO 12
<211> LENGTH: 134
<212> TYPE: PRT
<213> ORGANISM: Artificial Sequence
<220> FEATURE:
```

<223> OTHER INFORMATION: Synthetic sequence TCR29 alpha chain variable
      region with signal peptide

<400> SEQUENCE: 12

Met Glu Thr Leu Leu Gly Leu Leu Ile Leu Trp Leu Gln Leu Gln Trp
1               5                   10                  15

Val Ser Ser Lys Gln Glu Val Thr Gln Ile Pro Ala Ala Leu Ser Val
            20                  25                  30

Pro Glu Gly Glu Asn Leu Val Leu Asn Cys Ser Phe Thr Asp Ser Ala
        35                  40                  45

Ile Tyr Asn Leu Gln Trp Phe Arg Gln Asp Pro Gly Lys Gly Leu Thr
    50                  55                  60

Ser Leu Leu Leu Ile Gln Ser Ser Gln Arg Glu Gln Thr Ser Gly Arg
65                  70                  75                  80

Leu Asn Ala Ser Leu Asp Lys Ser Ser Gly Arg Ser Thr Leu Tyr Ile
                85                  90                  95

Ala Ala Ser Gln Pro Gly Asp Ser Ala Thr Tyr Leu Cys Ala Val Arg
            100                 105                 110

Gly Gly Thr Thr Ser Gly Thr Tyr Lys Tyr Ile Phe Gly Thr Gly Thr
        115                 120                 125

Arg Leu Lys Val Leu Ala
    130

<210> SEQ ID NO 13
<211> LENGTH: 14
<212> TYPE: PRT
<213> ORGANISM: Artificial Sequence
<220> FEATURE:
<223> OTHER INFORMATION: Synthetic sequence TCR1 beta chain CDR3

<400> SEQUENCE: 13

Cys Ala Ser Ser Ser Thr Gly Gly His Asn Glu Gln Phe Phe
1               5                   10

<210> SEQ ID NO 14
<211> LENGTH: 12
<212> TYPE: PRT
<213> ORGANISM: Artificial Sequence
<220> FEATURE:
<223> OTHER INFORMATION: Synthetic sequence TCR2 beta chain CDR3

<400> SEQUENCE: 14

Cys Ala Ser Ser Leu Val Lys Gly Glu Lys Leu Phe
1               5                   10

<210> SEQ ID NO 15
<211> LENGTH: 13
<212> TYPE: PRT
<213> ORGANISM: Artificial Sequence
<220> FEATURE:
<223> OTHER INFORMATION: Synthetic sequence TCR5 beta chain CDR3

<400> SEQUENCE: 15

Cys Ala Ser Ser Leu Thr Thr Leu Asp Glu Gln Tyr Val
1               5                   10

<210> SEQ ID NO 16
<211> LENGTH: 13
<212> TYPE: PRT
<213> ORGANISM: Artificial Sequence
<220> FEATURE:
<223> OTHER INFORMATION: Synthetic sequence TCR10 beta chain CDR3

```
<400> SEQUENCE: 16

Cys Ala Ser Ser Met Leu Thr Asn Tyr Glu Gln Tyr Phe
1               5                   10

<210> SEQ ID NO 17
<211> LENGTH: 13
<212> TYPE: PRT
<213> ORGANISM: Artificial Sequence
<220> FEATURE:
<223> OTHER INFORMATION: Synthetic sequence TCR16 beta chain CDR3

<400> SEQUENCE: 17

Cys Ala Ser Ser Leu Val Val Gly Asn Glu Gln Phe Phe
1               5                   10

<210> SEQ ID NO 18
<211> LENGTH: 177
<212> TYPE: PRT
<213> ORGANISM: Artificial Sequence
<220> FEATURE:
<223> OTHER INFORMATION: Synthetic sequence TCR1,5,10,13,16 beta chain
      constant region (Cys modified)

<400> SEQUENCE: 18

Glu Asp Leu Lys Asn Val Phe Pro Pro Glu Val Ala Val Phe Glu Pro
1               5                   10                  15

Ser Glu Ala Glu Ile Ser His Thr Gln Lys Ala Thr Leu Val Cys Leu
            20                  25                  30

Ala Thr Gly Phe Tyr Pro Asp His Val Glu Leu Ser Trp Trp Val Asn
        35                  40                  45

Gly Lys Glu Val His Ser Gly Val Cys Thr Asp Pro Gln Pro Leu Lys
    50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Glu Trp Thr Gln Asp
            100                 105                 110

Arg Ala Lys Pro Val Thr Gln Ile Val Ser Ala Glu Ala Trp Gly Arg
        115                 120                 125

Ala Asp Cys Gly Phe Thr Ser Glu Ser Tyr Gln Gln Gly Val Leu Ser
    130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Ser

<210> SEQ ID NO 19
<211> LENGTH: 141
<212> TYPE: PRT
<213> ORGANISM: Artificial Sequence
<220> FEATURE:
<223> OTHER INFORMATION: Synthetic sequence TCR1,13 alpha chain constant
      region

<400> SEQUENCE: 19

Asn Ile Gln Asn Pro Asp Pro Ala Val Tyr Gln Leu Arg Asp Ser Lys
1               5                   10                  15

Ser Ser Asp Lys Ser Val Cys Leu Phe Thr Asp Phe Asp Ser Gln Thr
```

```
                    20                  25                  30

Asn Val Ser Gln Ser Lys Asp Ser Asp Val Tyr Ile Thr Asp Lys Cys
                35                  40                  45

Val Leu Asp Met Arg Ser Met Asp Phe Lys Ser Asn Ser Ala Val Ala
        50                  55                  60

Trp Ser Asn Lys Ser Asp Phe Ala Cys Ala Asn Ala Phe Asn Asn Ser
65                  70                  75                  80

Ile Ile Pro Glu Asp Thr Phe Phe Pro Ser Pro Glu Ser Ser Cys Asp
                85                  90                  95

Val Lys Leu Val Glu Lys Ser Phe Glu Thr Asp Thr Asn Leu Asn Phe
            100                 105                 110

Gln Asn Leu Ser Val Ile Gly Phe Arg Ile Leu Leu Leu Lys Val Ala
            115                 120                 125

Gly Phe Asn Leu Leu Met Thr Leu Arg Leu Trp Ser Ser
            130                 135                 140

<210> SEQ ID NO 20
<211> LENGTH: 201
<212> TYPE: PRT
<213> ORGANISM: Artificial Sequence
<220> FEATURE:
<223> OTHER INFORMATION: Synthetic sequence TCR5 alpha chain constant
      region (Cys modified)

<400> SEQUENCE: 20

Asn Ile Gln Asn Pro Asp Pro Ala Val Tyr Gln Leu Arg Asp Ser Lys
1               5                   10                  15

Ser Ser Asp Lys Ser Val Cys Leu Phe Thr Asp Phe Asp Ser Gln Thr
                20                  25                  30

Asn Val Ser Gln Ser Lys Asp Ser Asp Val Tyr Ile Thr Asp Lys Cys
                35                  40                  45

Val Leu Asp Met Arg Ser Met Asp Phe Lys Ser Asn Ser Ala Val Ala
        50                  55                  60

Trp Ser Asn Lys Ser Asp Phe Ala Cys Ala Asn Ala Phe Asn Asn Ser
65                  70                  75                  80

Ile Ile Pro Glu Asp Thr Phe Phe Pro Ser Pro Glu Ser Ser Cys Asp
                85                  90                  95

Val Lys Leu Val Glu Lys Ser Phe Glu Thr Asp Thr Asn Leu Asn Phe
            100                 105                 110

Gln Asn Leu Ser Val Ile Gly Phe Arg Ile Leu Leu Leu Lys Val Ala
            115                 120                 125

Gly Phe Asn Leu Leu Met Thr Leu Arg Leu Trp Ser Ser Phe Ala Cys
            130                 135                 140

Ala Asn Ala Phe Asn Asn Ser Ile Ile Pro Glu Asp Thr Phe Phe Pro
145                 150                 155                 160

Ser Pro Glu Ser Ser Cys Asp Val Lys Leu Val Glu Lys Ser Phe Glu
                165                 170                 175

Thr Asp Thr Asn Leu Asn Phe Gln Asn Leu Ser Val Ile Gly Phe Arg
            180                 185                 190

Ile Leu Leu Leu Lys Val Ala Gly Phe
            195                 200

<210> SEQ ID NO 21
<211> LENGTH: 81
<212> TYPE: PRT
<213> ORGANISM: Artificial Sequence
<220> FEATURE:
```

<223> OTHER INFORMATION: Synthetic sequence TCR10 alpha chain constant
      region

<400> SEQUENCE: 21

Tyr Ile Gln Asn Pro Asp Pro Ala Val Tyr Gln Leu Arg Asp Ser Lys
1               5                   10                  15

Ser Ser Asp Lys Ser Val Cys Leu Phe Thr Asp Phe Asp Ser Gln Thr
            20                  25                  30

Asn Val Ser Gln Ser Lys Asp Ser Asp Val Tyr Ile Thr Asp Lys Cys
        35                  40                  45

Val Leu Asp Met Arg Ser Met Asp Phe Lys Ser Asn Ser Ala Val Ala
    50                  55                  60

Trp Ser Asn Lys Ser Asp Asn Leu Leu Met Thr Leu Arg Leu Trp Ser
65                  70                  75                  80

Ser

<210> SEQ ID NO 22
<211> LENGTH: 141
<212> TYPE: PRT
<213> ORGANISM: Artificial Sequence
<220> FEATURE:
<223> OTHER INFORMATION: Synthetic sequence TCR16 alpha chain constant
      region (Cys modified)

<400> SEQUENCE: 22

Asn Ile Gln Asn Pro Asp Pro Ala Val Tyr Gln Leu Arg Asp Ser Lys
1               5                   10                  15

Ser Ser Asp Lys Ser Val Cys Leu Phe Thr Asp Phe Asp Ser Gln Thr
            20                  25                  30

Asn Val Ser Gln Ser Lys Asp Ser Asp Val Tyr Ile Thr Asp Lys Cys
        35                  40                  45

Val Leu Asp Met Arg Ser Met Asp Phe Lys Ser Asn Ser Ala Val Ala
    50                  55                  60

Trp Ser Asn Lys Ser Asp Phe Ala Cys Ala Asn Ala Phe Asn Asn Ser
65                  70                  75                  80

Ile Ile Pro Glu Asp Thr Phe Phe Pro Ser Pro Glu Ser Ser Cys Asp
                85                  90                  95

Val Lys Leu Val Glu Lys Ser Phe Glu Thr Asp Thr Asn Leu Asn Phe
            100                 105                 110

Gln Asn Leu Ser Val Ile Gly Phe Arg Ile Leu Leu Leu Lys Val Ala
        115                 120                 125

Gly Phe Asn Leu Leu Met Thr Leu Arg Leu Trp Ser Ser
    130                 135                 140

<210> SEQ ID NO 23
<211> LENGTH: 176
<212> TYPE: PRT
<213> ORGANISM: Artificial Sequence
<220> FEATURE:
<223> OTHER INFORMATION: Synthetic sequence TCR2,14 beta chain constant
      region (Cys modified)

<400> SEQUENCE: 23

Glu Asp Leu Asn Lys Val Phe Pro Pro Glu Val Ala Val Phe Glu Pro
1               5                   10                  15

Ser Glu Ala Glu Ile Ser His Thr Gln Lys Ala Thr Leu Val Cys Leu
            20                  25                  30

Ala Thr Gly Phe Phe Pro Asp His Val Glu Leu Ser Trp Trp Val Asn
        35                  40                  45

-continued

Gly Lys Glu Val His Ser Gly Val Cys Thr Asp Pro Gln Pro Leu Lys
            50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Glu Trp Thr Gln Asp
            100                 105                 110

Arg Ala Lys Pro Val Thr Gln Ile Val Ser Ala Glu Ala Trp Gly Arg
        115                 120                 125

Ala Asp Cys Gly Phe Thr Ser Val Ser Tyr Gln Gln Gly Val Leu Ser
    130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

<210> SEQ ID NO 24
<211> LENGTH: 141
<212> TYPE: PRT
<213> ORGANISM: Artificial Sequence
<220> FEATURE:
<223> OTHER INFORMATION: Synthetic sequence TCR2,14 alpha chain constant
      region (Cys modified)

<400> SEQUENCE: 24

Asn Ile Gln Asn Pro Asp Pro Ala Val Tyr Gln Leu Arg Asp Ser Lys
1               5                   10                  15

Ser Ser Asp Lys Ser Val Cys Leu Phe Thr Asp Phe Asp Ser Gln Thr
            20                  25                  30

Asn Val Ser Gln Ser Lys Asp Ser Asp Val Tyr Ile Thr Asp Lys Cys
        35                  40                  45

Val Leu Asp Met Arg Ser Met Asp Phe Lys Ser Asn Ser Ala Val Ala
    50                  55                  60

Trp Ser Asn Lys Ser Asp Phe Ala Cys Ala Asn Ala Phe Asn Asn Ser
65                  70                  75                  80

Ile Ile Pro Glu Asp Thr Phe Phe Pro Ser Pro Glu Ser Ser Cys Asp
                85                  90                  95

Val Lys Leu Val Glu Lys Ser Phe Glu Thr Asp Thr Asn Leu Asn Phe
            100                 105                 110

Gln Asn Leu Ser Val Ile Gly Phe Arg Ile Leu Leu Leu Lys Val Ala
        115                 120                 125

Gly Phe Asn Leu Leu Met Thr Leu Arg Leu Trp Ser Ser
    130                 135                 140

<210> SEQ ID NO 25
<211> LENGTH: 177
<212> TYPE: PRT
<213> ORGANISM: Artificial Sequence
<220> FEATURE:
<223> OTHER INFORMATION: Synthetic sequence TCR29 beta chain constant
      region

<400> SEQUENCE: 25

Glu Asp Leu Asn Lys Val Phe Pro Pro Glu Val Ala Val Phe Glu Pro
1               5                   10                  15

Ser Glu Ala Glu Ile Ser His Thr Gln Lys Ala Thr Leu Val Cys Leu
            20                  25                  30

Ala Thr Gly Phe Phe Pro Asp His Val Glu Leu Ser Trp Trp Val Asn
             35                   40                  45

Gly Lys Glu Val His Ser Gly Val Ser Thr Asp Pro Gln Pro Leu Lys
 50                      55                  60

Glu Gln Pro Ala Leu Asn Asp Ser Arg Tyr Cys Leu Ser Ser Arg Leu
 65                  70                  75                  80

Arg Val Ser Ala Thr Phe Trp Gln Asn Pro Arg Asn His Phe Arg Cys
                 85                  90                  95

Gln Val Gln Phe Tyr Gly Leu Ser Glu Asn Asp Glu Trp Thr Gln Asp
                100                 105                 110

Arg Ala Lys Pro Val Thr Gln Ile Val Ser Ala Glu Ala Trp Gly Arg
                115                 120                 125

Ala Asp Cys Gly Phe Thr Ser Val Ser Tyr Gln Gln Gly Val Leu Ser
                130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Phe

<210> SEQ ID NO 26
<211> LENGTH: 141
<212> TYPE: PRT
<213> ORGANISM: Artificial Sequence
<220> FEATURE:
<223> OTHER INFORMATION: Synthetic sequence TCR29 alpha chain constant
      region

<400> SEQUENCE: 26

Asn Ile Gln Asn Pro Asp Pro Ala Val Tyr Gln Leu Arg Asp Ser Lys
 1               5                  10                  15

Ser Ser Asp Lys Ser Val Cys Leu Phe Thr Asp Phe Asp Ser Gln Thr
                 20                  25                  30

Asn Val Ser Gln Ser Lys Asp Ser Asp Val Tyr Ile Thr Asp Lys Thr
                 35                  40                  45

Val Leu Asp Met Arg Ser Met Asp Phe Lys Ser Asn Ser Ala Val Ala
 50                  55                  60

Trp Ser Asn Lys Ser Asp Phe Ala Cys Ala Asn Ala Phe Asn Asn Ser
 65                  70                  75                  80

Ile Ile Pro Glu Asp Thr Phe Phe Pro Ser Pro Glu Ser Ser Cys Asp
                 85                  90                  95

Val Lys Leu Val Glu Lys Ser Phe Glu Thr Asp Thr Asn Leu Asn Phe
                100                 105                 110

Gln Asn Leu Ser Val Ile Gly Phe Arg Ile Leu Leu Leu Lys Val Ala
                115                 120                 125

Gly Phe Asn Leu Leu Met Thr Leu Arg Leu Trp Ser Ser
                130                 135                 140

<210> SEQ ID NO 27
<211> LENGTH: 310
<212> TYPE: PRT
<213> ORGANISM: Artificial Sequence
<220> FEATURE:
<223> OTHER INFORMATION: Synthetic sequence TCR1,13 beta chain (full
      length) (Cys modified)

<400> SEQUENCE: 27

Met Gly Thr Ser Leu Leu Cys Trp Met Ala Leu Cys Leu Leu Gly Ala
1               5                   10                  15

Asp His Ala Asp Thr Gly Val Ser Gln Asp Pro Arg His Lys Ile Thr
            20                  25                  30

Lys Arg Gly Gln Asn Val Thr Phe Arg Cys Asp Pro Ile Ser Glu His
                35                  40                  45

Asn Arg Leu Tyr Trp Tyr Arg Gln Thr Leu Gly Gln Gly Pro Glu Phe
50                  55                  60

Leu Thr Tyr Phe Gln Asn Glu Ala Gln Leu Glu Lys Ser Arg Leu Leu
65                  70                  75                  80

Ser Asp Arg Phe Ser Ala Glu Arg Pro Lys Gly Ser Phe Ser Thr Leu
                85                  90                  95

Glu Ile Gln Arg Thr Glu Gln Gly Asp Ser Ala Met Tyr Leu Cys Ala
                100                 105                 110

Ser Ser Ser Thr Gly Gly His Asn Glu Gln Phe Phe Gly Pro Gly Thr
                115                 120                 125

Arg Leu Thr Val Leu Glu Asp Leu Lys Asn Val Phe Pro Pro Glu Val
            130                 135                 140

Ala Val Phe Glu Pro Ser Glu Ala Glu Ile Ser His Thr Gln Lys Ala
145                 150                 155                 160

Thr Leu Val Cys Leu Ala Thr Gly Phe Tyr Pro Asp His Val Glu Leu
                165                 170                 175

Ser Trp Trp Val Asn Gly Lys Glu Val His Ser Gly Val Cys Thr Asp
                180                 185                 190

Pro Gln Pro Leu Lys Glu Gln Pro Ala Leu Asn Asp Ser Arg Tyr Cys
                195                 200                 205

Leu Ser Ser Arg Leu Arg Val Ser Ala Thr Phe Trp Gln Asn Pro Arg
210                 215                 220

Asn His Phe Arg Cys Gln Val Gln Phe Tyr Gly Leu Ser Glu Asn Asp
225                 230                 235                 240

Glu Trp Thr Gln Asp Arg Ala Lys Pro Val Thr Gln Ile Val Ser Ala
                245                 250                 255

Glu Ala Trp Gly Arg Ala Asp Cys Gly Phe Thr Ser Glu Ser Tyr Gln
                260                 265                 270

Gln Gly Val Leu Ser Ala Thr Ile Leu Tyr Glu Ile Leu Leu Gly Lys
                275                 280                 285

Ala Thr Leu Tyr Ala Val Leu Val Ser Ala Leu Val Leu Met Ala Met
                290                 295                 300

Val Lys Arg Lys Asp Ser
305                 310

<210> SEQ ID NO 28
<211> LENGTH: 275
<212> TYPE: PRT
<213> ORGANISM: Artificial Sequence
<220> FEATURE:
<223> OTHER INFORMATION: Synthetic sequence TCR1,13 alpha chain (full
      length) (Cys modified) with signal peptide

<400> SEQUENCE: 28

Met Glu Thr Leu Leu Gly Val Ser Leu Val Ile Leu Trp Leu Gln Leu
1               5                   10                  15

Ala Arg Val Asn Ser Gln Gln Gly Glu Glu Asp Pro Gln Ala Leu Ser
            20                  25                  30

Ile Gln Glu Gly Glu Asn Ala Thr Met Asn Cys Ser Tyr Lys Thr Ser
            35                  40                  45

```
Ile Asn Asn Leu Gln Trp Tyr Arg Gln Asn Ser Gly Arg Gly Leu Val
 50                  55                  60

His Leu Ile Leu Ile Arg Ser Asn Glu Arg Glu Lys His Ser Gly Arg
 65                  70                  75                  80

Leu Arg Val Thr Leu Asp Thr Ser Lys Lys Ser Ser Leu Leu Ile
                 85                  90                  95

Thr Ala Ser Arg Ala Ala Asp Thr Ala Ser Tyr Phe Cys Ala Thr Lys
            100                 105                 110

Arg Asp Ser Gly Ala Gly Ser Tyr Gln Leu Thr Phe Gly Lys Gly Thr
        115                 120                 125

Lys Leu Ser Val Ile Pro Asn Ile Gln Asn Pro Asp Pro Ala Val Tyr
    130                 135                 140

Gln Leu Arg Asp Ser Lys Ser Ser Asp Lys Ser Val Cys Leu Phe Thr
145                 150                 155                 160

Asp Phe Asp Ser Gln Thr Asn Val Ser Gln Ser Lys Asp Ser Asp Val
                165                 170                 175

Tyr Ile Thr Asp Lys Cys Val Leu Asp Met Arg Ser Met Asp Phe Lys
            180                 185                 190

Ser Asn Ser Ala Val Ala Trp Ser Asn Lys Ser Asp Phe Ala Cys Ala
        195                 200                 205

Asn Ala Phe Asn Asn Ser Ile Ile Pro Glu Asp Thr Phe Phe Pro Ser
    210                 215                 220

Pro Glu Ser Ser Cys Asp Val Lys Leu Val Glu Lys Ser Phe Glu Thr
225                 230                 235                 240

Asp Thr Asn Leu Asn Phe Gln Asn Leu Ser Val Ile Gly Phe Arg Ile
                245                 250                 255

Leu Leu Leu Lys Val Ala Gly Phe Asn Leu Leu Met Thr Leu Arg Leu
            260                 265                 270

Trp Ser Ser
        275

<210> SEQ ID NO 29
<211> LENGTH: 308
<212> TYPE: PRT
<213> ORGANISM: Artificial Sequence
<220> FEATURE:
<223> OTHER INFORMATION: Synthetic sequence TCR2,14 beta chain (full
      length) (Cys modified) with signal peptide

<400> SEQUENCE: 29

Met Gly Thr Ser Leu Leu Cys Trp Met Ala Leu Cys Leu Leu Gly Ala
1                5                  10                  15

Asp His Ala Asp Thr Gly Val Ser Gln Asp Pro Arg His Lys Ile Thr
            20                  25                  30

Lys Arg Gly Gln Asn Val Thr Phe Arg Cys Asp Pro Ile Ser Glu His
        35                  40                  45

Asn Arg Leu Tyr Trp Tyr Arg Gln Thr Leu Gly Gln Gly Pro Glu Phe
    50                  55                  60

Leu Thr Tyr Phe Gln Asn Glu Ala Gln Leu Glu Lys Ser Arg Leu Leu
65                  70                  75                  80

Ser Asp Arg Phe Ser Ala Glu Arg Pro Lys Gly Ser Phe Ser Thr Leu
                85                  90                  95

Glu Ile Gln Arg Thr Glu Gln Gly Asp Ser Ala Met Tyr Leu Cys Ala
            100                 105                 110

Ser Ser Leu Val Lys Gly Glu Lys Leu Phe Phe Gly Ser Gly Thr Gln
```

```
                    115                 120                 125
Leu Ser Val Leu Glu Asp Leu Asn Lys Val Phe Pro Pro Glu Val Ala
            130                 135                 140
Val Phe Glu Pro Ser Glu Ala Glu Ile Ser His Thr Gln Lys Ala Thr
145                 150                 155                 160
Leu Val Cys Leu Ala Thr Gly Phe Phe Pro Asp His Val Glu Leu Ser
                165                 170                 175
Trp Trp Val Asn Gly Lys Glu Val His Ser Gly Val Cys Thr Asp Pro
            180                 185                 190
Gln Pro Leu Lys Glu Gln Pro Ala Leu Asn Asp Ser Arg Tyr Cys Leu
                195                 200                 205
Ser Ser Arg Leu Arg Val Ser Ala Thr Phe Trp Gln Asn Pro Arg Asn
            210                 215                 220
His Phe Arg Cys Gln Val Gln Phe Tyr Gly Leu Ser Glu Asn Asp Glu
225                 230                 235                 240
Trp Thr Gln Asp Arg Ala Lys Pro Val Thr Gln Ile Val Ser Ala Glu
                245                 250                 255
Ala Trp Gly Arg Ala Asp Cys Gly Phe Thr Ser Val Ser Tyr Gln Gln
            260                 265                 270
Gly Val Leu Ser Ala Thr Ile Leu Tyr Glu Ile Leu Leu Gly Lys Ala
                275                 280                 285
Thr Leu Tyr Ala Val Leu Val Ser Ala Leu Val Leu Met Ala Met Val
            290                 295                 300
Lys Arg Lys Asp
305

<210> SEQ ID NO 30
<211> LENGTH: 273
<212> TYPE: PRT
<213> ORGANISM: Artificial Sequence
<220> FEATURE:
<223> OTHER INFORMATION: Synthetic sequence TCR2,14 alpha chain (full
      length) (Cys modified) with signal peptide

<400> SEQUENCE: 30

Met Glu Thr Leu Leu Gly Leu Leu Ile Leu Trp Leu Gln Leu Gln Trp
1               5                   10                  15
Val Ser Ser Lys Gln Glu Val Thr Gln Ile Pro Ala Ala Leu Ser Val
            20                  25                  30
Pro Glu Gly Glu Asn Leu Val Leu Asn Cys Ser Phe Thr Asp Ser Ala
                35                  40                  45
Ile Tyr Asn Leu Gln Trp Phe Arg Gln Asp Pro Gly Lys Gly Leu Thr
50                  55                  60
Ser Leu Leu Leu Ile Gln Ser Ser Gln Arg Glu Gln Thr Ser Gly Arg
65                  70                  75                  80
Leu Asn Ala Ser Leu Asp Lys Ser Ser Gly Arg Ser Thr Leu Tyr Ile
                85                  90                  95
Ala Ala Ser Gln Pro Gly Asp Ser Ala Thr Tyr Leu Cys Ala Val Ile
            100                 105                 110
Gly Leu Gly Gly Thr Tyr Lys Tyr Ile Phe Gly Thr Gly Thr Arg Leu
                115                 120                 125
Lys Val Leu Ala Asn Ile Gln Asn Pro Asp Pro Ala Val Tyr Gln Leu
            130                 135                 140
Arg Asp Ser Lys Ser Ser Asp Lys Ser Val Cys Leu Phe Thr Asp Phe
145                 150                 155                 160
```

Asp Ser Gln Thr Asn Val Ser Gln Ser Lys Asp Ser Asp Val Tyr Ile
                165                 170                 175

Thr Asp Lys Cys Val Leu Asp Met Arg Ser Met Asp Phe Lys Ser Asn
            180                 185                 190

Ser Ala Val Ala Trp Ser Asn Lys Ser Asp Phe Ala Cys Ala Asn Ala
        195                 200                 205

Phe Asn Asn Ser Ile Ile Pro Glu Asp Thr Phe Phe Pro Ser Pro Glu
    210                 215                 220

Ser Ser Cys Asp Val Lys Leu Val Glu Lys Ser Phe Glu Thr Asp Thr
225                 230                 235                 240

Asn Leu Asn Phe Gln Asn Leu Ser Val Ile Gly Phe Arg Ile Leu Leu
                245                 250                 255

Leu Lys Val Ala Gly Phe Asn Leu Leu Met Thr Leu Arg Leu Trp Ser
            260                 265                 270

Ser

<210> SEQ ID NO 31
<211> LENGTH: 309
<212> TYPE: PRT
<213> ORGANISM: Artificial Sequence
<220> FEATURE:
<223> OTHER INFORMATION: Synthetic sequence TCR5 beta chain (full
      length) (Cys modified) with signal peptide

<400> SEQUENCE: 31

Met Gly Thr Ser Leu Leu Cys Trp Met Ala Leu Cys Leu Leu Gly Ala
1               5                   10                  15

Asp His Ala Asp Thr Gly Val Ser Gln Asp Pro Arg His Lys Ile Thr
            20                  25                  30

Lys Arg Gly Gln Asn Val Thr Phe Arg Cys Asp Pro Ile Ser Glu His
        35                  40                  45

Asn Arg Leu Tyr Trp Tyr Arg Gln Thr Leu Gly Gln Gly Pro Glu Phe
    50                  55                  60

Leu Thr Tyr Phe Gln Asn Glu Ala Gln Leu Glu Lys Ser Arg Leu Leu
65                  70                  75                  80

Ser Asp Arg Phe Ser Ala Glu Arg Pro Lys Gly Ser Phe Ser Thr Leu
                85                  90                  95

Glu Ile Gln Arg Thr Glu Gln Gly Asp Ser Ala Met Tyr Leu Cys Ala
            100                 105                 110

Ser Ser Leu Thr Thr Leu Asp Glu Gln Tyr Val Gly Pro Gly Thr Arg
        115                 120                 125

Leu Thr Val Thr Glu Asp Leu Lys Asn Val Phe Pro Pro Glu Val Ala
    130                 135                 140

Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
                165                 170                 175

Trp Trp Val Asn Gly Lys Glu Val His Ser Gly Val Cys Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
    210                 215                 220

His Phe Arg Cys Gln Val Gln Phe Tyr Gly Leu Ser Glu Asn Asp Glu
225                 230                 235                 240

```
Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Glu Ser Tyr Gln Gln
            260                 265                 270

Gly Val Leu Ser Ala Thr Ile Leu Tyr Glu Ile Leu Leu Gly Lys Ala
        275                 280                 285

Thr Leu Tyr Ala Val Leu Val Ser Ala Leu Val Leu Met Ala Met Val
    290                 295                 300

Lys Arg Lys Asp Ser
305

<210> SEQ ID NO 32
<211> LENGTH: 271
<212> TYPE: PRT
<213> ORGANISM: Artificial Sequence
<220> FEATURE:
<223> OTHER INFORMATION: Synthetic sequence TCR5 alpha chain (full
      length) (Cys modified) with signal peptide

<400> SEQUENCE: 32

Met Glu Thr Leu Leu Gly Val Ser Leu Val Ile Leu Trp Leu Gln Leu
1               5                   10                  15

Ala Arg Val Asn Ser Gln Gln Gly Glu Glu Asp Pro Gln Ala Leu Ser
            20                  25                  30

Ile Gln Glu Gly Glu Asn Ala Thr Met Asn Cys Ser Tyr Lys Thr Ser
        35                  40                  45

Ile Asn Asn Leu Gln Trp Tyr Arg Gln Asn Ser Gly Arg Gly Leu Val
    50                  55                  60

His Leu Ile Leu Ile Arg Ser Asn Glu Arg Glu Lys His Ser Gly Arg
65                  70                  75                  80

Leu Arg Val Thr Leu Asp Thr Ser Lys Lys Ser Ser Ser Leu Leu Ile
                85                  90                  95

Thr Ala Ser Arg Ala Ala Asp Thr Ala Ser Tyr Phe Cys Ala Thr Asn
            100                 105                 110

Ser Gly Asn Thr Pro Leu Val Phe Gly Lys Gly Thr Arg Leu Ser Val
        115                 120                 125

Ile Ala Asn Ile Gln Asn Pro Asp Pro Ala Val Tyr Gln Leu Arg Asp
    130                 135                 140

Ser Lys Ser Ser Asp Lys Ser Val Cys Leu Phe Thr Asp Phe Asp Ser
145                 150                 155                 160

Gln Thr Asn Val Ser Gln Ser Lys Asp Ser Asp Val Tyr Ile Thr Asp
                165                 170                 175

Lys Cys Val Leu Asp Met Arg Ser Met Asp Phe Lys Ser Asn Ser Ala
            180                 185                 190

Val Ala Trp Ser Asn Lys Ser Asp Phe Ala Cys Ala Asn Ala Phe Asn
        195                 200                 205

Asn Ser Ile Ile Pro Glu Asp Thr Phe Phe Pro Ser Pro Glu Ser Ser
    210                 215                 220

Cys Asp Val Lys Leu Val Glu Lys Ser Phe Glu Thr Asp Thr Asn Leu
225                 230                 235                 240

Asn Phe Gln Asn Leu Ser Val Ile Gly Phe Arg Ile Leu Leu Leu Lys
                245                 250                 255

Val Ala Gly Phe Asn Leu Leu Met Thr Leu Arg Leu Trp Ser Ser
            260                 265                 270

<210> SEQ ID NO 33
```

<211> LENGTH: 309
<212> TYPE: PRT
<213> ORGANISM: Artificial Sequence
<220> FEATURE:
<223> OTHER INFORMATION: Synthetic sequence TCR10 beta chain (full
      length) (Cys modified) with signal peptide

<400> SEQUENCE: 33

```
Met Gly Thr Ser Leu Leu Cys Trp Met Ala Leu Cys Leu Leu Gly Ala
1               5                   10                  15

Asp His Ala Asp Thr Gly Val Ser Gln Asp Pro Arg His Lys Ile Thr
            20                  25                  30

Lys Arg Gly Gln Asn Val Thr Phe Arg Cys Asp Pro Ile Ser Glu His
        35                  40                  45

Asn Arg Leu Tyr Trp Tyr Arg Gln Thr Leu Gly Gln Gly Pro Glu Phe
    50                  55                  60

Leu Thr Tyr Phe Gln Asn Glu Ala Gln Leu Glu Lys Ser Arg Leu Leu
65                  70                  75                  80

Ser Asp Arg Phe Ser Ala Glu Arg Pro Lys Gly Ser Phe Ser Thr Leu
                85                  90                  95

Glu Ile Gln Arg Thr Glu Gln Gly Asp Ser Ala Met Tyr Leu Cys Ala
            100                 105                 110

Ser Ser Met Leu Thr Asn Tyr Glu Gln Tyr Phe Gly Pro Gly Thr Arg
        115                 120                 125

Leu Thr Val Thr Glu Asp Leu Lys Asn Val Phe Pro Pro Glu Val Ala
130                 135                 140

Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
                165                 170                 175

Trp Trp Val Asn Gly Lys Glu Val His Ser Gly Val Cys Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
    210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Glu Ser Tyr Gln Gln
            260                 265                 270

Gly Val Leu Ser Ala Thr Ile Leu Tyr Glu Ile Leu Leu Gly Lys Ala
        275                 280                 285

Thr Leu Tyr Ala Val Leu Val Ser Ala Leu Val Leu Met Ala Met Val
    290                 295                 300

Lys Arg Lys Asp Ser
305
```

<210> SEQ ID NO 34
<211> LENGTH: 275
<212> TYPE: PRT
<213> ORGANISM: Artificial Sequence
<220> FEATURE:
<223> OTHER INFORMATION: Synthetic sequence TCR10 alpha chain (full
      length) (Cys modified) with signal peptide

<400> SEQUENCE: 34

```
Met Lys Lys His Leu Thr Thr Phe Leu Val Ile Leu Trp Leu Tyr Phe
1               5                   10                  15

Tyr Arg Gly Asn Gly Lys Asn Gln Val Glu Gln Ser Pro Gln Ser Leu
            20                  25                  30

Ile Ile Leu Glu Gly Lys Asn Cys Thr Leu Gln Cys Asn Tyr Thr Val
            35                  40                  45

Ser Pro Phe Ser Asn Leu Arg Trp Tyr Lys Gln Asp Thr Gly Arg Gly
50                  55                  60

Pro Val Ser Leu Thr Ile Met Thr Phe Ser Glu Asn Thr Lys Ser Asn
65                  70                  75                  80

Gly Arg Tyr Thr Ala Thr Leu Asp Ala Asp Thr Lys Gln Ser Ser Leu
                85                  90                  95

His Ile Thr Ala Ser Gln Leu Ser Asp Ser Ala Ser Tyr Ile Cys Val
            100                 105                 110

Val Asp Ser Gly Gly Gly Ala Asp Gly Leu Thr Phe Gly Lys Gly Thr
            115                 120                 125

His Leu Ile Ile Gln Pro Tyr Ile Gln Asn Pro Asp Pro Ala Val Tyr
    130                 135                 140

Gln Leu Arg Asp Ser Lys Ser Ser Asp Lys Ser Val Cys Leu Phe Thr
145                 150                 155                 160

Asp Phe Asp Ser Gln Thr Asn Val Ser Gln Ser Lys Asp Ser Asp Val
                165                 170                 175

Tyr Ile Thr Asp Lys Cys Val Leu Asp Met Arg Ser Met Asp Phe Lys
            180                 185                 190

Ser Asn Ser Ala Val Ala Trp Ser Asn Lys Ser Asp Phe Ala Cys Ala
            195                 200                 205

Asn Ala Phe Asn Asn Ser Ile Ile Pro Glu Asp Thr Phe Phe Pro Ser
    210                 215                 220

Pro Glu Ser Ser Cys Asp Val Lys Leu Val Glu Lys Ser Phe Glu Thr
225                 230                 235                 240

Asp Thr Asn Leu Asn Phe Gln Asn Leu Ser Val Ile Gly Phe Arg Ile
                245                 250                 255

Leu Leu Leu Lys Val Ala Gly Phe Asn Leu Leu Met Thr Leu Arg Leu
            260                 265                 270

Trp Ser Ser
    275

<210> SEQ ID NO 35
<211> LENGTH: 308
<212> TYPE: PRT
<213> ORGANISM: Artificial Sequence
<220> FEATURE:
<223> OTHER INFORMATION: Synthetic sequence TCR16 beta chain (full
      length) (Cys modified) with signal peptide

<400> SEQUENCE: 35

Met Gly Thr Ser Leu Leu Cys Trp Met Ala Leu Cys Leu Leu Gly Ala
1               5                   10                  15

Asp His Ala Asp Thr Gly Val Ser Gln Asp Pro Arg His Lys Ile Thr
            20                  25                  30

Lys Arg Gly Gln Asn Val Thr Phe Arg Cys Asp Pro Ile Ser Glu His
            35                  40                  45

Asn Arg Leu Tyr Trp Tyr Arg Gln Thr Leu Gly Gln Gly Pro Glu Phe
50                  55                  60

Leu Thr Tyr Phe Gln Asn Glu Ala Gln Leu Glu Lys Ser Arg Leu Leu
```

```
                65                  70                  75                  80
Ser Asp Arg Phe Ser Ala Glu Arg Pro Lys Gly Ser Phe Ser Thr Leu
                    85                  90                  95

Glu Ile Gln Arg Thr Glu Gln Gly Asp Ser Ala Met Tyr Leu Cys Ala
                100                 105                 110

Ser Ser Leu Val Val Gly Asn Glu Gln Phe Phe Gly Pro Gly Thr Arg
            115                 120                 125

Leu Thr Val Leu Glu Asp Leu Lys Asn Val Phe Pro Pro Glu Val Ala
        130                 135                 140

Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
                165                 170                 175

Trp Trp Val Asn Gly Lys Glu Val His Ser Gly Val Cys Thr Asp Pro
                    180                 185                 190

Gln Pro Leu Lys Glu Gln Pro Ala Leu Asn Asp Ser Arg Tyr Cys Leu
                195                 200                 205

Ser Ser Arg Leu Arg Val Ser Ala Thr Phe Trp Gln Asn Pro Arg Asn
210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Glu Ser Tyr Gln Gln
                260                 265                 270

Gly Val Leu Ser Ala Thr Ile Leu Tyr Glu Ile Leu Leu Gly Lys Ala
            275                 280                 285

Thr Leu Tyr Ala Val Leu Val Ser Ala Leu Val Leu Met Ala Met Val
        290                 295                 300

Lys Arg Lys Asp
305

<210> SEQ ID NO 36
<211> LENGTH: 272
<212> TYPE: PRT
<213> ORGANISM: Artificial Sequence
<220> FEATURE:
<223> OTHER INFORMATION: Synthetic sequence TCR16 alpha chain (full
      length) (Cys modified) with signal peptide

<400> SEQUENCE: 36

Met Glu Thr Leu Leu Gly Leu Leu Ile Leu Trp Leu Gln Leu Gln Trp
1               5                   10                  15

Val Ser Lys Gln Glu Val Thr Gln Ile Pro Ala Ala Leu Ser Val
                20                  25                  30

Pro Glu Gly Glu Asn Leu Val Leu Asn Cys Ser Phe Thr Asp Ser Ala
            35                  40                  45

Ile Tyr Asn Leu Gln Trp Phe Arg Gln Asp Pro Gly Lys Gly Leu Thr
        50                  55                  60

Ser Leu Leu Leu Ile Gln Ser Ser Gln Arg Glu Gln Thr Ser Gly Arg
65                  70                  75                  80

Leu Asn Ala Ser Leu Asp Lys Ser Ser Gly Arg Ser Thr Leu Tyr Ile
                85                  90                  95

Ala Ala Ser Gln Pro Gly Asp Ser Ala Thr Tyr Leu Cys Ala Val His
                100                 105                 110
```

```
Leu Leu Asn Asp Tyr Lys Leu Ser Phe Gly Ala Gly Thr Thr Val Thr
            115                 120                 125

Val Arg Ala Asn Ile Gln Asn Pro Asp Pro Ala Val Tyr Gln Leu Arg
        130                 135                 140

Asp Ser Lys Ser Ser Asp Lys Ser Val Cys Leu Phe Thr Asp Phe Asp
145                 150                 155                 160

Ser Gln Thr Asn Val Ser Gln Ser Lys Asp Ser Asp Val Tyr Ile Thr
                165                 170                 175

Asp Lys Cys Val Leu Asp Met Arg Ser Met Asp Phe Lys Ser Asn Ser
            180                 185                 190

Ala Val Ala Trp Ser Asn Lys Ser Asp Phe Ala Cys Ala Asn Ala Phe
        195                 200                 205

Asn Asn Ser Ile Ile Pro Glu Asp Thr Phe Phe Pro Ser Pro Glu Ser
210                 215                 220

Ser Cys Asp Val Lys Leu Val Glu Lys Ser Phe Glu Thr Asp Thr Asn
225                 230                 235                 240

Leu Asn Phe Gln Asn Leu Ser Val Ile Gly Phe Arg Ile Leu Leu Leu
                245                 250                 255

Lys Val Ala Gly Phe Asn Leu Leu Met Thr Leu Arg Leu Trp Ser Ser
            260                 265                 270

<210> SEQ ID NO 37
<211> LENGTH: 309
<212> TYPE: PRT
<213> ORGANISM: Artificial Sequence
<220> FEATURE:
<223> OTHER INFORMATION: Synthetic sequence TCR29 beta chain
      (full length) with signal peptide

<400> SEQUENCE: 37

Met Gly Thr Ser Leu Leu Cys Trp Met Ala Leu Cys Leu Leu Gly Ala
1               5                   10                  15

Asp His Ala Asp Thr Gly Val Ser Gln Asp Pro Arg His Lys Ile Thr
            20                  25                  30

Lys Arg Gly Gln Asn Val Thr Phe Arg Cys Asp Pro Ile Ser Glu His
        35                  40                  45

Asn Arg Leu Tyr Trp Tyr Arg Gln Thr Leu Gly Gln Gly Pro Glu Phe
    50                  55                  60

Leu Thr Tyr Phe Gln Asn Glu Ala Gln Leu Glu Lys Ser Arg Leu Leu
65                  70                  75                  80

Ser Asp Arg Phe Ser Ala Glu Arg Pro Lys Gly Ser Phe Ser Thr Leu
                85                  90                  95

Glu Ile Gln Arg Thr Glu Gln Gly Asp Ser Ala Met Tyr Leu Cys Ala
            100                 105                 110

Ser Ser Leu Val Ser Gly Asn Thr Ile Tyr Phe Gly Glu Gly Ser Trp
        115                 120                 125

Leu Thr Val Val Glu Asp Leu Asn Lys Val Phe Pro Pro Glu Val Ala
    130                 135                 140

Val Phe Glu Pro Ser Glu Ala Glu Ile Ser His Thr Gln Lys Ala Thr
145                 150                 155                 160

Leu Val Cys Leu Ala Thr Gly Phe Phe Pro Asp His Val Glu Leu Ser
                165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
        195                 200                 205
```

Ser Ser Arg Leu Arg Val Ser Ala Thr Phe Trp Gln Asn Pro Arg Asn
    210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Val Ser Tyr Gln Gln
                260                 265                 270

Gly Val Leu Ser Ala Thr Ile Leu Tyr Glu Ile Leu Leu Gly Lys Ala
            275                 280                 285

Thr Leu Tyr Ala Val Leu Val Ser Ala Leu Val Leu Met Ala Met Val
    290                 295                 300

Lys Arg Lys Asp Phe
305

<210> SEQ ID NO 38
<211> LENGTH: 275
<212> TYPE: PRT
<213> ORGANISM: Artificial Sequence
<220> FEATURE:
<223> OTHER INFORMATION: Synthetic sequence TCR29 alpha chain
      (full length) with signal peptide

<400> SEQUENCE: 38

Met Glu Thr Leu Leu Gly Leu Leu Ile Leu Trp Leu Gln Leu Gln Trp
1               5                   10                  15

Val Ser Ser Lys Gln Glu Val Thr Gln Ile Pro Ala Ala Leu Ser Val
            20                  25                  30

Pro Glu Gly Glu Asn Leu Val Leu Asn Cys Ser Phe Thr Asp Ser Ala
        35                  40                  45

Ile Tyr Asn Leu Gln Trp Phe Arg Gln Asp Pro Gly Lys Gly Leu Thr
    50                  55                  60

Ser Leu Leu Leu Ile Gln Ser Ser Gln Arg Glu Gln Thr Ser Gly Arg
65                  70                  75                  80

Leu Asn Ala Ser Leu Asp Lys Ser Ser Gly Arg Ser Thr Leu Tyr Ile
                85                  90                  95

Ala Ala Ser Gln Pro Gly Asp Ser Ala Thr Tyr Leu Cys Ala Val Arg
            100                 105                 110

Gly Gly Thr Thr Ser Gly Thr Tyr Lys Tyr Ile Phe Gly Thr Gly Thr
        115                 120                 125

Arg Leu Lys Val Leu Ala Asn Ile Gln Asn Pro Asp Pro Ala Val Tyr
    130                 135                 140

Gln Leu Arg Asp Ser Lys Ser Ser Asp Lys Ser Val Cys Leu Phe Thr
145                 150                 155                 160

Asp Phe Asp Ser Gln Thr Asn Val Ser Gln Ser Lys Asp Ser Asp Val
                165                 170                 175

Tyr Ile Thr Asp Lys Thr Val Leu Asp Met Arg Ser Met Asp Phe Lys
            180                 185                 190

Ser Asn Ser Ala Val Ala Trp Ser Asn Lys Ser Asp Phe Ala Cys Ala
        195                 200                 205

Asn Ala Phe Asn Asn Ser Ile Ile Pro Glu Asp Thr Phe Phe Pro Ser
    210                 215                 220

Pro Glu Ser Ser Cys Asp Val Lys Leu Val Glu Lys Ser Phe Glu Thr
225                 230                 235                 240

Asp Thr Asn Leu Asn Phe Gln Asn Leu Ser Val Ile Gly Phe Arg Ile

```
              245                 250                 255
Leu Leu Leu Lys Val Ala Gly Phe Asn Leu Leu Met Thr Leu Arg Leu
            260                 265                 270
Trp Ser Ser
        275
```

<210> SEQ ID NO 39
<211> LENGTH: 930
<212> TYPE: DNA
<213> ORGANISM: Artificial Sequence
<220> FEATURE:
<223> OTHER INFORMATION: Synthetic sequence TCR1,13 beta chain
      (codon optimized, Cys modified)

<400> SEQUENCE: 39

| | | | | | |
|---|---|---|---|---|---|
| atgggcacct | ccctgctgtg | ttggatggcc | ctgtgtctgc | tgggagccga | ccatgccgat | 60 |
| acagggtgt | cccaggaccc | ccggcacaag | attaccaagc | ggggccagaa | cgtgaccttc | 120 |
| agatgcgacc | ccatcagcga | gcacaaccgg | ctgtactggt | acaggcagac | cctgggccag | 180 |
| ggccccgagt | tcctgaccta | ctttcagaac | gaggcccagc | tggaaaagtc | ccggctgctg | 240 |
| agcgacagat | tcagcgccga | aagacccaag | ggcagcttca | gcaccctgga | aatccagcgg | 300 |
| accgagcagg | gcgatagcgc | catgtacctg | tgtgccagca | gcagcacagg | cggccacaac | 360 |
| gagcagttct | ttggccctgg | cacccggctg | accgtgctgg | aagatctgaa | gaacgtgttc | 420 |
| cccccagagg | tggccgtgtt | cgagccttct | gaggccgaga | tcagccacac | ccagaaagcc | 480 |
| accctcgtgt | gtctggccac | cggcttctac | cccgaccacg | tggaactgtc | ttggtgggtc | 540 |
| aacggcaaag | aggtgcactc | cggcgtgtgc | accgatcccc | agcctctgaa | agaacagccc | 600 |
| gccctgaacg | acagccggta | ctgcctgagc | agcagactga | gagtgtccgc | caccttctgg | 660 |
| cagaaccccc | ggaaccactt | cagatgccag | gtgcagttct | acggcctgag | cgagaacgac | 720 |
| gagtggaccc | aggacagagc | caagcccgtg | acccagatcg | tgtctgccga | agcctggggc | 780 |
| agagccgatt | gcggctttac | cagcgagagc | taccagcagg | gcgtgctgag | cgccaccatc | 840 |
| ctgtacgaga | tcctgctggg | caaggccacc | ctgtacgccg | tgctggtgtc | tgccctggtg | 900 |
| ctgatggcca | tggtcaagcg | gaaggacagc | | | | 930 |

<210> SEQ ID NO 40
<211> LENGTH: 828
<212> TYPE: DNA
<213> ORGANISM: Artificial Sequence
<220> FEATURE:
<223> OTHER INFORMATION: Synthetic sequence TCR1,13 alpha chain
      (codon optimized; Cys modified)

<400> SEQUENCE: 40

| | | | | | |
|---|---|---|---|---|---|
| atggaaacac | tgctgggcgt | gtccctcgtg | atcctgtggc | tgcagctggc | cagagtgaac | 60 |
| agccagcagg | gggaagagga | tcccccaggcc | ctgagcattc | aggaaggcga | aacgccacc | 120 |
| atgaactgca | gctacaagac | cagcatcaac | aacctgcagt | ggtacagaca | gaacagcggc | 180 |
| agaggcctgg | tgcacctgat | cctgatcaga | agcaacgaga | gagaagca | cagcggacgg | 240 |
| ctgagagtga | ccctggacac | ctccaagaag | tccagctccc | tgctgatcac | cgccagcaga | 300 |
| gccgccgata | ccgccagcta | cttctgtgcc | accaagcggg | attctggcgc | cggatcctac | 360 |
| cagctgacct | tcggcaaggg | caccaagctg | agcgtgatcc | ccaacatcca | gaaccccgac | 420 |
| cccgccgtgt | atcagctgag | agacagcaag | agcagcgaca | agagcgtgtg | cctgttcacc | 480 |
| gacttcgaca | gccagaccaa | cgtgtcccag | agcaaggaca | gcgacgtgta | catcaccgat | 540 |

```
aagtgcgtgc tggacatgcg agcatggac ttcaagagca acagcgccgt ggcctggtcc      600
aacaagagcg acttcgcctg cgccaacgcc ttcaacaaca gcatcatccc cgaggacacc      660
ttttccccca gccccgagag cagctgcgac gtgaaactgg tggagaagtc cttcgagaca      720
gacaccaatc tgaactttca gaacctgagc gtgatcggct ccggatcct gctgctgaaa      780 gtggccggct tcaatctgct gatgacccctg cggctgtgga gcagctga                  828
```

<210> SEQ ID NO 41
<211> LENGTH: 930
<212> TYPE: DNA
<213> ORGANISM: Artificial Sequence
<220> FEATURE:
<223> OTHER INFORMATION: Synthetic sequence TCR2,14 beta chain
      (codon optimized; Cys modified)

<400> SEQUENCE: 41

```
atgggcacct ccctgctgtg ttggatggcc ctgtgtctgc tgggagccga ccatgccgat       60
acaggggtgt cccaggaccc ccggcacaag attaccaagc ggggccagaa cgtgaccttc      120
agatgcgacc ccatcagcga gcacaaccgg ctgtactggt acaggcagac cctgggccag      180 ggcccccgagt tcctgaccta ctttcagaac gaggcccagc tggaaaagtc ccggctgctg      240
agcgacagat tcagcgccga aagacccaag ggcagcttca gcaccctgga aatccagcgg      300
accgagcagg gcgatagcgc catgtacctg tgtgccagca gcctcgtgaa gggcgagaag      360
ctgttcttcg gcagcggcac ccagctgagc gtgctggaag atctgaacaa ggtgttcccc      420
ccagaggtgg ccgtgttcga gccttctgag gccgagatca gccacaccca gaaagccacc      480
ctcgtgtgcc tggccaccgg cttttttccc gaccacgtgg aactgtcttg gtgggtcaac      540
ggcaaagagt gcactccgg cgtgtgcacc gatccccagc tctgaaaga acagcccgcc      600 ctgaacgaca gccggtactg cctgagcagc agactgagag tgtccgccac cttctggcag      660
aaccccggga accacttcag atgccaggtg cagttctacg gcctgagcga aacgacgag      720 tggacccagg acagagccaa gcccgtgacc cagatcgtgt ctgccgaagc tggggcaga      780 gccgattgcg gctttaccag cgtgtcctat cagcagggcg tgctgagcgc caccatcctg      840
tacgagatcc tgctgggcaa ggccacccctg tacgccgtgc tggtgtctgc cctggtgctg      900
atggccatgg tcaagcggaa ggactttggc                                      930
```

<210> SEQ ID NO 42
<211> LENGTH: 820
<212> TYPE: DNA
<213> ORGANISM: Artificial Sequence
<220> FEATURE:
<223> OTHER INFORMATION: Synthetic sequence TCR2,14 alpha chain
      (codon optimized; Cys modified)

<400> SEQUENCE: 42

```
atggaaacac tgctgggcct gctgatcctg tggctgcagc tgcagtgggt gtccagcaag       60
caggaagtga cacagatccc tgccgccctg tctgtgcccg agggcgaaaa tctggtgctg      120
aactgcagct tcaccgacag cgccatctac aacctgcagt ggttcagaca ggaccccggc      180
aagggcctga aagcctgct gctgattcag agcagccaga gagcagac cagcggcaga      240 ctgaacgcca gcctggataa gagcagcggc cgcagcaccc tgtatatcgc cgcttctcag      300
cctggcgact ctgccacata ctctgcgcc gtgatcggcc tggcggcac ctacaagtac      360 atctttggca ccggcaccag actgaaagtg ctggccaaca tccagaaccc cgacccgcc      420
```

```
gtgtaccagc tgagagacag caagtccagc gacaagagcg tgtgtctgtt caccgacttc      480
gacagccaga ccaacgtgtc ccagagcaag gacagcgacg tgtacatcac cgataagtgc      540
gtgctggaca tgcggagcat ggacttcaag agcaacagcg ccgtggcctg gtccaacaag      600
agcgacttcg cctgcgccaa cgccttcaac aacagcatca tccccgagga caccttttc       660 cccagccccg agagcagctg cgacgtgaaa ctggtggaga agtccttcga cagacacc        720 aatctgaact ttcagaacct gagcgtgatc ggcttccgga tcctgctgct gaaagtggcc      780
ggcttcaatc tgctgatgac cctgcggctg tggagcagcg                            820
```

<210> SEQ ID NO 43
<211> LENGTH: 933
<212> TYPE: DNA
<213> ORGANISM: Artificial Sequence
<220> FEATURE:
<223> OTHER INFORMATION: Synthetic sequence TCR5 beta chain
      (codon optimized; Cys modified)

<400> SEQUENCE: 43

```
atgggcacct ccctgctgtg ttggatggcc ctgtgtctgc tgggagccga ccatgccgat      60 acagggtgt cccaggaccc ccggcacaag attaccaagc ggggccagaa cgtgaccttc       120
agatgcgacc ccatcagcga gcacaaccgg ctgtactggt acaggcagac cctgggccag     180
ggccccgagt tcctgaccta ctttcagaac gaggcccagc tggaaaagtc ccggctgctg      240
agcgacagat tcagcgccga aagacccaag ggcagcttca gcaccctgga aatccagcgg     300
accgagcagg gggacagcgc catgtatctg tgtgccagct ccctgaccac cctggacgag      360
cagtatgtgg gccaggcac cagactgacc gtgaccgagg acctgaagaa cgtgttcccc      420
ccagaggtgg ccgtgttcga gccttctgag gccgagatca gccacaccca gaaagccacc      480
ctcgtgtgtc tggccaccgg cttctacccc gatcacgtgg agctgtcttg gtgggtgaac     540
ggcaaagagg tgcacagcgg cgtctgcacc gaccccagc ccctgaaaga gcagcccgcc      600
ctgaacgaca gccggtactg cctgagcagc cggctgagag tgagcgccac cttctggcag     660
aacccccgga accacttccg gtgccaggtg cagttctacg gcctgagcga aaacgacgag     720
tggacccagg acagagccaa gcccgtgacc cagatcgtga cgccgaggc ctgggggcaga     780 ccgactgcg gcttcaccag cgagagctac cagcagggcg tgctgtccgc cacaatcctg     840
tacgagatcc tgctgggcaa ggccacctg tacgccgtgc tggtgtccgc cctggtgctg      900
atggccatgg tgaagcggaa ggacagccgg ggc                                   933
```

<210> SEQ ID NO 44
<211> LENGTH: 816
<212> TYPE: DNA
<213> ORGANISM: Artificial Sequence
<220> FEATURE:
<223> OTHER INFORMATION: Synthetic sequence TCR5 alpha chain
      (codon optimized; Cys modified)

<400> SEQUENCE: 44

```
atggaaaccc tgctgggcgt gtccctcgtg atcctgtggc tgcagctggc cagagtgaac      60
agccagcagg gcgaagaaga tcccccaggcc ctgagcatcc aggaaggcga aaacgccaca     120
atgaactgca gctacaagac cagcatcaac aacctgcagt ggtacagaca gaacagcggc     180
agaggcctgg tgcacctgat cctgatcaga agcaacgaga gagaagca ctccggcaga       240 ctgagagtga ccctggacac cagcaagaag tccagcagcc tgctgatcac cgccagcaga     300
gccgccgata ccgccagcta cttctgcgcc accaactccg gcaacacccc cctggtgttt     360
```

```
ggcaagggca cccggctgag cgtgatcgcc aacatccaga accccgaccc cgccgtgtac    420
cagctgagag acagcaagag cagcgacaag agcgtgtgcc tgttcaccga cttcgacagc    480
cagaccaacg tgtcccagag caaggacagc gacgtgtaca tcaccgataa gtgcgtgctg    540
gacatgcgga gcatggactt caagagcaac agcgccgtgg cctggtccaa caagagcgac    600
ttcgcctgcg ccaacgcctt caacaacagc atcatccccg aggacacctt tttccccagc    660
cccgagagca gctgcgacgt gaaactggtg gagaagtcct tcgagacaga caccaatctg    720
aactttcaga acctgagcgt gatcggcttc cggatcctgc tgctgaaagt ggccggcttc    780
aatctgctga tgaccctgcg gctgtggagc agctga                              816

<210> SEQ ID NO 45
<211> LENGTH: 933
<212> TYPE: DNA
<213> ORGANISM: Artificial Sequence
<220> FEATURE:
<223> OTHER INFORMATION: Synthetic sequence TCR10 beta chain
      (codon optimized; Cys modified)

<400> SEQUENCE: 45
atgggcacct cctgctgtg ttggatggcc ctgtgtctgc tgggagccga ccatgccgat     60 acagggtgt cccaggaccc ccggcacaag attaccaagc ggggccagaa cgtgaccttc    120
agatgcgacc ccatcagcga gcacaaccgg ctgtactggt acaggcagac cctgggccag    180
ggccccgagt tcctgaccta ctttcagaac gaggcccagc tggaaaagtc ccggctgctg    240
agcgacagat tcagcgccga aagacccaag ggcagcttca gcaccctgga aatccagcgg    300
accgagcagg gcgatagcgc catgtacctg tgcgccagct ccatgctgac caactacgag    360
cagtacttcg gcctggcac ccggctgacc gtgaccgagg atctgaagaa cgtgttcccc    420
ccagaggtgg ccgtgttcga gccttctgag gccgagatca gccacaccca gaaagccacc    480
ctcgtgtgtc tggccaccgg cttctacccc gaccacgtgg aactgtcttg gtgggtcaac    540
ggcaaagagg tgcactccgg cgtgtgcacc gatccccagc ctctgaaaga acagcccgcc    600
ctgaacgaca gccggtactg cctgagcagc agactgagag tgtccgccac cttctggcag    660
aaccccggga ccacttcag atgccaggtg cagttctacg gcctgagcga aaacgacgag    720
tggacccagg acagagccaa gcccgtgacc cagatcgtgt ctgccgaagc tggggcaga    780 gccgattgcg gctttaccag cgagagctac cagcagggcg tgctgagcgc caccatcctg    840
tacgagatcc tgctgggcaa ggccacccct acgccgtgc tggtgtctgc cctggtgctg    900
atggccatgg tcaagcggaa ggacagcaga ggc                                 933

<210> SEQ ID NO 46
<211> LENGTH: 828
<212> TYPE: DNA
<213> ORGANISM: Artificial Sequence
<220> FEATURE:
<223> OTHER INFORMATION: Synthetic sequence TCR10 alpha chain
      (codon optimized; Cys modified)

<400> SEQUENCE: 46
atgaagaagc acctgaccac ctttctcgtg atcctgtggc tgtacttcta ccggggcaac     60
ggcaagaacc aggtggaaca gagcccccag agcctgatca tcctggaagg caagaattgc    120
accctgcagt gcaactacac cgtgtccccc ttcagcaacc tgcggtggta caagcaggac    180
accggcagag gccctgtgtc cctgaccatc atgaccttca gcgagaacac caagagcaac    240
```

| | |
|---|---:|
| ggccggtaca ccgccaccct ggatgccgat acaaagcaga gcagcctgca catcaccgcc | 300 |
| agccagctga gcgattccgc cagctacatc tgcgtggtgg attctggcgg cggagccgat | 360 |
| ggcctgacat ttggcaaggg cacccacctg atcattcagc cctacatcca gaaccccgac | 420 |
| cccgccgtgt accagctgag agacagcaag tccagcgaca gagcgtgtg cctgttcacc | 480 |
| gacttcgaca gccagaccaa cgtgtcccag agcaaggaca gcgacgtgta catcaccgat | 540 |
| aagtgcgtgc tggacatgcg gagcatggac ttcaagagca cagcgccgt ggcctggtcc | 600 |
| aacaagagcg acttcgcctg cgccaacgcc ttcaacaaca gcatcatccc cgaggacacc | 660 |
| tttttcccca gccccgagag cagctgcgac gtgaaactgg tggagaagtc cttcgagaca | 720 |
| gacaccaatc tgaactttca gaacctgagc gtgatcggct tccggatcct gctgctgaaa | 780 |
| gtggccggct tcaatctgct gatgacccty cggctgtgga gcagctga | 828 |

<210> SEQ ID NO 47
<211> LENGTH: 933
<212> TYPE: DNA
<213> ORGANISM: Artificial Sequence
<220> FEATURE:
<223> OTHER INFORMATION: Synthetic sequence TCR16 beta chain
(codon optimized; Cys modified)

<400> SEQUENCE: 47

| | |
|---|---:|
| atgggcacct ccctgctgtg ttggatggcc ctgtgtctgc tgggagccga ccatgccgat | 60 |
| acaggggtgt cccaggaccc ccggcacaag attaccaagc ggggccagaa cgtgaccttc | 120 |
| agatgcgacc ccatcagcga gcacaaccgg ctgtactggt acaggcagac cctgggccag | 180 |
| ggccccgagt tcctgaccta ctttcagaac gaggcccagc tggaaaagtc ccggctgctg | 240 |
| agcgacagat tcagcgccga aagacccaag ggcagcttca gcaccctgga atccagcgg | 300 |
| accgagcagg gcgatagcgc catgtacctg tgtgccagca gcctggtcgt gggcaacgag | 360 |
| cagttttttcg gccctggcac cagactgacc gtgctggaag atctgaagaa cgtgttcccc | 420 |
| ccagaggtgg ccgtgttcga gccttctgag gccgagatca gccacaccca gaaagccacc | 480 |
| ctcgtgtgtc tggccaccgg cttctacccc gaccacgtgg aactgtcttg gtgggtcaac | 540 |
| ggcaaagagg tgcactccgg cgtgtgcacc gatccccagc tctgaaaga cagcccgcc | 600 |
| ctgaacgaca gccggtactg cctgagcagc agactgagag tgtccgccac cttctggcag | 660 |
| aaccccgga accacttcag atgccaggtg cagttctacg gcctgagcga aaacgacgag | 720 |
| tggacccagg acagagccaa gcccgtgacc cagatcgtgt ctgccgaagc tggggcaga | 780 |
| gccgattgcg gctttaccag cgagagctac cagcagggcg tgctgagcgc caccatcctg | 840 |
| tacgagatcc tgctgggcaa ggccacccta tacgccgtgc tggtgtctgc cctggtgctg | 900 |
| atggccatgg tcaagcggaa ggacagcaga ggc | 933 |

<210> SEQ ID NO 48
<211> LENGTH: 819
<212> TYPE: DNA
<213> ORGANISM: Artificial Sequence
<220> FEATURE:
<223> OTHER INFORMATION: Synthetic sequence TCR16 alpha chain
(codon optimized; Cys modified)

<400> SEQUENCE: 48

| | |
|---|---:|
| atggaaacac tgctgggcct gctgatcctg tggctgcagc tgcagtgggt gtccagcaag | 60 |
| caggaagtga cacagatccc tgccgccctg tctgtgcccg agggcgaaaa tctggtgctg | 120 |
| aactgcagct tcaccgacag cgccatctac aacctgcagt ggttcagaca ggaccccggc | 180 |

| | |
|---|---|
| aagggcctga caagcctgct gctgattcag agcagccaga gagagcagac cagcggcaga | 240 |
| ctgaacgcca gcctggataa gagcagcggc cgcagcaccc tgtatatcgc cgcttctcag | 300 |
| cctggcgact ctgccacata tctgtgcgcc gtgcatctgc tgaacgacta caagctgagc | 360 |
| ttcggagccg gcaccaccgt gacagtgcgg gccaacatcc agaacccga ccctgccgtg | 420 |
| taccagctga gagacagcaa gtccagcgac aagagcgtgt gcctgttcac cgacttcgac | 480 |
| agccagacca acgtgtccca gagcaaggac agcgacgtgt acatcaccga taagtgcgtg | 540 |
| ctggacatgc ggagcatgga cttcaagagc aacagcgccg tggcctggtc caacaagagc | 600 |
| gacttcgcct gcgccaacgc cttcaacaac agcatcatcc ccgaggacac cttttcccc | 660 |
| agccccgaga gcagctgcga cgtgaaactg gtggagaagt ccttcgagac agacaccaat | 720 |
| ctgaactttc agaacctgag cgtgatcggc ttccggatcc tgctgctgaa agtggccggc | 780 |
| ttcaatctgc tgatgaccct gcggctgtgg agcagctga | 819 |

<210> SEQ ID NO 49
<211> LENGTH: 939
<212> TYPE: DNA
<213> ORGANISM: Artificial Sequence
<220> FEATURE:
<223> OTHER INFORMATION: Synthetic sequence TCR24 beta chain (wild type)

<400> SEQUENCE: 49

| | |
|---|---|
| atgggtcctg ggcttctcca ctggatggcc ctttgtctcc ttggaacagg tcatggggat | 60 |
| gccatggtca tccagaaccc aagataccag gttacccagt ttggaaagcc agtgaccctg | 120 |
| agttgttctc agactttgaa ccataacgtc atgtactggt accagcagaa gtcaagtcag | 180 |
| gccccaaagc tgctgttcca ctactatgac aaagatttta acaatgaagc agacacccct | 240 |
| gataacttcc aatccaggag gccgaacact tctttctgct ttcttgacat ccgctcacca | 300 |
| ggcctggggg acgcagccat gtacctgtgt gccaccagca agacacggat agctcaagag | 360 |
| acccagtact cgggccagg cacgcggctc ctggtgctcg aggacctgaa aaacgtgttc | 420 |
| ccacccgagg tcgctgtgtt tgagccatca gaagcagaga tctcccacac ccaaaaggcc | 480 |
| acactggtgt gcctggccac aggcttctac cccgaccacg tggagctgag ctggtgggtg | 540 |
| aatgggaagg aggtgcacag tggggtcagc acagacccgc agcccctcaa ggagcagccc | 600 |
| gccctcaatg actccagata ctgcctgagc agccgcctga gggtctcggc caccttctgg | 660 |
| cagaaccccc gcaaccactt ccgctgtcaa gtccagttct acgggctctc ggagaatgac | 720 |
| gagtggaccc aggatagggc caaacctgtc acccagatcg tcagcgccga ggcctggggt | 780 |
| agagcagact gtggcttcac ctccgagtct taccagcaag gggtcctgtc tgccaccatc | 840 |
| ctctatgaga tcttgctagg gaaggccacc ttgtatgccg tgctggtcag tgccctcgtg | 900 |
| ctgatggcca tggtcaagag aaaggattcc agaggctag | 939 |

<210> SEQ ID NO 50
<211> LENGTH: 825
<212> TYPE: DNA
<213> ORGANISM: Artificial Sequence
<220> FEATURE:
<223> OTHER INFORMATION: Synthetic sequence TCR24 alpha chain (wild type)

<400> SEQUENCE: 50

| | |
|---|---|
| atgctcctgg agcttatccc actgctgggg atacattttg tcctgagaac tgccagagcc | 60 |
| cagtcagtga cccagcctga catccacatc actgtgtctg aaggagcctc actggagttg | 120 |

```
agatgtaact attcctatgg ggcaacacct tatctcttct ggtatgtcca gtccccggc    180 caaggcctcc agctgctcct gaagtacttt tcaggagaca ctctggttca aggcattaaa  240
ggctttgagg ctgaatttaa gaggagtcaa tcttccttca acctgaggaa accctctgtg  300
cattggagtg atgctgctga gtacttctgt gctgtgggtt ataacaccaa tgcaggcaaa  360
tcaacctttg gggatgggac tacgctcact gtgaagccaa atatccagaa ccctgaccct  420
gccgtgtacc agctgagaga ctctaaatcc agtgacaagt ctgtctgcct attcaccgat  480
tttgattctc aaacaaatgt gtcacaaagt aaggattctg atgtgtatat cacagacaaa  540
actgtgctag acatgaggtc tatggacttc aagagcaaca gtgctgtggc ctggagcaac  600
aaatctgact ttgcatgtgc aaacgccttc aacaacagca ttattccaga agacaccttc  660
ttccccagcc agaaagttc ctgtgatgtc aagctggtcg agaaaagctt gaaacagat   720 acgaacctaa actttcaaaa cctgtcagtg attgggttcc gaatcctcct cctgaaagtg  780
gccgggttta atctgctcat gacgctgcgg ctgtggtcca gctga                 825

<210> SEQ ID NO 51
<211> LENGTH: 929
<212> TYPE: DNA
<213> ORGANISM: Artificial Sequence
<220> FEATURE:
<223> OTHER INFORMATION: Synthetic sequence TCR29 beta chain
      (codon optimized; Cys modified)

<400> SEQUENCE: 51
atgggcacaa gcctgctgtg ttggatggcc ctgtgtctgc tgggagccga tcatgccgat   60
acgggagtgt cccaggatcc tcggcacaag attaccaagc ggggccagaa cgtgaccttc  120
agatgcgacc ctatcagcga gcacaaccgg ctgtactggt acagacagac actcggccag  180
ggacctgagt tcctgaccta cttccagaac gaggcccagc tggaaaagag cagactgctg  240
agcgacagat tcagcgccga aagacccaag ggcagcttca gcaccctgga aatccagaga  300
accgagcagg gcgacagcgc catgtatctg tgtgccagct ctctggtgtc cggcaacacc  360
atctacttcg gcgaaggcag ctggctgaca gtggttaaga tctgaacaag gtgttccccc  420
cagaggtggc cgtgttcgag ccttctgagg ccgagatcag ccacacccag aaagccaccc  480
tcgtgtgcct ggccaccggc tttttccccg accacgtgga actgtcttgg tgggtcaacg  540
gcaaagaggt gcactccggc gtgtgcaccg atcccagcc tctgaaagaa cagcccgccc  600
tgaacgacag ccggtactgc ctgagcagca gactgagagt gtccgccacc ttctggcaga  660 accccggaa ccacttcaga tgccaggtgc agttctacgg cctgagcgag aacgacgagt  720
ggacccagga cagagccaag cccgtgaccc agatcgtgtc tgccgaagcc tggggcagag  780
ccgattgcgg ctttaccagc gtgtcctatc agcagggcgt gctgagcgcc accatcctgt  840
acgagatcct gctgggcaag gccacccctg tacgccgtgct ggtgtctgcc ctggtgctga  900
tggccatggt caagcggaag gactttggc                                    929

<210> SEQ ID NO 52
<211> LENGTH: 828
<212> TYPE: DNA
<213> ORGANISM: Artificial Sequence
<220> FEATURE:
<223> OTHER INFORMATION: Synthetic sequence TCR29 alpha chain
      (codon optimized; Cys modified)

<400> SEQUENCE: 52
```

```
atggaaacac tgctgggcct gctgatcctg tggctgcaac tgcaatgggt gtccagcaag    60
caagaagtga cacagatccc tgccgctctg tctgtgcctg agggcgaaaa cctggtgctg   120
aactgcagct tcaccgacag cgccatctac aacctgcagt ggttcagaca ggaccccggc   180
aagggactga caagcctgct gctgattcag agcagccaga gagagcagac cagcggcaga   240
ctgaatgcca gcctggataa gtcctccggc agaagcaccc tgtatatcgc cgcttctcag   300
cctggcgata cgccacata tctgtgtgcc gttagaggcg gcaccacctc cggcacctac   360
aagtacatct ttggcaccgg caccagactg aaggtgctgg ccaatatcca gaaccccgac   420
cccgccgtgt accagctgag agacagcaag tccagcgaca gagcgtgtg tctgttcacc   480
gacttcgaca gccagaccaa cgtgtcccag agcaaggaca gcgacgtgta catcaccgat   540
aagtgcgtgc tggacatgcg gagcatggac ttcaagagca cagcgccgt ggcctggtcc   600
aacaagagcg acttcgcctg cgccaacgcc ttcaacaaca gcatcatccc cgaggacacc   660
ttttttcccca gccccgagag cagctgcgac gtgaaactgg tggagaagtc cttcgagaca   720
gacaccaatc tgaactttca gaacctgagc gtgatcggct ccggatcct gctgctgaaa   780
gtggccggct tcaatctgct gatgaccctg cggctgtgga gcagctga                828
```

<210> SEQ ID NO 53
<211> LENGTH: 609
<212> TYPE: PRT
<213> ORGANISM: Artificial Sequence
<220> FEATURE:
<223> OTHER INFORMATION: Synthetic sequence TCR1/13 beta-P2A-alpha
      (Cys modified) with signal peptide

<400> SEQUENCE: 53

Met Gly Thr Ser Leu Leu Cys Trp Met Ala Leu Cys Leu Leu Gly Ala
1               5                   10                  15

Asp His Ala Asp Thr Gly Val Ser Gln Asp Pro Arg His Lys Ile Thr
            20                  25                  30

Lys Arg Gly Gln Asn Val Thr Phe Arg Cys Asp Pro Ile Ser Glu His
        35                  40                  45

Asn Arg Leu Tyr Trp Tyr Arg Gln Thr Leu Gly Gln Gly Pro Glu Phe
    50                  55                  60

Leu Thr Tyr Phe Gln Asn Glu Ala Gln Leu Glu Lys Ser Arg Leu Leu
65                  70                  75                  80

Ser Asp Arg Phe Ser Ala Glu Arg Pro Lys Gly Ser Phe Ser Thr Leu
                85                  90                  95

Glu Ile Gln Arg Thr Glu Gln Gly Asp Ser Ala Met Tyr Leu Cys Ala
            100                 105                 110

Ser Ser Ser Thr Gly Gly His Asn Glu Gln Phe Phe Gly Pro Gly Thr
        115                 120                 125

Arg Leu Thr Val Leu Glu Asp Leu Lys Asn Val Phe Pro Pro Glu Val
    130                 135                 140

Ala Val Phe Glu Pro Ser Glu Ala Glu Ile Ser His Thr Gln Lys Ala
145                 150                 155                 160

Thr Leu Val Cys Leu Ala Thr Gly Phe Tyr Pro Asp His Val Glu Leu
                165                 170                 175

Ser Trp Trp Val Asn Gly Lys Glu Val His Ser Gly Val Cys Thr Asp
            180                 185                 190

Pro Gln Pro Leu Lys Glu Gln Pro Ala Leu Asn Asp Ser Arg Tyr Cys
        195                 200                 205

Leu Ser Ser Arg Leu Arg Val Ser Ala Thr Phe Trp Gln Asn Pro Arg

```
                     210                 215                 220
Asn His Phe Arg Cys Gln Val Gln Phe Tyr Gly Leu Ser Glu Asn Asp
225                 230                 235                 240

Glu Trp Thr Gln Asp Arg Ala Lys Pro Val Thr Gln Ile Val Ser Ala
                    245                 250                 255

Glu Ala Trp Gly Arg Ala Asp Cys Gly Phe Thr Ser Glu Ser Tyr Gln
                260                 265                 270

Gln Gly Val Leu Ser Ala Thr Ile Leu Tyr Glu Ile Leu Leu Gly Lys
            275                 280                 285

Ala Thr Leu Tyr Ala Val Leu Val Ser Ala Leu Val Leu Met Ala Met
290                 295                 300

Val Lys Arg Lys Asp Ser Arg Gly Gly Ser Gly Ala Thr Asn Phe Ser
305                 310                 315                 320

Leu Leu Lys Gln Ala Gly Asp Val Glu Glu Asn Pro Gly Pro Met Glu
                325                 330                 335

Thr Leu Leu Gly Val Ser Leu Val Ile Leu Trp Leu Gln Leu Ala Arg
                340                 345                 350

Val Asn Ser Gln Gln Gly Glu Glu Asp Pro Gln Ala Leu Ser Ile Gln
                355                 360                 365

Glu Gly Glu Asn Ala Thr Met Asn Cys Ser Tyr Lys Thr Ser Ile Asn
370                 375                 380

Asn Leu Gln Trp Tyr Arg Gln Asn Ser Gly Arg Gly Leu Val His Leu
385                 390                 395                 400

Ile Leu Ile Arg Ser Asn Glu Arg Glu Lys His Ser Gly Arg Leu Arg
                405                 410                 415

Val Thr Leu Asp Thr Ser Lys Lys Ser Ser Ser Leu Leu Ile Thr Ala
                420                 425                 430

Ser Arg Ala Ala Asp Thr Ala Ser Tyr Phe Cys Ala Thr Lys Arg Asp
                435                 440                 445

Ser Gly Ala Gly Ser Tyr Gln Leu Thr Phe Gly Lys Gly Thr Lys Leu
                450                 455                 460

Ser Val Ile Pro Asn Ile Gln Asn Pro Asp Pro Ala Val Tyr Gln Leu
465                 470                 475                 480

Arg Asp Ser Lys Ser Ser Asp Lys Ser Val Cys Leu Phe Thr Asp Phe
                485                 490                 495

Asp Ser Gln Thr Asn Val Ser Gln Ser Lys Asp Ser Asp Val Tyr Ile
                500                 505                 510

Thr Asp Lys Cys Val Leu Asp Met Arg Ser Met Asp Phe Lys Ser Asn
                515                 520                 525

Ser Ala Val Ala Trp Ser Asn Lys Ser Asp Phe Ala Cys Ala Asn Ala
530                 535                 540

Phe Asn Asn Ser Ile Ile Pro Glu Asp Thr Phe Phe Pro Ser Pro Glu
545                 550                 555                 560

Ser Ser Cys Asp Val Lys Leu Val Glu Lys Ser Phe Glu Thr Asp Thr
                565                 570                 575

Asn Leu Asn Phe Gln Asn Leu Ser Val Ile Gly Phe Arg Ile Leu Leu
                580                 585                 590

Leu Lys Val Ala Gly Phe Asn Leu Leu Met Thr Leu Arg Leu Trp Ser
                595                 600                 605

Ser

<210> SEQ ID NO 54
<211> LENGTH: 604
```

```
<212> TYPE: PRT
<213> ORGANISM: Artificial Sequence
<220> FEATURE:
<223> OTHER INFORMATION: Synthetic sequence TCR2/14 beta-P2A-alpha
      (Cys modified) with signal peptide

<400> SEQUENCE: 54
```

Met Gly Thr Ser Leu Leu Cys Trp Met Ala Leu Cys Leu Leu Gly Ala
1               5                   10                  15

Asp His Ala Asp Thr Gly Val Ser Gln Asp Pro Arg His Lys Ile Thr
            20                  25                  30

Lys Arg Gly Gln Asn Val Thr Phe Arg Cys Asp Pro Ile Ser Glu His
        35                  40                  45

Asn Arg Leu Tyr Trp Tyr Arg Gln Thr Leu Gly Gln Gly Pro Glu Phe
    50                  55                  60

Leu Thr Tyr Phe Gln Asn Glu Ala Gln Leu Glu Lys Ser Arg Leu Leu
65                  70                  75                  80

Ser Asp Arg Phe Ser Ala Glu Arg Pro Lys Gly Ser Phe Ser Thr Leu
                85                  90                  95

Glu Ile Gln Arg Thr Glu Gln Gly Asp Ser Ala Met Tyr Leu Cys Ala
            100                 105                 110

Ser Ser Leu Val Lys Gly Glu Lys Leu Phe Phe Gly Ser Gly Thr Gln
        115                 120                 125

Leu Ser Val Leu Glu Asp Leu Asn Lys Val Phe Pro Pro Glu Val Ala
    130                 135                 140

Val Phe Glu Pro Ser Glu Ala Glu Ile Ser His Thr Gln Lys Ala Thr
145                 150                 155                 160

Leu Val Cys Leu Ala Thr Gly Phe Phe Pro Asp His Val Glu Leu Ser
                165                 170                 175

Trp Trp Val Asn Gly Lys Glu Val His Ser Gly Val Cys Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
    210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Val Ser Tyr Gln Gln
            260                 265                 270

Gly Val Leu Ser Ala Thr Ile Leu Tyr Glu Ile Leu Leu Gly Lys Ala
        275                 280                 285

Thr Leu Tyr Ala Val Leu Val Ser Ala Leu Val Leu Met Ala Met Val
    290                 295                 300

Lys Arg Lys Asp Phe Gly Ser Gly Ala Thr Asn Phe Ser Leu Leu Lys
305                 310                 315                 320

Gln Ala Gly Asp Val Glu Glu Asn Pro Gly Pro Met Glu Thr Leu Leu
                325                 330                 335

Gly Leu Leu Ile Leu Trp Leu Gln Leu Gln Trp Val Ser Ser Lys Gln
            340                 345                 350

Glu Val Thr Gln Ile Pro Ala Ala Leu Ser Val Pro Glu Gly Glu Asn
        355                 360                 365

Leu Val Leu Asn Cys Ser Phe Thr Asp Ser Ala Ile Tyr Asn Leu Gln
    370                 375                 380

Trp Phe Arg Gln Asp Pro Gly Lys Gly Leu Thr Ser Leu Leu Leu Ile
385                 390                 395                 400

Gln Ser Ser Gln Arg Glu Gln Thr Ser Gly Arg Leu Asn Ala Ser Leu
            405                 410                 415

Asp Lys Ser Ser Gly Arg Ser Thr Leu Tyr Ile Ala Ala Ser Gln Pro
        420                 425                 430

Gly Asp Ser Ala Thr Tyr Leu Cys Ala Val Ile Gly Leu Gly Gly Thr
            435                 440                 445

Tyr Lys Tyr Ile Phe Gly Thr Gly Thr Arg Leu Lys Val Leu Ala Asn
        450                 455                 460

Ile Gln Asn Pro Asp Pro Ala Val Tyr Gln Leu Arg Asp Ser Lys Ser
465                 470                 475                 480

Ser Asp Lys Ser Val Cys Leu Phe Thr Asp Phe Asp Ser Gln Thr Asn
            485                 490                 495

Val Ser Gln Ser Lys Asp Ser Asp Val Tyr Ile Thr Asp Lys Cys Val
        500                 505                 510

Leu Asp Met Arg Ser Met Asp Phe Lys Ser Asn Ser Ala Val Ala Trp
            515                 520                 525

Ser Asn Lys Ser Asp Phe Ala Cys Ala Asn Ala Phe Asn Asn Ser Ile
        530                 535                 540

Ile Pro Glu Asp Thr Phe Phe Pro Ser Pro Glu Ser Ser Cys Asp Val
545                 550                 555                 560

Lys Leu Val Glu Lys Ser Phe Glu Thr Asp Thr Asn Leu Asn Phe Gln
            565                 570                 575

Asn Leu Ser Val Ile Gly Phe Arg Ile Leu Leu Leu Lys Val Ala Gly
        580                 585                 590

Phe Asn Leu Leu Met Thr Leu Arg Leu Trp Ser Ser
            595                 600

<210> SEQ ID NO 55
<211> LENGTH: 604
<212> TYPE: PRT
<213> ORGANISM: Artificial Sequence
<220> FEATURE:
<223> OTHER INFORMATION: Synthetic sequence TCR5 beta-P2A-alpha
      (Cys modified) with signal peptide

<400> SEQUENCE: 55

Met Gly Thr Ser Leu Leu Cys Trp Met Ala Leu Cys Leu Leu Gly Ala
1               5                   10                  15

Asp His Ala Asp Thr Gly Val Ser Gln Asp Pro Arg His Lys Ile Thr
            20                  25                  30

Lys Arg Gly Gln Asn Val Thr Phe Arg Cys Asp Pro Ile Ser Glu His
        35                  40                  45

Asn Arg Leu Tyr Trp Tyr Arg Gln Thr Leu Gly Gln Gly Pro Glu Phe
    50                  55                  60

Leu Thr Tyr Phe Gln Asn Glu Ala Gln Leu Glu Lys Ser Arg Leu Leu
65                  70                  75                  80

Ser Asp Arg Phe Ser Ala Glu Arg Pro Lys Gly Ser Phe Ser Thr Leu
                85                  90                  95

Glu Ile Gln Arg Thr Glu Gln Gly Asp Ser Ala Met Tyr Leu Cys Ala
            100                 105                 110

Ser Ser Leu Thr Thr Leu Asp Glu Gln Tyr Val Gly Pro Gly Thr Arg
        115                 120                 125

Leu Thr Val Thr Glu Asp Leu Lys Asn Val Phe Pro Pro Glu Val Ala

-continued

```
            130                 135                 140
Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
                165                 170                 175

Trp Trp Val Asn Gly Lys Glu Val His Ser Gly Val Cys Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
    210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Glu Ser Tyr Gln Gln
                260                 265                 270

Gly Val Leu Ser Ala Thr Ile Leu Tyr Glu Ile Leu Leu Gly Lys Ala
            275                 280                 285

Thr Leu Tyr Ala Val Leu Val Ser Ala Leu Val Leu Met Ala Met Val
        290                 295                 300

Lys Arg Lys Asp Ser Arg Gly Ser Gly Ala Thr Asn Phe Ser Leu
305                 310                 315                 320

Leu Lys Gln Ala Gly Asp Val Glu Glu Asn Pro Gly Pro Met Glu Thr
                325                 330                 335

Leu Leu Gly Val Ser Leu Val Ile Leu Trp Leu Gln Leu Ala Arg Val
            340                 345                 350

Asn Ser Gln Gln Gly Glu Glu Asp Pro Gln Ala Leu Ser Ile Gln Glu
        355                 360                 365

Gly Glu Asn Ala Thr Met Asn Cys Ser Tyr Lys Thr Ser Ile Asn Asn
    370                 375                 380

Leu Gln Trp Tyr Arg Gln Asn Ser Gly Arg Gly Leu Val His Leu Ile
385                 390                 395                 400

Leu Ile Arg Ser Asn Glu Arg Glu Lys His Ser Gly Arg Leu Arg Val
                405                 410                 415

Thr Leu Asp Thr Ser Lys Lys Ser Ser Ser Leu Leu Ile Thr Ala Ser
                420                 425                 430

Arg Ala Ala Asp Thr Ala Ser Tyr Phe Cys Ala Thr Asn Ser Gly Asn
            435                 440                 445

Thr Pro Leu Val Phe Gly Lys Gly Thr Arg Leu Ser Val Ile Ala Asn
        450                 455                 460

Ile Gln Asn Pro Asp Pro Ala Val Tyr Gln Leu Arg Asp Ser Lys Ser
465                 470                 475                 480

Ser Asp Lys Ser Val Cys Leu Phe Thr Asp Phe Asp Ser Gln Thr Asn
                485                 490                 495

Val Ser Gln Ser Lys Asp Ser Asp Val Tyr Ile Thr Asp Lys Cys Val
            500                 505                 510

Leu Asp Met Arg Ser Met Asp Phe Lys Ser Asn Ser Ala Val Ala Trp
        515                 520                 525

Ser Asn Lys Ser Asp Phe Ala Cys Ala Asn Ala Phe Asn Asn Ser Ile
    530                 535                 540

Ile Pro Glu Asp Thr Phe Phe Pro Ser Pro Glu Ser Ser Cys Asp Val
545                 550                 555                 560
```

```
Lys Leu Val Glu Lys Ser Phe Glu Thr Asp Thr Asn Leu Asn Phe Gln
            565                 570                 575

Asn Leu Ser Val Ile Gly Phe Arg Ile Leu Leu Lys Val Ala Gly
            580                 585                 590

Phe Asn Leu Leu Met Thr Leu Arg Leu Trp Ser Ser
            595                 600
```

<210> SEQ ID NO 56
<211> LENGTH: 608
<212> TYPE: PRT
<213> ORGANISM: Artificial Sequence
<220> FEATURE:
<223> OTHER INFORMATION: Synthetic sequence TCR10 beta-P2A-alpha
      (Cys modified) with signal peptide

<400> SEQUENCE: 56

```
Met Gly Thr Ser Leu Leu Cys Trp Met Ala Leu Cys Leu Leu Gly Ala
1               5                   10                  15

Asp His Ala Asp Thr Gly Val Ser Gln Asp Pro Arg His Lys Ile Thr
            20                  25                  30

Lys Arg Gly Gln Asn Val Thr Phe Arg Cys Asp Pro Ile Ser Glu His
        35                  40                  45

Asn Arg Leu Tyr Trp Tyr Arg Gln Thr Leu Gly Gln Gly Pro Glu Phe
    50                  55                  60

Leu Thr Tyr Phe Gln Asn Glu Ala Gln Leu Glu Lys Ser Arg Leu Leu
65                  70                  75                  80

Ser Asp Arg Phe Ser Ala Glu Arg Pro Lys Gly Ser Phe Ser Thr Leu
            85                  90                  95

Glu Ile Gln Arg Thr Glu Gln Gly Asp Ser Ala Met Tyr Leu Cys Ala
        100                 105                 110

Ser Ser Met Leu Thr Asn Tyr Glu Gln Tyr Phe Gly Pro Gly Thr Arg
    115                 120                 125

Leu Thr Val Thr Glu Asp Leu Lys Asn Val Phe Pro Pro Glu Val Ala
            130                 135                 140

Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
            165                 170                 175

Trp Trp Val Asn Gly Lys Glu Val His Ser Gly Val Cys Thr Asp Pro
        180                 185                 190

Gln Pro Leu Lys Glu Gln Pro Ala Leu Asn Asp Ser Arg Tyr Cys Leu
    195                 200                 205

Ser Ser Arg Leu Arg Val Ser Ala Thr Phe Trp Gln Asn Pro Arg Asn
210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
            245                 250                 255

Ala Trp Gly Arg Ala Asp Cys Gly Phe Thr Ser Glu Ser Tyr Gln Gln
        260                 265                 270

Gly Val Leu Ser Ala Thr Ile Leu Tyr Glu Ile Leu Leu Gly Lys Ala
    275                 280                 285

Thr Leu Tyr Ala Val Leu Val Ser Ala Leu Val Leu Met Ala Met Val
290                 295                 300

Lys Arg Lys Asp Ser Arg Gly Gly Ser Gly Ala Thr Asn Phe Ser Leu
```

```
                305                 310                 315                 320
Leu Lys Gln Ala Gly Asp Val Glu Glu Asn Pro Gly Pro Met Lys Lys
                    325                 330                 335

His Leu Thr Thr Phe Leu Val Ile Leu Trp Leu Tyr Phe Tyr Arg Gly
                340                 345                 350

Asn Gly Lys Asn Gln Val Glu Gln Ser Pro Gln Ser Leu Ile Ile Leu
            355                 360                 365

Glu Gly Lys Asn Cys Thr Leu Gln Cys Asn Tyr Thr Val Ser Pro Phe
        370                 375                 380

Ser Asn Leu Arg Trp Tyr Lys Gln Asp Thr Gly Arg Gly Pro Val Ser
385                 390                 395                 400

Leu Thr Ile Met Thr Phe Ser Glu Asn Thr Lys Ser Asn Gly Arg Tyr
                405                 410                 415

Thr Ala Thr Leu Asp Ala Asp Thr Lys Gln Ser Ser Leu His Ile Thr
                420                 425                 430

Ala Ser Gln Leu Ser Asp Ser Ala Ser Tyr Ile Cys Val Val Asp Ser
            435                 440                 445

Gly Gly Gly Ala Asp Gly Leu Thr Phe Gly Lys Gly Thr His Leu Ile
        450                 455                 460

Ile Gln Pro Tyr Ile Gln Asn Pro Asp Pro Ala Val Tyr Gln Leu Arg
465                 470                 475                 480

Asp Ser Lys Ser Ser Asp Lys Ser Val Cys Leu Phe Thr Asp Phe Asp
                485                 490                 495

Ser Gln Thr Asn Val Ser Gln Ser Lys Asp Ser Asp Val Tyr Ile Thr
                500                 505                 510

Asp Lys Cys Val Leu Asp Met Arg Ser Met Asp Phe Lys Ser Asn Ser
            515                 520                 525

Ala Val Ala Trp Ser Asn Lys Ser Asp Phe Ala Cys Ala Asn Ala Phe
        530                 535                 540

Asn Asn Ser Ile Ile Pro Glu Asp Thr Phe Phe Pro Ser Pro Glu Ser
545                 550                 555                 560

Ser Cys Asp Val Lys Leu Val Glu Lys Ser Phe Glu Thr Asp Thr Asn
                565                 570                 575

Leu Asn Phe Gln Asn Leu Ser Val Ile Gly Phe Arg Ile Leu Leu Leu
                580                 585                 590

Lys Val Ala Gly Phe Asn Leu Leu Met Thr Leu Arg Leu Trp Ser Ser
            595                 600                 605

<210> SEQ ID NO 57
<211> LENGTH: 605
<212> TYPE: PRT
<213> ORGANISM: Artificial Sequence
<220> FEATURE:
<223> OTHER INFORMATION: Synthetic sequence TCR16 beta-P2A-alpha
      (Cys modified) with signal peptide

<400> SEQUENCE: 57

Met Gly Thr Ser Leu Leu Cys Trp Met Ala Leu Cys Leu Leu Gly Ala
1               5                   10                  15

Asp His Ala Asp Thr Gly Val Ser Gln Asp Pro Arg His Lys Ile Thr
                20                  25                  30

Lys Arg Gly Gln Asn Val Thr Phe Arg Cys Asp Pro Ile Ser Glu His
            35                  40                  45

Asn Arg Leu Tyr Trp Tyr Arg Gln Thr Leu Gly Gln Gly Pro Glu Phe
        50                  55                  60
```

-continued

```
Leu Thr Tyr Phe Gln Asn Glu Ala Gln Leu Glu Lys Ser Arg Leu Leu
 65                  70                  75                  80

Ser Asp Arg Phe Ser Ala Glu Arg Pro Lys Gly Ser Phe Ser Thr Leu
                 85                  90                  95

Glu Ile Gln Arg Thr Glu Gln Gly Asp Ser Ala Met Tyr Leu Cys Ala
            100                 105                 110

Ser Ser Leu Val Val Gly Asn Glu Gln Phe Phe Gly Pro Gly Thr Arg
        115                 120                 125

Leu Thr Val Leu Glu Asp Leu Lys Asn Val Phe Pro Pro Glu Val Ala
    130                 135                 140

Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
                165                 170                 175

Trp Trp Val Asn Gly Lys Glu Val His Ser Gly Val Cys Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
    210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Glu Ser Tyr Gln Gln
            260                 265                 270

Gly Val Leu Ser Ala Thr Ile Leu Tyr Glu Ile Leu Leu Gly Lys Ala
        275                 280                 285

Thr Leu Tyr Ala Val Leu Val Ser Ala Leu Val Leu Met Ala Met Val
    290                 295                 300

Lys Arg Lys Asp Ser Arg Gly Gly Ser Gly Ala Thr Asn Phe Ser Leu
305                 310                 315                 320

Leu Lys Gln Ala Gly Asp Val Glu Glu Asn Pro Gly Pro Met Glu Thr
                325                 330                 335

Leu Leu Gly Leu Leu Ile Leu Trp Leu Gln Leu Gln Trp Val Ser Ser
            340                 345                 350

Lys Gln Glu Val Thr Gln Ile Pro Ala Ala Leu Ser Val Pro Glu Gly
        355                 360                 365

Glu Asn Leu Val Leu Asn Cys Ser Phe Thr Asp Ser Ala Ile Tyr Asn
    370                 375                 380

Leu Gln Trp Phe Arg Gln Asp Pro Gly Lys Gly Leu Thr Ser Leu Leu
385                 390                 395                 400

Leu Ile Gln Ser Ser Gln Arg Glu Gln Thr Ser Gly Arg Leu Asn Ala
                405                 410                 415

Ser Leu Asp Lys Ser Ser Gly Arg Ser Thr Leu Tyr Ile Ala Ala Ser
            420                 425                 430

Gln Pro Gly Asp Ser Ala Thr Tyr Leu Cys Ala Val His Leu Leu Asn
        435                 440                 445

Asp Tyr Lys Leu Ser Phe Gly Ala Gly Thr Thr Val Thr Val Arg Ala
    450                 455                 460

Asn Ile Gln Asn Pro Asp Pro Ala Val Tyr Gln Leu Arg Asp Ser Lys
465                 470                 475                 480

Ser Ser Asp Lys Ser Val Cys Leu Phe Thr Asp Phe Asp Ser Gln Thr
```

```
                    485                 490                 495
Asn Val Ser Gln Ser Lys Asp Ser Asp Val Tyr Ile Thr Asp Lys Cys
                500                 505                 510

Val Leu Asp Met Arg Ser Met Asp Phe Lys Ser Asn Ser Ala Val Ala
                515                 520                 525

Trp Ser Asn Lys Ser Asp Phe Ala Cys Ala Asn Ala Phe Asn Asn Ser
        530                 535                 540

Ile Ile Pro Glu Asp Thr Phe Phe Pro Ser Glu Ser Ser Cys Asp
545                 550                 555                 560

Val Lys Leu Val Glu Lys Ser Phe Glu Thr Asp Thr Asn Leu Asn Phe
                565                 570                 575

Gln Asn Leu Ser Val Ile Gly Phe Arg Ile Leu Leu Lys Val Ala
                580                 585                 590

Gly Phe Asn Leu Leu Met Thr Leu Arg Leu Trp Ser Ser
                595                 600                 605

<210> SEQ ID NO 58
<211> LENGTH: 585
<212> TYPE: PRT
<213> ORGANISM: Artificial Sequence
<220> FEATURE:
<223> OTHER INFORMATION: Synthetic sequence Consensus sequence of the
      TCR beta-P2A-alpha

<400> SEQUENCE: 58

Met Gly Thr Ser Leu Leu Cys Trp Met Ala Leu Cys Leu Leu Gly Ala
1               5                   10                  15

Asp His Ala Asp Thr Gly Val Ser Gln Asp Pro Arg His Lys Ile Thr
                20                  25                  30

Lys Arg Gly Gln Asn Val Thr Phe Arg Cys Asp Pro Ile Ser Glu His
            35                  40                  45

Asn Arg Leu Tyr Trp Tyr Arg Gln Thr Leu Gly Gln Gly Pro Glu Phe
        50                  55                  60

Leu Thr Tyr Phe Gln Asn Glu Ala Gln Leu Glu Lys Ser Arg Leu Leu
65                  70                  75                  80

Ser Asp Arg Phe Ser Ala Glu Arg Pro Lys Gly Ser Phe Ser Thr Leu
                85                  90                  95

Glu Ile Gln Arg Thr Glu Gln Gly Asp Ser Ala Met Tyr Leu Cys Ala
            100                 105                 110

Ser Ser Leu Val Gly Glu Gln Phe Phe Gly Pro Gly Thr Arg Leu Thr
        115                 120                 125

Val Leu Glu Asp Leu Lys Asn Val Phe Pro Pro Glu Val Ala Val Phe
130                 135                 140

Glu Pro Ser Glu Ala Glu Ile Ser His Thr Gln Lys Ala Thr Leu Val
145                 150                 155                 160

Cys Leu Ala Thr Gly Phe Tyr Pro Asp His Val Glu Leu Ser Trp Trp
                165                 170                 175

Val Asn Gly Lys Glu Val His Ser Gly Val Cys Thr Asp Pro Gln Pro
            180                 185                 190

Leu Lys Glu Gln Pro Ala Leu Asn Asp Ser Arg Tyr Cys Leu Ser Ser
        195                 200                 205

Arg Leu Arg Val Ser Ala Thr Phe Trp Gln Asn Pro Arg Asn His Phe
210                 215                 220

Arg Cys Gln Val Gln Phe Tyr Gly Leu Ser Glu Asn Asp Glu Trp Thr
225                 230                 235                 240
```

Gln Asp Arg Ala Lys Pro Val Thr Gln Ile Val Ser Ala Glu Ala Trp
            245                 250                 255

Gly Arg Ala Asp Cys Gly Phe Thr Ser Glu Ser Tyr Gln Gln Gly Val
        260                 265                 270

Leu Ser Ala Thr Ile Leu Tyr Glu Ile Leu Leu Gly Lys Ala Thr Leu
    275                 280                 285

Tyr Ala Val Leu Val Ser Ala Leu Val Leu Met Ala Met Val Lys Arg
290                 295                 300

Lys Asp Ser Arg Gly Ser Gly Ala Thr Asn Phe Ser Leu Leu Lys
305                 310                 315                 320

Gln Ala Gly Asp Val Glu Glu Asn Pro Gly Pro Met Glu Thr Leu Leu
            325                 330                 335

Gly Leu Val Ile Leu Trp Leu Gln Leu Arg Val Asn Ser Lys Gln Gln
        340                 345                 350

Pro Gln Ala Leu Ser Ile Glu Gly Glu Asn Thr Leu Asn Cys Ser Tyr
    355                 360                 365

Thr Ser Ile Asn Leu Gln Trp Tyr Arg Gln Asp Ser Gly Arg Gly Leu
    370                 375                 380

Val Ser Leu Leu Leu Ile Ser Ser Glu Arg Glu Lys Thr Ser Gly Arg
385                 390                 395                 400

Leu Ala Thr Leu Asp Ser Ser Lys Ser Ser Leu Ile Thr Ala Ser Gln
            405                 410                 415

Gly Asp Ser Ala Ser Tyr Leu Cys Ala Val Ser Gly Gly Tyr Leu
        420                 425                 430

Thr Phe Gly Lys Gly Thr Arg Leu Ser Val Leu Ala Asn Ile Gln Asn
    435                 440                 445

Pro Asp Pro Ala Val Tyr Gln Leu Arg Asp Ser Lys Ser Ser Asp Lys
450                 455                 460

Ser Val Cys Leu Phe Thr Asp Phe Asp Ser Gln Thr Asn Val Ser Gln
465                 470                 475                 480

Ser Lys Asp Ser Asp Val Tyr Ile Thr Asp Lys Cys Val Leu Asp Met
            485                 490                 495

Arg Ser Met Asp Phe Lys Ser Asn Ser Ala Val Ala Trp Ser Asn Lys
        500                 505                 510

Ser Asp Phe Ala Cys Ala Asn Ala Phe Asn Asn Ser Ile Ile Pro Glu
    515                 520                 525

Asp Thr Phe Phe Pro Ser Pro Glu Ser Ser Cys Asp Val Lys Leu Val
530                 535                 540

Glu Lys Ser Phe Glu Thr Asp Thr Asn Leu Asn Phe Gln Asn Leu Ser
545                 550                 555                 560

Val Ile Gly Phe Arg Ile Leu Leu Leu Lys Val Ala Gly Phe Asn Leu
            565                 570                 575

Leu Met Thr Leu Arg Leu Trp Ser Ser
        580                 585

<210> SEQ ID NO 59
<211> LENGTH: 1830
<212> TYPE: DNA
<213> ORGANISM: Artificial Sequence
<220> FEATURE:
<223> OTHER INFORMATION: Synthetic sequence TCR1/13 beta-P2A-alpha
      (codon optimized; Cys modified)

<400> SEQUENCE: 59
atgggcacct ccctgctgtg ttggatggcc ctgtgtctgc tgggagccga ccatgccgat    60

```
acaggggtgt cccaggaccc ccggcacaag attaccaagc ggggccagaa cgtgaccttc    120
agatgcgacc ccatcagcga gcacaaccgg ctgtactggt acaggcagac cctgggccag    180
ggccccgagt tcctgaccta ctttcagaac gaggcccagc tggaaaagtc ccggctgctg    240
agcgacagat tcagcgccga aagacccaag ggcagcttca gcaccctgga aatccagcgg    300
accgagcagg gcgatagcgc catgtacctg tgtgccagca gcagcacagg cggccacaac    360
gagcagttct ttggccctgg cacccggctg accgtgctgg aagatctgaa gaacgtgttc    420
cccccagagg tggccgtgtt cgagccttct gaggccgaga tcagccacac ccagaaagcc    480
accctcgtgt gtctggccac cggcttctac cccgaccacg tggaactgtc ttggtgggtc    540
aacggcaaag aggtgcactc cggcgtgtgc accgatcccc agcctctgaa agaacagccc    600
gccctgaacg acagccggta ctgcctgagc agcagactga gagtgtccgc caccttctgg    660
cagaaccccc ggaaccactt cagatgccag gtgcagttct acggcctgag cgagaacgac    720
gagtggaccc aggacagagc caagcccgtg acccagatcg tgtctgccga agcctggggc    780
agagccgatt gcggctttac cagcgagagc taccagcagg gcgtgctgag cgccaccatc    840
ctgtacgaga tcctgctggg caaggccacc ctgtacgccg tgctggtgtc tgccctggtg    900
ctgatggcca tggtcaagcg gaaggacagc agaggcggaa gcggcgccac caacttcagc    960
ctgctgaaac aggccggcga cgtggaagag aaccctggcc tatggaaaac actgctgggc   1020
gtgtccctcg tgatcctgtg gctgcagctg gccagagtga cagccagca ggggggaagag   1080 gatccccagg ccctgagcat tcaggaaggc gagaacgcca ccatgaactg cagctacaag   1140
accagcatca caaacctgca gtggtacaga cagaacagcg gcagaggcct ggtgcacctg   1200
atcctgatca gaagcaacga gagagagaag cacagcggac ggctgagagt gacccctgga    1260
acctccaaga gtccagctc cctgctgatc accgccagca gagccgccga taccgccagc    1320
tacttctgtg ccaccaagcg ggattctggc gccggatcct accagctgac cttcggcaag    1380
ggcaccaagc tgagcgtgat ccccaacatc cagaaccccg accccgccgt gtatcagctg    1440
agagacagca gagcagcga caagagcgtg tgcctgttca ccgacttcga cagccagacc    1500
aacgtgtccc agagcaagga cagcgacgtg tacatcaccg ataagtgcgt gctggacatg    1560
cggagcatgg acttcaagag caacagcgcc gtggcctggt ccaacaagag cgacttcgcc    1620
tgcgccaacg ccttcaacaa cagcatcatc cccgaggaca ccttttttccc cagccccgag    1680 agcagctgcg acgtgaaact ggtggagaag tccttcgaga cagacaccaa tctgaacttt    1740
cagaacctga gcgtgatcgg cttccggatc ctgctgctga aagtggccgg cttcaatctg    1800
ctgatgaccc tgcggctgtg gagcagctga                                     1830
```

<210> SEQ ID NO 60
<211> LENGTH: 1813
<212> TYPE: DNA
<213> ORGANISM: Artificial Sequence
<220> FEATURE:
<223> OTHER INFORMATION: Synthetic sequence TCR2/14 beta-P2A-alpha
      (codon optimized; Cys modified)

<400> SEQUENCE: 60

```
atgggcacct ccctgctgtg ttggatggcc ctgtgtctgc tgggagccga ccatgccgat     60
acaggggtgt cccaggaccc ccggcacaag attaccaagc ggggccagaa cgtgaccttc    120
agatgcgacc ccatcagcga gcacaaccgg ctgtactggt acaggcagac cctgggccag    180
ggccccgagt tcctgaccta ctttcagaac gaggcccagc tggaaaagtc ccggctgctg    240
```

| | |
|---|---|
| agcgacagat tcagcgccga aagacccaag ggcagcttca gcaccctgga aatccagcgg | 300 |
| accgagcagg gcgatagcgc catgtacctg tgtgccagca gcctcgtgaa gggcgagaag | 360 |
| ctgttcttcg gcagcggcac ccagctgagc gtgctggaag atctgaacaa ggtgttcccc | 420 |
| ccagaggtgg ccgtgttcga gccttctgag gccgagatca gccacaccca gaaagccacc | 480 |
| ctcgtgtgcc tggccaccgg ctttttcccc gaccacgtgg aactgtcttg gtgggtcaac | 540 |
| ggcaaagagg tgcactccgg cgtgtgcacc gatccccagc ctctgaaaga cagcccgcc | 600 |
| ctgaacgaca gccggtactg cctgagcagc agactgagag tgtccgccac cttctggcag | 660 |
| aaccccggga accacttcag atgccaggtg cagttctacg gcctgagcga aaacgacgag | 720 |
| tggacccagg acagagccaa gcccgtgacc cagatcgtgt ctgccgaagc tgggggcaga | 780 |
| gccgattgcg gctttaccag cgtgtcctat cagcagggcg tgctgagcgc caccatcctg | 840 |
| tacgagatcc tgctgggcaa ggccaccctg tacgccgtgc tggtgtctgc cctggtgctg | 900 |
| atggccatgg tcaagcggaa ggactttggc agcggcgcca ccaacttcag cctgctgaaa | 960 |
| caggccggcg acgtggaaga gaaccctggc cctaatctga actttcagaa cctgagcgtg | 1020 |
| atcggcttcc ggatcctgct gctgaaagtg gccggcttca atctgctgat gaccctgcgg | 1080 |
| ctgtggagca gcgatggaaa cactgctggg cctgctgatc ctgtggctgc agctgcagtg | 1140 |
| ggtgtccagc aagcaggaag tgacacagat ccctgccgcc ctgtctgtgc ccagggcga | 1200 |
| aaatctggtg ctgaactgca gcttcaccga cagcgccatc tacaacctgc agtggttcag | 1260 |
| acaggacccc ggcaagggcc tgacaagcct gctgctgatt cagagcagcc agagagagca | 1320 |
| gaccagcggc agactgaacg ccagcctgga taagagcagc ggccgcagca ccctgtatat | 1380 |
| cgccgcttct cagcctggcg actctgccac atatctgtgc gccgtgatcg gcctgggcgg | 1440 |
| cacctacaag tacatctttg gcaccggcac cagactgaaa gtgctggcca acatccagaa | 1500 |
| ccccgacccc gccgtgtacc agctgagaga cagcaagtcc agcgacaaga gcgtgtgtct | 1560 |
| gttcaccgac ttcgacagcc agaccaacgt gtcccagagc aaggacagcg acgtgtacat | 1620 |
| caccgataag tgcgtgctgg acatgcggag catggacttc aagagcaaca gcgccgtggc | 1680 |
| ctggtccaac aagagcgact tcgcctgcgc caacgccttc aacaacagca tcatccccga | 1740 |
| ggacaccttt ttccccagcc ccgagagcag ctgcgacgtg aaactggtgg agaagtcctt | 1800 |
| cgagacagac acc | 1813 |

<210> SEQ ID NO 61
<211> LENGTH: 1815
<212> TYPE: DNA
<213> ORGANISM: Artificial Sequence
<220> FEATURE:
<223> OTHER INFORMATION: Synthetic sequence TCR5 beta-P2A-alpha
      (codon optimized; Cys modified)

<400> SEQUENCE: 61

| | |
|---|---|
| atgggcacct ccctgctgtg ttggatggcc ctgtgtctgc tgggagccga ccatgccgat | 60 |
| acagggggtgt cccaggaccc ccggcacaag attaccaagc ggggccagaa cgtgaccttc | 120 |
| agatgcgacc ccatcagcga gcacaaccgg ctgtactggt acaggcagac cctgggccag | 180 |
| ggccccgagt tcctgaccta ctttcagaac gaggcccagc tggaaaagtc ccggctgctg | 240 |
| agcgacagat tcagcgccga aagacccaag ggcagcttca gcaccctgga aatccagcgg | 300 |
| accgagcagg gggacagcgc catgtacctg tgtgccagct ccctgaccac cctggacgag | 360 |
| cagtatgtgg gccaggcac cagactgacc gtgaccgagg acctgaagaa cgtgttcccc | 420 |

```
ccagaggtgg ccgtgttcga gccttctgag gccgagatca gccacaccca gaaagccacc    480
ctcgtgtgtc tggccaccgg cttctacccc gatcacgtgg agctgtcttg gtgggtgaac    540
ggcaaagagg tgcacagcgg cgtctgcacc gaccccagc ccctgaaaga gcagcccgcc    600
ctgaacgaca gccggtactg cctgagcagc cggctgagag tgagcgccac cttctggcag    660
aaccccgga accacttccg gtgccaggtg cagttctacg gcctgagcga aaacgacgag    720
tggacccagg acagagccaa gcccgtgacc cagatcgtga cgccgaggc ctggggcaga    780
gccgactgcg gcttcaccag cgagagctac cagcagggcg tgctgtccgc cacaatcctg    840
tacgagatcc tgctgggcaa ggccaccctg tacgccgtgc tggtgtccgc cctggtgctg    900
atggccatgg tgaagcggaa ggacagccgg ggcggcagcg gcgccaccaa cttcagcctg    960
ctgaagcagg ccggcgacgt ggaggaaaac cctggcccca tggaaaccct gctgggcgtg   1020
tccctcgtga tcctgtggct gcagctggcc agagtgaaca gccagcaggg cgaagaagat   1080
ccccaggccc tgagcatcca ggaaggcgag aacgccacaa tgaactgcag ctacaagacc   1140
agcatcaaca acctgcagtg gtacagacag aacagcggca gggcctggt gcacctgatc   1200
ctgatcagaa gcaacgagag agaagaagcac tccggcagac tgagagtgac cctggacacc   1260
agcaagaagt ccagcagcct gctgatcacc gccagcagag ccgccgatac cgccagctac   1320
ttctgcgcca ccaactccgg caacaccccc ctggtgttg gcaagggcac ccggctgagc   1380
gtgatcgcca acatccagaa ccccgacccc gccgtgtacc agctgagaga cagcaagagc   1440
agcgacaaga gcgtgtgcct gttcaccgac ttcgacagcc agaccaacgt gtcccagagc   1500
aaggacagcg acgtgtacat caccgataag tgcgtgctgg acatgcggag catggacttc   1560
aagagcaaca gcgccgtggc ctggtccaac aagagcgact tcgcctgcgc caacgccttc   1620
aacaacagca tcatccccga ggacaccttt ttccccagcc ccgagagcag ctgcgacgtg   1680
aaactggtgg agaagtcctt cgagacagac accaatctga actttcagaa cctgagcgtg   1740
atcggcttcc ggatcctgct gctgaaagtg gccggcttca atctgctgat gaccctgcgg   1800
ctgtggagca gctga                                                   1815
```

<210> SEQ ID NO 62
<211> LENGTH: 1827
<212> TYPE: DNA
<213> ORGANISM: Artificial Sequence
<220> FEATURE:
<223> OTHER INFORMATION: Synthetic sequence TCR10 beta P2A-alpha
      (codon optimized; Cys modified)

<400> SEQUENCE: 62

```
atgggcacct ccctgctgtg ttggatggcc ctgtgtctgc tgggagccga ccatgccgat     60
acagggtgt cccaggaccc ccggcacaag attaccaagc ggggccagaa cgtgaccttc    120
agatgcgacc ccatcagcga gcacaaccgg ctgtactggt acaggcagac cctgggccag    180
ggccccgagt cctgaccta cttcagaac gaggcccagc tggaaaagtc ccggctgctg    240
agcgacagat tcagcgccga aagacccaag ggcagcttca gcaccctgga aatccagcgg    300
accgagcagg gcgatagcgc catgtacctg tgcgccagct ccatgctgac caactacgag    360
cagtacttcg gccctggcac ccggctgacc gtgaccgagg atctgaagaa cgtgttcccc    420
ccagaggtgg ccgtgttcga gccttctgag gccgagatca gccacaccca gaaagccacc    480
ctcgtgtgtc tggccaccgg cttctacccc gaccacgtgg aactgtcttg gtgggtcaac    540
ggcaaagagg tgcactccgg cgtgtgcacc gatccccagc ctctgaaaga acagcccgcc    600
```

```
ctgaacgaca gccggtactg cctgagcagc agactgagag tgtccgccac cttctggcag    660
aaccccggga accacttcag atgccaggtg cagttctacg gcctgagcga gaacgacgag    720
tggacccagg acagagccaa gcccgtgacc cagatcgtgt ctgccgaagc ctggggcaga    780
gccgattgcg gctttaccag cgagagctac cagcagggcg tgctgagcgc caccatcctg    840
tacgagatcc tgctgggcaa ggccaccctg tacgccgtgc tggtgtctgc cctggtgctg    900
atggccatgg tcaagcggaa ggacagcaga ggcggaagcg cgccaccaa cttcagcctg    960 ctgaaacagg ccggcgacgt ggaagagaac cctggcccca tgaagaagca cctgaccacc   1020
tttctcgtga tcctgtggct gtacttctac cggggcaacg gcaagaacca ggtgaacag   1080 agcccccaga gcctgatcat cctggaaggc aagaattgca ccctgcagtg caactacacc   1140 gtgtcccccct tcagcaacct gcggtggtac aagcaggaca ccggcagagg ccctgtgtcc   1200
ctgaccatca tgaccttcag cgagaacacc aagagcaacg gccggtacac cgccaccctg   1260
gatgccgata caaagcagag cagcctgcac atcaccgcca gcagctgag cgattccgcc   1320 agctacatct gcgtggtgga ttctggcggc ggagccgatg gcctgacatt tggcaagggc   1380
acccacctga tcattcagcc ctacatccaa aaccccgacc ccgccgtgta ccagctgaga   1440
gacagcaagt ccgcgacaa gagcgtgtgc ctgttcaccg acttcgacag ccagaccaac   1500
gtgtcccaga gcaaggacag cgacgtgtac atcaccgata gtgcgtgct ggacatgcgg   1560 agcatggact tcaagagcaa cagcgccgtg gcctggtcca acaagagcga cttcgcctgc   1620
gccaacgcct tcaacaacag catcatcccc gaggacacct tttcccccag ccccgagagc   1680
agctgcgacg tgaaactggt ggagaagtcc ttcgagacag acaccaatct gaactttcag   1740
aacctgagcg tgatcggctt ccggatcctg ctgctgaaag tggccggctt caatctgctg   1800
atgaccctgc ggctgtggag cagctga                                       1827

<210> SEQ ID NO 63
<211> LENGTH: 1818
<212> TYPE: DNA
<213> ORGANISM: Artificial Sequence
<220> FEATURE:
<223> OTHER INFORMATION: Synthetic sequence TCR16 beta-P2A-alpha
      (codon optimized; Cys modified)

<400> SEQUENCE: 63
atgggcacct ccctgctgtg ttggatggcc ctgtgtctgc tgggagccga ccatgccgat    60 acagggggtgt cccaggaccc ccggcacaag attaccaagc ggggccagaa cgtgaccttc    120
agatgcgacc ccatcagcga gcacaaccgg ctgtactggt acaggcagac cctgggccag    180
ggccccgagt tcctgaccta ctttcagaac gaggcccagc tggaaaagtc ccggctgctg    240
agcgacagat tcagcgccga aagacccaag ggcagcttca gcaccctgga aatccagcgg    300
accgagcagg gcgatagcgc catgtacctg tgtgccagca gcctggtcgt gggcaacgag    360
cagtttttcg gccctggcac cagactgacc gtgctggaag atctgaagaa cgtgttcccc    420
ccagaggtgg ccgtgttcga gccttctgag gccgagatca gccacaccca gaaagccacc    480
ctcgtgtgtc tggccaccgg cttctaccc gaccacgtgg aactgtcttg gtgggtcaac    540
ggcaaagagg tgcactccgg cgtgtgcacc gatccccagc tctgaaaga cagcccgcc    600 ctgaacgaca gccggtactg cctgagcagc agactgagag tgtccgccac cttctggcag    660
aaccccggga accacttcag atgccaggtg cagttctacg gcctgagcga gaacgacgag    720
tggacccagg acagagccaa gcccgtgacc cagatcgtgt ctgccgaagc ctggggcaga    780
```

```
gccgattgcg gctttaccag cgagagctac cagcagggcg tgctgagcgc caccatcctg    840
tacgagatcc tgctgggcaa ggccacccty tacgccgtgc tggtgtctgc cctggtgctg    900
atggccatgg tcaagcggaa ggacagcaga ggcggaagcg gcgccaccaa cttcagcctg    960
ctgaaacagg ccggcgacgt ggaagagaac cctggcccta tggaaacact gctgggcctg   1020
ctgatcctgt ggctgcagct gcagtgggtg tccagcaagc aggaagtgac acagatccct   1080
gccgccctgt ctgtgcccga gggcgaaaat ctggtgctga actgcagctt caccgacagc   1140
gccatctaca acctgcagtg gttcagacag gaccccggca agggcctgac aagcctgctg   1200
ctgattcaga gcagccagag agagcagacc agcggcagac tgaacgccag cctggataag   1260
agcagcggcc gcagcaccct gtatatcgcc gcttctcagc ctggcgactc tgccacatat   1320
ctgtgcgccg tgcatctgct gaacgactac aagctgagct cggagccgg caccaccgtg   1380
acagtgcggg ccaacatcca gaaccccgac cctgccgtgt accagctgag agacagcaag   1440
tccagcgaca gagcgtgtg cctgttcacc gacttcgaca gccagaccaa cgtgtcccag   1500
agcaaggaca gcgacgtgta catcaccgat aagtgcgtgc tggacatgcg gagcatggac   1560
ttcaagagca cagcgccgt ggcctggtcc aacaagagcg acttcgcctg cgccaacgcc   1620
ttcaacaaca gcatcatccc cgaggacacc ttttccca gccccgagag cagctgcgac   1680
gtgaaactgg tggagaagtc cttcgagaca gacaccaatc tgaactttca gaacctgagc   1740
gtgatcggct ccggatcct gctgctgaaa gtggccggct tcaatctgct gatgaccctg   1800
cggctgtgga gcagctga                                                 1818
```

<210> SEQ ID NO 64
<211> LENGTH: 1135
<212> TYPE: PRT
<213> ORGANISM: Artificial Sequence
<220> FEATURE:
<223> OTHER INFORMATION: Synthetic sequence HMHA1 (wt)

<400> SEQUENCE: 64

```
Met Phe Ser Arg Lys Lys Arg Glu Leu Met Lys Thr Pro Ser Ile Ser
1               5                   10                  15

Lys Lys Asn Arg Ala Gly Ser Pro Ser Pro Gln Pro Ser Gly Glu Leu
            20                  25                  30

Pro Arg Lys Asp Gly Ala Asp Ala Val Phe Pro Gly Pro Ser Leu Glu
        35                  40                  45

Pro Pro Ala Gly Ser Ser Gly Val Lys Ala Thr Gly Thr Leu Lys Arg
    50                  55                  60

Pro Thr Ser Leu Ser Arg His Ala Ser Ala Ala Gly Phe Pro Leu Ser
65                  70                  75                  80

Gly Ala Ala Ser Trp Thr Leu Gly Arg Ser His Arg Ser Pro Leu Thr
                85                  90                  95

Ala Ala Ser Pro Gly Glu Leu Pro Thr Glu Gly Ala Gly Pro Asp Val
            100                 105                 110

Val Glu Asp Ile Ser His Leu Ala Asp Val Ala Arg Phe Ala Glu
        115                 120                 125

Gly Leu Glu Lys Leu Lys Glu Cys Val Leu Arg Asp Asp Leu Leu Glu
    130                 135                 140

Ala Arg Arg Pro Arg Ala His Glu Cys Leu Gly Glu Ala Leu Arg Val
145                 150                 155                 160

Met His Gln Ile Ile Ser Lys Tyr Pro Leu Leu Asn Thr Val Glu Thr
                165                 170                 175
```

```
Leu Thr Ala Ala Gly Thr Leu Ile Ala Lys Val Lys Ala Phe His Tyr
            180                 185                 190

Glu Ser Asn Asn Asp Leu Glu Lys Gln Glu Phe Glu Lys Ala Leu Glu
        195                 200                 205

Thr Ile Ala Val Ala Phe Ser Ser Thr Val Ser Glu Phe Leu Met Gly
    210                 215                 220

Glu Val Asp Ser Ser Thr Leu Leu Ala Val Pro Pro Gly Asp Ser Ser
225                 230                 235                 240

Gln Ser Met Glu Ser Leu Tyr Gly Pro Gly Ser Glu Gly Thr Pro Pro
                245                 250                 255

Ser Leu Glu Asp Cys Asp Ala Gly Cys Leu Pro Ala Glu Glu Val Asp
            260                 265                 270

Val Leu Leu Gln Arg Cys Glu Gly Val Asp Ala Ala Leu Leu Tyr
        275                 280                 285

Ala Lys Asn Met Ala Lys Tyr Met Lys Asp Leu Ile Ser Tyr Leu Glu
    290                 295                 300

Lys Arg Thr Thr Leu Glu Met Glu Phe Ala Lys Gly Leu Gln Lys Ile
305                 310                 315                 320

Ala His Asn Cys Arg Gln Ser Val Met Gln Glu Pro His Met Pro Leu
                325                 330                 335

Leu Ser Ile Tyr Ser Leu Ala Leu Glu Gln Asp Leu Glu Phe Gly His
            340                 345                 350

Ser Met Val Gln Ala Val Gly Thr Leu Gln Thr Gln Thr Phe Met Gln
        355                 360                 365

Pro Leu Thr Leu Arg Arg Leu Glu His Glu Lys Arg Arg Lys Glu Ile
    370                 375                 380

Lys Glu Ala Trp His Arg Gln Arg Lys Leu Gln Glu Ala Glu Ser Asn
385                 390                 395                 400

Leu Arg Lys Ala Lys Gln Gly Tyr Val Gln Arg Cys Glu Asp His Asp
                405                 410                 415

Lys Ala Arg Phe Leu Val Ala Lys Ala Glu Glu Glu Gln Ala Gly Ser
            420                 425                 430

Ala Pro Gly Ala Gly Ser Thr Ala Thr Lys Thr Leu Asp Lys Arg Arg
        435                 440                 445

Arg Leu Glu Glu Glu Ala Lys Asn Lys Ala Glu Glu Ala Met Ala Thr
    450                 455                 460

Tyr Arg Thr Cys Val Ala Asp Ala Lys Thr Gln Lys Gln Glu Leu Glu
465                 470                 475                 480

Asp Thr Lys Val Thr Ala Leu Arg Gln Ile Gln Glu Val Ile Arg Gln
                485                 490                 495

Ser Asp Gln Thr Ile Lys Ser Ala Thr Ile Ser Tyr Tyr Gln Met Met
            500                 505                 510

His Met Gln Thr Ala Pro Leu Pro Val His Phe Gln Met Leu Cys Glu
        515                 520                 525

Ser Ser Lys Leu Tyr Asp Pro Gly Gln Gln Tyr Ala Ser His Val Arg
    530                 535                 540

Gln Leu Gln Arg Asp Gln Glu Pro Asp Val His Tyr Asp Phe Glu Pro
545                 550                 555                 560

His Val Ser Ala Asn Ala Trp Ser Pro Val Met Arg Ala Arg Lys Ser
                565                 570                 575

Ser Phe Asn Val Ser Asp Val Ala Arg Pro Glu Ala Ala Gly Ser Pro
            580                 585                 590

Pro Glu Glu Gly Gly Cys Thr Gly Thr Pro Ala Lys Asp His Arg
```

```
                    595                 600                 605
Ala Gly Arg Gly His Gln Val His Lys Ser Trp Pro Leu Ser Ile Ser
610                 615                 620

Asp Ser Asp Ser Gly Leu Asp Pro Gly Pro Ala Gly Asp Phe Lys
625                 630                 635                 640

Lys Phe Glu Arg Thr Ser Ser Gly Thr Met Ser Ser Thr Glu Glu
                    645                 650                 655

Leu Val Asp Pro Asp Gly Gly Ala Gly Ser Ala Phe Glu Gln Ala
                    660                 665                 670

Asp Leu Asn Gly Met Thr Pro Glu Leu Pro Val Ala Val Pro Ser Gly
                675                 680                 685

Pro Phe Arg His Glu Gly Leu Ser Lys Ala Ala Arg Thr His Arg Leu
690                 695                 700

Arg Lys Leu Arg Thr Pro Ala Lys Cys Arg Glu Cys Asn Ser Tyr Val
705                 710                 715                 720

Tyr Phe Gln Gly Ala Glu Cys Glu Glu Cys Cys Leu Ala Cys His Lys
                    725                 730                 735

Lys Cys Leu Glu Thr Leu Ala Ile Gln Cys Gly His Lys Lys Leu Gln
                    740                 745                 750

Gly Arg Leu Gln Leu Phe Gly Gln Asp Phe Ser His Ala Ala Arg Ser
                755                 760                 765

Ala Pro Asp Gly Val Pro Phe Ile Val Lys Lys Cys Val Cys Glu Ile
770                 775                 780

Glu Arg Arg Ala Leu Arg Thr Lys Gly Ile Tyr Arg Val Asn Gly Val
785                 790                 795                 800

Lys Thr Arg Val Glu Lys Leu Cys Gln Ala Phe Glu Asn Gly Lys Glu
                    805                 810                 815

Leu Val Glu Leu Ser Gln Ala Ser Pro His Asp Ile Ser Asn Val Leu
                    820                 825                 830

Lys Leu Tyr Leu Arg Gln Leu Pro Glu Pro Leu Ile Ser Phe Arg Leu
                835                 840                 845

Tyr His Glu Leu Val Gly Leu Ala Lys Asp Ser Leu Lys Ala Glu Ala
                850                 855                 860

Glu Ala Lys Ala Ala Ser Arg Gly Arg Gln Asp Gly Ser Glu Ser Glu
865                 870                 875                 880

Ala Val Ala Val Ala Leu Ala Gly Arg Leu Arg Glu Leu Leu Arg Asp
                    885                 890                 895

Leu Pro Pro Glu Asn Arg Ala Ser Leu Gln Tyr Leu Leu Arg His Leu
                    900                 905                 910

Arg Arg Ile Val Glu Val Glu Gln Asp Asn Lys Met Thr Pro Gly Asn
                915                 920                 925

Leu Gly Ile Val Phe Gly Pro Thr Leu Leu Arg Pro Arg Pro Thr Glu
            930                 935                 940

Ala Thr Val Ser Leu Ser Ser Leu Val Asp Tyr Pro His Gln Ala Arg
945                 950                 955                 960

Val Ile Glu Thr Leu Ile Val His Tyr Gly Leu Val Phe Glu Glu Glu
                    965                 970                 975

Pro Glu Glu Thr Pro Gly Gly Gln Asp Glu Ser Ser Asn Gln Arg Ala
                    980                 985                 990

Glu Val Val Val Gln Val Pro Tyr Leu Glu Ala Gly Glu Ala Val Val
                995                 1000                1005

Tyr Pro Leu Gln Glu Ala Ala Asp Gly Cys Arg Glu Ser Arg Val
            1010                1015                1020
```

```
Val Ser Asn Asp Ser Asp Ser Asp Leu Glu Glu Ala Ser Glu Leu Leu
1025                1030                1035                1040

Ser Ser Ser Glu Ala Ser Ala Leu Gly His Leu Ser Phe Leu Glu Gln
            1045                1050                1055

Gln Gln Ser Glu Ala Ser Leu Glu Val Ala Ser Gly Ser His Ser Gly
        1060                1065                1070

Ser Glu Glu Gln Leu Glu Ala Thr Ala Arg Glu Asp Gly Asp Gly Asp
    1075                1080                1085

Glu Asp Gly Pro Ala Gln Gln Leu Ser Gly Phe Asn Thr Asn Gln Ser
1090                1095                1100

Asn Asn Val Leu Gln Ala Pro Leu Pro Pro Met Arg Leu Arg Gly Gly
1105                1110                1115                1120

Arg Met Thr Leu Gly Ser Cys Arg Glu Arg Gln Pro Glu Phe Val
                1125                1130                1135

<210> SEQ ID NO 65
<211> LENGTH: 9
<212> TYPE: PRT
<213> ORGANISM: Artificial Sequence
<220> FEATURE:
<223> OTHER INFORMATION: Synthetic sequence HA-1 non-immunogenic peptide
      wild type

<400> SEQUENCE: 65

Val Leu Arg Asp Asp Leu Leu Glu Ala
1               5

<210> SEQ ID NO 66
<211> LENGTH: 9
<212> TYPE: PRT
<213> ORGANISM: Artificial Sequence
<220> FEATURE:
<223> OTHER INFORMATION: Synthetic sequence HA-1H antigen polymorphism

<400> SEQUENCE: 66

Val Leu His Asp Asp Leu Leu Glu Ala
1               5

<210> SEQ ID NO 67
<211> LENGTH: 1206
<212> TYPE: DNA
<213> ORGANISM: Artificial Sequence
<220> FEATURE:
<223> OTHER INFORMATION: Synthetic sequence Inducible Caspase9 (codon
      optimized)

<400> SEQUENCE: 67
atgctggaag gcgtgcaggt ggaaaccatc agccctggcg acggcagaac cttccctaag      60
aggggccaga cctgcgtggt gcactacacc ggaatgctgg aagatggcaa gaaggtggac     120
agcagccggg accggaacaa gcccttcaag ttcatgctgg gcaagcagga agtgatccgg     180
ggctggaaag agggcgtggc ccagatgtct gtgggccaga gagccaagct gaccatctcc     240
cccgattacg cctacggcgc cacaggccac cctggcatca ttcctccaca cgccacactg     300
gtgttcgacg tggaactgct gaagctgaa agcggcggag cagcggagt ggatggcttt      360 ggagatgtgg gcgccctgga aagcctgaga ggcaatgccg acctggccta catcctgagc     420
atggaacctt gcggccactg cctgattatc aacaacgtga acttctgcag agagagcggc     480
ctgcggacca gaaccggcag caacatcgac tgcgagaagc tgcggcggag attcagcagc     540
ctgcacttca tggtggaagt gaagggcgac ctgaccgcca gaaaatggt gctggccctg     600
```

```
ctggaactgg cccagcagga tcatggcgct ctggactgct gtgtggtcgt gatcctgagc      660
cacggctgcc aggccagcca tctgcagttc cctggcgccg tgtatggcac cgatggctgt      720
cctgtgtccg tggaaaagat cgtgaacatc ttcaacggca ccagctgccc cagcctgggc      780
ggaaagccca agctgttctt tattcaagcc tgcggaggcg agcagaagga ccacggattt      840
gaggtggcct ccaccagccc cgaggatgag agccctggaa gcaaccctga gcccgacgcc      900 acccccattttc aggaaggcct gagaaccttc gaccagctgg acgccatcag ctccctgccc      960 accccccagcg atatcttcgt gtcctacagc accttccccg gctttgtgtc ctggcgggat     1020
cccaagtccg gctcttggta cgtggaaacc ctggacgaca tcttcgagca gtgggcccat     1080
agcgaggacc tgcagagcct gctgctgaga gtggccaatg ccgtgtccgt gaagggcatc     1140
tacaagcaga tgcctggctg cttcaacttc ctgcggaaga agctgttttt caagaccagc     1200
gccagc                                                                1206
```

```
<210> SEQ ID NO 68
<211> LENGTH: 159
<212> TYPE: DNA
<213> ORGANISM: Artificial Sequence
<220> FEATURE:
<223> OTHER INFORMATION: Synthetic sequence RQR (codon optimized)

<400> SEQUENCE: 68
gcctgcccct acagcaaccc tagcctgtgt tctggcggcg aggcagcga actgcctacc       60 cagggcacct tcagcaacgt gtccaccaat gtgtctggcg gaggcggctc tgcctgccct     120
tactccaatc catccctgtg cagcggaggg ggcggaagc                            159
```

```
<210> SEQ ID NO 69
<211> LENGTH: 53
<212> TYPE: PRT
<213> ORGANISM: Artificial Sequence
<220> FEATURE:
<223> OTHER INFORMATION: Synthetic sequence RQR

<400> SEQUENCE: 69

Ala Cys Pro Tyr Ser Asn Pro Ser Leu Cys Ser Gly Gly Gly Gly Ser
1               5                   10                  15

Glu Leu Pro Thr Gln Gly Thr Phe Ser Asn Val Ser Thr Asn Val Ser
            20                  25                  30

Gly Gly Gly Gly Ser Ala Cys Pro Tyr Ser Asn Pro Ser Leu Cys Ser
        35                  40                  45

Gly Gly Gly Gly Ser
    50
```

```
<210> SEQ ID NO 70
<211> LENGTH: 235
<212> TYPE: PRT
<213> ORGANISM: Artificial Sequence
<220> FEATURE:
<223> OTHER INFORMATION: Synthetic sequence CD8 co-receptor alpha chain
      with signal peptide

<400> SEQUENCE: 70

Met Ala Leu Pro Val Thr Ala Leu Leu Leu Pro Leu Ala Leu Leu Leu
1               5                   10                  15

His Ala Ala Arg Pro Ser Gln Phe Arg Val Ser Pro Leu Asp Arg Thr
            20                  25                  30

Trp Asn Leu Gly Glu Thr Val Glu Leu Lys Cys Gln Val Leu Leu Ser
```

```
            35                  40                  45
Asn Pro Thr Ser Gly Cys Ser Trp Leu Phe Gln Pro Arg Gly Ala Ala
 50                  55                  60

Ala Ser Pro Thr Phe Leu Leu Tyr Leu Ser Gln Asn Lys Pro Lys Ala
 65                  70                  75                  80

Ala Glu Gly Leu Asp Thr Gln Arg Phe Ser Gly Lys Arg Leu Gly Asp
                 85                  90                  95

Thr Phe Val Leu Thr Leu Ser Asp Phe Arg Arg Glu Asn Glu Gly Tyr
            100                 105                 110

Tyr Phe Cys Ser Ala Leu Ser Asn Ser Ile Met Tyr Phe Ser His Phe
        115                 120                 125

Val Pro Val Phe Leu Pro Ala Lys Pro Thr Thr Thr Pro Ala Pro Arg
    130                 135                 140

Pro Pro Thr Pro Ala Pro Thr Ile Ala Ser Gln Pro Leu Ser Leu Arg
145                 150                 155                 160

Pro Glu Ala Cys Arg Pro Ala Ala Gly Gly Ala Val His Thr Arg Gly
                165                 170                 175

Leu Asp Phe Ala Cys Asp Ile Tyr Ile Trp Ala Pro Leu Ala Gly Thr
            180                 185                 190

Cys Gly Val Leu Leu Leu Ser Leu Val Ile Thr Leu Tyr Cys Asn His
        195                 200                 205

Arg Asn Arg Arg Arg Val Cys Lys Cys Pro Arg Pro Val Val Lys Ser
    210                 215                 220

Gly Asp Lys Pro Ser Leu Ser Ala Arg Tyr Val
225                 230                 235

<210> SEQ ID NO 71
<211> LENGTH: 210
<212> TYPE: PRT
<213> ORGANISM: Artificial Sequence
<220> FEATURE:
<223> OTHER INFORMATION: Synthetic sequence CD8 co-receptor beta chain
      isoform 1 with signal peptide

<400> SEQUENCE: 71

Met Arg Pro Arg Leu Trp Leu Leu Leu Ala Ala Gln Leu Thr Val Leu
 1               5                  10                  15

His Gly Asn Ser Val Leu Gln Gln Thr Pro Ala Tyr Ile Lys Val Gln
                 20                  25                  30

Thr Asn Lys Met Val Met Leu Ser Cys Glu Ala Lys Ile Ser Leu Ser
            35                  40                  45

Asn Met Arg Ile Tyr Trp Leu Arg Gln Arg Gln Ala Pro Ser Ser Asp
 50                  55                  60

Ser His His Glu Phe Leu Ala Leu Trp Asp Ser Ala Lys Gly Thr Ile
 65                  70                  75                  80

His Gly Glu Glu Val Glu Gln Glu Lys Ile Ala Val Phe Arg Asp Ala
                 85                  90                  95

Ser Arg Phe Ile Leu Asn Leu Thr Ser Val Lys Pro Glu Asp Ser Gly
            100                 105                 110

Ile Tyr Phe Cys Met Ile Val Gly Ser Pro Glu Leu Thr Phe Gly Lys
        115                 120                 125

Gly Thr Gln Leu Ser Val Val Asp Phe Leu Pro Thr Thr Ala Gln Pro
    130                 135                 140

Thr Lys Lys Ser Thr Leu Lys Lys Arg Val Cys Arg Leu Pro Arg Pro
145                 150                 155                 160
```

```
Glu Thr Gln Lys Gly Pro Leu Cys Ser Pro Ile Thr Leu Gly Leu Leu
                165                 170                 175

Val Ala Gly Val Leu Val Leu Leu Val Ser Leu Gly Val Ala Ile His
            180                 185                 190

Leu Cys Cys Arg Arg Arg Ala Arg Leu Arg Phe Met Lys Gln Phe
        195                 200                 205

Tyr Lys
    210

<210> SEQ ID NO 72
<211> LENGTH: 221
<212> TYPE: PRT
<213> ORGANISM: Artificial Sequence
<220> FEATURE:
<223> OTHER INFORMATION: Synthetic sequence CD8 co-receptor beta chain
      isoform 2 with signal peptide

<400> SEQUENCE: 72

Met Arg Pro Arg Leu Trp Leu Leu Leu Ala Ala Gln Leu Thr Val Leu
1               5                   10                  15

His Gly Asn Ser Val Leu Gln Gln Thr Pro Ala Tyr Ile Lys Val Gln
            20                  25                  30

Thr Asn Lys Met Val Met Leu Ser Cys Glu Ala Lys Ile Ser Leu Ser
        35                  40                  45

Asn Met Arg Ile Tyr Trp Leu Arg Gln Arg Gln Ala Pro Ser Ser Asp
50                  55                  60

Ser His His Glu Phe Leu Ala Leu Trp Asp Ser Ala Lys Gly Thr Ile
65                  70                  75                  80

His Gly Glu Glu Val Glu Gln Glu Lys Ile Ala Val Phe Arg Asp Ala
                85                  90                  95

Ser Arg Phe Ile Leu Asn Leu Thr Ser Val Lys Pro Glu Asp Ser Gly
            100                 105                 110

Ile Tyr Phe Cys Met Ile Val Gly Ser Pro Glu Leu Thr Phe Gly Lys
        115                 120                 125

Gly Thr Gln Leu Ser Val Val Asp Phe Leu Pro Thr Thr Ala Gln Pro
    130                 135                 140

Thr Lys Lys Ser Thr Leu Lys Lys Arg Val Cys Arg Leu Pro Arg Pro
145                 150                 155                 160

Glu Thr Gln Lys Gly Pro Leu Cys Ser Pro Ile Thr Leu Gly Leu Leu
                165                 170                 175

Val Ala Gly Val Leu Val Leu Leu Val Ser Leu Gly Val Ala Ile His
            180                 185                 190

Leu Cys Cys Arg Arg Arg Ala Arg Leu Arg Phe Met Lys Gln Leu
        195                 200                 205

Arg Leu His Pro Leu Glu Lys Cys Ser Arg Met Asp Tyr
    210                 215                 220

<210> SEQ ID NO 73
<211> LENGTH: 246
<212> TYPE: PRT
<213> ORGANISM: Artificial Sequence
<220> FEATURE:
<223> OTHER INFORMATION: Synthetic sequence CD8 co-receptor beta chain
      isoform 3 with signal peptide

<400> SEQUENCE: 73

Met Arg Pro Arg Leu Trp Leu Leu Leu Ala Ala Gln Leu Thr Val Leu
1               5                   10                  15
```

His Gly Asn Ser Val Leu Gln Gln Thr Pro Ala Tyr Ile Lys Val Gln
            20                  25                  30

Thr Asn Lys Met Val Met Leu Ser Cys Glu Ala Lys Ile Ser Leu Ser
        35                  40                  45

Asn Met Arg Ile Tyr Trp Leu Arg Gln Arg Gln Ala Pro Ser Ser Asp
    50                  55                  60

Ser His His Glu Phe Leu Ala Leu Trp Asp Ser Ala Lys Gly Thr Ile
65                  70                  75                  80

His Gly Glu Glu Val Glu Gln Glu Lys Ile Ala Val Phe Arg Asp Ala
                85                  90                  95

Ser Arg Phe Ile Leu Asn Leu Thr Ser Val Lys Pro Glu Asp Ser Gly
            100                 105                 110

Ile Tyr Phe Cys Met Ile Val Gly Ser Pro Glu Leu Thr Phe Gly Lys
        115                 120                 125

Gly Thr Gln Leu Ser Val Val Asp Phe Leu Pro Thr Thr Ala Gln Pro
    130                 135                 140

Thr Lys Lys Ser Thr Leu Lys Lys Arg Val Cys Arg Leu Pro Arg Pro
145                 150                 155                 160

Glu Thr Gln Lys Gly Pro Leu Cys Ser Pro Ile Thr Leu Gly Leu Leu
                165                 170                 175

Val Ala Gly Val Leu Val Leu Leu Val Ser Leu Gly Val Ala Ile His
            180                 185                 190

Leu Cys Cys Arg Arg Arg Arg Ala Arg Leu Arg Phe Met Lys Gln Lys
        195                 200                 205

Phe Asn Ile Val Cys Leu Lys Ile Ser Gly Phe Thr Thr Cys Cys Cys
    210                 215                 220

Phe Gln Ile Leu Gln Ile Ser Arg Glu Tyr Gly Phe Gly Val Leu Leu
225                 230                 235                 240

Gln Lys Asp Ile Gly Gln
                245

<210> SEQ ID NO 74
<211> LENGTH: 246
<212> TYPE: PRT
<213> ORGANISM: Artificial Sequence
<220> FEATURE:
<223> OTHER INFORMATION: Synthetic sequence CD8 co-receptor beta chain
      isoform 4 with signal peptide

<400> SEQUENCE: 74

Met Arg Pro Arg Leu Trp Leu Leu Leu Ala Ala Gln Leu Thr Val Leu
1               5                   10                  15

His Gly Asn Ser Val Leu Gln Gln Thr Pro Ala Tyr Ile Lys Val Gln
            20                  25                  30

Thr Asn Lys Met Val Met Leu Ser Cys Glu Ala Lys Ile Ser Leu Ser
        35                  40                  45

Asn Met Arg Ile Tyr Trp Leu Arg Gln Arg Gln Ala Pro Ser Ser Asp
    50                  55                  60

Ser His His Glu Phe Leu Ala Leu Trp Asp Ser Ala Lys Gly Thr Ile
65                  70                  75                  80

His Gly Glu Glu Val Glu Gln Glu Lys Ile Ala Val Phe Arg Asp Ala
                85                  90                  95

Ser Arg Phe Ile Leu Asn Leu Thr Ser Val Lys Pro Glu Asp Ser Gly
            100                 105                 110

Ile Tyr Phe Cys Met Ile Val Gly Ser Pro Glu Leu Thr Phe Gly Lys
        115                 120                 125

```
Gly Thr Gln Leu Ser Val Val Asp Phe Leu Pro Thr Thr Ala Gln Pro
            130                 135                 140

Thr Lys Lys Ser Thr Leu Lys Lys Arg Val Cys Arg Leu Pro Arg Pro
145                 150                 155                 160

Glu Thr Gln Lys Gly Pro Leu Cys Ser Pro Ile Thr Leu Gly Leu Leu
                165                 170                 175

Val Ala Gly Val Leu Val Leu Leu Val Ser Leu Gly Val Ala Ile His
            180                 185                 190

Leu Cys Cys Arg Arg Arg Ala Arg Leu Arg Phe Met Lys Gln Lys
            195                 200             205

Phe Asn Ile Val Cys Leu Lys Ile Ser Gly Phe Thr Thr Cys Cys
            210                 215                 220

Phe Gln Ile Leu Gln Ile Ser Arg Glu Tyr Gly Phe Gly Val Leu Leu
225                 230                 235                 240

Gln Lys Asp Ile Gly Gln
                245
```

```
<210> SEQ ID NO 75
<211> LENGTH: 243
<212> TYPE: PRT
<213> ORGANISM: Artificial Sequence
<220> FEATURE:
<223> OTHER INFORMATION: Synthetic sequence CD8 co-receptor beta chain
      isoform 5 with signal peptide

<400> SEQUENCE: 75
```

```
Met Arg Pro Arg Leu Trp Leu Leu Leu Ala Ala Gln Leu Thr Val Leu
1               5                   10                  15

His Gly Asn Ser Val Leu Gln Gln Thr Pro Ala Tyr Ile Lys Val Gln
            20                  25                  30

Thr Asn Lys Met Val Met Leu Ser Cys Glu Ala Lys Ile Ser Leu Ser
            35                  40                  45

Asn Met Arg Ile Tyr Trp Leu Arg Gln Arg Gln Ala Pro Ser Ser Asp
50                  55                  60

Ser His His Glu Phe Leu Ala Leu Trp Asp Ser Ala Lys Gly Thr Ile
65                  70                  75                  80

His Gly Glu Glu Val Glu Gln Glu Lys Ile Ala Val Phe Arg Asp Ala
            85                  90                  95

Ser Arg Phe Ile Leu Asn Leu Thr Ser Val Lys Pro Glu Asp Ser Gly
            100                 105                 110

Ile Tyr Phe Cys Met Ile Val Gly Ser Pro Glu Leu Thr Phe Gly Lys
            115                 120                 125

Gly Thr Gln Leu Ser Val Val Asp Phe Leu Pro Thr Thr Ala Gln Pro
            130                 135                 140

Thr Lys Lys Ser Thr Leu Lys Lys Arg Val Cys Arg Leu Pro Arg Pro
145                 150                 155                 160

Glu Thr Gln Lys Gly Pro Leu Cys Ser Pro Ile Thr Leu Gly Leu Leu
                165                 170                 175

Val Ala Gly Val Leu Val Leu Leu Val Ser Leu Gly Val Ala Ile His
            180                 185                 190

Leu Cys Cys Arg Arg Arg Ala Arg Leu Arg Phe Met Lys Gln Pro
            195                 200             205

Gln Gly Glu Gly Ile Ser Gly Thr Phe Val Pro Gln Cys Leu His Gly
            210                 215                 220

Tyr Tyr Ser Asn Thr Thr Thr Ser Gln Lys Leu Leu Asn Pro Trp Ile
```

Leu Lys Thr

<210> SEQ ID NO 76
<211> LENGTH: 66
<212> TYPE: DNA
<213> ORGANISM: Artificial Sequence
<220> FEATURE:
<223> OTHER INFORMATION: Synthetic sequence P2A-1 (codon-optimized)

<400> SEQUENCE: 76

```
ggaagtggag ctacgaattt ttctttatta aaacaagcag gagatgttga ggagaatccc    60
ggtcca                                                                66
```

<210> SEQ ID NO 77
<211> LENGTH: 63
<212> TYPE: DNA
<213> ORGANISM: Artificial Sequence
<220> FEATURE:
<223> OTHER INFORMATION: Synthetic sequence P2A-2 (codon-optimized)

<400> SEQUENCE: 77

```
agcggcgcca ccaacttcag cctgctgaaa caggccggcg acgtggaaga gaaccctggc    60
cct                                                                   63
```

<210> SEQ ID NO 78
<211> LENGTH: 65
<212> TYPE: DNA
<213> ORGANISM: Artificial Sequence
<220> FEATURE:
<223> OTHER INFORMATION: Synthetic sequence P2A-3 (codon-optimized)

<400> SEQUENCE: 78

```
gaagcggcgc cacaaatttc agcctgctga agcaggccgg cgacgtggaa gagaaccctg    60
gccct                                                                 65
```

<210> SEQ ID NO 79
<211> LENGTH: 66
<212> TYPE: DNA
<213> ORGANISM: Artificial Sequence
<220> FEATURE:
<223> OTHER INFORMATION: Synthetic sequence P2A-4 (codon-optimized)

<400> SEQUENCE: 79

```
ggctccggcg ccaccaactt ttcactgctg aaacaggctg ggatgtgga agaaaatccc     60 ggccca                                                                66
```

<210> SEQ ID NO 80
<211> LENGTH: 66
<212> TYPE: DNA
<213> ORGANISM: Artificial Sequence
<220> FEATURE:
<223> OTHER INFORMATION: Synthetic sequence P2A-5

<400> SEQUENCE: 80

```
ggcagcggcg ccaccaactt tagcctgctg aaacaggctg gcgacgtgga agagaacccc    60
ggacct                                                                66
```

<210> SEQ ID NO 81
<211> LENGTH: 66
<212> TYPE: DNA
<213> ORGANISM: Artificial Sequence

```
<220> FEATURE:
<223> OTHER INFORMATION: Synthetic sequence P2A-6

<400> SEQUENCE: 81
ggctctggcg ccaccaactt tagcctgctg aaacaggctg gcgacgtgga agagaacccc      60
ggacct                                                                66

<210> SEQ ID NO 82
<211> LENGTH: 63
<212> TYPE: DNA
<213> ORGANISM: Artificial Sequence
<220> FEATURE:
<223> OTHER INFORMATION: Synthetic sequence T2A

<400> SEQUENCE: 82
ggaagcggag agggcagagg aagtctgcta acatgcggtg acgtcgagga gaatcctgga      60
cct                                                                   63

<210> SEQ ID NO 83
<211> LENGTH: 69
<212> TYPE: DNA
<213> ORGANISM: Artificial Sequence
<220> FEATURE:
<223> OTHER INFORMATION: Synthetic sequence E2A

<400> SEQUENCE: 83
ggaagcggac agtgtactaa ttatgctctc ttgaaattgg ctggagatgt tgagagcaac      60
cctggacct                                                             69

<210> SEQ ID NO 84
<211> LENGTH: 75
<212> TYPE: DNA
<213> ORGANISM: Artificial Sequence
<220> FEATURE:
<223> OTHER INFORMATION: Synthetic sequence F2A

<400> SEQUENCE: 84
ggaagcggag tgaaacagac tttgaatttt gaccttctca agttggcggg agacgtggag      60
tccaaccctg gacct                                                      75

<210> SEQ ID NO 85
<211> LENGTH: 4713
<212> TYPE: DNA
<213> ORGANISM: Artificial Sequence
<220> FEATURE:
<223> OTHER INFORMATION: Synthetic sequence iC9-HA1-TCR2-RQR-CD8

<400> SEQUENCE: 85
atgctggaag gcgtgcaggt ggaaaccatc agccctggcg acggcagaac cttccctaag      60
aggggccaga cctgcgtggt gcactacacc ggaatgctgg aagatggcaa gaaggtggac     120
agcagccggg accggaacaa gcccttcaag ttcatgctgg gcaagcagga agtgatccgg     180
ggctgggaag agggcgtggc ccagatgtct gtgggccaga gagccaagct gaccatctcc     240
cccgattacg cctacggcgc cacaggccac cctggcatca ttcctccaca cgccacactg     300
gtgttcgacg tggaactgct gaagctggaa agcggcggag cagcggagt ggatggcttt      360 ggagatgtgg gcgccctgga aagcctgaga ggcaatgccg acctggccta catcctgagc     420
atggaacctt gcggccactg cctgattatc aacaacgtga acttctgcag agagagcggc     480
ctgcggacca gaaccggcag caacatcgac tgcgagaagc tgcggcggag attcagcagc     540
```

```
ctgcacttca tggtggaagt gaagggcgac ctgaccgcca agaaaatggt gctggccctg    600
ctggaactgg cccagcagga tcatggcgct ctggactgct gtgtggtcgt gatcctgagc    660
cacggctgcc aggccagcca tctgcagttc cctggcgccg tgtatggcac cgatggctgt    720
cctgtgtccg tggaaaagat cgtgaacatc ttcaacggca ccagctgccc cagcctgggc    780
ggaaagccca agctgttctt tattcaagcc tgcggaggcg agcagaagga ccacggattt    840
gaggtggcct ccaccagccc cgaggatgag agccctggaa gcaaccctga gcccgacgcc    900
accccatttc aggaaggcct gagaaccttc gaccagctgg acgccatcag ctccctgccc    960
acccccagcg atatcttcgt gtcctacagc accttccccg ctttgtgtc ctggcgggat    1020
cccaagtccg gctcttggta cgtggaaacc ctggacgaca tcttcgagca gtgggcccat    1080
agcgaggacc tgcagagcct gctgctgaga gtggccaatg ccgtgtccgt gaagggcatc    1140
tacaagcaga tgcctggctg cttcaacttc ctgcggaaga agctgttttt caagaccagc    1200
gccagcggaa gtggagctac gattttttct ttattaaaac aagcaggaga tgttgaggag    1260
aatcccggtc caatgggcac ctccctgctg tgttggatgg ccctgtgtct gctgggagcc    1320
gaccatgccg atacaggggt gtcccaggac ccccggcaca agattaccaa gcggggccag    1380
aacgtgacct tcagatgcga ccccatcagc gagcacaacc ggctgtactg gtacaggcag    1440
accctgggcc agggcccccga gttcctgacc tactttcaga cgaggcccca gctggaaaag    1500
tcccggctgc tgagcgacag attcagcgcc gaaagaccca agggcagctt cagcaccctg    1560
gaaatccagc ggaccgagca gggcgatagc gccatgtacc tgtgtgccag cagcctcgtg    1620
aagggcgaga agctgttctt cggcagcggc acccagctga gcgtgctgga gatctgaac    1680
aaggtgttcc ccccagaggt ggccgtgttc gagccttctg aggccgagat cagccacacc    1740
cagaaagcca cctcgtgtg cctggccacc ggctttttcc ccgaccacgt ggaactgtct    1800
tggtgggtca acggcaaaga ggtgcactcc ggcgtgtgca ccgatcccca gcctctgaaa    1860
gaacagcccg ccctgaacga cagcggtac tgcctgagca gcagactgag agtgtccgcc    1920
accttctggc agaaccccccg gaaccacttc agatgccagg tgcagttcta cggcctgagc    1980
gagaacgacg agtggaccca ggacagagcc aagcccgtga cccagatcgt gtctgccgaa    2040
gcctggggca gagccgattg cggctttacc agcgtgtcct atcagcaggg cgtgctgagc    2100
gccaccatcc tgtacgagat cctgctgggc aaggccaccc tgtacgccgt gctggtgtct    2160
gccctggtgc tgatggccat ggtcaagcgg aaggactttg gcagcggcgc caccaacttc    2220
agcctgctga acaggccgg cgacgtggaa gagaaccctg ccctatgga aacactgctg    2280
ggcctgctga tcctgtggct gcagctgcag tgggtgtcca gcaagcagga agtgacacag    2340
atccctgccg ccctgtctgt gcccgagggc gaaaatctgg tgctgaactg cagcttcacc    2400
gacagcgcca tctacaacct gcagtggttc agacaggacc ccggcaaggg cctgacaagc    2460
ctgctgctga ttcagagcag ccagagagag cagaccagcg gcagactgaa cgccagcctg    2520
gataagagca gcggccgcag caccctgtat atcgccgctt tcagcctggc gactctgcc    2580
acatatctgt gcgccgtgat cggcctgggc ggcacctaca gtacatctt tggcaccggc    2640
accagactga aagtgctggc caacatccag aaccccgacc ccgccgtgta ccagctgaga    2700
gacagcaagt ccagcgacaa gagcgtgtgt ctgttcaccg acttcgacag ccagaccaac    2760
gtgtcccaga gcaaggacag cgacgtgtac atcaccgata gtgcgtgct ggacatgcgg    2820
agcatggact tcaagagcaa cagcgccgtg gcctggtcca caagagcga cttcgcctgc    2880
gccaacgcct tcaacaacag catcatcccc gaggacacct tttccccag cccgagagc    2940
```

```
agctgcgacg tgaaactggt ggagaagtcc ttcgagacag acaccaatct gaactttcag    3000
aacctgagcg tgatcggctt ccggatcctg ctgctgaaaa tggccggctt caatctgctg    3060
atgaccctgc ggctgtggag cagcggaagc ggcgccacaa atttcagcct gctgaagcag    3120
gccggcgacg tggaagagaa ccctggccct atgaggccca gactgtggct gctgctggcc    3180
gctcagctga cagtgctgca cggcaatagc gtggcctgcc cctacagcaa ccctagcctg    3240
tgttctggcg gcggaggcag cgaactgcct acccagggca ccttcagcaa cgtgtccacc    3300
aatgtgtctg gcggaggcgg ctctgcctgc ccttactcca atccatccct gtgcagcgga    3360
ggggcggaa gcctgcagca gacaccagcc tacatcaagg tgcagaccaa caagatggtc    3420
atgctgagct gcgaggccaa gatcagcctg agcaacatgc ggatctactg gctgcggcag    3480
agacaggccc ctagcagcga tagccaccac gagtttctgg ccctgtggga cagcgccaag    3540
ggcaccattc acggcgagga agtggaacag gaaaagatcg ccgtgttccg ggacgccagc    3600
cggttcatcc tgaacctgac cagcgtgaag cccgaggact ccggcatcta tttctgcatg    3660
atcgtgggct cccccgagct gaccttcggc aagggaacac agctgtccgt ggtggacttc    3720
ctgcctacca cagcccagcc caccaagaag tctaccctga gaaaagagt gtgccggctg    3780
cccagacccg agacacagaa aggccctctg tgcagcccta tcaccctggg actgctggtg    3840
gctgccgtgc tggtgctgct ggtgtctctg ggagtggcca tccacctgtg ctgcagaaga    3900
aggcgggcca gactgcggtt catgaagcag ttctacaagg gctccggcgc caccaacttt    3960
tcactgctga acaggctggg ggatgtggaa gaaaatcccg gcccaatggc cctgcctgtg    4020
accgctctgc tgctgcctct ggcactgctg ctgcatgccg ccagacccag ccagttcaga    4080
gtgtccccc tggacagaac ctggaacctg ggcgagacag tggaactgaa gtgccaggtg    4140
ctgctgagca accccaccag cggctgcagc tggctgttcc agcctagagg cgctgccgcc    4200
agccctacct ttctgctgta cctgagccag aacaagccca aggccgccga gggcctggac    4260
acccagagat tcagcggcaa gagactgggc gacaccttcg tgctgaccct gtccgacttc    4320
agaagagaga cgagggcta ctacttctgc tccgccctga gcaatagcat catgtacttc    4380
agccacttcg tgcccgtgtt tctgcccgcc aagcctacaa ccaccctgc cccaagacct    4440
cccacacccg cccctacaat tgccagccag cctctgtctc tgaggcccga ggcttgtaga    4500
ccagctgctg gcggagccgt gcacaccaga ggactggact ttgcctgcga catctacatc    4560
tgggcccctc tggccggcac ttgcggagtg ctgctgctga gtctcgtgat caccctgtac    4620
tgcaaccacc ggaaccggcg gagagtgtgc aagtgcccta ggcccgtcgt gaagtccggc    4680
gacaagcctt ctctgagcgc cagatatgtc tga                                 4713
```

<210> SEQ ID NO 86
<211> LENGTH: 13
<212> TYPE: PRT
<213> ORGANISM: Artificial Sequence
<220> FEATURE:
<223> OTHER INFORMATION: Synthetic sequence TCR1 alpha chain CDR3

<400> SEQUENCE: 86

Cys Ala Ser Ser Leu Val Ser Gly Asn Thr Ile Tyr Phe
1               5                   10

<210> SEQ ID NO 87
<211> LENGTH: 15
<212> TYPE: PRT
<213> ORGANISM: Artificial Sequence

```
<220> FEATURE:
<223> OTHER INFORMATION: Synthetic sequence TCR1 alpha chain CDR3

<400> SEQUENCE: 87

Cys Ala Thr Lys Arg Asp Ser Gly Ala Gly Ser Tyr Gln Leu Thr
1               5                   10                  15

<210> SEQ ID NO 88
<211> LENGTH: 14
<212> TYPE: PRT
<213> ORGANISM: Artificial Sequence
<220> FEATURE:
<223> OTHER INFORMATION: Synthetic sequence TCR2 alpha chain CDR3

<400> SEQUENCE: 88

Cys Ala Val Ile Gly Leu Gly Gly Thr Tyr Lys Tyr Ile Phe
1               5                   10

<210> SEQ ID NO 89
<211> LENGTH: 12
<212> TYPE: PRT
<213> ORGANISM: Artificial Sequence
<220> FEATURE:
<223> OTHER INFORMATION: Synthetic sequence TCR5 alpha chain CDR3

<400> SEQUENCE: 89

Cys Ala Thr Asn Ser Gly Asn Thr Pro Leu Val Phe
1               5                   10

<210> SEQ ID NO 90
<211> LENGTH: 14
<212> TYPE: PRT
<213> ORGANISM: Artificial Sequence
<220> FEATURE:
<223> OTHER INFORMATION: Synthetic sequence TCR10 alpha chain CDR3

<400> SEQUENCE: 90

Cys Val Val Asp Ser Gly Gly Gly Ala Asp Gly Leu Thr Phe
1               5                   10

<210> SEQ ID NO 91
<211> LENGTH: 13
<212> TYPE: PRT
<213> ORGANISM: Artificial Sequence
<220> FEATURE:
<223> OTHER INFORMATION: Synthetic sequence TCR16 alpha chain CDR3

<400> SEQUENCE: 91

Cys Ala Val His Leu Leu Asn Asp Tyr Lys Leu Ser Phe
1               5                   10

<210> SEQ ID NO 92
<211> LENGTH: 16
<212> TYPE: PRT
<213> ORGANISM: Artificial Sequence
<220> FEATURE:
<223> OTHER INFORMATION: Synthetic sequence TCR29 alpha chain CDR3

<400> SEQUENCE: 92

Cys Ala Val Arg Gly Gly Thr Thr Ser Gly Thr Tyr Lys Tyr Ile Phe
1               5                   10                  15

<210> SEQ ID NO 93
<211> LENGTH: 21
<212> TYPE: DNA
<213> ORGANISM: Artificial Sequence
<220> FEATURE:
```

<223> OTHER INFORMATION: TCR alpha-chain primer

<400> SEQUENCE: 93
ggtgaatagg cagacagact t                                             21

<210> SEQ ID NO 94
<211> LENGTH: 20
<212> TYPE: DNA
<213> ORGANISM: Artificial Sequence
<220> FEATURE:
<223> OTHER INFORMATION: TCR beta-chain primer

<400> SEQUENCE: 94
gtggccaggc acaccagtgt                                               20

<210> SEQ ID NO 95
<211> LENGTH: 402
<212> TYPE: PRT
<213> ORGANISM: Artificial Sequence
<220> FEATURE:
<223> OTHER INFORMATION: Synthetic sequence inducible caspase-9

<400> SEQUENCE: 95

```
Met Leu Glu Gly Val Gln Val Glu Thr Ile Ser Pro Gly Asp Gly Arg
 1               5                  10                  15

Thr Phe Pro Lys Arg Gly Gln Thr Cys Val Val His Tyr Thr Gly Met
            20                  25                  30

Leu Glu Asp Gly Lys Lys Val Asp Ser Ser Arg Asp Arg Asn Lys Pro
        35                  40                  45

Phe Lys Phe Met Leu Gly Lys Gln Glu Val Ile Arg Gly Trp Glu Glu
    50                  55                  60

Gly Val Ala Gln Met Ser Val Gly Gln Arg Ala Lys Leu Thr Ile Ser
65                  70                  75                  80

Pro Asp Tyr Ala Tyr Gly Ala Thr Gly His Pro Gly Ile Ile Pro Pro
                85                  90                  95

His Ala Thr Leu Val Phe Asp Val Glu Leu Leu Lys Leu Glu Ser Gly
            100                 105                 110

Gly Gly Ser Gly Val Asp Gly Phe Gly Asp Val Gly Ala Leu Glu Ser
        115                 120                 125

Leu Arg Gly Asn Ala Asp Leu Ala Tyr Ile Leu Ser Met Glu Pro Cys
    130                 135                 140

Gly His Cys Leu Ile Ile Asn Asn Val Asn Phe Cys Arg Glu Ser Gly
145                 150                 155                 160

Leu Arg Thr Arg Thr Gly Ser Asn Ile Asp Cys Glu Lys Leu Arg Arg
                165                 170                 175

Arg Phe Ser Ser Leu His Phe Met Val Glu Val Lys Gly Asp Leu Thr
            180                 185                 190

Ala Lys Lys Met Val Leu Ala Leu Leu Glu Leu Ala Gln Gln Asp His
        195                 200                 205

Gly Ala Leu Asp Cys Cys Val Val Val Ile Leu Ser His Gly Cys Gln
    210                 215                 220

Ala Ser His Leu Gln Phe Pro Gly Ala Val Tyr Gly Thr Asp Gly Cys
225                 230                 235                 240

Pro Val Ser Val Glu Lys Ile Val Asn Ile Phe Asn Gly Thr Ser Cys
                245                 250                 255

Pro Ser Leu Gly Gly Lys Pro Lys Leu Phe Phe Ile Gln Ala Cys Gly
            260                 265                 270
```

Gly Glu Gln Lys Asp His Gly Phe Glu Val Ala Ser Thr Ser Pro Glu
            275                 280                 285

Asp Glu Ser Pro Gly Ser Asn Pro Glu Pro Asp Ala Thr Pro Phe Gln
        290                 295                 300

Glu Gly Leu Arg Thr Phe Asp Gln Leu Asp Ala Ile Ser Ser Leu Pro
305                 310                 315                 320

Thr Pro Ser Asp Ile Phe Val Ser Tyr Ser Thr Phe Pro Gly Phe Val
                325                 330                 335

Ser Trp Arg Asp Pro Lys Ser Gly Ser Trp Tyr Val Glu Thr Leu Asp
            340                 345                 350

Asp Ile Phe Glu Gln Trp Ala His Ser Glu Asp Leu Gln Ser Leu Leu
        355                 360                 365

Leu Arg Val Ala Asn Ala Val Ser Val Lys Gly Ile Tyr Lys Gln Met
370                 375                 380

Pro Gly Cys Phe Asn Phe Leu Arg Lys Lys Leu Phe Phe Lys Thr Ser
385                 390                 395                 400

Ala Ser

<210> SEQ ID NO 96
<211> LENGTH: 112
<212> TYPE: PRT
<213> ORGANISM: Artificial Sequence
<220> FEATURE:
<223> OTHER INFORMATION: Synthetic sequence TCR1,13 beta chain variable
      region (mature)

<400> SEQUENCE: 96

Gly Val Ser Gln Asp Pro Arg His Lys Ile Thr Lys Arg Gly Gln Asn
1               5                   10                  15

Val Thr Phe Arg Cys Asp Pro Ile Ser Glu His Asn Arg Leu Tyr Trp
            20                  25                  30

Tyr Arg Gln Thr Leu Gly Gln Gly Pro Glu Phe Leu Thr Tyr Phe Gln
        35                  40                  45

Asn Glu Ala Gln Leu Glu Lys Ser Arg Leu Leu Ser Asp Arg Phe Ser
    50                  55                  60

Ala Glu Arg Pro Lys Gly Ser Phe Ser Thr Leu Glu Ile Gln Arg Thr
65                  70                  75                  80

Glu Gln Gly Asp Ser Ala Met Tyr Leu Cys Ala Ser Ser Ser Thr Gly
                85                  90                  95

Gly His Asn Glu Gln Phe Phe Gly Pro Gly Thr Arg Leu Thr Val Leu
            100                 105                 110

<210> SEQ ID NO 97
<211> LENGTH: 113
<212> TYPE: PRT
<213> ORGANISM: Artificial Sequence
<220> FEATURE:
<223> OTHER INFORMATION: Synthetic sequence TCR1,13 alpha chain variable
      region (mature)

<400> SEQUENCE: 97

Gln Gln Gly Glu Glu Asp Pro Gln Ala Leu Ser Ile Gln Glu Gly Glu
1               5                   10                  15

Asn Ala Thr Met Asn Cys Ser Tyr Lys Thr Ser Ile Asn Asn Leu Gln
            20                  25                  30

Trp Tyr Arg Gln Asn Ser Gly Arg Gly Leu Val His Leu Ile Leu Ile
        35                  40                  45

Arg Ser Asn Glu Arg Glu Lys His Ser Gly Arg Leu Arg Val Thr Leu

```
                50                  55                  60
Asp Thr Ser Lys Lys Ser Ser Leu Leu Ile Thr Ala Ser Arg Ala
 65                  70                  75                  80

Ala Asp Thr Ala Ser Tyr Phe Cys Ala Thr Lys Arg Asp Ser Gly Ala
                 85                  90                  95

Gly Ser Tyr Gln Leu Thr Phe Gly Lys Gly Thr Lys Leu Ser Val Ile
                100                 105                 110

Pro

<210> SEQ ID NO 98
<211> LENGTH: 111
<212> TYPE: PRT
<213> ORGANISM: Artificial Sequence
<220> FEATURE:
<223> OTHER INFORMATION: Synthetic sequence TCR2,14 beta chain variable
      region (mature)

<400> SEQUENCE: 98

Gly Val Ser Gln Asp Pro Arg His Lys Ile Thr Lys Arg Gly Gln Asn
 1               5                  10                  15

Val Thr Phe Arg Cys Asp Pro Ile Ser Glu His Asn Arg Leu Tyr Trp
                20                  25                  30

Tyr Arg Gln Thr Leu Gly Gln Gly Pro Glu Phe Leu Thr Tyr Phe Gln
             35                  40                  45

Asn Glu Ala Gln Leu Glu Lys Ser Arg Leu Leu Ser Asp Arg Phe Ser
 50                  55                  60

Ala Glu Arg Pro Lys Gly Ser Phe Ser Thr Leu Glu Ile Gln Arg Thr
 65                  70                  75                  80

Glu Gln Gly Asp Ser Ala Met Tyr Leu Cys Ala Ser Ser Leu Val Lys
                 85                  90                  95

Gly Glu Lys Leu Phe Phe Gly Ser Gly Thr Gln Leu Ser Val Leu
                100                 105                 110

<210> SEQ ID NO 99
<211> LENGTH: 113
<212> TYPE: PRT
<213> ORGANISM: Artificial Sequence
<220> FEATURE:
<223> OTHER INFORMATION: Synthetic sequence TCR2,14 alpha chain variable
      region (mature)

<400> SEQUENCE: 99

Lys Gln Glu Val Thr Gln Ile Pro Ala Ala Leu Ser Val Pro Glu Gly
 1               5                  10                  15

Glu Asn Leu Val Leu Asn Cys Ser Phe Thr Asp Ser Ala Ile Tyr Asn
                20                  25                  30

Leu Gln Trp Phe Arg Gln Asp Pro Gly Lys Gly Leu Thr Ser Leu Leu
             35                  40                  45

Leu Ile Gln Ser Ser Gln Arg Glu Gln Thr Ser Gly Arg Leu Asn Ala
             50                  55                  60

Ser Leu Asp Lys Ser Ser Gly Arg Ser Thr Leu Tyr Ile Ala Ala Ser Gln
 65                  70                  75                  80

Pro Gly Asp Ser Ala Thr Tyr Leu Cys Ala Val Ile Gly Leu Gly Gly
                 85                  90                  95

Thr Tyr Lys Tyr Ile Phe Gly Thr Gly Thr Arg Leu Lys Val Leu Ala
                100                 105                 110

<210> SEQ ID NO 100
```

```
<211> LENGTH: 111
<212> TYPE: PRT
<213> ORGANISM: Artificial Sequence
<220> FEATURE:
<223> OTHER INFORMATION: Synthetic sequence TCR5 beta chain variable
      region (mature)

<400> SEQUENCE: 100

Gly Val Ser Gln Asp Pro Arg His Lys Ile Thr Lys Arg Gly Gln Asn
1               5                   10                  15

Val Thr Phe Arg Cys Asp Pro Ile Ser Glu His Asn Arg Leu Tyr Trp
            20                  25                  30

Tyr Arg Gln Thr Leu Gly Gln Gly Pro Glu Phe Leu Thr Tyr Phe Gln
        35                  40                  45

Asn Glu Ala Gln Leu Glu Lys Ser Arg Leu Leu Ser Asp Arg Phe Ser
    50                  55                  60

Ala Glu Arg Pro Lys Gly Ser Phe Ser Thr Leu Glu Ile Gln Arg Thr
65                  70                  75                  80

Glu Gln Gly Asp Ser Ala Met Tyr Leu Cys Ala Ser Ser Leu Thr Thr
                85                  90                  95

Leu Asp Glu Gln Tyr Val Gly Pro Gly Thr Arg Leu Thr Val Thr
            100                 105                 110

<210> SEQ ID NO 101
<211> LENGTH: 109
<212> TYPE: PRT
<213> ORGANISM: Artificial Sequence
<220> FEATURE:
<223> OTHER INFORMATION: Synthetic sequence TCR5 alpha chain variable
      region (mature)

<400> SEQUENCE: 101

Gln Gln Gly Glu Glu Asp Pro Gln Ala Leu Ser Ile Gln Glu Gly Glu
1               5                   10                  15

Asn Ala Thr Met Asn Cys Ser Tyr Lys Thr Ser Ile Asn Asn Leu Gln
            20                  25                  30

Trp Tyr Arg Gln Asn Ser Gly Arg Gly Leu Val His Leu Ile Leu Ile
        35                  40                  45

Arg Ser Asn Glu Arg Glu Lys His Ser Gly Arg Leu Arg Val Thr Leu
    50                  55                  60

Asp Thr Ser Lys Lys Ser Ser Ser Leu Leu Ile Thr Ala Ser Arg Ala
65                  70                  75                  80

Ala Asp Thr Ala Ser Tyr Phe Cys Ala Thr Asn Ser Gly Asn Thr Pro
                85                  90                  95

Leu Val Phe Gly Lys Gly Thr Arg Leu Ser Val Ile Ala
            100                 105

<210> SEQ ID NO 102
<211> LENGTH: 111
<212> TYPE: PRT
<213> ORGANISM: Artificial Sequence
<220> FEATURE:
<223> OTHER INFORMATION: Synthetic sequence TCR10 beta chain variable
      region (mature)

<400> SEQUENCE: 102

Gly Val Ser Gln Asp Pro Arg His Lys Ile Thr Lys Arg Gly Gln Asn
1               5                   10                  15

Val Thr Phe Arg Cys Asp Pro Ile Ser Glu His Asn Arg Leu Tyr Trp
            20                  25                  30
```

```
Tyr Arg Gln Thr Leu Gly Gln Gly Pro Glu Phe Leu Thr Tyr Phe Gln
            35                  40                  45

Asn Glu Ala Gln Leu Glu Lys Ser Arg Leu Leu Ser Asp Arg Phe Ser
 50                  55                  60

Ala Glu Arg Pro Lys Gly Ser Phe Ser Thr Leu Glu Ile Gln Arg Thr
 65                  70                  75                  80

Glu Gln Gly Asp Ser Ala Met Tyr Leu Cys Ala Ser Ser Met Leu Thr
                85                  90                  95

Asn Tyr Glu Gln Tyr Phe Gly Pro Gly Thr Arg Leu Thr Val Thr
                100                 105                 110

<210> SEQ ID NO 103
<211> LENGTH: 113
<212> TYPE: PRT
<213> ORGANISM: Artificial Sequence
<220> FEATURE:
<223> OTHER INFORMATION: Synthetic sequence TCR10 alpha chain variable
      region (mature)

<400> SEQUENCE: 103

Lys Asn Gln Val Glu Gln Ser Pro Gln Ser Leu Ile Ile Leu Glu Gly
 1               5                  10                  15

Lys Asn Cys Thr Leu Gln Cys Asn Tyr Thr Val Ser Pro Phe Ser Asn
                20                  25                  30

Leu Arg Trp Tyr Lys Gln Asp Thr Gly Arg Gly Pro Val Ser Leu Thr
                35                  40                  45

Ile Met Thr Phe Ser Glu Asn Thr Lys Ser Asn Gly Arg Tyr Thr Ala
 50                  55                  60

Thr Leu Asp Ala Asp Thr Lys Gln Ser Ser Leu His Ile Thr Ala Ser
 65                  70                  75                  80

Gln Leu Ser Asp Ser Ala Ser Tyr Ile Cys Val Val Ser Gly Gly
                85                  90                  95

Gly Ala Asp Gly Leu Thr Phe Gly Lys Gly Thr His Leu Ile Ile Gln
                100                 105                 110

Pro

<210> SEQ ID NO 104
<211> LENGTH: 111
<212> TYPE: PRT
<213> ORGANISM: Artificial Sequence
<220> FEATURE:
<223> OTHER INFORMATION: Synthetic sequence TCR16 beta chain variable
      region (mature)

<400> SEQUENCE: 104

Gly Val Ser Gln Asp Pro Arg His Lys Ile Thr Lys Arg Gly Gln Asn
 1               5                  10                  15

Val Thr Phe Arg Cys Asp Pro Ile Ser Glu His Asn Arg Leu Tyr Trp
                20                  25                  30

Tyr Arg Gln Thr Leu Gly Gln Gly Pro Glu Phe Leu Thr Tyr Phe Gln
                35                  40                  45

Asn Glu Ala Gln Leu Glu Lys Ser Arg Leu Leu Ser Asp Arg Phe Ser
 50                  55                  60

Ala Glu Arg Pro Lys Gly Ser Phe Ser Thr Leu Glu Ile Gln Arg Thr
 65                  70                  75                  80

Glu Gln Gly Asp Ser Ala Met Tyr Leu Cys Ala Ser Ser Leu Val Val
                85                  90                  95

Gly Asn Glu Gln Phe Phe Gly Pro Gly Thr Arg Leu Thr Val Leu
```

<210> SEQ ID NO 105
<211> LENGTH: 112
<212> TYPE: PRT
<213> ORGANISM: Artificial Sequence
<220> FEATURE:
<223> OTHER INFORMATION: Synthetic sequence TCR16 alpha chain variable
      region (mature)

<400> SEQUENCE: 105

Lys Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Gln Ser Ser Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val His Leu Leu Asn
                85                  90                  95

Asp Tyr Lys Leu Ser Phe Gly Ala Gly Thr Thr Val Thr Val Arg Ala
            100                 105                 110

<210> SEQ ID NO 106
<211> LENGTH: 111
<212> TYPE: PRT
<213> ORGANISM: Artificial Sequence
<220> FEATURE:
<223> OTHER INFORMATION: Synthetic sequence TCR29 beta chain variable
      region (mature)

<400> SEQUENCE: 106

Gly Val Ser Gln Asp Pro Arg His Lys Ile Thr Lys Arg Gly Gln Asn
1               5                   10                  15

Val Thr Phe Arg Cys Asp Pro Ile Ser Glu His Asn Arg Leu Tyr Trp
            20                  25                  30

Tyr Arg Gln Thr Leu Gly Gln Gly Pro Glu Phe Leu Thr Tyr Phe Gln
        35                  40                  45

Asn Glu Ala Gln Leu Glu Lys Ser Arg Leu Leu Ser Asp Arg Phe Ser
    50                  55                  60

Ala Glu Arg Pro Lys Gly Ser Phe Ser Thr Leu Glu Ile Gln Arg Thr
65                  70                  75                  80

Glu Gln Gly Asp Ser Ala Met Tyr Leu Cys Ala Ser Ser Leu Val Ser
                85                  90                  95

Gly Asn Thr Ile Tyr Phe Gly Glu Gly Ser Trp Leu Thr Val Val
            100                 105                 110

<210> SEQ ID NO 107
<211> LENGTH: 115
<212> TYPE: PRT
<213> ORGANISM: Artificial Sequence
<220> FEATURE:
<223> OTHER INFORMATION: Synthetic sequence TCR29 alpha chain variable
      region (mature)

<400> SEQUENCE: 107

Lys Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
                20                  25                  30

Leu Gln Trp Phe Arg Gln Asp Pro Gly Lys Gly Leu Thr Ser Leu Leu
        35                  40                  45

Leu Ile Gln Ser Ser Gln Arg Glu Gln Thr Ser Gly Arg Leu Asn Ala
50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Gly Gly Thr
                85                  90                  95

Thr Ser Gly Thr Tyr Lys Tyr Ile Phe Gly Thr Gly Thr Arg Leu Lys
                100                 105                 110

Val Leu Ala
        115

<210> SEQ ID NO 108
<211> LENGTH: 289
<212> TYPE: PRT
<213> ORGANISM: Artificial Sequence
<220> FEATURE:
<223> OTHER INFORMATION: Synthetic sequence TCR1,13 beta chain (full
      length) (Cys modified) (mature)

<400> SEQUENCE: 108

Gly Val Ser Gln Asp Pro Arg His Lys Ile Thr Lys Arg Gly Gln Asn
1               5                   10                  15

Val Thr Phe Arg Cys Asp Pro Ile Ser Glu His Asn Arg Leu Tyr Trp
                20                  25                  30

Tyr Arg Gln Thr Leu Gly Gln Gly Pro Glu Phe Leu Thr Tyr Phe Gln
        35                  40                  45

Asn Glu Ala Gln Leu Glu Lys Ser Arg Leu Leu Ser Asp Arg Phe Ser
50                  55                  60

Ala Glu Arg Pro Lys Gly Ser Phe Ser Thr Leu Glu Ile Gln Arg Thr
65                  70                  75                  80

Glu Gln Gly Asp Ser Ala Met Tyr Leu Cys Ala Ser Ser Ser Thr Gly
                85                  90                  95

Gly His Asn Glu Gln Phe Phe Gly Pro Gly Thr Arg Leu Thr Val Leu
                100                 105                 110

Glu Asp Leu Lys Asn Val Phe Pro Pro Glu Val Ala Val Phe Glu Pro
        115                 120                 125

Ser Glu Ala Glu Ile Ser His Thr Gln Lys Ala Thr Leu Val Cys Leu
        130                 135                 140

Ala Thr Gly Phe Tyr Pro Asp His Val Glu Leu Ser Trp Trp Val Asn
145                 150                 155                 160

Gly Lys Glu Val His Ser Gly Val Cys Thr Asp Pro Gln Pro Leu Lys
                165                 170                 175

Glu Gln Pro Ala Leu Asn Asp Ser Arg Tyr Cys Leu Ser Ser Arg Leu
        180                 185                 190

Arg Val Ser Ala Thr Phe Trp Gln Asn Pro Arg Asn His Phe Arg Cys
        195                 200                 205

Gln Val Gln Phe Tyr Gly Leu Ser Glu Asn Asp Glu Trp Thr Gln Asp
        210                 215                 220

Arg Ala Lys Pro Val Thr Gln Ile Val Ser Ala Glu Ala Trp Gly Arg
225                 230                 235                 240

Ala Asp Cys Gly Phe Thr Ser Glu Ser Tyr Gln Gln Gly Val Leu Ser

```
                    245                 250                 255

Ala Thr Ile Leu Tyr Glu Ile Leu Leu Gly Lys Ala Thr Leu Tyr Ala
                260                 265                 270

Val Leu Val Ser Ala Leu Val Leu Met Ala Met Val Lys Arg Lys Asp
            275                 280                 285

Ser

<210> SEQ ID NO 109
<211> LENGTH: 254
<212> TYPE: PRT
<213> ORGANISM: Artificial Sequence
<220> FEATURE:
<223> OTHER INFORMATION: Synthetic sequence TCR1,13 alpha chain (full
      length)(Cys modified)(mature)

<400> SEQUENCE: 109

Gln Gln Gly Glu Glu Asp Pro Gln Ala Leu Ser Ile Gln Glu Gly Glu
1               5                   10                  15

Asn Ala Thr Met Asn Cys Ser Tyr Lys Thr Ser Ile Asn Asn Leu Gln
            20                  25                  30

Trp Tyr Arg Gln Asn Ser Gly Arg Gly Leu Val His Leu Ile Leu Ile
        35                  40                  45

Arg Ser Asn Glu Arg Glu Lys His Ser Gly Arg Leu Arg Val Thr Leu
50                  55                  60

Asp Thr Ser Lys Lys Ser Ser Ser Leu Leu Ile Thr Ala Ser Arg Ala
65                  70                  75                  80

Ala Asp Thr Ala Ser Tyr Phe Cys Ala Thr Lys Arg Asp Ser Gly Ala
                85                  90                  95

Gly Ser Tyr Gln Leu Thr Phe Gly Lys Gly Thr Lys Leu Ser Val Ile
            100                 105                 110

Pro Asn Ile Gln Asn Pro Asp Pro Ala Val Tyr Gln Leu Arg Asp Ser
        115                 120                 125

Lys Ser Ser Asp Lys Ser Val Cys Leu Phe Thr Asp Phe Asp Ser Gln
130                 135                 140

Thr Asn Val Ser Gln Ser Lys Asp Ser Asp Val Tyr Ile Thr Asp Lys
145                 150                 155                 160

Cys Val Leu Asp Met Arg Ser Met Asp Phe Lys Ser Asn Ser Ala Val
                165                 170                 175

Ala Trp Ser Asn Lys Ser Asp Phe Ala Cys Ala Asn Ala Phe Asn Asn
            180                 185                 190

Ser Ile Ile Pro Glu Asp Thr Phe Phe Pro Ser Pro Glu Ser Ser Cys
        195                 200                 205

Asp Val Lys Leu Val Glu Lys Ser Phe Glu Thr Asp Thr Asn Leu Asn
210                 215                 220

Phe Gln Asn Leu Ser Val Ile Gly Phe Arg Ile Leu Leu Leu Lys Val
225                 230                 235                 240

Ala Gly Phe Asn Leu Leu Met Thr Leu Arg Leu Trp Ser Ser
                245                 250

<210> SEQ ID NO 110
<211> LENGTH: 287
<212> TYPE: PRT
<213> ORGANISM: Artificial Sequence
<220> FEATURE:
<223> OTHER INFORMATION: Synthetic sequence TCR2,14 beta chain (full
      length) (Cys modified) (mature)

<400> SEQUENCE: 110
```

```
Gly Val Ser Gln Asp Pro Arg His Lys Ile Thr Lys Arg Gly Gln Asn
1               5                   10                  15

Val Thr Phe Arg Cys Asp Pro Ile Ser Glu His Asn Arg Leu Tyr Trp
            20                  25                  30

Tyr Arg Gln Thr Leu Gly Gln Gly Pro Glu Phe Leu Thr Tyr Phe Gln
        35                  40                  45

Asn Glu Ala Gln Leu Glu Lys Ser Arg Leu Leu Ser Asp Arg Phe Ser
50                  55                  60

Ala Glu Arg Pro Lys Gly Ser Phe Ser Thr Leu Glu Ile Gln Arg Thr
65                  70                  75                  80

Glu Gln Gly Asp Ser Ala Met Tyr Leu Cys Ala Ser Ser Leu Val Lys
                85                  90                  95

Gly Glu Lys Leu Phe Phe Gly Ser Gly Thr Gln Leu Ser Val Leu Glu
                100                 105                 110

Asp Leu Asn Lys Val Phe Pro Pro Glu Val Ala Val Phe Glu Pro Ser
            115                 120                 125

Glu Ala Glu Ile Ser His Thr Gln Lys Ala Thr Leu Val Cys Leu Ala
130                 135                 140

Thr Gly Phe Phe Pro Asp His Val Glu Leu Ser Trp Trp Val Asn Gly
145                 150                 155                 160

Lys Glu Val His Ser Gly Val Cys Thr Asp Pro Gln Pro Leu Lys Glu
                165                 170                 175

Gln Pro Ala Leu Asn Asp Ser Arg Tyr Cys Leu Ser Ser Arg Leu Arg
            180                 185                 190

Val Ser Ala Thr Phe Trp Gln Asn Pro Arg Asn His Phe Arg Cys Gln
            195                 200                 205

Val Gln Phe Tyr Gly Leu Ser Glu Asn Asp Glu Trp Thr Gln Asp Arg
210                 215                 220

Ala Lys Pro Val Thr Gln Ile Val Ser Ala Glu Ala Trp Gly Arg Ala
225                 230                 235                 240

Asp Cys Gly Phe Thr Ser Val Ser Tyr Gln Gln Gly Val Leu Ser Ala
                245                 250                 255

Thr Ile Leu Tyr Glu Ile Leu Leu Gly Lys Ala Thr Leu Tyr Ala Val
                260                 265                 270

Leu Val Ser Ala Leu Val Leu Met Ala Met Val Lys Arg Lys Asp
                275                 280                 285

<210> SEQ ID NO 111
<211> LENGTH: 254
<212> TYPE: PRT
<213> ORGANISM: Artificial Sequence
<220> FEATURE:
<223> OTHER INFORMATION: Synthetic sequence TCR2,14 alpha chain (full
      length)(Cys modified) (mature)

<400> SEQUENCE: 111

Lys Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Gln Ser Ser Gln Arg Glu Gln Thr Ser Gly Arg Leu Asn Ala
50                  55                  60

Ser Leu Asp Lys Ser Ser Gly Arg Ser Thr Leu Tyr Ile Ala Ala Ser
```

```
                65                   70                  75                  80
        Gln Pro Gly Asp Ser Ala Thr Tyr Leu Cys Ala Val Ile Gly Leu Gly
                        85                  90                  95

Gly Thr Tyr Lys Tyr Ile Phe Gly Thr Gly Thr Arg Leu Lys Val Leu
                        100                 105                 110

Ala Asn Ile Gln Asn Pro Asp Pro Ala Val Tyr Gln Leu Arg Asp Ser
                        115                 120                 125

Lys Ser Ser Asp Lys Ser Val Cys Leu Phe Thr Asp Phe Asp Ser Gln
                        130                 135                 140

Thr Asn Val Ser Gln Ser Lys Asp Ser Asp Val Tyr Ile Thr Asp Lys
        145                 150                 155                 160

Cys Val Leu Asp Met Arg Ser Met Asp Phe Lys Ser Asn Ser Ala Val
                        165                 170                 175

Ala Trp Ser Asn Lys Ser Asp Phe Ala Cys Ala Asn Ala Phe Asn Asn
                        180                 185                 190

Ser Ile Ile Pro Glu Asp Thr Phe Phe Pro Ser Pro Glu Ser Ser Cys
                        195                 200                 205

Asp Val Lys Leu Val Glu Lys Ser Phe Glu Thr Asp Thr Asn Leu Asn
                        210                 215                 220

Phe Gln Asn Leu Ser Val Ile Gly Phe Arg Ile Leu Leu Leu Lys Val
        225                 230                 235                 240

Ala Gly Phe Asn Leu Leu Met Thr Leu Arg Leu Trp Ser Ser
                        245                 250

<210> SEQ ID NO 112
<211> LENGTH: 288
<212> TYPE: PRT
<213> ORGANISM: Artificial Sequence
<220> FEATURE:
<223> OTHER INFORMATION: Synthetic sequence TCR5 beta chain (full
      length) (Cys modified) (mature)

<400> SEQUENCE: 112

Gly Val Ser Gln Asp Pro Arg His Lys Ile Thr Lys Arg Gly Gln Asn
        1               5                   10                  15

Val Thr Phe Arg Cys Asp Pro Ile Ser Glu His Asn Arg Leu Tyr Trp
                        20                  25                  30

Tyr Arg Gln Thr Leu Gly Gln Gly Pro Glu Phe Leu Thr Tyr Phe Gln
                        35                  40                  45

Asn Glu Ala Gln Leu Glu Lys Ser Arg Leu Leu Ser Asp Arg Phe Ser
        50                  55                  60

Ala Glu Arg Pro Lys Gly Ser Phe Ser Thr Leu Glu Ile Gln Arg Thr
        65                  70                  75                  80

Glu Gln Gly Asp Ser Ala Met Tyr Leu Cys Ala Ser Ser Leu Thr Thr
                        85                  90                  95

Leu Asp Glu Gln Tyr Val Gly Pro Gly Thr Arg Leu Thr Val Thr Glu
                        100                 105                 110

Asp Leu Lys Asn Val Phe Pro Pro Glu Val Ala Val Phe Glu Pro Ser
                        115                 120                 125

Glu Ala Glu Ile Ser His Thr Gln Lys Ala Thr Leu Val Cys Leu Ala
                        130                 135                 140

Thr Gly Phe Tyr Pro Asp His Val Glu Leu Ser Trp Trp Val Asn Gly
        145                 150                 155                 160

Lys Glu Val His Ser Gly Val Cys Thr Asp Pro Gln Pro Leu Lys Glu
                        165                 170                 175
```

```
Gln Pro Ala Leu Asn Asp Ser Arg Tyr Cys Leu Ser Ser Arg Leu Arg
                180                 185                 190

Val Ser Ala Thr Phe Trp Gln Asn Pro Arg Asn His Phe Arg Cys Gln
            195                 200                 205

Val Gln Phe Tyr Gly Leu Ser Glu Asn Asp Glu Trp Thr Gln Asp Arg
        210                 215                 220

Ala Lys Pro Val Thr Gln Ile Val Ser Ala Glu Ala Trp Gly Arg Ala
225                 230                 235                 240

Asp Cys Gly Phe Thr Ser Glu Ser Tyr Gln Gln Gly Val Leu Ser Ala
                245                 250                 255

Thr Ile Leu Tyr Glu Ile Leu Leu Gly Lys Ala Thr Leu Tyr Ala Val
            260                 265                 270

Leu Val Ser Ala Leu Val Leu Met Ala Met Val Lys Arg Lys Asp Ser
        275                 280                 285

<210> SEQ ID NO 113
<211> LENGTH: 250
<212> TYPE: PRT
<213> ORGANISM: Artificial Sequence
<220> FEATURE:
<223> OTHER INFORMATION: Synthetic sequence TCR5 alpha chain (full
      length)(Cys modified) (mature)

<400> SEQUENCE: 113

Gln Gln Gly Glu Glu Asp Pro Gln Ala Leu Ser Ile Gln Glu Gly Glu
1               5                   10                  15

Asn Ala Thr Met Asn Cys Ser Tyr Lys Thr Ser Ile Asn Asn Leu Gln
            20                  25                  30

Trp Tyr Arg Gln Asn Ser Gly Arg Gly Leu Val His Leu Ile Leu Ile
        35                  40                  45

Arg Ser Asn Glu Arg Glu Lys His Ser Gly Arg Leu Arg Val Thr Leu
    50                  55                  60

Asp Thr Ser Lys Lys Ser Ser Ser Leu Leu Ile Thr Ala Ser Arg Ala
65                  70                  75                  80

Ala Asp Thr Ala Ser Tyr Phe Cys Ala Thr Asn Ser Gly Asn Thr Pro
                85                  90                  95

Leu Val Phe Gly Lys Gly Thr Arg Leu Ser Val Ile Ala Asn Ile Gln
            100                 105                 110

Asn Pro Asp Pro Ala Val Tyr Gln Leu Arg Asp Ser Lys Ser Ser Asp
        115                 120                 125

Lys Ser Val Cys Leu Phe Thr Asp Phe Asp Ser Gln Thr Asn Val Ser
145                 150                 155                 160

Gln Ser Lys Asp Ser Asp Val Tyr Ile Thr Asp Lys Cys Val Leu Asp
145                 150                 155                 160

Met Arg Ser Met Asp Phe Lys Ser Asn Ser Ala Val Ala Trp Ser Asn
                165                 170                 175

Lys Ser Asp Phe Ala Cys Ala Asn Ala Phe Asn Asn Ser Ile Ile Pro
            180                 185                 190

Glu Asp Thr Phe Phe Pro Ser Pro Glu Ser Ser Cys Asp Val Lys Leu
        195                 200                 205

Val Glu Lys Ser Phe Glu Thr Asp Thr Asn Leu Asn Phe Gln Asn Leu
    210                 215                 220

Ser Val Ile Gly Phe Arg Ile Leu Leu Leu Lys Val Ala Gly Phe Asn
225                 230                 235                 240

Leu Leu Met Thr Leu Arg Leu Trp Ser Ser
                245                 250
```

<210> SEQ ID NO 114
<211> LENGTH: 288
<212> TYPE: PRT
<213> ORGANISM: Artificial Sequence
<220> FEATURE:
<223> OTHER INFORMATION: Synthetic sequence TCR10 beta chain (full
      length) (Cys modified) (mature)

<400> SEQUENCE: 114

```
Gly Val Ser Gln Asp Pro Arg His Lys Ile Thr Lys Arg Gly Gln Asn
1               5                   10                  15

Val Thr Phe Arg Cys Asp Pro Ile Ser Glu His Asn Arg Leu Tyr Trp
            20                  25                  30

Tyr Arg Gln Thr Leu Gly Gln Gly Pro Glu Phe Leu Thr Tyr Phe Gln
        35                  40                  45

Asn Glu Ala Gln Leu Glu Lys Ser Arg Leu Leu Ser Asp Arg Phe Ser
    50                  55                  60

Ala Glu Arg Pro Lys Gly Ser Phe Ser Thr Leu Glu Ile Gln Arg Thr
65                  70                  75                  80

Glu Gln Gly Asp Ser Ala Met Tyr Leu Cys Ala Ser Ser Met Leu Thr
                85                  90                  95

Asn Tyr Glu Gln Tyr Phe Gly Pro Gly Thr Arg Leu Thr Val Thr Glu
            100                 105                 110

Asp Leu Lys Asn Val Phe Pro Pro Glu Val Ala Val Phe Glu Pro Ser
        115                 120                 125

Glu Ala Glu Ile Ser His Thr Gln Lys Ala Thr Leu Val Cys Leu Ala
    130                 135                 140

Thr Gly Phe Tyr Pro Asp His Val Glu Leu Ser Trp Trp Val Asn Gly
145                 150                 155                 160

Lys Glu Val His Ser Gly Val Cys Thr Asp Pro Gln Pro Leu Lys Glu
                165                 170                 175

Gln Pro Ala Leu Asn Asp Ser Arg Tyr Cys Leu Ser Ser Arg Leu Arg
            180                 185                 190

Val Ser Ala Thr Phe Trp Gln Asn Pro Arg Asn His Phe Arg Cys Gln
        195                 200                 205

Val Gln Phe Tyr Gly Leu Ser Glu Asn Asp Glu Trp Thr Gln Asp Arg
    210                 215                 220

Ala Lys Pro Val Thr Gln Ile Val Ser Ala Glu Ala Trp Gly Arg Ala
225                 230                 235                 240

Asp Cys Gly Phe Thr Ser Glu Ser Tyr Gln Gln Gly Val Leu Ser Ala
                245                 250                 255

Thr Ile Leu Tyr Glu Ile Leu Leu Gly Lys Ala Thr Leu Tyr Ala Val
            260                 265                 270

Leu Val Ser Ala Leu Val Leu Met Ala Met Val Lys Arg Lys Asp Ser
        275                 280                 285
```

<210> SEQ ID NO 115
<211> LENGTH: 254
<212> TYPE: PRT
<213> ORGANISM: Artificial Sequence
<220> FEATURE:
<223> OTHER INFORMATION: Synthetic sequence TCR10 alpha chain (full
      length)(Cys modified) (mature)

<400> SEQUENCE: 115

```
Lys Asn Gln Val Glu Gln Ser Pro Gln Ser Leu Ile Ile Leu Glu Gly
1               5                   10                  15
```

Lys Asn Cys Thr Leu Gln Cys Asn Tyr Thr Val Ser Pro Phe Ser Asn
            20                  25                  30

Leu Arg Trp Tyr Lys Gln Asp Thr Gly Arg Gly Pro Val Ser Leu Thr
        35                  40                  45

Ile Met Thr Phe Ser Glu Asn Thr Lys Ser Asn Gly Arg Tyr Thr Ala
    50                  55                  60

Thr Leu Asp Ala Asp Thr Lys Gln Ser Ser Leu His Ile Thr Ala Ser
65                  70                  75                  80

Gln Leu Ser Asp Ser Ala Ser Tyr Ile Cys Val Val Asp Ser Gly Gly
                85                  90                  95

Gly Ala Asp Gly Leu Thr Phe Gly Lys Gly Thr His Leu Ile Ile Gln
            100                 105                 110

Pro Tyr Ile Gln Asn Pro Asp Pro Ala Val Tyr Gln Leu Arg Asp Ser
        115                 120                 125

Lys Ser Ser Asp Lys Ser Val Cys Leu Phe Thr Asp Phe Asp Ser Gln
130                 135                 140

Thr Asn Val Ser Gln Ser Lys Asp Ser Asp Val Tyr Ile Thr Asp Lys
145                 150                 155                 160

Cys Val Leu Asp Met Arg Ser Met Asp Phe Lys Ser Asn Ser Ala Val
                165                 170                 175

Ala Trp Ser Asn Lys Ser Asp Phe Ala Cys Ala Asn Ala Phe Asn Asn
            180                 185                 190

Ser Ile Ile Pro Glu Asp Thr Phe Phe Pro Ser Pro Glu Ser Ser Cys
        195                 200                 205

Asp Val Lys Leu Val Glu Lys Ser Phe Glu Thr Asp Thr Asn Leu Asn
    210                 215                 220

Phe Gln Asn Leu Ser Val Ile Gly Phe Arg Ile Leu Leu Leu Lys Val
225                 230                 235                 240

Ala Gly Phe Asn Leu Leu Met Thr Leu Arg Leu Trp Ser Ser
                245                 250

<210> SEQ ID NO 116
<211> LENGTH: 287
<212> TYPE: PRT
<213> ORGANISM: Artificial Sequence
<220> FEATURE:
<223> OTHER INFORMATION: Synthetic sequence TCR16 beta chain (full
      length) (Cys modified) (mature)

<400> SEQUENCE: 116

Gly Val Ser Gln Asp Pro Arg His Lys Ile Thr Lys Arg Gly Gln Asn
1               5                   10                  15

Val Thr Phe Arg Cys Asp Pro Ile Ser Glu His Asn Arg Leu Tyr Trp
            20                  25                  30

Tyr Arg Gln Thr Leu Gly Gln Gly Pro Glu Phe Leu Thr Tyr Phe Gln
        35                  40                  45

Asn Glu Ala Gln Leu Glu Lys Ser Arg Leu Leu Ser Asp Arg Phe Ser
    50                  55                  60

Ala Glu Arg Pro Lys Gly Ser Phe Ser Thr Leu Glu Ile Gln Arg Thr
65                  70                  75                  80

Glu Gln Gly Asp Ser Ala Met Tyr Leu Cys Ala Ser Ser Leu Val Val
                85                  90                  95

Gly Asn Glu Gln Phe Phe Gly Pro Gly Thr Arg Leu Thr Val Leu Glu
            100                 105                 110

Asp Leu Lys Asn Val Phe Pro Pro Glu Val Ala Val Phe Glu Pro Ser

```
              115                 120                 125
Glu Ala Glu Ile Ser His Thr Gln Lys Ala Thr Leu Val Cys Leu Ala
        130                 135                 140

Thr Gly Phe Tyr Pro Asp His Val Glu Leu Ser Trp Trp Val Asn Gly
145                 150                 155                 160

Lys Glu Val His Ser Gly Val Cys Thr Asp Pro Gln Pro Leu Lys Glu
                165                 170                 175

Gln Pro Ala Leu Asn Asp Ser Arg Tyr Cys Leu Ser Ser Arg Leu Arg
            180                 185                 190

Val Ser Ala Thr Phe Trp Gln Asn Pro Arg Asn His Phe Arg Cys Gln
        195                 200                 205

Val Gln Phe Tyr Gly Leu Ser Glu Asn Asp Glu Trp Thr Gln Asp Arg
    210                 215                 220

Ala Lys Pro Val Thr Gln Ile Val Ser Ala Glu Ala Trp Gly Arg Ala
225                 230                 235                 240

Asp Cys Gly Phe Thr Ser Glu Ser Tyr Gln Gln Gly Val Leu Ser Ala
                245                 250                 255

Thr Ile Leu Tyr Glu Ile Leu Leu Gly Lys Ala Thr Leu Tyr Ala Val
            260                 265                 270

Leu Val Ser Ala Leu Val Leu Met Ala Met Val Lys Arg Lys Asp
        275                 280                 285

<210> SEQ ID NO 117
<211> LENGTH: 253
<212> TYPE: PRT
<213> ORGANISM: Artificial Sequence
<220> FEATURE:
<223> OTHER INFORMATION: Synthetic sequence TCR16 alpha chain (full
      length) (Cys modified) (mature)

<400> SEQUENCE: 117

Lys Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Gln Ser Ser Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val His Leu Leu Asn
                85                  90                  95

Asp Tyr Lys Leu Ser Phe Gly Ala Gly Thr Thr Val Thr Val Arg Ala
            100                 105                 110

Asn Ile Gln Asn Pro Asp Pro Ala Val Tyr Gln Leu Arg Asp Ser Lys
        115                 120                 125

Ser Ser Asp Lys Ser Val Cys Leu Phe Thr Asp Phe Asp Ser Gln Thr
    130                 135                 140

Asn Val Ser Gln Ser Lys Asp Ser Asp Val Tyr Ile Thr Asp Lys Cys
145                 150                 155                 160

Val Leu Asp Met Arg Ser Met Asp Phe Lys Ser Asn Ser Ala Val Ala
                165                 170                 175

Trp Ser Asn Lys Ser Asp Phe Ala Cys Ala Asn Ala Phe Asn Asn Ser
            180                 185                 190
```

```
Ile Ile Pro Glu Asp Thr Phe Phe Pro Ser Pro Glu Ser Ser Cys Asp
            195                 200                 205

Val Lys Leu Val Glu Lys Ser Phe Glu Thr Asp Thr Asn Leu Asn Phe
210                 215                 220

Gln Asn Leu Ser Val Ile Gly Phe Arg Ile Leu Leu Leu Lys Val Ala
225                 230                 235                 240

Gly Phe Asn Leu Leu Met Thr Leu Arg Leu Trp Ser Ser
            245                 250
```

<210> SEQ ID NO 118
<211> LENGTH: 288
<212> TYPE: PRT
<213> ORGANISM: Artificial Sequence
<220> FEATURE:
<223> OTHER INFORMATION: Synthetic sequenceTCR29 beta chain (full length) (mature)

<400> SEQUENCE: 118

```
Gly Val Ser Gln Asp Pro Arg His Lys Ile Thr Lys Arg Gly Gln Asn
1               5                   10                  15

Val Thr Phe Arg Cys Asp Pro Ile Ser Glu His Asn Arg Leu Tyr Trp
                20                  25                  30

Tyr Arg Gln Thr Leu Gly Gln Gly Pro Glu Phe Leu Thr Tyr Phe Gln
            35                  40                  45

Asn Glu Ala Gln Leu Glu Lys Ser Arg Leu Leu Ser Asp Arg Phe Ser
    50                  55                  60

Ala Glu Arg Pro Lys Gly Ser Phe Ser Thr Leu Glu Ile Gln Arg Thr
65                  70                  75                  80

Glu Gln Gly Asp Ser Ala Met Tyr Leu Cys Ala Ser Ser Leu Val Ser
                85                  90                  95

Gly Asn Thr Ile Tyr Phe Gly Glu Gly Ser Trp Leu Thr Val Val Glu
            100                 105                 110

Asp Leu Asn Lys Val Phe Pro Pro Glu Val Ala Val Phe Glu Pro Ser
    115                 120                 125

Glu Ala Glu Ile Ser His Thr Gln Lys Ala Thr Leu Val Cys Leu Ala
130                 135                 140

Thr Gly Phe Phe Pro Asp His Val Glu Leu Ser Trp Trp Val Asn Gly
145                 150                 155                 160

Lys Glu Val His Ser Gly Val Ser Thr Asp Pro Gln Pro Leu Lys Glu
                165                 170                 175

Gln Pro Ala Leu Asn Asp Ser Arg Tyr Cys Leu Ser Ser Arg Leu Arg
            180                 185                 190

Val Ser Ala Thr Phe Trp Gln Asn Pro Arg Asn His Phe Arg Cys Gln
    195                 200                 205

Val Gln Phe Tyr Gly Leu Ser Glu Asn Asp Glu Trp Thr Gln Asp Arg
210                 215                 220

Ala Lys Pro Val Thr Gln Ile Val Ser Ala Glu Ala Trp Gly Arg Ala
225                 230                 235                 240

Asp Cys Gly Phe Thr Ser Val Ser Tyr Gln Gln Gly Val Leu Ser Ala
                245                 250                 255

Thr Ile Leu Tyr Glu Ile Leu Leu Gly Lys Ala Thr Leu Tyr Ala Val
            260                 265                 270

Leu Val Ser Ala Leu Val Leu Met Ala Met Val Lys Arg Lys Asp Phe
    275                 280                 285
```

<210> SEQ ID NO 119

<211> LENGTH: 256
<212> TYPE: PRT
<213> ORGANISM: Artificial Sequence
<220> FEATURE:
<223> OTHER INFORMATION: Synthetic sequence TCR29 alpha chain (full length) (mature)

<400> SEQUENCE: 119

Lys Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Gln Ser Ser Gln Arg Glu Gln Thr Ser Gly Arg Leu Asn Ala
50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Gly Gly Thr
                85                  90                  95

Thr Ser Gly Thr Tyr Lys Tyr Ile Phe Gly Thr Gly Thr Arg Leu Lys
            100                 105                 110

Val Leu Ala Asn Ile Gln Asn Pro Asp Pro Ala Val Tyr Gln Leu Arg
        115                 120                 125

Asp Ser Lys Ser Ser Asp Lys Ser Val Cys Leu Phe Thr Asp Phe Asp
130                 135                 140

Ser Gln Thr Asn Val Ser Gln Ser Lys Asp Ser Asp Val Tyr Ile Thr
145                 150                 155                 160

Asp Lys Thr Val Leu Asp Met Arg Ser Met Asp Phe Lys Ser Asn Ser
                165                 170                 175

Ala Val Ala Trp Ser Asn Lys Ser Asp Phe Ala Cys Ala Asn Ala Phe
            180                 185                 190

Asn Asn Ser Ile Ile Pro Glu Asp Thr Phe Phe Pro Ser Pro Glu Ser
        195                 200                 205

Ser Cys Asp Val Lys Leu Val Glu Lys Ser Phe Glu Thr Asp Thr Asn
210                 215                 220

Leu Asn Phe Gln Asn Leu Ser Val Ile Gly Phe Arg Ile Leu Leu Leu
225                 230                 235                 240

Lys Val Ala Gly Phe Asn Leu Leu Met Thr Leu Arg Leu Trp Ser Ser
                245                 250                 255

<210> SEQ ID NO 120
<211> LENGTH: 214
<212> TYPE: PRT
<213> ORGANISM: Artificial Sequence
<220> FEATURE:
<223> OTHER INFORMATION: Synthetic sequence CD8 co-receptor alpha chain (mature)

<400> SEQUENCE: 120

Ser Gln Phe Arg Val Ser Pro Leu Asp Arg Thr Trp Asn Leu Gly Glu
1               5                   10                  15

Thr Val Glu Leu Lys Cys Gln Val Leu Leu Ser Asn Pro Thr Ser Gly
            20                  25                  30

Cys Ser Trp Leu Phe Gln Pro Arg Gly Ala Ala Ala Ser Pro Thr Phe
        35                  40                  45

Leu Leu Tyr Leu Ser Gln Asn Lys Pro Lys Ala Ala Glu Gly Leu Asp
50                  55                  60

Thr Gln Arg Phe Ser Gly Lys Arg Leu Gly Asp Thr Phe Val Leu Thr
65                  70                  75                  80

Leu Ser Asp Phe Arg Arg Glu Asn Glu Gly Tyr Tyr Phe Cys Ser Ala
            85                  90                  95

Leu Ser Asn Ser Ile Met Tyr Phe Ser His Phe Val Pro Val Phe Leu
        100                 105                 110

Pro Ala Lys Pro Thr Thr Thr Pro Ala Pro Arg Pro Pro Thr Pro Ala
        115                 120                 125

Pro Thr Ile Ala Ser Gln Pro Leu Ser Leu Arg Pro Glu Ala Cys Arg
    130                 135                 140

Pro Ala Ala Gly Gly Ala Val His Thr Arg Gly Leu Asp Phe Ala Cys
145                 150                 155                 160

Asp Ile Tyr Ile Trp Ala Pro Leu Ala Gly Thr Cys Gly Val Leu Leu
                165                 170                 175

Leu Ser Leu Val Ile Thr Leu Tyr Cys Asn His Arg Asn Arg Arg Arg
            180                 185                 190

Val Cys Lys Cys Pro Arg Pro Val Val Lys Ser Gly Asp Lys Pro Ser
        195                 200                 205

Leu Ser Ala Arg Tyr Val
    210

<210> SEQ ID NO 121
<211> LENGTH: 189
<212> TYPE: PRT
<213> ORGANISM: Artificial Sequence
<220> FEATURE:
<223> OTHER INFORMATION: Synthetic sequence CD8 co-receptor beta chain
      isoform 1 (mature)

<400> SEQUENCE: 121

Leu Gln Gln Thr Pro Ala Tyr Ile Lys Val Gln Thr Asn Lys Met Val
1               5                   10                  15

Met Leu Ser Cys Glu Ala Lys Ile Ser Leu Ser Asn Met Arg Ile Tyr
            20                  25                  30

Trp Leu Arg Gln Arg Gln Ala Pro Ser Ser Asp Ser His His Glu Phe
        35                  40                  45

Leu Ala Leu Trp Asp Ser Ala Lys Gly Thr Ile His Gly Glu Glu Val
    50                  55                  60

Glu Gln Glu Lys Ile Ala Val Phe Arg Asp Ala Ser Arg Phe Ile Leu
65                  70                  75                  80

Asn Leu Thr Ser Val Lys Pro Glu Asp Ser Gly Ile Tyr Phe Cys Met
            85                  90                  95

Ile Val Gly Ser Pro Glu Leu Thr Phe Gly Lys Gly Thr Gln Leu Ser
        100                 105                 110

Val Val Asp Phe Leu Pro Thr Thr Ala Gln Pro Thr Lys Lys Ser Thr
    115                 120                 125

Leu Lys Lys Arg Val Cys Arg Leu Pro Arg Pro Glu Thr Gln Lys Gly
130                 135                 140

Pro Leu Cys Ser Pro Ile Thr Leu Gly Leu Leu Val Ala Gly Val Leu
145                 150                 155                 160

Val Leu Leu Val Ser Leu Gly Val Ala Ile His Leu Cys Cys Arg Arg
                165                 170                 175

Arg Arg Ala Arg Leu Arg Phe Met Lys Gln Phe Tyr Lys
                180                 185

-continued

```
<210> SEQ ID NO 122
<211> LENGTH: 200
<212> TYPE: PRT
<213> ORGANISM: Artificial Sequence
<220> FEATURE:
<223> OTHER INFORMATION: Synthetic sequence CD8 co-receptor beta chain
      isoform 2 (mature)

<400> SEQUENCE: 122

Leu Gln Gln Thr Pro Ala Tyr Ile Lys Val Gln Thr Asn Lys Met Val
1               5                   10                  15

Met Leu Ser Cys Glu Ala Lys Ile Ser Leu Ser Asn Met Arg Ile Tyr
            20                  25                  30

Trp Leu Arg Gln Arg Gln Ala Pro Ser Ser Asp Ser His His Glu Phe
        35                  40                  45

Leu Ala Leu Trp Asp Ser Ala Lys Gly Thr Ile His Gly Glu Glu Val
    50                  55                  60

Glu Gln Glu Lys Ile Ala Val Phe Arg Asp Ala Ser Arg Phe Ile Leu
65                  70                  75                  80

Asn Leu Thr Ser Val Lys Pro Glu Asp Ser Gly Ile Tyr Phe Cys Met
                85                  90                  95

Ile Val Gly Ser Pro Glu Leu Thr Phe Gly Lys Gly Thr Gln Leu Ser
            100                 105                 110

Val Val Asp Phe Leu Pro Thr Thr Ala Gln Pro Thr Lys Lys Ser Thr
        115                 120                 125

Leu Lys Lys Arg Val Cys Arg Leu Pro Arg Pro Glu Thr Gln Lys Gly
    130                 135                 140

Pro Leu Cys Ser Pro Ile Thr Leu Gly Leu Leu Val Ala Gly Val Leu
145                 150                 155                 160

Val Leu Leu Val Ser Leu Gly Val Ala Ile His Leu Cys Cys Arg Arg
                165                 170                 175

Arg Arg Ala Arg Leu Arg Phe Met Lys Gln Leu Arg Leu His Pro Leu
            180                 185                 190

Glu Lys Cys Ser Arg Met Asp Tyr
        195                 200

<210> SEQ ID NO 123
<211> LENGTH: 225
<212> TYPE: PRT
<213> ORGANISM: Artificial Sequence
<220> FEATURE:
<223> OTHER INFORMATION: Synthetic sequence CD8 co-receptor beta chain
      isoform 3 (mature)

<400> SEQUENCE: 123

Leu Gln Gln Thr Pro Ala Tyr Ile Lys Val Gln Thr Asn Lys Met Val
1               5                   10                  15

Met Leu Ser Cys Glu Ala Lys Ile Ser Leu Ser Asn Met Arg Ile Tyr
            20                  25                  30

Trp Leu Arg Gln Arg Gln Ala Pro Ser Ser Asp Ser His His Glu Phe
        35                  40                  45

Leu Ala Leu Trp Asp Ser Ala Lys Gly Thr Ile His Gly Glu Glu Val
    50                  55                  60

Glu Gln Glu Lys Ile Ala Val Phe Arg Asp Ala Ser Arg Phe Ile Leu
65                  70                  75                  80

Asn Leu Thr Ser Val Lys Pro Glu Asp Ser Gly Ile Tyr Phe Cys Met
                85                  90                  95

Ile Val Gly Ser Pro Glu Leu Thr Phe Gly Lys Gly Thr Gln Leu Ser
```

```
            100                 105                 110
Val Val Asp Phe Leu Pro Thr Thr Ala Gln Pro Thr Lys Lys Ser Thr
            115                 120                 125

Leu Lys Lys Arg Val Cys Arg Leu Pro Arg Pro Glu Thr Gln Lys Gly
            130                 135                 140

Pro Leu Cys Ser Pro Ile Thr Leu Gly Leu Leu Val Ala Gly Val Leu
145                 150                 155                 160

Val Leu Leu Val Ser Leu Gly Val Ala Ile His Leu Cys Cys Arg Arg
                165                 170                 175

Arg Arg Ala Arg Leu Arg Phe Met Lys Gln Lys Phe Asn Ile Val Cys
                180                 185                 190

Leu Lys Ile Ser Gly Phe Thr Thr Cys Cys Cys Phe Gln Ile Leu Gln
                195                 200                 205

Ile Ser Arg Glu Tyr Gly Phe Gly Val Leu Leu Gln Lys Asp Ile Gly
                210                 215                 220

Gln
225

<210> SEQ ID NO 124
<211> LENGTH: 225
<212> TYPE: PRT
<213> ORGANISM: Artificial Sequence
<220> FEATURE:
<223> OTHER INFORMATION: Synthetic sequence CD8 co-receptor beta chain
      isoform 4 (mature)

<400> SEQUENCE: 124

Leu Gln Gln Thr Pro Ala Tyr Ile Lys Val Gln Thr Asn Lys Met Val
1               5                   10                  15

Met Leu Ser Cys Glu Ala Lys Ile Ser Leu Ser Asn Met Arg Ile Tyr
            20                  25                  30

Trp Leu Arg Gln Arg Gln Ala Pro Ser Ser Asp Ser His His Glu Phe
            35                  40                  45

Leu Ala Leu Trp Asp Ser Ala Lys Gly Thr Ile His Gly Glu Glu Val
        50                  55                  60

Glu Gln Glu Lys Ile Ala Val Phe Arg Asp Ala Ser Arg Phe Ile Leu
65                  70                  75                  80

Asn Leu Thr Ser Val Lys Pro Glu Asp Ser Gly Ile Tyr Phe Cys Met
                85                  90                  95

Ile Val Gly Ser Pro Glu Leu Thr Phe Gly Lys Gly Thr Gln Leu Ser
            100                 105                 110

Val Val Asp Phe Leu Pro Thr Thr Ala Gln Pro Thr Lys Lys Ser Thr
            115                 120                 125

Leu Lys Lys Arg Val Cys Arg Leu Pro Arg Pro Glu Thr Gln Lys Gly
            130                 135                 140

Pro Leu Cys Ser Pro Ile Thr Leu Gly Leu Leu Val Ala Gly Val Leu
145                 150                 155                 160

Val Leu Leu Val Ser Leu Gly Val Ala Ile His Leu Cys Cys Arg Arg
                165                 170                 175

Arg Arg Ala Arg Leu Arg Phe Met Lys Gln Lys Phe Asn Ile Val Cys
                180                 185                 190

Leu Lys Ile Ser Gly Phe Thr Thr Cys Cys Cys Phe Gln Ile Leu Gln
                195                 200                 205

Ile Ser Arg Glu Tyr Gly Phe Gly Val Leu Leu Gln Lys Asp Ile Gly
                210                 215                 220
```

Gln
225

<210> SEQ ID NO 125
<211> LENGTH: 222
<212> TYPE: PRT
<213> ORGANISM: Artificial Sequence
<220> FEATURE:
<223> OTHER INFORMATION: Synthetic sequence CD8 co-receptor beta chain
      isoform 5 (mature)

<400> SEQUENCE: 125

Leu Gln Gln Thr Pro Ala Tyr Ile Lys Val Gln Thr Asn Lys Met Val
1               5                   10                  15

Met Leu Ser Cys Glu Ala Lys Ile Ser Leu Ser Asn Met Arg Ile Tyr
            20                  25                  30

Trp Leu Arg Gln Arg Gln Ala Pro Ser Ser Asp Ser His His Glu Phe
        35                  40                  45

Leu Ala Leu Trp Asp Ser Ala Lys Gly Thr Ile His Gly Glu Glu Val
    50                  55                  60

Glu Gln Glu Lys Ile Ala Val Phe Arg Asp Ala Ser Arg Phe Ile Leu
65                  70                  75                  80

Asn Leu Thr Ser Val Lys Pro Glu Asp Ser Gly Ile Tyr Phe Cys Met
                85                  90                  95

Ile Val Gly Ser Pro Glu Leu Thr Phe Gly Lys Gly Thr Gln Leu Ser
            100                 105                 110

Val Val Asp Phe Leu Pro Thr Thr Ala Gln Pro Thr Lys Lys Ser Thr
        115                 120                 125

Leu Lys Lys Arg Val Cys Arg Leu Pro Arg Pro Glu Thr Gln Lys Gly
    130                 135                 140

Pro Leu Cys Ser Pro Ile Thr Leu Gly Leu Leu Val Ala Gly Val Leu
145                 150                 155                 160

Val Leu Leu Val Ser Leu Gly Val Ala Ile His Leu Cys Cys Arg Arg
                165                 170                 175

Arg Arg Ala Arg Leu Arg Phe Met Lys Gln Pro Gln Gly Glu Gly Ile
            180                 185                 190

Ser Gly Thr Phe Val Pro Gln Cys Leu His Gly Tyr Tyr Ser Asn Thr
        195                 200                 205

Thr Thr Ser Gln Lys Leu Leu Asn Pro Trp Ile Leu Lys Thr
    210                 215                 220

<210> SEQ ID NO 126
<211> LENGTH: 930
<212> TYPE: DNA
<213> ORGANISM: Artificial Sequence
<220> FEATURE:
<223> OTHER INFORMATION: Synthetic sequence TCR 29 beta chain (wild-
      type)

<400> SEQUENCE: 126
atgggcacca gcctcctctg ctggatggcc ctgtgtctcc tgggggcaga tcacgcagat      60
actggagtct cccaggaccc cagacacaag atcacaaaga gggacagaa tgtaactttc      120 aggtgtgatc caatttctga acacaaccgc ctttattggt accgacagac cctggggcag     180
ggcccagagt ttctgactta cttccagaat gaagctcaac tagaaaaatc aaggctgctc     240
agtgatcggt tctctgcaga gaggcctaag ggatctttct ccaccttgga gatccagcgc     300
acagagcagg gggactcggc catgtatctc tgtgccagca gcttagtatc cggaaacacc     360

```
atatattttg gagagggaag ttggctcact gttgtagagg acctgaacaa ggtgttccca      420
cccgaggtcg ctgtgtttga gccatcagaa gcagagatct cccacaccca aaaggccaca      480
ctggtgtgcc tggccacagg cttcttcccc gaccacgtgg agctgagctg gtgggtgaat      540
gggaaggagg tgcacagtgg ggtcagcaca gacccgcagc ccctcaagga gcagcccgcc      600
ctcaatgact ccagatactg cctgagcagc cgcctgaggg tctcggccac cttctggcag      660 aaccccgca accacttccg ctgtcaagtc cagttctacg gctctcgga gaatgacgag        720 tggacccagg atagggccaa acccgtcacc cagatcgtca gcgccgaggc ctggggtaga      780
gcagactgtg gctttacctc ggtgtcctac cagcaagggg tcctgtctgc caccatcctc      840
tatgagatcc tgctagggaa ggccaccctg tatgctgtgc tggtcagcgc ccttgtgttg      900
atggccatgg tcaagagaaa ggatttctga                                       930
```

```
<210> SEQ ID NO 127
<211> LENGTH: 828
<212> TYPE: DNA
<213> ORGANISM: Artificial Sequence
<220> FEATURE:
<223> OTHER INFORMATION: Synthetic sequence TCR 29 alpha chain (wild-
      type)

<400> SEQUENCE: 127
atggagaccc tcttgggcct gcttatcctt tggctgcagc tgcaatgggt gagcagcaaa       60
caggaggtga cgcagattcc tgcagctctg agtgtcccag aaggagaaaa cttggttctc      120
aactgcagtt tcactgatag cgctatttac aacctccagt ggtttaggca ggaccctggg      180
aaaggtctca catctctgtt gcttattcag tcaagtcaga gagagcaaac aagtggaaga      240
cttaatgcct cgctggataa atcatcagga cgtagtactt tatacattgc agcttctcag      300
cctggtgact cagccaccta cctctgtgct gtgagagggg ggactacctc aggaacctac      360
aaatacatct ttggaacagg caccaggctg aaggttttag caaatatcca gaaccctgac      420
cctgccgtgt accagctgag agactctaaa tccagtgaca gtctgtctg cctattcacc       480 gattttgatt ctcaaacaaa tgtgtcacaa agtaaggatt ctgatgtgta tatcacagac      540
aaaactgtgc tagacatgag gtctatggac ttcaagagca cagtgctgt ggcctggagc       600 aacaaatctg actttgcatg tgcaaacgcc ttcaacaaca gcattattcc agaagacacc      660
ttcttcccca gcccagaaag ttcctgtgat gtcaagctgg tcgagaaaag ctttgaaaca      720
gatacgaacc taaactttca aaacctgtca gtgattgggt tccgaatcct cctcctgaaa      780
gtggccgggt taatctgct catgacgctg cggctgtggt ccagctga                    828
```

```
<210> SEQ ID NO 128
<211> LENGTH: 9
<212> TYPE: PRT
<213> ORGANISM: Artificial Sequence
<220> FEATURE:
<223> OTHER INFORMATION: Control clone specific for a Y
      chromosome-associated minor H antigen

<400> SEQUENCE: 128

Phe Ile Asp Ser Tyr Ile Cys Gln Val
1               5
```

```
<210> SEQ ID NO 129

<400> SEQUENCE: 129

000
```

<210> SEQ ID NO 130
<211> LENGTH: 14
<212> TYPE: PRT
<213> ORGANISM: Artificial Sequence
<220> FEATURE:
<223> OTHER INFORMATION: Synthetic sequence TCR24 beta chain CDR3

<400> SEQUENCE: 130

Ala Thr Ser Lys Thr Arg Ile Ala Gln Glu Thr Gln Tyr Phe
1               5                   10

<210> SEQ ID NO 131
<211> LENGTH: 9
<212> TYPE: PRT
<213> ORGANISM: Artificial Sequence
<220> FEATURE:
<223> OTHER INFORMATION: Synthetic Meganuclease sequence

<400> SEQUENCE: 131

Leu Ala Gly Leu Ile Asp Ala Asp Gly
1               5

<210> SEQ ID NO 132
<211> LENGTH: 5
<212> TYPE: PRT
<213> ORGANISM: Artificial Sequence
<220> FEATURE:
<223> OTHER INFORMATION: Synthetic Meganuclease sequence
<220> FEATURE:
<221> NAME/KEY: VARIANT
<222> LOCATION: 3
<223> OTHER INFORMATION: Xaa  = D or E
<220> FEATURE:
<221> NAME/KEY: VARIANT
<222> LOCATION: 4
<223> OTHER INFORMATION: Xaa = any amino aicd

<400> SEQUENCE: 132

Pro Asp Xaa Xaa Lys
1               5

<210> SEQ ID NO 133
<211> LENGTH: 5
<212> TYPE: PRT
<213> ORGANISM: Artificial Sequence
<220> FEATURE:
<223> OTHER INFORMATION: Synthetic sequence - TCR2, 14 Vb CDR1

<400> SEQUENCE: 133

Ser Glu His Asn Arg
1               5

<210> SEQ ID NO 134
<211> LENGTH: 6
<212> TYPE: PRT
<213> ORGANISM: Artificial Sequence
<220> FEATURE:
<223> OTHER INFORMATION: Synthetic sequence - TCR2, 14 Vb CDR2

<400> SEQUENCE: 134

Phe Gln Asn Glu Ala Gln
1               5

<210> SEQ ID NO 135
<211> LENGTH: 6
<212> TYPE: PRT
<213> ORGANISM: Artificial Sequence -continued

```
<220> FEATURE:
<223> OTHER INFORMATION: Synthetic sequence - TCR2, 14 Va CDR1

<400> SEQUENCE: 135

Asp Ser Ala Ile Tyr Asn
1               5

<210> SEQ ID NO 136
<211> LENGTH: 7
<212> TYPE: PRT
<213> ORGANISM: Artificial Sequence
<220> FEATURE:
<223> OTHER INFORMATION: Synthetic sequence - TCR2, 14 Va CDR2

<400> SEQUENCE: 136

Ile Gln Ser Ser Gln Arg Glu
1               5
```